(12) United States Patent
Sette et al.

(10) Patent No.: US 10,703,784 B2
(45) Date of Patent: Jul. 7, 2020

(54) ANTIGENS AND EPITOPES DERIVED FROM MYCOBACTERIUM TUBERCULOSIS

(71) Applicant: LA JOLLA INSTITUTE FOR ALLERGY AND IMMUNOLOGY, La Jolla, CA (US)

(72) Inventors: Alessandro Sette, La Jolla, CA (US); Cecilia Arlehamm, Del Mar, CA (US); Bjoern Peters, San Diego, CA (US); Howard Grey, La Jolla, CA (US); John Sidney, San Diego, CA (US)

(73) Assignee: LA JOLLA INSTITUTE FOR ALLERGY AND IMMUNOLOGY, La Jolla, CA (US)

(*) Notice: Subject to any disclaimer, the term of this patent is extended or adjusted under 35 U.S.C. 154(b) by 0 days.

(21) Appl. No.: 13/632,281

(22) Filed: Oct. 1, 2012

(65) Prior Publication Data

US 2014/0004151 A1 Jan. 2, 2014

Related U.S. Application Data

(60) Provisional application No. 61/541,892, filed on Sep. 30, 2011.

(51) Int. Cl.
| | |
|---|---|
| *A61K 39/04* | (2006.01) |
| *A61K 39/02* | (2006.01) |
| *A61K 39/00* | (2006.01) |
| *C07K 14/35* | (2006.01) |
| *A61K 45/06* | (2006.01) |

(52) U.S. Cl.
CPC .............. *C07K 14/35* (2013.01); *A61K 39/04* (2013.01); *A61K 45/06* (2013.01); *A61K 2039/57* (2013.01)

(58) Field of Classification Search
CPC ........ A61K 38/00; A61K 39/00; A61K 39/02; A61K 39/04; C07K 1/00; C07K 2/00; C07K 14/00
USPC ..... 424/184.1, 185.1, 234.1, 248.1; 530/300, 530/350
See application file for complete search history.

(56) References Cited

U.S. PATENT DOCUMENTS

| | | | |
|---|---|---|---|
| 6,555,653 B2 * | 4/2003 | Alderson ................ | C07K 14/35 424/168.1 |
| 7,238,359 B2 * | 7/2007 | Hasnain et al. ........... | 424/248.1 |
| 7,393,539 B2 * | 7/2008 | James et al. .............. | 424/248.1 |
| 7,670,609 B2 * | 3/2010 | Shafferman et al. ...... | 424/248.1 |
| 2006/0002941 A1 * | 1/2006 | Mahairas ................ | A61K 39/00 424/178.1 |
| 2006/0078566 A1 * | 4/2006 | Hasnain et al. .......... | 424/190.1 |
| 2006/0182685 A1 * | 8/2006 | Bishai et al. ............ | 424/9.2 |
| 2006/0228712 A1 * | 10/2006 | Nakagawa et al. ........ | 435/6 |
| 2008/0260763 A1 * | 10/2008 | Felgner et al. ........... | 424/186.1 |
| 2009/0082296 A1 * | 3/2009 | James et al. .............. | 514/44 |
| 2009/0285847 A1 * | 11/2009 | Felgner et al. ........... | 424/190.1 |

FOREIGN PATENT DOCUMENTS

| | | | |
|---|---|---|---|
| WO | WO97/11966 | * | 4/1997 |
| WO | WO2008124646 | * | 10/2008 |
| WO | WO2009/039854 | * | 4/2009 |

OTHER PUBLICATIONS

Skjot, R.L.V., et al., Epitope Mapping of the Immunodominant Antigen TB10.4 and the Two Homologous Proteins TB10.3 and TB12.9, Which Constitute a Subfamily of the esat-6 Gene Family, Infect Immun, 2002, 70: 5446-5453.
Li Pira, G., et al., Evaluation of Antigen-Specific T-Cell Responses with a Miniaturized and Automated Method, Clin Vaccine Immunol, 2008, 15:1811-1818.
Alderson, M. R., et al., Expression Cloning of an immunodominant Family of *Mycobacterium tuberculosis* Antigens Using Human Cd4+ T Cells. J Exp Med, 2000, 191:551-560.
Mustafa, A. S., Comparative evaluation of MPT83 (Rv2873) for T helper-1 cell reactivity and identification of HLA-promiscuous peptides: studies in M. bovis BCG-vaccinated healthy subjects, Clin Vaccine Immunol, 2011, CVI.05260-05211.
Al-Attiya, R.F.A., et al., Synthetic Peptides Identify Promiscuous Human Th1 Cell Epitopes of the Secreted *Mycobacterial* Antigen MPB70, Infection and Immunity, 2003, 71:1953-1960.
De Groot, A.S., et al., Developing an epitope-driven tuberculosis (TB) vaccine, Vaccine, 2005, 23:2121-2131.
Mustafa, A. S., et al., ProPred analysis and experimental evaluation of promiscuous T-cell epitopes of three major secreted antigens of *Mycobacterium tuberculosis*, Tuberculosis, 2006, 86:115-124.
Arend, S.M., et al., Antigenic Equivalence of Human T-Cell Responses to *Mycobacterium tuberculosis*-Specific RD1-Encoded Protein Antigens ESAT-6 and Culture Filtrate Protein 10 and to Mixtures of Synthetic Peptides, Infect Immun, 2000, 68:3314-3321.
Shams, H.P., Characterization of a *Mycobacterium tuberculosis* Peptide That Is Recognized by Human CD4+ and CD8+ T Cells in the Context of Multiple HLA Alleles, J Immunol, 2004, 173:1966-1977.
Mustafa, A.S., et al., Multiple Epitopes from the *Mycobacterium tuberculosis* ESAT-6 Antigen Are Recognized by Antigen-Specific Human T Cell Lines. Clinical Infectious Diseases, 2000, 30:S201

(56) References Cited

OTHER PUBLICATIONS

Launois, P., et al., T-cell-epitope mapping of the major secreted *Mycobacterial* antigen Ag85A in tuberculosis and leprosy. Infection and Immunity, 1994, 62:3879-3687.

Roche, P.W., et al., T-cell determinants and antibody binding sites on the major *Mycobacterial* secretory protein MPB59 of *Mycobacterium bovis*. Infection and Immunity, 1994, 62:5319-5326.

Hiemstra, H.S., et al., Definition of Natural T Cell Antigens with Mimicry Epitopes Obtained from Dedicated Synthetic Peptide Libraries. J Immunol, 1998, 161:4078-4082.

Silver, R. et al., Mapping of T cel epitopes of the 30-kDa alpha antigen of *Mycobacterium bovis* strain bacillus Calmette-Guerin in purified protein derivative (PPD)-positive individuals. J Immunol, 1995, 154:4665-4674.

Valle, M.T., Epitope focus, clonal composition and Th1 phenotype of the human CD4 response to the secretory *Mycobacterial* antigen Ag85. Clinical & Experimental Immunology, 2001, 123:226-232.

Dillon, D.C., et al., Molecular Characterization and Human T-Cell Responses to a Member of a Novel *Mycobacterium tuberculosis* mtb39 Gene Family. Infection and Immunity, 1999, 67:2941-2950.

Chaitra, M.G., et al., Characterization of T-cell immunogenicity of two PE/PPE proteins of *Mycobacterium tuberculosis*. J Med Microbiol, 2008, 57:1079-1086.

Mustafa, A.S., et al., Efficient Testing of Large Pools of *Mycobacterium tuberculosis* RD1 Peptides and Identification of Major Antigens and Immunodominant Peptides Recognized by Human Th1 Cells. Clin. Vaccine Immunol, 2008, 15:916-924.

Okkels, L., et al., PPE protein (Rv3873) from DNA segment RD1 of *Mycobacterium tuberculosis*: strong recognition of both specific T-cell epitopes and epitopes conserved within the PPE family. Infect Immun, 2003, 71:6116-6123.

Munk, M.E., et al., Epitopes of the *Mycobacterial* Heat Shock Protein 65 for Human T Cells Comprise Different Structures. Immunobiology, 1990, 180:272-277.

Oftung, F., et al., Epitopes of the *Mycobacterium tuberculosis* 65-kilodalton protein antigen as recognized by human T cells. J Immunol, 1988, 141:2749-2754.

Haanen, J.B., et al., *Mycobacterium leprae*-specific T cells from a tuberculoid leprosy patient suppress HLA-DR3-restricted T cell responses to an immunodominant epitope on 65-kDa hsp of *Mycobacteria*. J Immunol, 1990, 145:3898-3904.

Geluk, A., et al., Evolutionary conservation of major histocompatibility complex-DR/peptide/T cell interactions in primates. J Exp Med, 1993, 177:979-987.

Agrewala, J.N., et al., Influence of HLA-DR on the phenotype of CD4+ T lymphocytes specific for an epitope of the 16-kDa α-crystallin antigen of *Mycobacterium tuberculosis*. European Journal of Immunology, 1999, 29:1753-1761.

Caccamo, N., et al., Cytokine profile, HLA restriction and TCR sequence analysis of human CD4+ T clones specific for an immunodominant epitope of *Mycobacterium tuberculosis* 16-kDa protein. Clinical & Experimental Immunology, 2003, 133:260-266.

Friscia, G., et al., Human T cell responses to peptide epitopes of the 16-kD antigen in tuberculosis. Clin Exp Immunol, 1995, 102:53-57.

Wilkinson, D., et al., Human T- and B-Cell Reactivity to the 16 kDa α-Crystallin Protein of *Mycobacterium tuberculosis*. Scandinavian Journal of Immunology, 1998, 48:403-409.

Hussain, R., et al., Immune profiling of leprosy and tuberculosis patients to 15-mer peptides of *Mycobacterium leprae* and *M. tuberculosis* GroES in a BCG vaccinated area: implications for development of vaccine and diagnostic reagents. Immunology, 2004, 111:462-471.

Chua, I., et al., Predominant recognition of species-specific determinants of the GroES homologues from *Mycobacterium leprae* and *M. tuberculosis*. Immunology, 1998, 93:64-72.

Kim, J., et al., Determinants of T cell reactivity to the *Mycobacterium leprae* GroES homologue. J Immunol, 1997, 159:335-343.

Matsushita, S., et al., Evidence for self and nonself peptide partial agonists that prolong clonal survival of mature T cells in vitro. J Immunol, 1997, 158:5685-5691.

\* cited by examiner

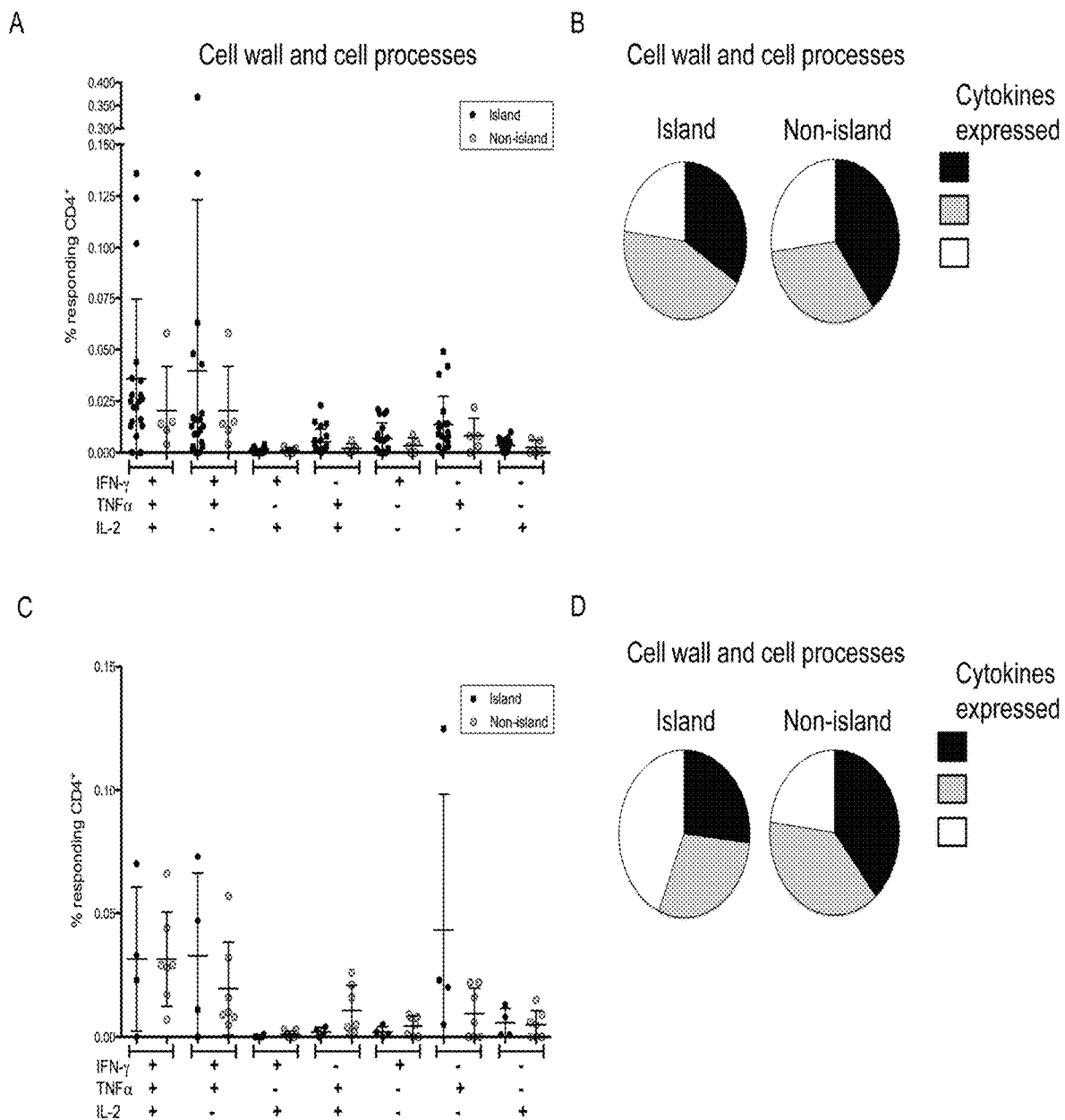
Figure 6 A-D

ANTIGENS AND EPITOPES DERIVED FROM *MYCOBACTERIUM TUBERCULOSIS*

RELATED APPLICATION INFORMATION

This application claims priority to and provisional application 61/541,892, filed Sep. 30, 2011, and which application is expressly incorporated herein by reference in its entirety.

GOVERNMENT SUPPORT

This invention received government support from the National Institutes of Health Contract HHSN272200900042C. The government has certain rights in the invention.

SEQUENCE LISTING

The instant application contains a Sequence Listing which has been submitted in ASCII format via EFS-Web and hereby incorporated by reference in its entirety. Said ASCII copy, created on Jun. 26, 2014, is named 2011-08-02_SEQ_ST25.txt and is 198,614 bytes in size.

FIELD OF THE INVENTION

The present invention relates to *M. tuberculosis* proteins and peptides, and subsequences, portions or modifications thereof and methods and compounds for eliciting, stimulating, inducing, promoting, increasing, or enhancing an anti-*M. tuberculosis* immune response.

BACKGROUND OF INVENTION

Tuberculosis is a major threat to global health and one of the major causes of death from infectious disease. One-third of the world's population is latently infected with *M. tuberculosis* (MTB). Most cases of active disease will arise from this enormous reservoir of latent TB, resulting in further spread of the disease, which embodies a major obstacle in achieving worldwide control of TB (WHO, 2011). Current diagnostics cannot distinguish between active and latent infection, and the only available vaccine against TB has limited efficacy. Further the increasing incidence of drug resistant strains has prompted their inclusion in the list of A-C pathogens, and heightened interest in development of effective vaccines. Therefore, there is a need for the development of novel vaccines and diagnostic strategies (Wallis et al., 2010).

Human T cell responses to MTB involve CD4+, CD8+ and γδ T cells (Boom, 1996). CD4 T cells have been shown to be central to the defense against MTB through the discovery that HIV infected patients are more susceptible to primary TB infection, re-infection and re-activation (Barnes et al., 1991). Different types of CD4 T helper (Th) cells develop from naïve T cells under the influence of polarizing signals and master transcription factors. Seminal studies showed that human memory T cells directed against MTB secreted IFN-γ, thus representing the human counterpart of mouse Th1 cells (Del Prete et al., 1991). IFN-γ has an essential role in the protective immunity to mycobacteria, as demonstrated by the increased susceptibility to mycobacteria in individuals with genetic defects in the IFN-γ receptor (Newport et al., 1996). Furthermore, different Th cell subsets differ in expression of chemokine receptors and therefore in migratory capacity and tissue localization (Sallusto et al., 2000). Th1 cells mainly express CCR5 and CXCR3 (Sallusto et al., 1998), while Th17 cells co-express CCR6 and CCR4 and Th22 cells co-express CCR6 and CCR10 (Acosta-Rodriguez et al., 2007; Duhen et al., 2009)

The MTB genome encodes more than 4,000 different ORFs, generally highly conserved amongst different strains, including drug resistant ones. Yet, only a handful of them have been reported as targets of human CD4+ T cells, the key cellular effector of MTB immunity. A genome-wide study determining which MTB antigens are immunodominant is to date lacking.

SUMMARY OF THE INVENTION

The invention is based, in part, on the present inventors' discovery of novel MTB proteins and peptides that are novel MTB antigens and epitopes and characterization of the genome-wide antigen response in latently infected individuals.

Thus the invention provides proteins and peptides, and subsequences, portions or modifications thereof and methods and compounds for eliciting, stimulating, inducing, promoting, increasing, or enhancing an anti-MTB immune response.

Thus in one aspect, there is presently provided a method of providing a subject with protection against a *M. tuberculosis* (MTB) infection or pathology, or one or more physiological conditions, disorders, illnesses, diseases, symptoms or complications caused by or associated with MTB infection or pathology, the method comprising administering to the subject an amount of a protein or peptide comprising, consisting of or consisting essentially of an amino acid sequence of a *M. tuberculosis* (MTB) protein or peptide set forth in Table 1 or Table 5, or a subsequence, portion, or modification thereof, sufficient to provide the subject with protection against the MTB infection or pathology, or one or more physiological conditions, disorders, illnesses, diseases, symptoms or complications caused by or associated with MTB infection or pathology. In particular aspects of the present invention, the method comprises vaccinating a subject against a *M. tuberculosis* (MTB) infection.

In certain embodiments, the protein or peptide of the presently provided methods comprises, consists of or consists essentially of an amino acid sequence of a MTB protein Rv3024c, Rv0289, Rv0290, Rv3330, Rv1788, Rv1791, Rv3125c, Rv0294, Rv2874, Rv3022c, Rv3135, Rv3876, Rv0124, Rv0291, Rv0292, Rv0293c, Rv0297, Rv0299, Rv3012c, Rv3025c, Rv0278c, Rv0279c, Rv0298, Rv0442c, Rv0690c, Rv0985c, Rv0987, Rv1172c, Rv1243c, Rv1317c, Rv1366, Rv1441c, Rv2490c or Rv2853, or a subsequence, portion, homologue, variant or derivative thereof.

In different embodiments of the presently provided methods, the amino acid sequence of the *M. tuberculosis* (MTB) protein or peptide comprises, consists of or consists essentially of an amino acid sequence derived from or based upon an amino acid sequence of *Mycobacterium tuberculosis* H37Rv, *Mycobacterium tuberculosis* CDC1551, *Mycobacterium tuberculosis* H37Ra. *Mycobacterium tuberculosis* F11, *Mycobacterium tuberculosis* KZN 1435, *Mycobacterium tuberculosis* KZN 605, *Mycobacterium tuberculosis* C, *Mycobacterium tuberculosis* str. Haarlem, *Mycobacterium tuberculosis* KZN 4207, *Mycobacterium tuberculosis* 94_M4241A, *Mycobacterium tuberculosis* 02_1987, *Mycobacterium tuberculosis* T92, *Mycobacterium tuberculosis* EAS054, *Mycobacterium tuberculosis* T85, *Mycobacterium tuberculosis* GM 1503, *Mycobacterium tuberculosis* T17,

*Mycobacterium tuberculosis* '98-R604 INH-RIF-EM', *Mycobacterium tuberculosis* T46, *Mycobacterium tuberculosis* CPHL_A or *Mycobacterium tuberculosis* K85.

In different embodiments, the methods of the present invention comprises administering to the subject the protein or peptide in combination with an immunological agent, wherein the subject is administered an amount of the protein or peptide sufficient to vaccinate the subject against the MTB infection when the protein or peptide is administered in combination with the immunological agent.

In certain embodiments, the method comprises eliciting, stimulating, inducing, promoting, increasing or enhancing a T cell response against *M. tuberculosis* (MTB). In particular embodiments, the method comprises eliciting, stimulating, inducing, promoting, increasing or enhancing a CD4+ T cell response against *M. tuberculosis* (MTB). In further embodiments, the method comprises eliciting, stimulating, inducing, promoting, increasing or enhancing a CXCR3$^+$CCR6$^+$ memory Th1 cell response against *M. tuberculosis* (MTB). In still further embodiments of the present methods, the subject is a mammal.

In another aspect, there is presently provided a method of eliciting, stimulating, inducing, promoting, increasing or enhancing an immune response against *M. tuberculosis* (MTB) in a subject, the method comprising administering to the subject an amount of a protein or peptide comprising, consisting of or consisting essentially of an amino acid sequence of a *M. tuberculosis* (MTB) protein or peptide set forth in Table 1 or Table 5, or a subsequence, portion, or modification thereof, sufficient to elicit, stimulate, induce, promote, increase or enhance an immune response against MTB in the subject.

In certain embodiments, the protein or peptide of the presently described methods comprises, consists of or consists essentially of an amino acid sequence of a MTB protein Rv3024c, Rv0289, Rv0290, Rv3330, Rv1788, Rv1791, Rv3125c, Rv0294, Rv2874, Rv3022c, Rv3135, Rv3876, Rv0124, Rv0291, Rv0292, Rv0293c, Rv0297, Rv0299, Rv3012c, Rv3025c, Rv0278c, Rv0279c, Rv0298, Rv0442c, Rv0690c, Rv0985c, Rv0987, Rv1172c, Rv1243c, Rv1317c, Rv1366, Rv1441c, Rv2490c or Rv2853, or a subsequence, portion, homologue, variant or derivative thereof.

In different embodiments of the present methods, the amino acid sequence of the *M. tuberculosis* (MTB) protein or peptide comprises, consists of or consists essentially of an amino acid sequence derived from or based upon an amino acid sequence of *Mycobacterium tuberculosis* H37Rv, *Mycobacterium tuberculosis* CDC1551, *Mycobacterium tuberculosis* H37Ra. *Mycobacterium tuberculosis* F11, *Mycobacterium tuberculosis* KZN 1435, *Mycobacterium tuberculosis* KZN 605, *Mycobacterium tuberculosis* C, *Mycobacterium tuberculosis* str. Haarlem, *Mycobacterium tuberculosis* KZN 4207, *Mycobacterium tuberculosis* 94_M4241A, *Mycobacterium tuberculosis* 02_1987, *Mycobacterium tuberculosis* T92, *Mycobacterium tuberculosis* EAS054, *Mycobacterium tuberculosis* T85, *Mycobacterium tuberculosis* GM 1503, *Mycobacterium tuberculosis* T17, *Mycobacterium tuberculosis* '98-R604 INH-RIF-EM', *Mycobacterium tuberculosis* T46, *Mycobacterium tuberculosis* CPHL_A or *Mycobacterium tuberculosis* K85.

In certain embodiments, the method comprises treating a subject for a *M. tuberculosis* (MTB) infection, the method comprising administering to the subject an amount of a protein or peptide comprising, consisting of or consisting essentially of an amino acid sequence of a *M. tuberculosis* (MTB) protein or peptide set forth in Table 1 or Table 5, or a subsequence, portion, or modification thereof, sufficient to treat the subject for the MTB infection.

In particular embodiments of the presently described method of eliciting, stimulating, inducing, promoting, increasing or enhancing an immune response against *M. tuberculosis* (MTB) in a subject, the immune response against *M. tuberculosis* (MTB) comprises a CD4+ T cell response. In further embodiments, the immune response against *M. tuberculosis* (MTB) comprises a CXCR3$^+$CCR6$^+$ memory Th1 cell response. In particular embodiments, the subject is a mammal.

In yet another aspect of the present invention, there is provided a protein or peptide comprising, consisting of or consisting essentially of an amino acid sequence of a *M. tuberculosis* (MTB) protein or peptide set forth in Table 1 or Table 5, or a subsequence, portion, or modification thereof, wherein the protein or peptide, elicits, stimulates, induces, promotes, increases or enhances an anti-MTB immune response.

In particular embodiments, the present invention provides a protein or peptide comprising, consisting of or consisting essentially of an amino acid sequence of a MTB protein Rv3024c, Rv0289, Rv0290, Rv3330, Rv1788, Rv1791, Rv3125c, Rv0294, Rv2874, Rv3022c, Rv3135, Rv3876, Rv0124, Rv0291, Rv0292, Rv0293c, Rv0297, Rv0299, Rv3012c, Rv3025c, Rv0278c, Rv0279c, Rv0298, Rv0442c, Rv0690c, Rv0985c, Rv0987, Rv1172c, Rv1243c, Rv1317c, Rv1366, Rv1441c, Rv2490c or Rv2853, or a subsequence, portion, homologue, variant or derivative thereof.

In different embodiments of the present invention, the protein or peptide consists of or consists essentially of an amino acid sequence derived from or based upon an amino acid sequence of *Mycobacterium tuberculosis* H37Rv, *Mycobacterium tuberculosis* CDC1551, *Mycobacterium tuberculosis* H37Ra. *Mycobacterium tuberculosis* F11, *Mycobacterium tuberculosis* KZN 1435, *Mycobacterium tuberculosis* KZN 605, *Mycobacterium tuberculosis* C, *Mycobacterium tuberculosis* str. Haarlem, *Mycobacterium tuberculosis* KZN 4207, *Mycobacterium tuberculosis* 94_M4241A, *Mycobacterium tuberculosis* 02_1987, *Mycobacterium tuberculosis* T92, *Mycobacterium tuberculosis* EAS054, *Mycobacterium tuberculosis* T85, *Mycobacterium tuberculosis* GM 1503, *Mycobacterium tuberculosis* T17, *Mycobacterium tuberculosis* '98-R604 INH-RIF-EM', *Mycobacterium tuberculosis* T46, *Mycobacterium tuberculosis* CPHL_A or *Mycobacterium tuberculosis* K85.

In a further embodiment of the present invention, the protein or peptide elicits, stimulates, induces, promotes, increases or enhances CD4+ T cell response. In a particular embodiment, the protein or peptide elicits, stimulates, induces, promotes, increases or enhances a CXCR3$^+$CCR6$^+$ memory Th1 cell response.

In yet another aspect of the present invention, there is provided a pharmaceutical composition comprising a protein or peptide described herein.

Other aspects and features of the present invention will become apparent to those of ordinary skill in the art upon review of the following description of specific embodiments of the invention in conjunction with the accompanying figures.

DESCRIPTION OF DRAWINGS

In the figures, which illustrate, by way of example only, embodiments of the present invention:

FIG. 1. T cell responses to MTB are restricted to a CXCR3$_+$CCR6$_+$ memory subset. Memory CD4 T cells were sorted into five subsets, 1) CXCR3+CCR6−, 2) CXCR3+CCR6+, 3) CCR4+CCR6−, 4) CCR4+CCR6+, and 5) CCR6+CCR10+. The sorted T cells were polyclonally expanded and analyzed for the presence of MTB-, Influenza A and C. albicans-specific T cells by stimulation with whole cell lysates in the presence of autologous monocytes and assessed for $_3$H-thymidine incorporation. (A) Shown is proliferation of individual cultures as cpm. Dotted lines represent the cut-off value. (B) Shown is the estimated frequency of antigen-specific T cells per $10^6$ cells in each Th cell subset for the three organisms used for stimulation.

FIG. 2. The T cell response to MTB is restricted to a CXCR3+CCR6+ memory subset. (A, B) Three CD45RA−CD25−CD4+ memory T cell subsets from four LTBI donors were sorted; 1) CCR6+CXCR3−; 2) CCR6+CXCR3+; and 3) CCR6−. (A) Representative dot plot from one donor; (B) Mean percentages of the T cell subsets on total CD4+ memory T cells. Error bars indicate SD (n=4). (C) T cell libraries were set up from the sorted subsets by polyclonal stimulation and expansion for 3-4 weeks. Libraries were analyzed by stimulation with autologous monocytes with or without MTB whole cell lysate and proliferative response was measured by $^3$H-thymidine incorporation. Shown is the estimated frequency of MTB-specific T cells per $10_6$ CD4 memory T cells for LTBI donors. (D) Distribution of MTB-specific T cells in the three memory T cell subsets. Data represent mean±SD from four donors. ***, p<0.0001.

FIG. 3. Breadth and dominance at the epitope and antigen level. (A) Epitopes ranked on the basis of magnitude of response. LTBI (black line—% of total response, grey line—total SFC) and TB uninfected (grey dashed line—total SFC) donors. Black dashed lines indicate the top 80 and 175 epitopes. (B) Antigens ranked on the basis of the response frequency for LTBI donors. Black dashed line indicates antigens recognized by >10% of LTBI donors. (C) Antigens ranked on the basis of magnitude of response and response frequency (black line—% of total response, grey line—total SFC). Black dashed line indicates the top 82 antigens.

FIG. 4. Protein categories of identified antigens. The identified antigens (black bars) were divided into protein categories (TuberculList) and compared to the MTB genome (grey bars). Chi-square test, *, p<0.001, **, p<0.0001.

FIG. 5. Antigens cluster in antigenic islands in the MTB genome. (A) All antigens recognized on the H37Rv genome map, % donors responding (black bars) and % of total response (dotted grey line). (B) Antigenic islands identified by a 5-gene window spanning the entire MTB genome (top panel); Binomial distribution and Bonferroni correction, *, p<0.01. Proteins within each antigenic island, % donors responding (black bars) and % of total island response (grey bars) and the % of total (all antigens recognized) response per island (middle panel). Cartoons show relative length of proteins, direction of transcription and protein category of each protein. Esx proteins are part of the cell wall and cell processes category.

FIG. 6. Cell wall/cell processes and PE/PPE specific CD4 T cells have a multifunctional phenotype. Epitope-specific IFN-γ, TNFα and IL-2 production by PBMCs from LTBI donors measured after 6 h peptide stimulation. (A, C) % of responding CD4+ expressing each of the seven possible combinations of IFN-γ, TNFα and IL-2 (A) cell wall and cell processes proteins, (C) PE/PPE proteins. Island proteins (black dots) and non-island (grey dots). Each dot represents one donor/epitope combination mean±SD is indicated. (B, D) The fraction of the total cytokine response against (B) cell wall and cell processes, (D) PE/PPE proteins, expressing all 3, 2 or 1 cytokine. (E) Heat-map of each of the seven possible combinations of IFN-γ, TNFα and IL-2 for each individual donor and epitope tested grouped by protein category and island localization. Each column represents one donor. Epitopes tested are SEQ ID Nos: 404, 38 41, 40, 42, 48, 405, 96, 321, 318, 324, 357, 340, 313 in order of appearance.

FIG. 7. Memory phenotype of MTB-specific CD4 T cells using HLA class II tetramers. (A) HLA class II tetramer stained CD4-purified cells from LTBI donors. Tetramer+ cells were isolated following magnetic bead enrichment. Plots are gated on CD4+ T cells, and the numbers indicate the percentage of tetramer+ cells isolated from each of 4 representative donors CD4+ population. DPB1*04:01 AGCQTYKWETFLTSE (SEQ ID No: 293) n=4 donors, DRB1*15:01 MHVSFVMAYPEMLAA (SEQ ID No: 340) n=3, DRB1*15:01MSQIMYNYPAMMAHA (SEQ ID No: 41) n=5 and DRB1*01:01 GEEYLILSARDVLAV (SEQ ID No: 399) n=2. (B) Memory phenotype of tetramer+ cells for one representative donor per tetramer. Plots are gated on total CD4+ T cells (black background) or epitope-specific CD4+ T cells (grey dots). The numbers represent the percentages of tetramer+CD4+ T cells in the gate. (C) Pie chart representation of the proportion of CCR7−CD45RA− (effector memory), CCR7+CD45RA− (central memory), CCR7+CD45RA+ (naïve), and CCR7−CD45RA+ (effector) CD4+ T cells for each tetramer.

FIG. 8. The T cell library approach complements the ex vivo IFN-γ ELISPOT assay. CCR6+CXCR3+ T cell libraries were set up for 4 representative donors. The sorted T cells were polyclonally expanded and analyzed for the presence of antigen-specific T cells by stimulation with peptide pools and measurement of $^3$H-thymidine incorporation. Shown is proliferation (cpm) of individual cultures from 4 different donors. Dotted lines represent the cut-off value. Response to antigens within genomic islands is shown in black or light grey and labelled Island 1, Island 2 or Island 3; response to antigens outside antigenic islands is shown in white. Antigenic islands are indicated by capped lines.

FIG. 9. Experimental design. Summary of the steps involved in the antigen identification pipeline, showing number of genomes, 15-mer peptides and selected peptides.

FIG. 10. Novelty of the antigens identified as a source of CD4 epitopes in humans. (A) Comparison with IEDB and literature, antigens were divided into four categories; novel, targets of CD4 T cells, CD8 T cells or undefined T cell type. 41% of defined antigens are novel. (B) Overlap of antigens described in this study with antigens described as sources of HLA class I restricted epitopes in the IEDB. (C) Overlap of antigens described in this study with antigens described as serologically reactive by Kunnath-Velayudhan et al. p-values calculated using a Chi-square test.

FIG. 11. Gating strategy for multifunctionality analysis. Cells were first gated based on forward vs. side-scatter, then CD3 vs. CD4 and finally for each cytokine (IFN-γ, TNFα, IL-2). Gates for each cytokine were based on the negative control and they were used for subsequent Boolean gating.

DETAILED DESCRIPTION

Figure 1:
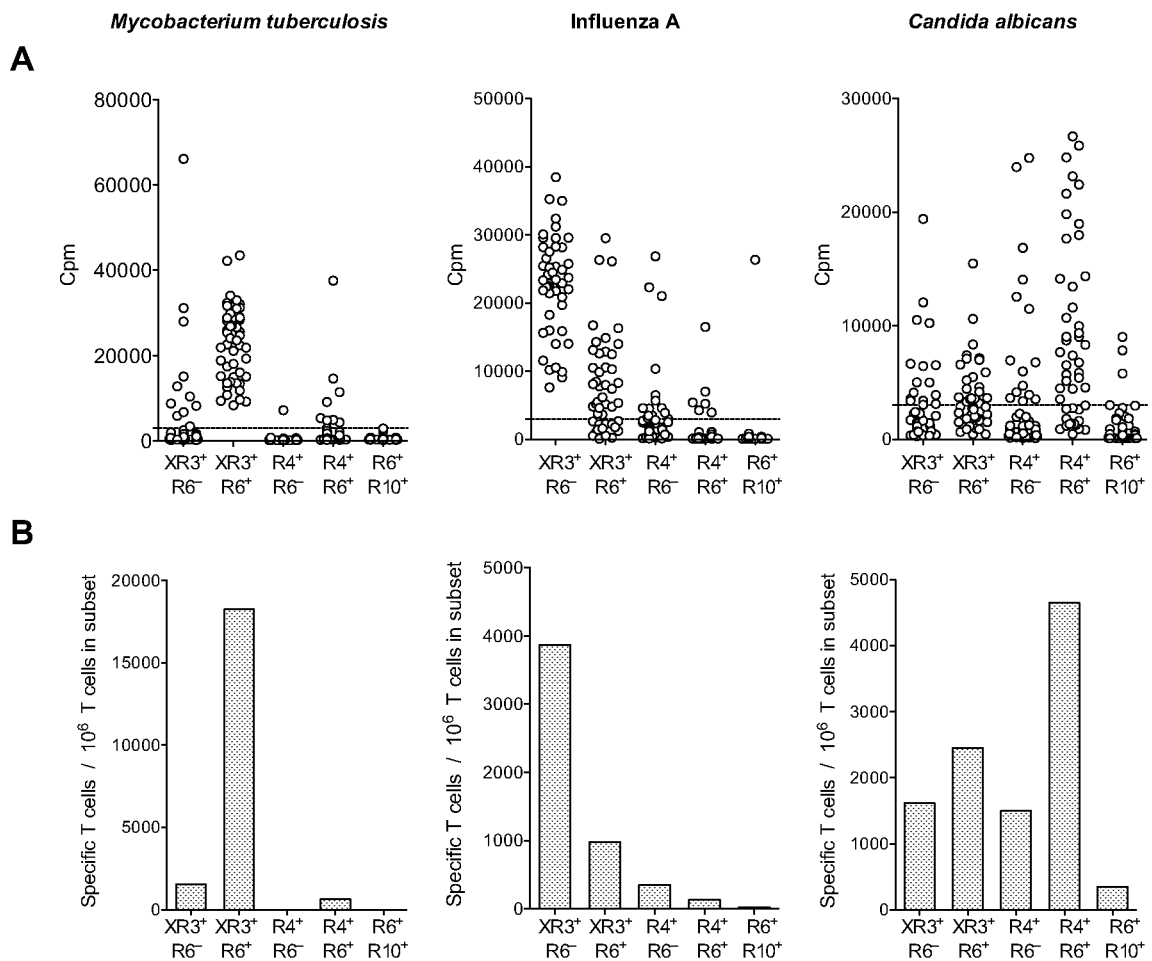

While immune reactive antigens have been described for *M. tuberculosis* (MTB), prior to the present invention the immunological footprint of MTB CD4 T cell recognition was incomplete. As disclosed herein, the present inventors have conducted the first unbiased, truly genome-wide screen for epitopes from MTB by the combined use of epitope predictions and high throughput ELISPOT and T cell library assays using PBMC from individuals latently infected with MTB.

Thus there are presently provided proteins and peptides, and subsequences, portions or modifications thereof, and methods and compounds for eliciting, stimulating, inducing, promoting, increasing, or enhancing an anti-MTB immune response. In particular aspects, there is provided several novel T cell antigens and epitopes which may be used in methods for MTB diagnosis, treatment and vaccination.

Previously identified T cell antigens from MTB are derived from all main protein categories, for about 2% of the approximately 4,000 ORFs of the MTB genome ((Blythe et al., 2007) and Immune Epitope Database (IEDB, iedb.org)), suggesting that protein function or cellular location per se does not determine which proteins can be recognized by the immune system. Previous studies in several complex pathogen systems have identified broad immune responses directed against a relatively large fraction of the genome (Oseroff et al., 2005; Pasquetto et al., 2005; Snyder et al., 2004). These studies were based on bioinformatics predictions and screening of exposed individuals for immune reactivity. By combining HLA class II peptide predictions and modern high throughput techniques such as ex vivo direct analysis, and screening of T cell libraries (Geiger et al., 2009), the present inventors have identified and characterized for the first time the genome-wide antigen response in latently infected individuals. The definition of breadth of responses is key for the design of preventive and therapeutic vaccination strategies that mirrors natural immunity (Kaech et al., 2002; Svenson et al., 2010). In addition, it provides important knowledge for the evaluation of disease progression and performance of vaccine candidates, as well as for development of diagnostics.

As used herein, an "antigen" refers to a substance, including but not limited to a protein, or a subsequence, portion or modification thereof that elicits an immune response when administered to a subject. In particular embodiments, an antigen may be a bacterial protein or peptide (e.g. a MTB protein or peptide). As used herein an "epitope" refers to a region or part of an antigen that elicits an immune response when administered to a subject. In particular embodiments, an epitope may be comprised of a region or part of an MTB protein or peptide.

In certain embodiments of the present invention, the MTB proteins or peptides described herein elicit an immune response. As will be understood by a person skilled in the art, an immune response may be a cellular or humoral immune response and may comprise an antibody response, a T cell response or both an antibody and T cell response. In particular embodiments of the present invention, the MTB protein or peptide is a T cell antigen or epitope.

A MTB protein or peptide as described herein includes a MTB protein or peptide, or a subsequence or portion or modification thereof. In some embodiments, the MTB protein is or peptide is derived from an MTB intermediary metabolism and respiration protein, cell wall and cell processes protein, lipid metabolism protein, information pathway protein, virulence, detoxification or adaptation protein, regulatory protein, PE/PPE protein, insertion sequence and phage protein, Esx protein, secreted protein, secretion system protein or conserved hypothetical protein. As would be understood by a person of skill in the art, a conserved hypothetical protein refers to a protein that is predicted to be expressed by an organism based on nucleic acid or amino acid sequence conservation with a protein of one or more other organisms.

In certain embodiments of the present invention, the MTB protein or peptide, or subsequence, portion or modification thereof, comprises a sequence set forth in Table 1 or Table 5, or a subsequence, portion or a modification thereof.

In further embodiments of the present invention, the MTB protein or peptide, or subsequence, portion or modification thereof, comprises an amino acid sequence of protein Rv3024c, Rv0289, Rv0290, Rv3330, Rv1788, Rv1791, Rv3125c, Rv0294, Rv2874, Rv3022c, Rv3135, Rv3876, Rv0124, Rv0291, Rv0292, Rv0293c, Rv0297, Rv0299, Rv3012c, Rv3025c, Rv0278c, Rv0279c, Rv0298, Rv0442c, Rv0690c, Rv0985c, Rv0987, Rv1172c, Rv1243c, Rv1317c, Rv1366, Rv1441c, Rv2490c or Rv2853.

In accordance with the present invention, the MTB protein or peptide, or subsequence, portion or modification thereof, may be derived from or based upon a sequence from any MTB strain, including but not limited to *Mycobacterium tuberculosis* H37Rv, *Mycobacterium tuberculosis* CDC1551, *Mycobacterium tuberculosis* H37Ra. *Mycobacterium tuberculosis* F11, *Mycobacterium tuberculosis* KZN 1435, *Mycobacterium tuberculosis* KZN 605, *Mycobacterium tuberculosis* C, *Mycobacterium tuberculosis* str. Haarlem, *Mycobacterium tuberculosis* KZN 4207, *Mycobacterium tuberculosis* 94_M4241A, *Mycobacterium tuberculosis* 02_1987, *Mycobacterium tuberculosis* T92, *Mycobacterium tuberculosis* EAS054, *Mycobacterium tuberculosis* T85, *Mycobacterium tuberculosis* GM 1503, *Mycobacterium tuberculosis* T17, *Mycobacterium tuberculosis* '98-R604 INH-RIF-EM', *Mycobacterium tuberculosis* T46, *Mycobacterium tuberculosis* CPHL_A and *Mycobacterium tuberculosis* K85.

As will be understood by a person skilled in the art, the amino acid sequence or nucleic acid sequence of MTB bacteria of the same strain may, for example due to mutations of the nucleic acid sequence between or within generations. In certain embodiments of the present invention, the MTB protein or peptide, or subsequence, portion or modification thereof, may be derived from or based upon the sequence of *Mycobacterium tuberculosis* H37Rv set forth in GenBank accession No. NC_000962, the sequence of *Mycobacterium tuberculosis* CDC1551 set forth in GenBank accession No. NC_002755, the sequence of *Mycobacterium tuberculosis* H37Ra set forth in GenBank accession No. NC_009525, the sequence of *Mycobacterium tuberculosis* F11 set forth in GenBank accession No. NC_009565, the sequence of *Mycobacterium tuberculosis* KZN 1435 set forth in GenBank accession No. NC_012943, the sequence of *Mycobacterium tuberculosis* set forth in GenBank accession No. KZN 605 NZ_ABGN00000000, the sequence of *Mycobacterium tuberculosis* C set forth in GenBank accession No. NZ_AAKR00000000, the sequence of *Mycobacterium tuberculosis* str. Haarlem set forth in GenBank accession No. NZ_AASN00000000, the sequence of *Mycobacterium tuberculosis* H37Ra set forth in GenBank accession No. NZ_AAYK00000000, the sequence of *Mycobacterium tuberculosis* KZN 4207 set forth in GenBank accession No. NZ_ABGL00000000, the sequence of *Mycobacterium tuberculosis* 94_M4241A set forth in GenBank accession No. NZ_ABLL00000000, the sequence of *Mycobacterium tuberculosis* 02_1987 set forth in GenBank accession No. NZ_ABLM00000000, the sequence of *Mycobacterium tuberculosis* T92 set forth in GenBank accession No. NZ_ABLN00000000, the sequence of *Mycobacterium tuberculosis* EAS054 set forth in GenBank accession No. NZ_ABOV00000000, the sequence of *Mycobacterium tuberculosis* T85 set forth in GenBank accession No. NZ_ABOW00000000, the sequence of *Mycobacterium* tuberculosis GM 1503 set forth in GenBank accession No. NZ_ABQG00000000, the sequence of Mycobacterium tuberculosis T17 set forth in GenBank accession No. NZ_ABQH00000000, the sequence of Mycobacterium tuberculosis '98-R604 INH-RIF-EM' set forth in GenBank accession No. NZ_ABVM00000000, the sequence of Mycobacterium tuberculosis T46 set forth in GenBank accession No. NZ_ACHO00000000, the sequence of Mycobacterium tuberculosis CPHL_A set forth in GenBank accession No. NZ_ACHP00000000 or the sequence of Mycobacterium tuberculosis K85 M4241A set forth in GenBank accession No. NZ_ACHQ00000000.

In certain embodiments of the compositions and methods of the present invention, the MTB protein or peptide, or subsequence, portion or modification thereof, comprises an amino acid sequence of protein Rv3024c of *Mycobacterium tuberculosis* H37Rv, *Mycobacterium tuberculosis* CDC1551, *Mycobacterium tuberculosis* H37Ra. *Mycobacterium tuberculosis* F11, *Mycobacterium tuberculosis* KZN 1435, *Mycobacterium tuberculosis* KZN 605, *Mycobacterium tuberculosis* C, *Mycobacterium tuberculosis* str. Haarlem, *Mycobacterium tuberculosis* KZN 4207, *Mycobacterium tuberculosis* 94_M4241A, *Mycobacterium tuberculosis* 02_1987, *Mycobacterium tuberculosis* T92, *Mycobacterium tuberculosis* EAS054, *Mycobacterium tuberculosis* T85, *Mycobacterium tuberculosis* GM 1503, *Mycobacterium tuberculosis* T17, *Mycobacterium tuberculosis* '98-R604 INH-RIF-EM', *Mycobacterium tuberculosis* T46, *Mycobacterium tuberculosis* CPHL_A or *Mycobacterium tuberculosis* K85. In other embodiments of the compositions and methods of the present invention, the MTB protein or peptide, or subsequence, portion or modification thereof, comprises an amino acid sequence of protein Rv0289 of *Mycobacterium tuberculosis* H37Rv, *Mycobacterium tuberculosis* CDC1551, *Mycobacterium tuberculosis* H37Ra. *Mycobacterium tuberculosis* F11, *Mycobacterium tuberculosis* KZN 1435, *Mycobacterium tuberculosis* KZN 605, *Mycobacterium tuberculosis* C, *Mycobacterium tuberculosis* str. Haarlem, *Mycobacterium tuberculosis* KZN 4207, *Mycobacterium tuberculosis* 94_M4241A, *Mycobacterium tuberculosis* 02_1987, *Mycobacterium tuberculosis* T92, *Mycobacterium tuberculosis* EAS054, *Mycobacterium tuberculosis* T85, *Mycobacterium tuberculosis* GM 1503, *Mycobacterium tuberculosis* T17, *Mycobacterium tuberculosis* '98-R604 INH-RIF-EM', *Mycobacterium tuberculosis* T46, *Mycobacterium tuberculosis* CPHL_A or *Mycobacterium tuberculosis* K85. In other embodiments of the compositions and methods of the present invention, the MTB protein or peptide, or subsequence, portion or modification thereof, comprises an amino acid sequence of protein Rv0290 of *Mycobacterium tuberculosis* H37Rv, *Mycobacterium tuberculosis* CDC1551, *Mycobacterium tuberculosis* H37Ra. *Mycobacterium tuberculosis* F11, *Mycobacterium tuberculosis* KZN 1435, *Mycobacterium tuberculosis* KZN 605, *Mycobacterium tuberculosis* C, *Mycobacterium tuberculosis* str. Haarlem, *Mycobacterium tuberculosis* KZN 4207, *Mycobacterium tuberculosis* 94_M4241A, *Mycobacterium tuberculosis* 02_1987, *Mycobacterium tuberculosis* T92, *Mycobacterium tuberculosis* EAS054, *Mycobacterium tuberculosis* T85, *Mycobacterium tuberculosis* GM 1503, *Mycobacterium tuberculosis* T17, *Mycobacterium tuberculosis* '98-R604 INH-RIF-EM', *Mycobacterium tuberculosis* T46, *Mycobacterium tuberculosis* CPHL_A or *Mycobacterium tuberculosis* K85. In other embodiments of the compositions and methods of the present invention, the MTB protein or peptide, or subsequence, portion or modification thereof, comprises an amino acid sequence of protein Rv3330 of *Mycobacterium tuberculosis* H37Rv, *Mycobacterium tuberculosis* CDC1551, *Mycobacterium tuberculosis* H37Ra. *Mycobacterium tuberculosis* F11, *Mycobacterium tuberculosis* KZN 1435, *Mycobacterium tuberculosis* KZN 605, *Mycobacterium tuberculosis* C, *Mycobacterium tuberculosis* str. Haarlem, *Mycobacterium tuberculosis* KZN 4207, *Mycobacterium tuberculosis* 94_M4241A, *Mycobacterium tuberculosis* 02_1987, *Mycobacterium tuberculosis* T92, *Mycobacterium tuberculosis* EAS054, *Mycobacterium tuberculosis* T85, *Mycobacterium tuberculosis* GM 1503, *Mycobacterium tuberculosis* T17, *Mycobacterium tuberculosis* '98-R604 INH-RIF-EM', *Mycobacterium tuberculosis* T46, *Mycobacterium tuberculosis* CPHL_A or *Mycobacterium tuberculosis* K85. In other embodiments of the compositions and methods of the present invention, the MTB protein or peptide, or subsequence, portion or modification thereof, comprises an amino acid sequence of protein Rv1788 of *Mycobacterium tuberculosis* H37Rv, *Mycobacterium tuberculosis* CDC1551, *Mycobacterium tuberculosis* H37Ra. *Mycobacterium tuberculosis* F11, *Mycobacterium tuberculosis* KZN 1435, *Mycobacterium tuberculosis* KZN 605, *Mycobacterium tuberculosis* C, *Mycobacterium tuberculosis* str. Haarlem, *Mycobacterium tuberculosis* KZN 4207, *Mycobacterium tuberculosis* 94_M4241A, *Mycobacterium tuberculosis* 02_1987, *Mycobacterium tuberculosis* T92, *Mycobacterium tuberculosis* EAS054, *Mycobacterium tuberculosis* T85, *Mycobacterium tuberculosis* GM 1503, *Mycobacterium tuberculosis* T17, *Mycobacterium tuberculosis* '98-R604 INH-RIF-EM', *Mycobacterium tuberculosis* T46, *Mycobacterium tuberculosis* CPHL_A or *Mycobacterium tuberculosis* K85. In other embodiments of the compositions and methods of the present invention, the MTB protein or peptide, or subsequence, portion or modification thereof, comprises an amino acid sequence of protein Rv1791 of *Mycobacterium tuberculosis* H37Rv, *Mycobacterium tuberculosis* CDC1551, *Mycobacterium tuberculosis* H37Ra. *Mycobacterium tuberculosis* F11, *Mycobacterium tuberculosis* KZN 1435, *Mycobacterium tuberculosis* KZN 605, *Mycobacterium tuberculosis* C, *Mycobacterium tuberculosis* str. Haarlem, *Mycobacterium tuberculosis* KZN 4207, *Mycobacterium tuberculosis* 94_M4241A, *Mycobacterium tuberculosis* 02_1987, *Mycobacterium tuberculosis* T92, *Mycobacterium tuberculosis* EAS054, *Mycobacterium tuberculosis* T85, *Mycobacterium tuberculosis* GM 1503, *Mycobacterium tuberculosis* T17, *Mycobacterium tuberculosis* '98-R604 INH-RIF-EM', *Mycobacterium tuberculosis* T46, *Mycobacterium tuberculosis* CPHL_A or *Mycobacterium tuberculosis* K85. In other embodiments of the compositions and methods of the present invention, the MTB protein or peptide, or subsequence, portion or modification thereof, comprises an amino acid sequence of protein Rv3125c of *Mycobacterium tuberculosis* H37Rv, *Mycobacterium tuberculosis* CDC1551, *Mycobacterium tuberculosis* H37Ra. *Mycobacterium tuberculosis* F11, *Mycobacterium tuberculosis* KZN 1435, *Mycobacterium tuberculosis* KZN 605, *Mycobacterium tuberculosis* C, *Mycobacterium tuberculosis* str. Haarlem, *Mycobacterium tuberculosis* KZN 4207, *Mycobacterium tuberculosis* 94_M4241A, *Mycobacterium tuberculosis* 02_1987, *Mycobacterium tuberculosis* T92, *Mycobacterium tuberculosis* EAS054, *Mycobacterium tuberculosis* T85, *Mycobacterium tuberculosis* GM 1503, *Mycobacterium tuberculosis* T17, *Mycobacterium tuberculosis* '98-R604 INH-RIF-EM', *Mycobacterium tuberculosis* T46, *Mycobacterium tuberculosis* CPHL_A or *Mycobacterium tuberculosis* K85. In other embodiments of the compositions and methods of the present invention, the MTB protein or peptide, or subsequence, portion or modification thereof, comprises an amino acid sequence of protein Rv0294 of *Mycobacterium tuberculosis* H37Rv, *Mycobacterium tuberculosis* CDC1551, *Mycobacterium tuberculosis* H37Ra. *Mycobacterium tuberculosis* F11, *Mycobacterium tuberculosis* KZN 1435, *Mycobacterium tuberculosis* KZN 605, *Mycobacterium tuberculosis* C, *Mycobacterium tuberculosis* str. Haarlem, *Mycobacterium tuberculosis* KZN 4207, *Mycobacterium tuberculosis* 94_M4241A, *Mycobacterium tuberculosis* 02_1987, *Mycobacterium tuberculosis* T92, *Mycobacterium tuberculosis* EAS054, *Mycobacterium tuberculosis* T85, *Mycobacterium tuberculosis* GM 1503, *Mycobacterium tuberculosis* T17, *Mycobacterium tuberculosis* '98-R604 INH-RIF-EM', *Mycobacterium tuberculosis* T46, *Mycobacterium tuberculosis* CPHL_A or *Mycobacterium tuberculosis* K85. In other embodiments of the compositions and methods of the present invention, the MTB protein or peptide, or subsequence, portion or modification thereof, comprises an amino acid sequence of protein Rv2874 of *Mycobacterium tuberculosis* H37Rv, *Mycobacterium tuberculosis* CDC1551, *Mycobacterium tuberculosis* H37Ra. *Mycobacterium tuberculosis* F11, *Mycobacterium tuberculosis* KZN 1435, *Mycobacterium tuberculosis* KZN 605, *Mycobacterium tuberculosis* C, *Mycobacterium tuberculosis* str. Haarlem, *Mycobacterium tuberculosis* KZN 4207, *Mycobacterium tuberculosis* 94_M4241A, *Mycobacterium tuberculosis* 02_1987, *Mycobacterium tuberculosis* T92, *Mycobacterium tuberculosis* EAS054, *Mycobacterium tuberculosis* T85, *Mycobacterium tuberculosis* GM 1503, *Mycobacterium tuberculosis* T17, *Mycobacterium tuberculosis* '98-R604 INH-RIF-EM', *Mycobacterium tuberculosis* T46, *Mycobacterium tuberculosis* CPHL_A or *Mycobacterium tuberculosis* K85. In other embodiments of the compositions and methods of the present invention, the MTB protein or peptide, or subsequence, portion or modification thereof, comprises an amino acid sequence of protein Rv3022c of *Mycobacterium tuberculosis* H37Rv, *Mycobacterium tuberculosis* CDC1551, *Mycobacterium tuberculosis* H37Ra. *Mycobacterium tuberculosis* F11, *Mycobacterium tuberculosis* KZN 1435, *Mycobacterium tuberculosis* KZN 605, *Mycobacterium tuberculosis* C, *Mycobacterium tuberculosis* str. Haarlem, *Mycobacterium tuberculosis* KZN 4207, *Mycobacterium tuberculosis* 94_M4241A, *Mycobacterium tuberculosis* 02_1987, *Mycobacterium tuberculosis* T92, *Mycobacterium tuberculosis* EAS054, *Mycobacterium tuberculosis* T85, *Mycobacterium tuberculosis* GM 1503, *Mycobacterium tuberculosis* T17, *Mycobacterium tuberculosis* '98-R604 INH-RIF-EM', *Mycobacterium tuberculosis* T46, *Mycobacterium tuberculosis* CPHL_A or *Mycobacterium tuberculosis* K85. In other embodiments of the compositions and methods of the present invention, the MTB protein or peptide, or subsequence, portion or modification thereof, comprises an amino acid sequence of protein Rv3135 of *Mycobacterium tuberculosis* H37Rv, *Mycobacterium tuberculosis* CDC1551, *Mycobacterium tuberculosis* H37Ra. *Mycobacterium tuberculosis* F11, *Mycobacterium tuberculosis* KZN 1435, *Mycobacterium tuberculosis* KZN 605, *Mycobacterium tuberculosis* C, *Mycobacterium tuberculosis* str. Haarlem, *Mycobacterium tuberculosis* KZN 4207, *Mycobacterium tuberculosis* 94_M4241A, *Mycobacterium tuberculosis* 02_1987, *Mycobacterium tuberculosis* T92, *Mycobacterium tuberculosis* EAS054, *Mycobacterium tuberculosis* T85, *Mycobacterium tuberculosis* GM 1503, *Mycobacterium tuberculosis* T17, *Mycobacterium tuberculosis* '98-R604 INH-RIF-EM', *Mycobacterium tuberculosis* T46, *Mycobacterium tuberculosis* CPHL_A or *Mycobacterium tuberculosis* K85. In other embodiments of the compositions and methods of the present invention, the MTB protein or peptide, or subsequence, portion or modification thereof, comprises an amino acid sequence of protein Rv3876 of *Mycobacterium tuberculosis* H37Rv, *Mycobacterium tuberculosis* CDC1551, *Mycobacterium tuberculosis* H37Ra. *Mycobacterium tuberculosis* F11, *Mycobacterium tuberculosis* KZN 1435, *Mycobacterium tuberculosis* KZN 605, *Mycobacterium tuberculosis* C, *Mycobacterium tuberculosis* str. Haarlem, *Mycobacterium tuberculosis* KZN 4207, *Mycobacterium tuberculosis* 94_M4241A, *Mycobacterium tuberculosis* 02_1987, *Mycobacterium tuberculosis* T92, *Mycobacterium tuberculosis* EAS054, *Mycobacterium tuberculosis* T85, *Mycobacterium tuberculosis* GM 1503, *Mycobacterium tuberculosis* T17, *Mycobacterium tuberculosis* '98-R604 INH-RIF-EM', *Mycobacterium tuberculosis* T46, *Mycobacterium tuberculosis* CPHL_A or *Mycobacterium tuberculosis* K85. In other embodiments of the compositions and methods of the present invention, the MTB protein or peptide, or subsequence, portion or modification thereof, comprises an amino acid sequence of protein Rv0124 of *Mycobacterium tuberculosis* H37Rv, *Mycobacterium tuberculosis* CDC1551, *Mycobacterium tuberculosis* H37Ra. *Mycobacterium tuberculosis* F11, *Mycobacterium tuberculosis* KZN 1435, *Mycobacterium tuberculosis* KZN 605, *Mycobacterium tuberculosis* C, *Mycobacterium tuberculosis* str. Haarlem, *Mycobacterium tuberculosis* KZN 4207, *Mycobacterium tuberculosis* 94_M4241A, *Mycobacterium tuberculosis* 02_1987, *Mycobacterium tuberculosis* T92, *Mycobacterium tuberculosis* EAS054, *Mycobacterium tuberculosis* T85, *Mycobacterium tuberculosis* GM 1503, *Mycobacterium tuberculosis* T17, *Mycobacterium tuberculosis* '98-R604 INH-RIF-EM', *Mycobacterium tuberculosis* T46, *Mycobacterium tuberculosis* CPHL_A or *Mycobacterium tuberculosis* K85. In other embodiments of the compositions and methods of the present invention, the MTB protein or peptide, or subsequence, portion or modification thereof, comprises an amino acid sequence of protein Rv0291 of *Mycobacterium tuberculosis* H37Rv, *Mycobacterium tuberculosis* CDC1551, *Mycobacterium tuberculosis* H37Ra. *Mycobacterium tuberculosis* F11, *Mycobacterium tuberculosis* KZN 1435, *Mycobacterium tuberculosis* KZN 605, *Mycobacterium tuberculosis* C, *Mycobacterium tuberculosis* str. Haarlem, *Mycobacterium tuberculosis* KZN 4207, *Mycobacterium tuberculosis* 94_M4241A, *Mycobacterium tuberculosis* 02_1987, *Mycobacterium tuberculosis* T92, *Mycobacterium tuberculosis* EAS054, *Mycobacterium tuberculosis* T85, *Mycobacterium tuberculosis* GM 1503, *Mycobacterium tuberculosis* T17, *Mycobacterium tuberculosis* '98-R604 INH-RIF-EM', *Mycobacterium tuberculosis* T46, *Mycobacterium tuberculosis* CPHL_A or *Mycobacterium tuberculosis* K85. In other embodiments of the compositions and methods of the present invention, the MTB protein or peptide, or subsequence, portion or modification thereof, comprises an amino acid sequence of protein Rv0292 of *Mycobacterium tuberculosis* H37Rv, *Mycobacterium tuberculosis* CDC1551, *Mycobacterium tuberculosis* H37Ra. *Mycobacterium tuberculosis* F11, *Mycobacterium tuberculosis* KZN 1435, *Mycobacterium tuberculosis* KZN 605, *Mycobacterium tuberculosis* C, *Mycobacterium tuberculosis* str. Haarlem, *Mycobacterium tuberculosis* KZN 4207, *Mycobacterium tuberculosis* 94_M4241A, *Mycobacterium tuberculosis* 02_1987, *Mycobacterium tuberculosis* T92, *Mycobacterium tuberculosis* EAS054, *Mycobacterium tuberculosis* T85, *Mycobacterium tuberculosis* GM 1503, *Mycobacterium tuberculosis* T17, *Mycobacterium tuberculosis* '98-R604 INH-RIF-EM', *Mycobacterium tuberculosis* T46, *Mycobacterium tuberculosis* CPHL_A or *Mycobacterium tuberculosis* K85. In other embodiments of the compositions and methods of the present invention, the MTB protein or peptide, or subsequence, portion or modification thereof, comprises an amino acid sequence of protein Rv0293c of *Mycobacterium tuberculosis* H37Rv, *Mycobacterium tuberculosis* CDC1551, *Mycobacterium tuberculosis* H37Ra. *Mycobacterium tuberculosis* F11, *Mycobacterium tuberculosis* KZN 1435, *Mycobacterium tuberculosis* KZN 605, *Mycobacterium tuberculosis* C, *Mycobacterium tuberculosis* str. Haarlem, *Mycobacterium tuberculosis* KZN 4207, *Mycobacterium tuberculosis* 94_M4241A, *Mycobacterium tuberculosis* 02_1987, *Mycobacterium tuberculosis* T92, *Mycobacterium tuberculosis* EAS054, *Mycobacterium tuberculosis* T85, *Mycobacterium tuberculosis* GM 1503, *Mycobacterium tuberculosis* T17, *Mycobacterium tuberculosis* '98-R604 INH-RIF-EM', *Mycobacterium tuberculosis* T46, *Mycobacterium tuberculosis* CPHL_A or *Mycobacterium tuberculosis* K85. In other embodiments of the compositions and methods of the present invention, the MTB protein or peptide, or subsequence, portion or modification thereof, comprises an amino acid sequence of protein Rv0297 of *Mycobacterium tuberculosis* H37Rv, *Mycobacterium tuberculosis* CDC1551, *Mycobacterium tuberculosis* H37Ra. *Mycobacterium tuberculosis* F11, *Mycobacterium tuberculosis* KZN 1435, *Mycobacterium tuberculosis* KZN 605, *Mycobacterium tuberculosis* C, *Mycobacterium tuberculosis* str. Haarlem, *Mycobacterium tuberculosis* KZN 4207, *Mycobacterium tuberculosis* 94_M4241A, *Mycobacterium tuberculosis* 02_1987, *Mycobacterium tuberculosis* T92, *Mycobacterium tuberculosis* EAS054, *Mycobacterium tuberculosis* T85, *Mycobacterium tuberculosis* GM 1503, *Mycobacterium tuberculosis* T17, *Mycobacterium tuberculosis* '98-R604 INH-RIF-EM', *Mycobacterium tuberculosis* T46, *Mycobacterium tuberculosis* CPHL_A or *Mycobacterium tuberculosis* K85. In other embodiments of the compositions and methods of the present invention, the MTB protein or peptide, or subsequence, portion or modification thereof, comprises an amino acid sequence of protein Rv0299 of *Mycobacterium tuberculosis* H37Rv, *Mycobacterium tuberculosis* CDC1551, *Mycobacterium tuberculosis* H37Ra. *Mycobacterium tuberculosis* F11, *Mycobacterium tuberculosis* KZN 1435, *Mycobacterium tuberculosis* KZN 605, *Mycobacterium tuberculosis* C, *Mycobacterium tuberculosis* str. Haarlem, *Mycobacterium tuberculosis* KZN 4207, *Mycobacterium tuberculosis* 94_M4241A, *Mycobacterium tuberculosis* 02_1987, *Mycobacterium tuberculosis* T92, *Mycobacterium tuberculosis* EAS054, *Mycobacterium tuberculosis* T85, *Mycobacterium tuberculosis* GM 1503, *Mycobacterium tuberculosis* T17, *Mycobacterium tuberculosis* '98-R604 INH-RIF-EM', *Mycobacterium tuberculosis* T46, *Mycobacterium tuberculosis* CPHL_A or *Mycobacterium tuberculosis* K85. In other embodiments of the compositions and methods of the present invention, the MTB protein or peptide, or subsequence, portion or modification thereof, comprises an amino acid sequence of protein Rv3012c of *Mycobacterium tuberculosis* H37Rv, *Mycobacterium tuberculosis* CDC1551, *Mycobacterium tuberculosis* H37Ra. *Mycobacterium tuberculosis* F11, *Mycobacterium tuberculosis* KZN 1435, *Mycobacterium tuberculosis* KZN 605, *Mycobacterium tuberculosis* C, *Mycobacterium tuberculosis* str. Haarlem, *Mycobacterium tuberculosis* KZN 4207, *Mycobacterium tuberculosis* 94_M4241A, *Mycobacterium tuberculosis* 02_1987, *Mycobacterium tuberculosis* T92, *Mycobacterium tuberculosis* EAS054, *Mycobacterium tuberculosis* T85, *Mycobacterium tuberculosis* GM 1503, *Mycobacterium tuberculosis* T17, *Mycobacterium tuberculosis* '98-R604 INH-RIF-EM', *Mycobacterium tuberculosis* T46, *Mycobacterium tuberculosis* CPHL_A or *Mycobacterium tuberculosis* K85. In other embodiments of the compositions and methods of the present invention, the MTB protein or peptide, or subsequence, portion or modification thereof, comprises an amino acid sequence of protein Rv3025c of *Mycobacterium tuberculosis* H37Rv, *Mycobacterium tuberculosis* CDC1551, *Mycobacterium tuberculosis* H37Ra. *Mycobacterium tuberculosis* F11, *Mycobacterium tuberculosis* KZN 1435, *Mycobacterium tuberculosis* KZN 605, *Mycobacterium tuberculosis* C, *Mycobacterium tuberculosis* str. Haarlem, *Mycobacterium tuberculosis* KZN 4207, *Mycobacterium tuberculosis* 94_M4241A, *Mycobacterium tuberculosis* 02_1987, *Mycobacterium tuberculosis* T92, *Mycobacterium tuberculosis* EAS054, *Mycobacterium tuberculosis* T85, *Mycobacterium tuberculosis* GM 1503, *Mycobacterium tuberculosis* T17, *Mycobacterium tuberculosis* '98-R604 INH-RIF-EM', *Mycobacterium tuberculosis* T46, *Mycobacterium tuberculosis* CPHL_A or *Mycobacterium tuberculosis* K85. In other embodiments of the compositions and methods of the present invention, the MTB protein or peptide, or subsequence, portion or modification thereof, comprises an amino acid sequence of protein Rv0278c of *Mycobacterium tuberculosis* H37Rv, *Mycobacterium tuberculosis* CDC1551, *Mycobacterium tuberculosis* H37Ra. *Mycobacterium tuberculosis* F11, *Mycobacterium tuberculosis* KZN 1435, *Mycobacterium tuberculosis* KZN 605, *Mycobacterium tuberculosis* C, *Mycobacterium tuberculosis* str. Haarlem, *Mycobacterium tuberculosis* KZN 4207, *Mycobacterium tuberculosis* 94_M4241A, *Mycobacterium tuberculosis* 02_1987, *Mycobacterium tuberculosis* T92, *Mycobacterium tuberculosis* EAS054, *Mycobacterium tuberculosis* T85, *Mycobacterium tuberculosis* GM 1503, *Mycobacterium tuberculosis* T17, *Mycobacterium tuberculosis* '98-R604 INH-RIF-EM', *Mycobacterium tuberculosis* T46, *Mycobacterium tuberculosis* CPHL_A or *Mycobacterium tuberculosis* K85. In other embodiments of the compositions and methods of the present invention, the MTB protein or peptide, or subsequence, portion or modification thereof, comprises an amino acid sequence of protein Rv0279c of *Mycobacterium tuberculosis* H37Rv, *Mycobacterium tuberculosis* CDC1551, *Mycobacterium tuberculosis* H37Ra. *Mycobacterium tuberculosis* F11, *Mycobacterium tuberculosis* KZN 1435, *Mycobacterium tuberculosis* KZN 605, *Mycobacterium tuberculosis* C, *Mycobacterium tuberculosis* str. Haarlem, *Mycobacterium tuberculosis* KZN 4207, *Mycobacterium tuberculosis* 94_M4241A, *Mycobacterium tuberculosis* 02_1987, *Mycobacterium tuberculosis* T92, *Mycobacterium tuberculosis* EAS054, *Mycobacterium tuberculosis* T85, *Mycobacterium tuberculosis* GM 1503, *Mycobacterium tuberculosis* T17, *Mycobacterium tuberculosis* '98-R604 INH-RIF-EM', *Mycobacterium tuberculosis* T46, *Mycobacterium tuberculosis* CPHL_A or *Mycobacterium tuberculosis* K85. In other embodiments of the compositions and methods of the present invention, the MTB protein or peptide, or subsequence, portion or modification thereof, comprises an amino acid sequence of protein Rv0298 of *Mycobacterium tuberculosis* H37Rv, *Mycobacterium tuberculosis* CDC1551, *Mycobacterium tuberculosis* H37Ra. *Mycobacterium tuberculosis* F11, *Mycobacterium tuberculosis* KZN 1435, *Mycobacterium tuberculosis* KZN 605, *Mycobacterium tuberculosis* C, *Mycobacterium tuberculosis* str. Haarlem, *Mycobacterium tuberculosis* KZN 4207, *Mycobacterium tuberculosis* 94_M4241A, *Mycobacterium tuberculosis* 02_1987, *Mycobacterium tuberculosis* T92, *Mycobacterium tuberculosis* EAS054, *Mycobacterium tuberculosis* T85, *Mycobacterium tuberculosis* GM 1503, *Mycobacterium tuberculosis* T17, *Mycobacterium tuberculosis* '98-R604 INH-RIF-EM', *Mycobacterium tuberculosis*

T46, *Mycobacterium tuberculosis* CPHL_A or *Mycobacterium tuberculosis* K85. In other embodiments of the compositions and methods of the present invention, the MTB protein or peptide, or subsequence, portion or modification thereof, comprises an amino acid sequence of protein Rv0442c of *Mycobacterium tuberculosis* H37Rv, *Mycobacterium tuberculosis* CDC1551, *Mycobacterium tuberculosis* H37Ra. *Mycobacterium tuberculosis* F11, *Mycobacterium tuberculosis* KZN 1435, *Mycobacterium tuberculosis* KZN 605, *Mycobacterium tuberculosis* C, *Mycobacterium tuberculosis* str. Haarlem, *Mycobacterium tuberculosis* KZN 4207, *Mycobacterium tuberculosis* 94_M4241A, *Mycobacterium tuberculosis* 02_1987, *Mycobacterium tuberculosis* T92, *Mycobacterium tuberculosis* EAS054, *Mycobacterium tuberculosis* T85, *Mycobacterium tuberculosis* GM 1503, *Mycobacterium tuberculosis* T17, *Mycobacterium tuberculosis* '98-R604 INH-RIF-EM', *Mycobacterium tuberculosis* T46, *Mycobacterium tuberculosis* CPHL_A or *Mycobacterium tuberculosis* K85. In other embodiments of the compositions and methods of the present invention, the MTB protein or peptide, or subsequence, portion or modification thereof, comprises an amino acid sequence of protein Rv0690c of *Mycobacterium tuberculosis* H37Rv, *Mycobacterium tuberculosis* CDC1551, *Mycobacterium tuberculosis* H37Ra. *Mycobacterium tuberculosis* F11, *Mycobacterium tuberculosis* KZN 1435, *Mycobacterium tuberculosis* KZN 605, *Mycobacterium tuberculosis* C, *Mycobacterium tuberculosis* str. Haarlem, *Mycobacterium tuberculosis* KZN 4207, *Mycobacterium tuberculosis* 94_M4241A, *Mycobacterium tuberculosis* 02_1987, *Mycobacterium tuberculosis* T92, *Mycobacterium tuberculosis* EAS054, *Mycobacterium tuberculosis* T85, *Mycobacterium tuberculosis* GM 1503, *Mycobacterium tuberculosis* T17, *Mycobacterium tuberculosis* '98-R604 INH-RIF-EM', *Mycobacterium tuberculosis* T46, *Mycobacterium tuberculosis* CPHL_A or *Mycobacterium tuberculosis* K85. In other embodiments of the compositions and methods of the present invention, the MTB protein or peptide, or subsequence, portion or modification thereof, comprises an amino acid sequence of protein Rv0985c of *Mycobacterium tuberculosis* H37Rv, *Mycobacterium tuberculosis* CDC1551, *Mycobacterium tuberculosis* H37Ra. *Mycobacterium tuberculosis* F11, *Mycobacterium tuberculosis* KZN 1435, *Mycobacterium tuberculosis* KZN 605, *Mycobacterium tuberculosis* C, *Mycobacterium tuberculosis* str. Haarlem, *Mycobacterium tuberculosis* KZN 4207, *Mycobacterium tuberculosis* 94_M4241A, *Mycobacterium tuberculosis* 02_1987, *Mycobacterium tuberculosis* T92, *Mycobacterium tuberculosis* EAS054, *Mycobacterium tuberculosis* T85, *Mycobacterium tuberculosis* GM 1503, *Mycobacterium tuberculosis* T17, *Mycobacterium tuberculosis* '98-R604 INH-RIF-EM', *Mycobacterium tuberculosis* T46, *Mycobacterium tuberculosis* CPHL_A or *Mycobacterium tuberculosis* K85. In other embodiments of the compositions and methods of the present invention, the MTB protein or peptide, or subsequence, portion or modification thereof, comprises an amino acid sequence of protein Rv0987 of *Mycobacterium tuberculosis* H37Rv, *Mycobacterium tuberculosis* CDC1551, *Mycobacterium tuberculosis* H37Ra. *Mycobacterium tuberculosis* F11, *Mycobacterium tuberculosis* KZN 1435, *Mycobacterium tuberculosis* KZN 605, *Mycobacterium tuberculosis* C, *Mycobacterium tuberculosis* str. Haarlem, *Mycobacterium tuberculosis* KZN 4207, *Mycobacterium tuberculosis* 94_M4241A, *Mycobacterium tuberculosis* 02_1987, *Mycobacterium tuberculosis* T92, *Mycobacterium tuberculosis* EAS054, *Mycobacterium tuberculosis* T85, *Mycobacterium tuberculosis* GM 1503, *Mycobacterium tuberculosis* T17, *Mycobacterium tuberculosis* '98-R604 INH-RIF-EM', *Mycobacterium tuberculosis* T46, *Mycobacterium tuberculosis* CPHL_A or *Mycobacterium tuberculosis* K85. In other embodiments of the compositions and methods of the present invention, the MTB protein or peptide, or subsequence, portion or modification thereof, comprises an amino acid sequence of protein Rv1172c of *Mycobacterium tuberculosis* H37Rv, *Mycobacterium tuberculosis* CDC1551, *Mycobacterium tuberculosis* H37Ra. *Mycobacterium tuberculosis* F11, *Mycobacterium tuberculosis* KZN 1435, *Mycobacterium tuberculosis* KZN 605, *Mycobacterium tuberculosis* C, *Mycobacterium tuberculosis* str. Haarlem, *Mycobacterium tuberculosis* KZN 4207, *Mycobacterium tuberculosis* 94_M4241A, *Mycobacterium tuberculosis* 02_1987, *Mycobacterium tuberculosis* T92, *Mycobacterium tuberculosis* EAS054, *Mycobacterium tuberculosis* T85, *Mycobacterium tuberculosis* GM 1503, *Mycobacterium tuberculosis* T17, *Mycobacterium tuberculosis* '98-R604 INH-RIF-EM', *Mycobacterium tuberculosis* T46, *Mycobacterium tuberculosis* CPHL_A or *Mycobacterium tuberculosis* K85. In other embodiments of the compositions and methods of the present invention, the MTB protein or peptide, or subsequence, portion or modification thereof, comprises an amino acid sequence of protein Rv1243c of *Mycobacterium tuberculosis* H37Rv, *Mycobacterium tuberculosis* CDC1551, *Mycobacterium tuberculosis* H37Ra. *Mycobacterium tuberculosis* F11, *Mycobacterium tuberculosis* KZN 1435, *Mycobacterium tuberculosis* KZN 605, *Mycobacterium tuberculosis* C, *Mycobacterium tuberculosis* str. Haarlem, *Mycobacterium tuberculosis* KZN 4207, *Mycobacterium tuberculosis* 94_M4241A, *Mycobacterium tuberculosis* 02_1987, *Mycobacterium tuberculosis* T92, *Mycobacterium tuberculosis* EAS054, *Mycobacterium tuberculosis* T85, *Mycobacterium tuberculosis* GM 1503, *Mycobacterium tuberculosis* T17, *Mycobacterium tuberculosis* '98-R604 INH-RIF-EM', *Mycobacterium tuberculosis* T46, *Mycobacterium tuberculosis* CPHL_A or *Mycobacterium tuberculosis* K85. In other embodiments of the compositions and methods of the present invention, the MTB protein or peptide, or subsequence, portion or modification thereof, comprises an amino acid sequence of protein Rv1317c of *Mycobacterium tuberculosis* H37Rv, *Mycobacterium tuberculosis* CDC1551, *Mycobacterium tuberculosis* H37Ra. *Mycobacterium tuberculosis* F11, *Mycobacterium tuberculosis* KZN 1435, *Mycobacterium tuberculosis* KZN 605, *Mycobacterium tuberculosis* C, *Mycobacterium tuberculosis* str. Haarlem, *Mycobacterium tuberculosis* KZN 4207, *Mycobacterium tuberculosis* 94_M4241A, *Mycobacterium tuberculosis* 02_1987, *Mycobacterium tuberculosis* T92, *Mycobacterium tuberculosis* EAS054, *Mycobacterium tuberculosis* T85, *Mycobacterium tuberculosis* GM 1503, *Mycobacterium tuberculosis* T17, *Mycobacterium tuberculosis* '98-R604 INH-RIF-EM', *Mycobacterium tuberculosis* T46, *Mycobacterium tuberculosis* CPHL_A or *Mycobacterium tuberculosis* K85. In other embodiments of the compositions and methods of the present invention, the MTB protein or peptide, or subsequence, portion or modification thereof, comprises an amino acid sequence of protein Rv1366 of *Mycobacterium tuberculosis* H37Rv, *Mycobacterium tuberculosis* CDC1551, *Mycobacterium tuberculosis* H37Ra. *Mycobacterium tuberculosis* F11, *Mycobacterium tuberculosis* KZN 1435, *Mycobacterium tuberculosis* KZN 605, *Mycobacterium tuberculosis* C, *Mycobacterium tuberculosis* str. Haarlem, *Mycobacterium tuberculosis* KZN 4207, *Mycobacterium tuberculosis* 94_M4241A, *Mycobacterium tuberculosis* 02_1987, *Mycobacterium tuberculosis* T92, *Mycobacterium tuberculosis* EAS054, *Mycobacterium tuberculosis* T85, *Mycobacterium tuberculosis* GM 1503,

*Mycobacterium tuberculosis* T17, *Mycobacterium tuberculosis* '98-R604 INH-RIF-EM', *Mycobacterium tuberculosis* T46, *Mycobacterium tuberculosis* CPHL_A or *Mycobacterium tuberculosis* K85. In other embodiments of the compositions and methods of the present invention, the MTB protein or peptide, or subsequence, portion or modification thereof, comprises an amino acid sequence of protein Rv1441c of *Mycobacterium tuberculosis* H37Rv, *Mycobacterium tuberculosis* CDC1551, *Mycobacterium tuberculosis* H37Ra. *Mycobacterium tuberculosis* F11, *Mycobacterium tuberculosis* KZN 1435, *Mycobacterium tuberculosis* KZN 605, *Mycobacterium tuberculosis* C, *Mycobacterium tuberculosis* str. Haarlem, *Mycobacterium tuberculosis* KZN 4207, *Mycobacterium tuberculosis* 94_M4241A, *Mycobacterium tuberculosis* 02_1987, *Mycobacterium tuberculosis* T92, *Mycobacterium tuberculosis* EAS054, *Mycobacterium tuberculosis* T85, *Mycobacterium tuberculosis* GM 1503, *Mycobacterium tuberculosis* T17, *Mycobacterium tuberculosis* '98-R604 INH-RIF-EM', *Mycobacterium tuberculosis* T46, *Mycobacterium tuberculosis* CPHL_A or *Mycobacterium tuberculosis* K85. In other embodiments of the compositions and methods of the present invention, the MTB protein or peptide, or subsequence, portion or modification thereof, comprises an amino acid sequence of protein Rv2490c of *Mycobacterium tuberculosis* H37Rv, *Mycobacterium tuberculosis* CDC1551, *Mycobacterium tuberculosis* H37Ra. *Mycobacterium tuberculosis* F11, *Mycobacterium tuberculosis* KZN 1435, *Mycobacterium tuberculosis* KZN 605, *Mycobacterium tuberculosis* C, *Mycobacterium tuberculosis* str. Haarlem, *Mycobacterium tuberculosis* KZN 4207, *Mycobacterium tuberculosis* 94_M4241A, *Mycobacterium tuberculosis* 02_1987, *Mycobacterium tuberculosis* T92, *Mycobacterium tuberculosis* EAS054, *Mycobacterium tuberculosis* T85, *Mycobacterium tuberculosis* GM 1503, *Mycobacterium tuberculosis* T17, *Mycobacterium tuberculosis* '98-R604 INH-RIF-EM', *Mycobacterium tuberculosis* T46, *Mycobacterium tuberculosis* CPHL_A or *Mycobacterium tuberculosis* K85. In other embodiments of the compositions and methods of the present invention, the MTB protein or peptide, or subsequence, portion or modification thereof, comprises an amino acid sequence of protein Rv2853 of *Mycobacterium tuberculosis* H37Rv, *Mycobacterium tuberculosis* CDC1551, *Mycobacterium tuberculosis* H37Ra. *Mycobacterium tuberculosis* F11, *Mycobacterium tuberculosis* KZN 1435, *Mycobacterium tuberculosis* KZN 605, *Mycobacterium tuberculosis* C, *Mycobacterium tuberculosis* str. Haarlem, *Mycobacterium tuberculosis* KZN 4207, *Mycobacterium tuberculosis* 94_M4241A, *Mycobacterium tuberculosis* 02_1987, *Mycobacterium tuberculosis* T92, *Mycobacterium tuberculosis* EAS054, *Mycobacterium tuberculosis* T85, *Mycobacterium tuberculosis* GM 1503, *Mycobacterium tuberculosis* T17, *Mycobacterium tuberculosis* '98-R604 INH-RIF-EM', *Mycobacterium tuberculosis* T46, *Mycobacterium tuberculosis* CPHL_A or *Mycobacterium tuberculosis* K85.

As disclosed herein, a MTB protein or peptide, or subsequence, portion or modification thereof may elicit a cellular or humoral immune response. In particular embodiments of the present invention, a MTB protein or peptide, or subsequence, portion or modification thereof described herein, elicits, stimulates, promotes or induces an immune response. In certain embodiments, a MTB protein or peptide, or subsequence, portion or modification thereof, elicits, stimulates, promotes or induces a T cell response (e.g. a CD4+ T cell response, including but not limited to a $CXCR3^+CCR6^+$ memory Th1 cell response). Such responses can provide protection against (e.g., prophylaxis) an initial MTB infection, or a secondary or subsequent MTB infection. Such T cell responses can also be effective in treatment (e.g., therapeutic) of an initial MTB infection, or a secondary or subsequent MTB infection.

As used herein a "modification" of a MTB protein or peptide, or subsequence, or portion thereof, refers to a modified or variant form of the protein or peptide, or subsequence, or portion thereof. Such modified forms, such as amino acid deletions, additions and substitutions, can also be used in the invention methods and compositions for eliciting, stimulating, inducing, promoting, increasing or enhancing an anti-MTB immune response or protecting, vaccinating or immunizing a subject against MTB, or treatment of a subject for MTB, as set forth herein.

As used herein, a subsequence of a MTB protein or peptide includes or consists of one or more amino acids less than the full length MTB protein or peptide. The term "subsequence" means a fragment or part of the full length molecule. A subsequence of a MTB protein or peptide has one or more amino acids less than the full length MTB protein or peptide (e.g. one or more internal or terminal amino acid deletions from either amino or carboxy-termini). Subsequences therefore can be any length up to the full length native molecule, provided said length is at least one amino acid less than full length native molecule.

Subsequences can vary in size. For example a subsequence of a protein or peptide can be as small as an epitope capable of binding an antibody (i.e., about five amino acids) up to a polypeptide that is one amino acid less than the entire length of a reference polypeptide such as a MTB protein or peptide.

In various embodiments of the present invention, a MTB subsequence is characterized as including or consisting of a subsequence of a protein or amino acid sequence set forth in Table 1 or Table 5. In particular embodiments of the present invention, a MTB subsequence is characterized as including or consisting of a subsequence of an amino acid sequence of protein Rv3024c, Rv0289, Rv0290, Rv3330, Rv1788, Rv1791, Rv3125c, Rv0294, Rv2874, Rv3022c, Rv3135, Rv3876, Rv0124, Rv0291, Rv0292, Rv0293c, Rv0297, Rv0299, Rv3012c, Rv3025c, Rv0278c, Rv0279c, Rv0298, Rv0442c, Rv0690c, Rv0985c, Rv0987, Rv1172c, Rv1243c, Rv1317c, Rv1366, Rv1441c, Rv2490c or Rv2853.

In various embodiments, a MTB subsequence is characterized as including or consisting of a Rv3024c sequence with less than 367 amino acids in length identical to Rv3024c, a Rv0289 sequence with less than 295 amino acids in length identical to Rv0289, a Rv0290 sequence with less than 472 amino acids in length identical to Rv0290, a Rv3330 sequence with less than 405 amino acids in length identical to Rv3330, a Rv1788 sequence with less than 99 amino acids in length identical to Rv1788, a Rv1791 sequence with less than 99 amino acids in length identical to Rv1791, a Rv3125c sequence with less than 391 amino acids in length identical to Rv3125c, a Rv0294 sequence with less than 261 amino acids in length identical to Rv0294, a Rv2874 sequence with less than 695 amino acids in length identical to Rv2874, a Rv3022 sequence with less than 81 amino acids in length identical to Rv3022c, a Rv3135 sequence with less than 409 amino acids in length identical to Rv3135, a Rv3976 sequence with less than 666 amino acids in length identical to Rv3876, a Rv0124 sequence with less than 487 amino acids in length identical to Rv0124, a Rv0291 sequence with less than 461 amino acids in length identical to Rv0291, a Rv0292 sequence with less than 331 amino acids in length identical to Rv0292, a Rv0293c sequence with less than 400 amino acids in length identical to Rv0293c, a Rv0297 sequence with less than 591 amino acids in length identical to Rv0297, a Rv0299 sequence with less than 100 amino acids in length identical to Rv0299, a Rv3012c sequence with less than 99 amino acids in length identical to Rv3012c, a Rv3025c sequence with less than 393 amino acids in length identical to Rv3025c, a Rv0278c sequence with less than 957 amino acids in length identical to Rv0278c, a Rv0279c sequence with less than 837 amino acids in length identical to Rv0279c, a Rv0298 sequence with less than 75 amino acids in length identical to Rv0298, a Rv0442c sequence with less than 487 amino acids in length identical to Rv0442c, a Rv0690c sequence with less than 349 amino acids in length identical to Rv0690c, a Rv0985c sequence with less than 151 amino acids in length identical to Rv0985c, a Rv0987 sequence with less than 855 amino acids in length identical to Rv0987, a Rv1172c sequence with less than 308 amino acids in length identical to Rv1172c, a Rv1243c sequence with less than 562 amino acids in length identical to Rv1243c, a Rv1317c sequence with less than 496 amino acids in length identical to Rv1317c, a Rv166 sequence with less than 273 amino acids in length identical to Rv1366, a Rv1441c sequence with less than 491 amino acids in length identical to Rv1441c, a Rv2490c sequence with less than 111 amino acids in length identical Rv2490c or a Rv2853 sequence with less than 615 amino acids in length identical to Rv2853.

As used herein, subsequences may also include or consist of one or more amino acid additions or deletions, wherein the subsequence does not comprise the full length native/wild type MTB protein or peptide sequence. Accordingly, total subsequence lengths can be greater than the length of the full length native/wild type MTB protein or peptide, for example, where a MTB protein or peptide subsequence is fused or forms a chimera with another polypeptide.

In other embodiments, the methods and compositions described herein may comprise a MTB protein or peptide comprising or consisting of a subsequence, or an amino acid modification of MTB protein or peptide sequence, wherein the protein or peptide elicits, stimulates, induces, promotes, increases or enhances and anti-MTB T cell response (e.g. anti-MTB vCD4$^+$ T cell response), as described herein.

A non-limiting example of a MTB protein or peptide, or subsequence, portion or modification thereof, includes, comprises or consists of a subsequence or portion of a MTB intermediary metabolism and respiration protein, cell wall and cell processes protein, lipid metabolism protein, information pathway protein, virulence, detoxification, or adaptation protein, regulatory proteins PE/PPE protein, insertion sequence and phage protein, Esx protein, secreted protein, secretion system protein or conserved hypothetical protein.

Non-limiting examples of a MTB protein or peptide, or a subsequence, portion or modification thereof includes, comprises or consists of an amino acid sequence of protein Rv3024c, Rv0289, Rv0290, Rv3330, Rv1788, Rv1791, Rv3125c, Rv0294, Rv2874, Rv3022c, Rv3135, Rv3876, Rv0124, Rv0291, Rv0292, Rv0293c, Rv0297, Rv0299, Rv3012c, Rv3025c, Rv0278c, Rv0279c, Rv0298, Rv0442c, Rv0690c, Rv0985c, Rv0987, Rv1172c, Rv1243c, Rv1317c, Rv1366, Rv1441c, Rv2490c or Rv2853.

A non-limiting Rv3024c sequence of or from which a protein or peptide, or subsequence, portion or modification thereof can be based upon is a sequence set forth as:

(SEQ ID No: 1)
MKVLAAMSGGVDSSVAAARMVDAGHEVVGVHMALSTAPGTLRTGSRGCCSK

EDAADARRVADVLGIPFYVWDFAEKFKEDVINDFVSSYARGETPNPCVRCN

QQIKFAALSARAVALGFDTVATGHYARLSGGRLRRAVDRDKDQSYVLAVLT

-continued

AQQLRHAAFPIGDTPKRQIRAEAARRGLAVANKPDSHDICFIPSGNTKAFL

GERIGVRRGVVVDADGVVLASHDGVHGFTIGQRRGLGIAGPGPNGRPRYVT

AIDADTATVHVGDVTDLDVQTLTGRAPVFTAGAAPSGPVDCVVQVRAHGET

VSAVAELIGDALFVQLHAPLRGVARGQTLVLYRPDPAGDEVLGS ATIAGA

SGLSTGGNPGA

A non-limiting Rv0289 sequence of or from which a protein or peptide, or subsequence, portion or modification thereof can be based upon is a sequence set forth as:

(SEQ ID No: 2)
MDATPNAVELTVDNAWFIAETIGAGTFPWVLAITMPYSDAAQRGAFVDRQR

DELTRMGLLSPQGVINPAVADWIKVVCFPDRWLDLRYVGPASADGACELLR

GIVALRTGTGKTSNKTGNGVVALRNAQLVTFTAMDIDDPRALVPILGVGLA

HRPPARFDEFSLPTRVGARADERLRSGVPLGEVVDYLGIPASARPVVESVF

SGPRSYVEIVAGCNRDGRHTTTEVGLSIVDTSAGRVLVSPSRAFDGEWVST

FSPGTPFAIAVAIQTLTACLPDGQW FPGQRVSRDFSTQSS

A non-limiting Rv0290 sequence of or from which a protein or peptide, or subsequence, portion or modification thereof can be based upon is a sequence set forth as:

(SEQ ID No: 3)
MSGTVMQIVRVAILADSRLTEMALPAELPLREILPAVQRLVVPSAQNGDGG

QADSGAAVQLSLAPVGGQPFSLDASLDTVGVVDGDLLVLQPVPAGPAAPGI

VEDIADAAMIFSTSRLKPWGIAHIQRGALAAVIAVALLATGLTVTYRVATG

VLAGLLAVAGIAVASALAGLLITIRSPRSGIALSIAALVPIGAALALAVPG

KFGPAQVLLGAAGVAAWSLIALMIPSAERERVVAFFTAAAVVGASVALAAG

AQLLWQLPLLSIGCGLIVAALLVTIQAAQLSALWARFPLPVIPAPGDPTPS

APPLRLLEDLPRRVRVSDAHQSGFIAAAVLLSVLGSVAIAVRPEALSVVGW

YLVAATAAAATLRARVWDSAACKAWLLAQPYLVAGVLLVFYTATGRYVAAF

GAVLVLAVLMLAWVVVALNPGIASPESYSLPLRRLLGLVAAGLDVSLIPVM

AYLVGLFAWVLNR

A non-limiting Rv3330 sequence of or from which a protein or peptide, or subsequence, portion or modification thereof can be based upon is a sequence set forth as:

(SEQ ID No: 4)
MAFLRSVSCLAAAVFAVGTGIGLPTAAGEPNAAPAACPYKVSTPPAVDSSE

VPAAGEPPLPLVVPPTPVGGNALGGCGIITAPGSAPAPGDVSAEAWLVADL

DSGAVIAARDPHGRHRPASVIKVLVAMASINTLTLNKSVAGTADDAAVEGT

KVGVNTGGTYTVNQLLHGLLMHSGNDAAYALARQLGGMPAALEKINLLAAK

LGGRDTRVATPSGLDGPGMSTSAYDIGLFYRYAWQNPVFADIVATRTFDFP

GHGDHPGYELENDNQLLYNYPGALGGKTGYTDDAGQTFVGAANRDGRRLMT

VLLHGTRQPIPPWEQAAHLLDYGFNTPAGTQIGTLIEPDPSLMSTDRNPAD

RQRVDPQAAARISAADALPVRVGVAVIGALIVFGLIMVARAMNRRPQH

A non-limiting Rv1788 sequence of or from which a protein or peptide, or subsequence, portion or modification thereof can be based upon is a sequence set forth as:

A non-limiting Rv1791 sequence of or from which a protein or peptide, or subsequence, portion or modification thereof can be based upon is a sequence set forth as:

(SEQ ID No: 5)
MSFVTTQPEALAAAAGSLQGIGSALNAQNAAAATPTTGVVPAAADEVSA

LTAAQFAAHAQIYQAVSAQAA AIHEMFVNTLQMSSGSYAATEAANAAA

AG

A non-limiting Rv3125c sequence of or from which a protein or peptide, or subsequence, portion or modification thereof can be based upon is a sequence set forth as:

(SEQ ID No: 6)
MSFVTTQPEALAAAAANLQGIGTTMNAQNAAAAAPTTGVVPAAADEVSA

LTAAQFAAHAQMYQTVSAQAA AIHEMFVNTLVASSGSYAATEAANAAA

AG (SEQ ID No: 7)
MVLGFSWLPPEINSARMFAGAGSGPLFAAASAWEGLAADLWASASSFES

VLAALTTGPWTGPASMSMAAAASPYVGWLSTVASQAQLAAIQARAAATA

FEAALAATVHPTAVTANRVSLASLIAANVLGQNTPAIAATEFDYLEMWA

QDVAAMVGYHAGAKSVAATLAPFSLPPVSLAGLAAQVGTQVAGMATTAS

AAVTPVVEGAMASVPTVMSGMQSLVSQLPLQHASMLFLPVRILTSPITT

LASMARESATRLGPPAGGLAAANTPNPSGAAIPAFKPLGGRELGAGMSA

GLGQAQLVGSMSVPPTWQGSIPISMASSAMSGLGVPPNPVALTQAAGAA

GGGMPMMLMPMSISGAGAGMPGGLMDRDGAGWHVTQARLTVIPRTGVG

A non-limiting Rv0294 sequence of or from which a protein or peptide, or subsequence, portion or modification thereof can be based upon is a sequence set forth as:

(SEQ ID No: 8)
MWDPDVYLAFSGHRNRPFYELVSRVGLERARRVVDLGCGPGHLTRYLAR

RWPGAVIEALDSSPEMVAAAAERGIDATTGDLRDWKPKPDTDVVVSNAA

LHWVPEHSDLLVRWVDELAPGSWIAVQIPGNFETPSHAAVRALARREPY

AKLMRDIPFRVGAVVQSPAYYAELLMDTGCKVDVWETTYLHQLTGEHPV

LDWITGSALVPVRERLSDESWQQFRQELIPLLNDAYPPRADGSTIFPFR

RLFMVAEVGGARRSGG

A non-limiting Rv2874 sequence of or from which a protein or peptide, or subsequence, portion or modification thereof can be based upon is a sequence set forth as:

(SEQ ID No: 9)
MVESRRAAAAASAYASRCGIAPATSQRSLATPPTISVPSGEGRCRCHVA

RGAGRDPRRRLRRRRWCGRCGYHSHLTGGEFDVNRLCQQRSERSCQLV

AVPADPRPKRQRITDVLTLALVGFLGGLITGISPCILPVLPVIFFSGAQ

SVDAAQVAKPEGAVAVRRKRALSATLRPYRVIGGLVLSFGMVTLLGSAL

LSVLHLPQDAIRWAALVALVAIGAGLIFPRFEQLLEKPFSRIPKQIVT

RSNGFGLGLALGVLYVPCAGPILAAIVVAGATATIGLGTVVLTATFALG

AALPLLFFALAGQRIAERVGAFRRRQREIRIATGSVTILLAVALVFDLP

AALQRAIPDYTASLQQQISTGTEIREQLNLGGIVNAQNAQLSNCSDGAA

QLESCGTAPDLKGITGWLNTPGNKPIDLKSLRGKVVLIDFWAYSCINCQ

RAIPHVVGWYQAYKDSGLAVIGVHTPEYAFEKVPGNVAKGAANLGISYP

IALDNNYATWTNYRNRYWPAEYLIDATGTVRHIKFGEGDYNVTETLVRQ

LLNDAKPGVKLPQPSSTTTPDLTPRAALTPETYFGVGKVVNYGGGGAYD

EGSAVFDYPPSLAANSFALRGRWALDYQGATSDGNDAAIKLNYHAKDVY

IVVGGTGTLTVVRDGKPATLPISGPPTTHQVVAGYRLASETLEVRPSKG

LQVFSFTYG

A non-limiting Rv3022c sequence of or from which a protein or peptide, or subsequence, portion or modification thereof can be based upon is a sequence set forth as:

(SEQ ID No: 10)
VTAPVWLASPPEVHSALLSAGPGPGSLQAAAAGWSALSAEYAAVAQELS

VVVAAVGAGVWQGPSAELFVA AYVPYVAWLVQ

A non-limiting Rv3135 sequence of or from which a protein or peptide, or subsequence, portion or modification thereof can be based upon is a sequence set forth as:

(SEQ ID No: 11)
MVLGFSWLPPEINSARMFAGAGSGPLFAAASAWEGLAADLWASASSFES

VLAALTTGPWTGPASMSMAAAASPYVGWLSTVASQAQLAAIQARAAATA

FEAALAATVHPTAVTANRVSLASLIAANVLGQNTPAIAATEFDYLEMWA

QDVAAMVGYHAGAKSVAATLAPFSLPPVSLAGLAAQVGTQVAGMATTAS

AAVTPVVEGAMASVPTVMSGMQSLVSQLPLQHASMLFLPVRILTSPITT

LASMARESATRLGPPAGGLAAANTPNPSGAAIPAFKPLGGRELGAGMSA

GLGQAQLVGSMSVPPTWQGSIPISMASSAMSGLGVPPNPVALTQAAGAA

GGGMPMMLMPMSISGAGAGMPGGLMDRDGAGWHVTQARLTVIPRTGVG

A non-limiting Rv3876 sequence of or from which a protein or peptide, or subsequence, portion or modification thereof can be based upon is a sequence set forth as:

(SEQ ID No: 12)
MAADYDKLFRPHEGMEAPDDMAAQPFFDPSASFPPAPASANLPKPNGQT

PPPTSDDLSERFVSAPPPPPPPPPPPPPTPMPIAAGEPPSPEPAASKPP

TPPMPIAGPEPAPPKPPTPPMPIAGPEPAPPKPPTPPMPIAGPAPTPTE

SQLAPPRPPTPQTPTGAPQQPESPAPHVPSHGPHQPRRTAPAPPWAKMP

IGEPPPAPSRPSASPAEPPTRPAPQHSRRARRGHRYRTDTERNVGKVAT

GPSIQARLRAEEASGAQLAPGTEPSPAPLGQPRSYLAPPTRPAPTEPPP

SPSPQRNSGRRAERRVHPDLAAQHAAAQPDSITAATTGGRRRKRAAPDL

DATQKSLRPAAKGPKVKKVKPQKPKATKPPKVVSQRGWRHWVHALTRIN

LGLSPDEKYELDLHARVRRNPRGSYQIAVVGLKGGAGKTTLTAALGSTL

AQVRADRILALDADPGAGNLADRVGRQSGATIADVLAEKELSHYNDIRA

HTSVNAVNLEVLPAPEYSSAQRALSDADWHFIADPASRFYNLVLADCGA

-continued
GFFDPLTRGVLSTVSGVVVVASVSIDGAQQASVALDWLRNNGYQDLASR

ACVVINHIMPGEPNVAVKDLVRHFEQQVQPGRVVVMPWDRHIAAGTEIS

LDLLLDPIYKRKVLELAAALSDDFERAGRR

A non-limiting Rv0124 sequence of or from which a protein or peptide, or subsequence, portion or modification thereof can be based upon is a sequence set forth as:

(SEQ ID No: 13)
MSFVSVAPEIVVAAATDLAGIGSAISAANAAAAAPTTAVLAAGADEVSA

AIAALSGHAQAYQALSAQAAAFHQQFVQTLAGGAGAYAAAEAQVEQQLL

AAINAPTQALLGRPLIGNGADGAPGTGQAGGAGGILYGNGGNGGSGAAG

QAGGAGGPAGLIGHGGSGGAGGSGAAGGAGGHGGWLWGNGGVGGSGGAG

VGAGVAGGHGGAGGAAGLWGAGGGGGNGGNGADANIVSGGDGGLGGAGG

GGGWLYGDGGAGGHGGQGAIGLGGGAGGDGGQGGAGRGLWGTGGAGGHG

GQGGGTGGPPLPGQAGMGAAGGAGGLIGNGGAGGDGGVGASGGVAGVGG

AGGNAMLIGHGGAGGAGGDSSFANGAAGGAGGAGGHLFGNGGSGGHGGA

VTAGNTGIGGAGGVGGDARLIGHGGAGGAGGDRAGALVGRDGGPGGNGG

AGGQLYGNGGDGAPGTGGTLQAAVSGLVTALFGAPGQPGDTGQPG

A non-limiting Rv0291 sequence of or from which a protein or peptide, or subsequence, portion or modification thereof can be based upon is a sequence set forth as:

(SEQ ID No: 14)
MIRAAFACLAATVVVAGWWTPPAWAIGPPVVDAAAQPPSGDPGPVAPME

QRGACSVSGVIPGTDAGVPTPSQTMLNLPAAWQFSRGEGQLVAIIDTGV

QPGPRLPNVDAGGDFVESTDGLTDCDGHGTLVAGIVAGQPGNDGFSGVA

PAARLLSIRAMSTKFSPRTSGGDPQLAQATLDVAVLAGAIVHAADLGAK

VINVSTITCLPADRMVDQAALGAAIRYAAVDKDAVIVAAAGNTGASGSV

SASCDSNPLTDLSRPDDPRNWAGVTSVSIPSWWQPYVLSVASLTSAGQP

SKFSMPGPWVGIAAPGENIASVSNSGDGALANGLPDAHQKLVALSGTSY

AAGYVSGVAALVRSRYPGLNATEVVRRLTATAHRGARESSNIVGAGNLD

AVAALTWQLPAEPGGGAAPAKPVADPPVPAPKDTTPRNVAFAGAAALSV

LVGLTAATVAIARRRREPTE

A non-limiting Rv0292 sequence of or from which a protein or peptide, or subsequence, portion or modification thereof can be based upon is a sequence set forth as:

(SEQ ID No: 15)
MNPIPSWPGRGRVTLVLLAVVPVALAYPWQSTRDYVLLGVAAAVVIGLF

GFWRGLYFTTIARRGLAILRRRRRIAEPATCTRTTVLVWVGPPASDTNV

LPLTLIARYLDRYGIRADTIRITSRVTASGDCRTWVGLTVVADDNLAAL

QARSARIPLQETAQVAARRLADHLREIGWEAGTAAPDEIPALVAADSRE

TWRGMRHTDSDYVAAYRVSANAELPDTLPAIRSRPAQETWIALEIAYAA

GSSTRYTVAAACALRTDWRPGGTAPVAGLLPQHGNHVPALTALDPRSTR

RLDGHTDAPADLLTRLHWPTPTAGAHRAPLTNAVSRT

A non-limiting Rv0293c sequence of or from which a protein or peptide, or subsequence, portion or modification thereof can be based upon is a sequence set forth as:

(SEQ ID No: 16)
MSGTFTADAIGPPVPIPDVPGADAGAEGLPSRSVLSARQRILVESSAIA

DVALRTAVASVLSATVTPAVVANALRHVNEGSERSNLNFYAELAAAHDP

AKSFPAPTELPKVTSRPASPLTEWVARGTVDNIAFASGFRAINPTMRQR

WSALTANNIVHAQHWRHRDGPRPTLCVIHGFMGSSYLLNGLFFSLPWYY

GRSGYDVLLYTLPFHGQRAEKFSPFSGFGYFTSLSGFAEAMAQAVYDFR

SIVDYLRHIGVDRIALTGISLGGYTSALLASVESRLEAVIPNCPVVMPA

KLFDEWFPANKLVKLGLRLTNISRDELIAGLAYHGPLNYRPLLPKDRRM

IITGLGDRMAPPEHAVTLWKQWDRCALHWFPGSHLLHVSQLDYLRRMTV

FLQGLMFD

A non-limiting Rv0297 sequence of or from which a protein or peptide, or subsequence, portion or modification thereof can be based upon is a sequence set forth as:

(SEQ ID No: 17)
MSFVIAQPEMIAAAAGELASIRSAINAANAAAAAQTTGVMSAAADEVST

AVAALFSSHAQAYQAASAQAAAFHAQVVRTLTVDAGAYASAEAANAGPN

MLAAVNAPAQALLGRPLIGNGANGAPGTGQAGGDGGLLFGNGGNGGSGA

PGQAGGAGGAAGFFGNGGNGGDGGAGANGGAGGTAGWFFGFGGNGGAGG

IGVAGINGGLGGAGGDGGNAGFFGNGGNGGMGGAGAAGVNAVNPGLATP

VTPAANGGNGLNLVGVPGTAGGGADGANGSAIGQAGGAGGDGGNASTSG

GIGIAQTGGAGGAGGAGGDGAPGGNGGNGGSVEHTGATGSSASGGNGAT

GGNGGVGAPGGAGGNGGHVSGGSVNTAGAGGKGGNGGTGGAGGPGGHGG

SVLSGPVGDSGNGGAGGDGGAGVSATDIAGTGGRGGNGGHGGLWIGNGG

DGGAGGVGGVGGAGAAGAIGGHGGDGGSVNTPIGGSEAGDGGKGGLGGD

GGGRGIFGQFGAGGAGGAGGVGGAGGAGGTGGGGNGGAIFNAGTPGAA

GTGGDGGVGGTGAAGGKGGAGGSGGVNGATGADGAKGLDGATGGKGNNG

NPG

A non-limiting Rv0299 sequence of or from which a protein or peptide, or subsequence, portion or modification thereof can be based upon is a sequence set forth as:

(SEQ ID No: 18)
MIAPGDIAPRRDSEHELYVAVLSNALHRAADTGRVITCPFIPGRVPEDL

LAMVVAVEQPNGTLLPELVQW LHVAALGAPLGNAGVAALREAASVVTA

LLC

A non-limiting Rv3012c sequence of or from which a protein or peptide, or subsequence, portion or modification thereof can be based upon is a sentience set forth as:

(SEQ ID No: 19)
MSQISRDEVAHLARLARLALTETELDSFAGQLDAILTHVSQIQAVDVTG

VQATDNPLKDVNVTRPDETVP CLTQRQVLDQAPDAVDGRFAVPQILGD

A non-limiting Rv3025c sequence of or from which a protein or peptide, or subsequence, portion or modification thereof can be based upon is a sequence set forth as:

(SEQ ID No: 20)
MAYLDHAATTPMHPAAIEAMAAVQRTIGNASSLHTSGRSARRRIEEARE

LIADKLGARPSEVIFTAGGTESDNLAVKGIYWARRDAEPHRRRIVTTEV

EHHAVLDSVNWLVEHEGAHVTWLPTAADGSVSATALREALQSHDDVALV

SVMWANNEVGTILPIAEMSVVAMEFGVPMHSDAIQAVGQLPLDFGASGL

SAMSVAGHKFGGPPGVGALLLRRDVTCVPLMHGGGQERDIRSGTPDVAS

AVGMATAAQIAVDGLEENSARLRLLRDRLVEGVLAEIDDVCLNGADDPM

RLAGNAHFTFRGCEGDALLMLLDANGIECSTGSACTAGVAQPSHVLIAM

GVDAASARGSLRLSLGHTSVEADVDAALEVLPGAVARARRAALAAAGAS

R

A non-limiting Rv0278c sequence of or from which a protein or peptide, or subsequence, portion or modification thereof can be based upon is a sequence set forth as:

(SEQ ID No: 21)
MSFVIAAPEVIAAAATDLASLGSSISAANAAAAANTTALMAAGADEVST

AIAALFGAHGQAYQALSAQAQAFHAQFVQALTSGGGAYAAAEAAAVSPL

LDPINEFFLANTGRPLIGNGANGAPGTGANGGDGGWLIGNGGAGGSGAA

GVNGGAGGNGGAGGNGGAGGLIGNGGAGGAGGVASSGIGGSGGAGGNAM

LFGAGGAGGAGGGVVALTGGAGGAGGAGGNAGLLFGAAGVGGAGGFTNG

SALGGAGGAGGAGGLFATGGVGGSGGAGSSGGAGGAGGAGGLFGAGGTG

GHGGFADSSFGGVGGAGGAGGLFGAGGEGGSGGHSLVAGGDGGAGGNAG

MLALGAAGGAGGIGGDGGTLTAGGIGGAGGAGGNAGLLFGSGGSGGAGG

FGFADGGQGGPGGNAGTVFGSGGAGGNGGVGQGFAGGIGGAGGTPGLIG

NGGNGGNGGASAVTGGNGGIGGTGVLIGNGGNGGSGGIGAGKAGVGGVS

GLLLGLDGFNAPASTSPLHTLQQNVLNVVNEPFQTLTGRPLIGNGANGT

PGTGADGGAGGWLFGNGANGTPGTGAAGGAGGWLFGNGGNGGHGATNTA

ATATGGAGGAGGILFGTGGNGGTGGIATGAGGIGGAGGAGGVSLLIGSG

GTGGNGGNSIGVAGIGGAGGRGGDAGLLFGAAGTGGHGAAGGVPAGVGG

AGGNGGLFANGGAGGAGGFNAAGGNGGNGGLFGTGGTGGAGTNFGAGGN

GGNGGLFGAGGTGGAAGSGGSGITTGGGHGGNAGLLSLGASGGAGGSG

GASSLAGGAGGTGGNGALLFGFRGAGGAGGHGGAALTSIQQGGAGGAGG

NGGLLFGSAGAGGAGGSGANALGAGTGGTGGDGGHAGVFGNGGDGGCRR

VWRRYRRQRWCRRQRRADRQRRQRRQRRQSRGHARCRRHRRAAARRERT

QRLAIAGRPATTRGVEGISCSPQMMP

EQ

A non-limiting Rv0279c sequence of or from which a protein or peptide, or subsequence, portion or modification thereof can be based upon is a sequence set forth as:

(SEQ ID No: 22)
MSFVIAAPEVIAAAATDLASLESSIAAANAAAAANTTALLAAGADEVST

AVAALFGAHGQAYQALSAQAQAFHAQFVQALTSGGGAYAAAEAAATSPL

LAPINEFFLANTGRPLIGNGTNGAPGTGANGGDGGWLIGNGGAGGSGAA

GVNGGAGGNGGAGGLIGNGGAGGAGGRASTGTGGAGGAGGAAGMLFGAA

GVGGPGGFAAAFGATGGAGGAGGNGGLFADGGVGGAGGATDAGTGGAGG

SGGNGGLFGAGGTGGPGGFGIFGGGAGGDGGSGGLFGAGGTGGSGGTSI

INVGGNGGAGGDAGMLSLGAAGGAGGSGGSNPDGGGGAGGIGGDGGTLF

GSGGAGGVCGLGFDAGGAGGAGGKAGLLIGAGGAGGAGGGSFAGAGGTG

GAGGAPGLVGNAGNGGNGGASANGAGAAGGAGGSGVLIGNGGNGGSGGT

GAPAGTAGAGGLGGQLLGRDGFNAPASTPLHTLQQQILNAINEPTQALT

GRPLIGNGANGTPGTGADGGAGGWLFGNGGNGGHGATGADGGDGGSGGA

GGILSGIGGTGGSGGIGTTGQGGTGGTGGAALLIGSGGTGGSGGFGLDT

GGAGGRGGDAGLFLGAAGTGGQAALSQNFIGAGGTAGAGGTGGLFANGG

AAGGAGGFGANGGTGGNGLLFGGGTGGAGTLGADGGAGGHGGLFGAGGT

GGAGGSSGGTFGGNGGSGGNAGLLALGASGGAGGSGGSALNVGGTGGVG

GNGGSGGSLFGFGGAGGTGGSSGIGSSGGTGGDGGTAGVFGNGGDGGAG

GFGADTGGNSSSVPNAVLIGNGGNGGNGGKAGGTPGAGGTSGLIIGENG

LNGL

A non-limiting Rv0298 sequence of or from which a protein or peptide, or subsequence, portion or modification thereof can be based upon is a sequence set forth as:

(SEQ ID No: 23)
MTKEKISVTVDAAVLAAIDADARAAGLNRSEMIEQALRNEHLRVALRDY

TAKTVPALDIDAYAQRVYQAN RAAGS

A non-limiting Rv0442c sequence of or from which a protein or peptide, or subsequence, portion or modification thereof can be based upon is a sequence set forth as:

(SEQ ID No 24)
MTSPHFAWLPPEINSALMFAGPGSGPLIAAATAWGELAEKLLASIASLG

SVTSELTSGAWLGPSAAAMMAVATQYLAWLSTAAAQAEQAAAQAMAIAT

AFEAALAATVQPAVVAANRGLMQLLAATNWFGQNAPALMDVEAAYEQMW

ALDVAAMAGYHFDASAAVAQLAPWQQVLRNLGIDIGKNGQINLGFGNTG

SGNIGNNNIGNNNIGSGNTGTGNIGSGNTGSGNLGLGNLGDGNIGFGNT

GSGNIGFGITGDHQMGFGGFNSGSGNIGFGNSGTGNVGLFNSGSGNIGI

GNSGSLNSGIGTSGTINAGLSGSAGSLNTSFWNAGMQNAALGSAAGSEAA

LVSSAGYATGGMSTAALSSGILASALGSTGGLQHGLANVLNSGLTNTPV

AAPASAPVGGLDSGNPNPGSGSAAAGSGANPGLRSPGTSYPSFVNSGSN

DSGLRNTAVREPSTPGSGIPKSNFYPSPDRESAYASPRIGQPVGSE

A non-limiting Rv0690c sequence of or from which a protein or peptide, or subsequence, portion or modification thereof can be based upon is a sequence set forth as:

(SEQ ID No: 25)
MTGTEHLVHTLRSQGRVCTSSGSPMYRELLELVAADVESGGVFASILAD

QKGAPEGQAVPLRLLGGLHRMVLDGRAPVLRRWYPSTGGTWQAEAAWPD

IVRTATDQPESLRAALDRPPQTNEVGRSAALIGGLLIACLQFDLPIRLF

EIGSSAGLNLRPDRYRYRYLGGEWGLADSPVRIDNAWLGELPPTATVRI

VERHGYDIAPIDVTSPDGELNALSYIWPDQTDRLERLRGAIAVARNIPA

DLHRQAAHAAVAGMTLTDDALTVLWHSITWQYLPADERAAIRAGIDALA

AQADAHCPFVHLTLEPAHQRPGAQIKYLVRMRSWPGGHARVLGECHPHG

PPVTWQ

A non-limiting Rv0985c sequence of or from which a protein or peptide, or subsequence, portion or modification thereof can be based upon is a sequence set forth as:

(SEQ ID No: 26)
MLKGFKEFLARGNIVDLAVAVVIGTAFTALVTKFTDSIITPLINRIGVN

AQSDVGILRIGIGGGQTIDLNVLLSAAINFFLIAFAVYFLVVLPYNTLR

KKGEVEQPGDTQVVLLTEIRDLLAQTNGDSPGRHGGRGTPSP

TDGPRASTESQ

A non-limiting Rv0987 sequence of or from which a protein or peptide, or subsequence, portion or modification thereof can be based upon is a sequence set forth as:

(SEQ ID No: 27)
MNDQAPVAYAPLWRTAWRRLRQRPFQYILLVLGIALGVAMIVAIDVSSN

SAQRAFDLSAAAITGKSTHRLVSGPAGVDQQLYVDLRRHGYDFSAPVIE

GYVLARGLGNRAMQFMGTDPFAESAFRSPLWSNQNIAELGGFLTRPNGV

VLSRQVAQKYGLAVGDRIALQVKGAPTTVTLVGLLTPADEVSNQKLSDL

IIADISTAQELFHMPGRLSHIDLIIKDEATATRIQQRLPAGVRMETSDT

QRDTVKQMTDAFTVNLTALSLIALLVGIFLIYNTVTFNVVQRRPFFAIL

RCLGVTREQLFWLIMTESLVAGLIGTGLGLLIGIWLGEGLIGLVTQTIN

DFYFVINVRNVSVSAESLLKGLIIGIFAAMLATLPPAIEAMRTVPASTL

RRSSLESKITKLMPWLWVAWFGLGSFGVLMLWLPGNNLVVAFVGLFSVL

IALALIAPPLTRFVMLRLAPGLGRLLGPIGRMAPRNIVRSLSRTSIAIA

ALMMAVSLMVGVSISVGSFRQTLANWLEVTLKSDVYVSPPTLTSGRPSG

NLPVDAVRNISKWPGVRDAVMARYSSVFAPDWGREVELMAVSGDISDGK

RPYRWIDGNKDTLWPRFLAGKGVMLSEPMVSRQHLQMPPRPITLMTDSG

PQTFPVLAVFSDYTSDQGVILMDRASYRAHWQDDDVTTMFLFLASGANS

GALIDQLQAAFAGREDIVIQSTHSVREASMFIFDRSFTITIALQLVATV

VAFIGVLSALMSLELDRAHELGVFRAIGMTTRQLWKLMFIETGLMGGMA

GLMALPTGCILAWILVRIINVRSFGWTLQMHFESAHFLRALLVAVVAAL

AAGMYPA WRLGRMTIRTAIREE

A non-limiting Rv1172c sequence of or from which a protein or peptide, or subsequence, portion or modification thereof can be based upon is a sequence set forth as:

(SEQ ID No: 28)
MSFVFAAPEALAAAAADMAGIGSTLNAANVVAAVPTTGVLAAAADEVST

QVAALLSAHAQGYQQLSRQMMTAFHDQFVQALRASADAYATAEASAAQT

MVNAVNAPARALLGHPLISADASTGGGSNALSRVQSMFLGTGGSSALGG

SAAANAAASGALQLQPTGGASGLSAVGALLPRAGAAAAAALPALAAESI

GNAIKNLYNAVEPWVQYGFNLTAWAVGWLPYIGILAPQINFFYYLGEPI

VQAVLFNAIDFVDGTVTFSQALTNIETATAASINQ FINTEINWIRGFL

PPLPPISPPGFPSLP

A non-limiting Rv1243c sequence of or from which a protein or peptide, or subsequence, portion or modification thereof can be based upon is a sequence set forth as:

(SEQ ID No: 29)
MEYLIAAQDVLVAAAADLEGIGSALAAANRAAEAPTTGLLAAGADEVSA

AIASLFSGNAQAYQALSAQAAAFHQQFVRALSSAAGSYAAAEAANASPM

QAVLDVVNGPTQLLLGRPLIGDGANGGPGQNGGDGGLLYGNGGNGGSSS

TPGQPGGRGGAAGLIGNGGAGGAGGPGANGGAGGNGGWLYGNGGLGGNG

GAATQIGGNGGNGGHGGNAGLWGNGGAGGAGAAGAAGANGQNPVSHQVT

HATDGADGTTGPDGNGTDAGSGSNAVNPGVGGGAGGIGGDGTNLGQTDV

SGGAGGDGGDGANFASGGAGGNGGAAQSGFGDAVGGNGGAGGNGGAGGG

GGLGGAGGSANVANAGNSIGGNGGAGGNGGIGAPGGAGGAGGNANQDNP

PGGNSTGGNGGAGGDGGVGASADVGGAGGFGGSGGRGGLLLGTGGAGGD

GGVGGDGGIGAQGGSGGNGGNGGIGADGMANQDGDGGDGGNGGDGGAGG

AGGVGGNGGATGGAGGLFGQSGSPGSGAAGGLGGAGGNGGGGGGGTGFN

PGAPGDPGTQGATGANGQHGLNG

A non-limiting Rv1317c sequence of or from which a protein or peptide, or subsequence, portion or modification thereof can be based upon is a sequence set forth as:

(SEQ ID No: 30)
MHDDFERCYRAIQSKDARFDGWFVVAVLTTGVYCRPSCPVRPPFARNVR

FLPTAAAQGEGFRACKRCRPDASPGSPEWNVRSDVVARAMRLIADGTV

DRDGVSGLAAQLGYTIRQLERLLQAVVGAGPLALARAQRMQTARVLIET

TNLPFGDVAFAAGFSSIRQFNDTVRLACDGTPTALRARAAARFESATAS

AGTVSLRLPVRAPFAFEGVFGHLAATAVPGCEEVRDGAYRRTLRLPWGN

GIVSLTPAPDHVRCLLVLDDFRDLMTATARCRRLLDLDADPEAIVEALG

ADPDLRAVVGKAPGQRIPRTVDEAEFAVRAVLAQQVSTKAASTHAGRLV

AAYGRPVHDRHGALTHTFPSIEQLAEIDPGHLAVPKARQRTINALVASL

ADKSLVLDAGCDWQRARGQLLALPGVGPWTAEVIAMRGLGDPDAFPASD

LGLRLAAKKLGLPAQRRALTVHSARWRPWRSYATQHLWTTLEHPVNQWP

PQEKIA

A non-limiting Rv1366 sequence of or from which a protein or peptide, or subsequence, portion or modification thereof can be based upon is a sequence set forth as:

(SEQ ID No: 31)
MVVALVGSAIVDLHSRPPWSNNAVRRLGVALRDGVDPPVDCPSYAEVML

WHADLAAEVQDRIEGRSWSASELLVTSRAKSQDTLLAKLRRRPYLQLNT

IQDIAGVRIDADLLLGEQTRLAREIADHFGADQPAIHDLRDHPHAGYRA

VHVWLRLPAGRVEIQIRTILQSLWANFYELLADAYGRGIRYDERPEQLA

AGVVPAQLQELVGVMQDASADLAMHEAEWQHCAEIEYPGQRAMALGEAS

KNKATVLATTKFRLERAINEAESAGGGG

A non-limiting Rv1441c sequence of or from which a protein or peptide, or subsequence, portion or modification thereof can be based upon is a sequence set forth as:

(SEQ ID No: 32)
MSNVMVVPGMLSAAAADVASIGAALSAANGAAAPTTAGVLAAGADEVSA

AIASLFSGYARDYQALSAQMARFHQQFVQALTASVGSYAAAEAANASPL

QALEQQVLAAINAPTQTLLGRPLIGNGADGLPGQNGGAGGLLWGNGGNG

GAGDAAHPNGGNGGDAGMFGNGGAGGAGYSPAAGTGAAGGAGGAGGAGG

WLSGNGGAGGNGGTGASGADGGGGLPPVPASPGGNGGGDAGGAAGMFG

TGGAGGTGGDGGAGGAGDSPNSGANGARGGDGGNGAAGGAGGRLFGNGG

AGGNGGTAGQGGDGGTALGAGGIGGDGGTGGAGGTGGTAGIGGSSAGAG

GAGGDGGAGGTGGGSSMIGGKGGTGGNGGVGGTGGASALTIGNGSSAGA

GGAGGAGGTGGTGGYIESLDGKGQAGNGGNGGNGAAGGAGGGGTGAGGN

GGAGGNGGDGGPSQGGGNPGFGGDGGTGGPGGVGVPDGIGGANGAQGKH

G

A non-limiting Rv2490c sequence of or from which a protein or peptide, or subsequence, portion or modification thereof can be based upon is a sequence set forth as:

(SEQ ID No: 33)
MQSMSFDPAVADIGSQVVNNAFQGLQAGAVAWVSLSSLLPAGAEEVSAW

AVTAFTTAATGLLALNQAAQEELRKAGEVFTAIARMYSDADVRAAACLL

EAIPRPGQTLARE

A non-limiting Rv2853 sequence of or from which a protein or peptide, or subsequence, portion or modification thereof can be based upon is a sequence set forth as:

(SEQ ID No: 34)
MLYVVASPDLMTAAATNLAEIGSAISTANGAAALPTVEVVAAAADEVST

QIAALFGAHARSYQTLSTQAAAFHSRFVQALTTAAASYASVEAANASPL

QVALDVINAPAQTLLGRPLIGNGADGSTPGQAGGPGGLLYGNGGNGAAG

GPNQAGGAGGNAGLIGNGGAGGAGGVGAVGGKRGTGGLLFGNGGAGGQG

GLGLAGINGGSGGQGGHGGNAILFGQGGAGGPGGTGAMGVAGTNPTPIG

TAAPGSDGVNQIGNGGNTDLTGGAGGDGNAGSTTVNGGNGGTGGAARNS

SGGTGNSFGGAGGAGGDGANGGDGGAGGEALTEGGATAVSGAGGKGGNA

EASGGAGGNGGKGGFAQATTSVTGGNGGNGGNGHDSNAPGGAGGSGGVG

GDGGRGGLLAGNGGTGGAGGNGGTGGAGAPGGAGGAGGKADIANSLGDN

ATVTGGNGGTGGDGGSALGTGGAGGAGGLGGHGGAGGLLIGNGGAGGAG

GLGGAGGAGGAGGEGGAGGAGGEAIPGGASTNSAGGDGGAGGTGGNGGD

GGAGGAPGLGGAGGAGGWLIGQSGSTGGGGAGGAGGAGGAGGAGGSGGA

GGHGDTTSGKNGSSGTAGFDGNPGQPG

As disclosed herein, presently provided MTB proteins and peptides, or subsequences, portions or modifications thereof include those having all or at least partial sequence identity to one or more exemplary MTB proteins, subsequences, portions or modifications thereof (e.g., sequences set forth in Table 1 or Table 5.). The percent identity of such sequences can be as little as 60%, or can be greater (e.g., 65%, 70%, 75%, 80%, 85%, 90%, 95%, 96%, 97%, 98%, 99%, etc.). The percent identity can extend over the entire sequence length or a portion of the sequence. In particular aspects, the length of the sequence sharing the percent identity is 2, 3, 4, 5 or more contiguous amino acids, e.g., 6, 7, 8, 9, 10, 11, 12, 13, 14, 15, 16, 17, 18, 19, 20, etc. contiguous amino acids. In additional particular aspects, the length of the sequence sharing the percent identity is 20 or more contiguous amino acids, e.g., 20, 21, 22, 23, 24, 25, 26, 27, 28, 29, 30, 31, 32, 33, 34, 35, etc. contiguous amino acids. In further particular aspects, the length of the sequence sharing the percent identity is 35 or more contiguous amino acids, e.g., 35, 36, 37, 38, 39, 40, 41, 42, 43, 44, 45, 45, 47, 48, 49, 50, etc., contiguous amino acids. In yet further particular aspects, the length of the sequence sharing the percent identity is 50 or more contiguous amino acids, e.g., 50-55, 55-60, 60-65, 65-70, 70-75, 75-80, 80-85, 85-90, 90-95, 95-100, 100-110, etc. contiguous amino acids.

The term "identity" and grammatical variations thereof, mean that two or more referenced entities are the same. Thus, where two MTB proteins and peptides, or subsequences, portions or modifications thereof are identical, they have the same amino acid sequence. The identity can be over a defined area (region or domain) of the sequence. "Areas, regions or domains" of homology or identity mean that a portion of two or more referenced entities share homology or are the same.

The extent of identity between two sequences can be ascertained using a computer program and mathematical algorithm known in the art. Such algorithms that calculate percent sequence identity (homology) generally account for sequence gaps and mismatches over the comparison region or area. For example, a BLAST (e.g., BLAST 2.0) search algorithm (see, e.g., Altschul et al., *J. Mol. Biol.* 215:403 (1990), publicly available through NCBI) has exemplary search parameters as follows: Mismatch −2; gap open 5; gap extension 2. For polypeptide sequence comparisons, a BLASTP algorithm is typically used in combination with a scoring matrix, such as PAM100, PAM 250, BLOSUM 62 or BLOSUM 50. FASTA (e.g., FASTA2 and FASTA3) and SSEARCH sequence comparison programs are also used to quantitate the extent of identity (Pearson et al., *Proc. Natl. Acad. Sci. USA* 85:2444 (1988); Pearson, *Methods Mol Biol.* 132:185 (2000); and Smith et al., *J. Mol. Biol.* 147:195 (1981)). Programs for quantitating protein structural similarity using Delaunay-based topological mapping have also been developed (Bostick et al., *Biochem Biophys Res Commun.* 304:320 (2003)).

In accordance with the invention, modified and variant forms of MTB proteins and peptides, or subsequences or portions thereof are provided. Such forms, referred to as "modifications" or "variants" and grammatical variations thereof, are a MTB protein or peptide, or subsequence or portion thereof that deviates from a reference sequence. For example, certain sequences set forth in Table 5 are considered a modification or variant of MTB protein or peptide, or subsequence or portion thereof. Such modifications may have greater or less activity or function than a reference MTB protein or peptide, or subsequence or portion thereof, such as ability to elicit, stimulate, induce, promote, increase, enhance or activate a CD4+ T cell response. Thus, MTB proteins and peptides, or subsequences or portions thereof include sequences having substantially the same, greater or less relative activity or function as a T cell epitope than a reference T cell epitope (e.g., any of the sequences in Table 5) for example, an ability to elicit, stimulate, induce, promote, increase, enhance or activate an anti-MTB $CD4^+$ T cell response in vitro or in vivo.

Non-limiting examples of modifications include one or more amino acid substitutions (e.g., 1, 2, 3, 4, 5, 6, 7, 8, 9, 10, 1, 12, 13, 14, 15, 16, 17, 18, 19, 20, 20-25, 25-30, 30-50, 50-100, or more residues), additions and insertions (e.g., 1, 2, 3, 4, 5, 6, 7, 8, 9, 10, 1, 12, 13, 14, 15, 16, 17, 18, 19, 20, 20-25, 25-30, 30-50, 50-100, or more residues) and deletions (e.g., 1, 2, 3, 4, 5, 6, 7, 8, 9, 10, 1, 12, 13, 14, 15, 16, 17, 18, 19, 20, 20-25, 25-30, 30-50, 50-100) of a reference MTB protein or peptide, or subsequence or portion thereof. In particular embodiments, a modified or variant sequence retains at least part of a function or an activity of unmodified sequence, and can have less than, approximately the same, or greater, but at least a part of, a function or activity of a reference sequence, for example, the ability to elicit, stimulate, induce, promote, increase, enhance or activate an anti-MTB $CD4^+$ T cell response in vitro or in vivo. Such $CD4^+$ T cell responses elicited include, for example, among others, induced, increased, enhanced, stimulate or activate expression or production of a cytokine (e.g., IFN-gamma, TNF, IL-2 or CD40L), release of a cytotoxin (perforin or granulysin), or apoptosis of a target (e.g. MTB infected) cell.

Specific non-limiting examples of substitutions include conservative and non-conservative amino acid substitutions. A "conservative substitution" is the replacement of one amino acid by a biologically, chemically or structurally similar residue. Biologically similar means that the substitution does not destroy a biological activity. Structurally similar means that the amino acids have side chains with similar length, such as alanine, glycine and serine, or a similar size. Chemical similarity means that the residues have the same charge, or are both hydrophilic or hydrophobic. Particular examples include the substitution of one hydrophobic residue, such as isoleucine, valine, leucine or methionine for another, or the substitution of one polar residue for another, such as the substitution of arginine for lysine, glutamic for aspartic acids, or glutamine for asparagine, serine for threonine, and the like.

An addition can be the covalent or non-covalent attachment of any type of molecule to the sequence. Specific examples of additions include glycosylation, acetylation, phosphorylation, amidation, formylation, ubiquitination, and derivatization by protecting/blocking groups and any of numerous chemical modifications. Additional specific non-limiting examples of an addition are one or more additional amino acid residues. Accordingly, MTB sequences including MTB proteins peptides, T cell epitopes, subsequences, portions, and modifications thereof can be a part of or contained within a larger molecule, such as another protein or peptide sequence, such as a fusion or chimera with a different MTB sequence, or a non-MTB protein or peptide, or subsequence or portion or modification thereof. In particular embodiments, an addition is a fusion (chimeric) sequence, an amino acid sequence having one or more molecules not normally present in a reference native (wild type) sequence covalently attached to the sequence.

The term "chimeric" and grammatical variations thereof, when used in reference to a sequence, means that the sequence contains one or more portions that are derived from, obtained or isolated from, or based upon other physical or chemical entities. For example, a chimera of two or more different proteins may have one part a MTB peptide, subsequence, portion or modification, and a second part of the chimera may be from a different MTB protein sequence, or a non-MTB sequence.

Another particular example of a modified sequence having an amino acid addition is one in which a second heterologous sequence, i.e., heterologous functional domain is attached (covalent or non-covalent binding) that confers a distinct or complementary function. Heterologous functional domains are not restricted to amino acid residues. Thus, a heterologous functional domain can consist of any of a variety of different types of small or large functional moieties. Such moieties include nucleic acid, peptide, carbohydrate, lipid or small organic compounds, such as a drug (e.g., an antiviral), a metal (gold, silver), and radioisotope. For example, a tag such as T7 or polyhistidine can be attached in order to facilitate purification or detection of a T cell epitope. Thus, in other embodiments, there is presently provided a MTB protein or peptide, or subsequence or portion thereof and a heterologous domain, wherein the heterologous functional domain confers a distinct function, on the MTB protein or peptide, or subsequence or portion thereof. Such constructs containing a MTB protein or peptide, or subsequence or portion thereof and a heterologous domain are also referred to as chimeras.

Linkers, such as amino acid or peptidomimetic sequences may be inserted between the sequence and the addition (e.g., heterologous functional domain) so that the two entities maintain, at least in part, a distinct function or activity. Linkers may have one or more properties that include a flexible conformation, an inability to form an ordered secondary structure or a hydrophobic or charged character, which could promote or interact with either domain. Amino acids typically found in flexible protein regions include Gly, Asn and Ser. Other near neutral amino acids, such as Thr and Ala, may also be used in the linker sequence. The length of the linker sequence may vary without significantly affecting a function or activity of the fusion protein (see, e.g., U.S. Pat. No. 6,087,329). Linkers further include chemical moieties and conjugating agents, such as sulfo-succinimidyl derivatives (sulfo-SMCC, sulfo-SMPB), disuccinimidyl suberate (DSS), disuccinimidyl glutarate (DSG) and disuccinimidyl tartrate (DST).

Further non-limiting examples of additions are detectable labels. Thus, in another embodiment, the invention provides MTB proteins or peptides, or subsequence or portion thereof that are detectably labeled. Specific examples of detectable labels include fluorophores, chromophores, radioactive isotopes (e.g., $S^{35}$, $P^{32}$, $I^{125}$), electron-dense reagents, enzymes, ligands and receptors. Enzymes are typically detected by their activity. For example, horseradish peroxidase is usually detected by its ability to convert a substrate such as 3,3-',5,5-'-tetramethylbenzidine (TMB) to a blue pigment, which can be quantified.

Another non-limiting example of an addition is an insertion of an amino acid within any MTB protein or peptide, or subsequence or portion thereof (e.g., any MTB protein or sequence set forth herein, such as in Table 1 or Table 5). In particular embodiments, an insertion is of one or more amino acid residues inserted into the amino acid sequence of a MTB protein or peptide, or subsequence or portion thereof, such as any protein or sequence set forth herein, such as in Tables 1 or 5.

Modified and variant MTB proteins or peptides, or subsequences or portions thereof also include one or more D-amino acids substituted for L-amino acids (and mixtures thereof), structural and functional analogues, for example, peptidomimetics having synthetic or non-natural amino acids or amino acid analogues and derivatized forms. Modifications include cyclic structures such as an end-to-end amide bond between the amino and carboxy-terminus of the molecule or intra- or inter-molecular disulfide bond. MTB proteins or peptides, or subsequences or portions thereof may be modified in vitro or in vivo, e.g., post-translationally modified to include, for example, sugar residues, phosphate groups, ubiquitin, fatty acids, lipids, etc.

Specific non-limiting examples of MTB proteins or peptides, or subsequences or portions thereof include an amino acid sequence comprising at least one amino acid deletion from a full length MTB protein sequence. In particular embodiments, a protein subsequence or portion is from about 2 to 957 amino acids in length, provided that said subsequence or portion is at least one amino acid less in length than the full-length mtB protein sequence. In additional particular embodiments, a protein subsequence or portion is from about 2 to 5, 5 to 10, 10 to 15, 15 to 20, 20 to 25, 25 to 50, 50 to 100, 100 to 150, 150 to 200, 200 to 250, 250 to 300, 300 to 350, 350 to 400, 400 to 450, 450 to 500, 500 to 550, 550 to 600, 600 to 650, 650 to 700, 700 to 750, 750 to 800, 800 to 850, 850 to 900, 900 to 950 or 950 to 957 amino acids in length, provided that said subsequence or portion is at least one amino acid less in length than the full-length MTB protein sequence.

MTB proteins or peptides, or subsequences, portions or modifications thereof can be produced by any of a variety of standard protein purification or recombinant expression techniques. For example, a MTB protein or peptide, or a subsequence, portion or modification thereof can be produced by standard peptide synthesis techniques, such as solid-phase synthesis. A portion of the protein may contain an amino acid sequence such as a T7 tag or polyhistidine sequence to facilitate purification of expressed or synthesized protein. The protein may be expressed in a cell and purified. The protein may be expressed as a part of a larger protein (e.g., a fusion or chimera) by recombinant methods.

MTB proteins or peptides, or subsequences, portions or modifications thereof can be made using recombinant DNA technology via cell expression or in vitro translation. Polypeptide sequences including modified forms can also be produced by chemical synthesis using methods known in the art, for example, an automated peptide synthesis apparatus (see, e.g., Applied Biosystems, Foster City, Calif.).

The invention provides isolated and/or purified MTB proteins or peptides, or subsequences, portions or modifications thereof including, comprising or consisting of amino acid sequence of a protein, peptide, subsequence, portion or modification of an MTB intermediary metabolism and respiration protein, cell wall and cell processes protein, lipid metabolism proteins, information pathway protein, virulence, detoxification or adaptation protein, regulatory protein, PE/PPE protein, insertion sequence and phage protein, Esx protein, secreted protein, secretion system protein or conserved hypothetical protein.

In particular embodiments, the present invention provides isolated and/or purified MTB proteins or peptides, or subsequences, portions or modifications thereof that include, comprise or consist of the protein and peptides set forth in Table 1 or Table 5.

In certain embodiments, the present invention provides isolated and/or purified MTB proteins or peptides, or subsequences, portions or modifications thereof that include, comprise or consist of an amino acid sequence of protein Rv3024c, Rv0289, Rv0290, Rv3330, Rv1788, Rv1791, Rv3125c, Rv0294, Rv2874, Rv3022c, Rv3135, Rv3876, Rv0124, Rv0291, Rv0292, Rv0293c, Rv0297, Rv0299, Rv3012c, Rv3025c, Rv0278c, Rv0279c, Rv0298, Rv0442c, Rv0690c, Rv0985c, Rv0987, Rv1172c, Rv1243c, Rv1317c, Rv1366, Rv1441c, Rv2490c or Rv2853.

In particular embodiments, an isolated and/or purified MTB protein or peptide, or subsequence, portion or modification thereof includes a T cell epitope, e.g., as set forth in Tables 1 or 5.

The term "isolated," when used as a modifier of a composition (e.g., MTB proteins or peptides, or subsequences, portions or modifications thereof, nucleic acids encoding same, etc.), means that the compositions are made by the hand of man or are separated, completely or at least in part, from their naturally occurring in vivo environment. Generally, isolated compositions are substantially free of one or more materials with which they normally associate with in nature, for example, one or more protein, nucleic acid, lipid, carbohydrate, cell membrane. The term "isolated" does not exclude alternative physical forms of the composition, such as fusions/chimeras, multimers/oligomers, modifications (e.g., phosphorylation, glycosylation, lipidation) or derivatized forms, or forms expressed in host cells produced by the hand of man.

An "isolated" composition (e.g., MTB proteins or peptides, or subsequences, portions or modifications thereof) can also be "substantially pure" or "purified" when free of most or all of the materials with which it typically associates with in nature. Thus, an isolated MTB proteins or peptides, or subsequences, portions or modifications thereof, that also is substantially pure or purified does not include polypeptides or polynucleotides present among millions of other sequences, such as peptides of an peptide library or nucleic acids in a genomic or cDNA library, for example.

A "substantially pure" or "purified" composition can be combined with one or more other molecules. Thus, "substantially pure" or "purified" does not exclude combinations of compositions, such as combinations of MTB proteins or peptides, or subsequences, portions or modifications thereof (e.g., multiple, T cell epitopes), and other antigens, agents, drugs or therapies.

The invention also provides nucleic acids encoding MTB proteins or peptides, or subsequences, portions or modifications thereof. Such nucleic acid sequences encode a sequence at least 60% or more (e.g., 65%, 70%, 75%, 80%, 85%, 90%, 95%, etc.) identical to a MTB proteins or peptides, or subsequences, portions or modifications thereof. In an additional embodiment, a nucleic acid encodes a sequence having a modification, such as one or more amino acid additions (insertions), deletions or substitutions of a MTB proteins or peptides, or subsequences, portions or modifications thereof, such as set forth in Tables 1 or 5.

The terms "nucleic acid," "polynucleotide" and "polynucleoside" and the like refer to at least two or more ribo- or deoxy-ribonucleic acid base pairs (nucleotides/nucleosides) that are linked through a phosphoester bond or equivalent. Nucleic acids include polynucleotides and polynucleosides. Nucleic acids include single, double or triplex, circular or linear, molecules. Exemplary nucleic acids include but are not limited to: RNA, DNA, cDNA, genomic nucleic acid, naturally occurring and non naturally occurring nucleic acid, e.g., synthetic nucleic acid.

Nucleic acids can be of various lengths. Nucleic acid lengths typically range from about 20 bases to 20 Kilobases (Kb), or any numerical value or range within or encompassing such lengths, 10 bases to 10 Kb, 1 to 5 Kb or less, 1000 to about 500 bases or less in length. Nucleic acids can also be shorter, for example, 100 to about 500 bases, or from about 12 to 25, 25 to 50, 50 to 100, 100 to 250, or about 250 to 500 bases in length, or any numerical value or range or value within or encompassing such lengths. In particular aspects, a nucleic acid sequence has a length from about 10-20, 20-30, 30-50, 50-100, 100-150, 150-200, 200-250, 250-300, 300-400, 400-500, 500-1000, 1000-2000 bases, or any numerical value or range within or encompassing such lengths. Shorter nucleic acids are commonly referred to as "oligonucleotides" or "probes" of single- or double-stranded DNA. However, there is no upper limit to the length of such oligonucleotides.

Nucleic acid sequences further include nucleotide and nucleoside substitutions, additions and deletions, as well as derivatized forms and fusion/chimeric sequences (e.g., encoding recombinant polypeptide). For example, due to the degeneracy of the genetic code, nucleic acids include sequences and subsequences degenerate with respect to nucleic acids that encode MTB proteins or peptides, or subsequences, portions or modifications thereof, as well as variants and modifications thereof (e.g., substitutions, additions, insertions and deletions).

Nucleic acids can be produced using various standard cloning and chemical synthesis techniques. Techniques include, but are not limited to nucleic acid amplification, e.g., polymerase chain reaction (PCR), with genomic DNA or cDNA targets using primers (e.g., a degenerate primer mixture) capable of annealing to the encoding sequence. Nucleic acids can also be produced by chemical synthesis (e.g., solid phase phosphoramidite synthesis) or transcription from a gene. The sequences produced can then be translated in vitro, or cloned into a plasmid and propagated and then expressed in a cell (e.g., a host cell such as eukaryote or mammalian cell, yeast or bacteria, in an animal or in a plant).

Nucleic acid may be inserted into a nucleic acid construct in which expression of the nucleic acid is influenced or regulated by an "expression control element." An "expression control element" refers to a nucleic acid sequence element that regulates or influences expression of a nucleic acid sequence to which it is operatively linked. Expression control elements include, as appropriate, promoters, enhancers, transcription terminators, gene silencers, a start codon (e.g., ATG) in front of a protein-encoding gene, etc.

An expression control element operatively linked to a nucleic acid sequence controls transcription and, as appropriate, translation of the nucleic acid sequence. Expression control elements include elements that activate transcription constitutively, that are inducible (i.e., require an external signal for activation), or derepressible (i.e., require a signal to turn transcription off; when the signal is no longer present, transcription is activated or "derepressed"), or specific for cell-types or tissues (i.e., tissue-specific control elements).

Nucleic acid can also be inserted into a plasmid for propagation into a host cell and for subsequent genetic manipulation. A plasmid is a nucleic acid that can be propagated in a host cell, plasmids may optionally contain expression control elements in order to drive expression of the nucleic acid encoding MTB proteins or peptides, or subsequences, portions or modifications thereof in the host cell. A vector is used herein synonymously with a plasmid and may also include an expression control element for expression in a host cell (e.g., expression vector). Plasmids and vectors generally contain at least an origin of replication for propagation in a cell and a promoter. Plasmids and vectors are therefore useful for genetic manipulation and expression of MTB proteins or peptides, or subsequences, portions or modifications thereof. Accordingly, vectors that include nucleic acids encoding or complementary to MTB proteins or peptides, or subsequences, portions or modifications thereof, are provided.

In accordance with the invention, there are provided particles (e.g., viral particles) and transformed host cells that express and/or are transformed with a nucleic acid that encodes and/or express MTB proteins or peptides, or subsequences, portions or modifications thereof. Particles and transformed host cells include but are not limited to virions, and prokaryotic and eukaryotic cells such as bacteria, fungi (yeast), plant, insect, and animal (e.g., mammalian, including primate and human, CHO cells and hybridomas) cells. For example, bacteria transformed with recombinant bacteriophage nucleic acid, plasmid nucleic acid or cosmid nucleic acid expression vectors; yeast transformed with recombinant yeast expression vectors; plant cell systems infected with recombinant virus expression vectors (e.g., cauliflower mosaic virus, CaMV; tobacco mosaic virus, TMV) or transformed with recombinant plasmid expression vectors (e.g., Ti plasmid); insect cell systems infected with recombinant virus expression vectors (e.g., baculovirus); and animal cell systems infected with recombinant virus expression vectors (e.g., retroviruses, adenovirus, vaccinia virus), or transformed animal cell systems engineered for stable expression. The cells may be a primary cell isolate, cell culture (e.g., passaged, established or immortalized cell line), or part of a plurality of cells, or a tissue or organ ex vivo or in a subject (in vivo).

The term "transformed" or "transfected" when used in reference to a cell (e.g., a host cell) or organism, means a genetic change in a cell following incorporation of an exogenous molecule, for example, a protein or nucleic acid (e.g., a transgene) into the cell. Thus, a "transfected" or "transformed" cell is a cell into which, or a progeny thereof in which an exogenous molecule has been introduced by the hand of man, for example, by recombinant DNA techniques.

The nucleic acid or protein can be stably or transiently transfected or transformed (expressed) in the host cell and progeny thereof. The cell(s) can be propagated and the introduced protein expressed, or nucleic acid transcribed. A progeny of a transfected or transformed cell may not be identical to the parent cell, since there may be mutations that occur during replication.

Expression of MTB proteins or peptides, or subsequences, portions or modifications thereof, and nucleic acid in particles or introduction into target cells (e.g., host cells) can also be carried out by methods known in the art. Non-limiting examples include osmotic shock (e.g., calcium phosphate), electroporation, microinjection, cell fusion, etc. Introduction of nucleic acid and polypeptide in vitro, ex vivo and in vivo can also be accomplished using other techniques. For example, a polymeric substance, such as polyesters, polyamine acids, hydrogel, polyvinyl pyrrolidone, ethylene-vinylacetate, methylcellulose, carboxymethylcellulose, protamine sulfate, or lactide/glycolide copolymers, polylactide/glycolide copolymers, or ethylenevinylacetate copolymers. A nucleic acid can be entrapped in microcapsules prepared by coacervation techniques or by interfacial polymerization, for example, by the use of hydroxymethylcellulose or gelatin-microcapsules, or poly (methylmethacrolate) microcapsules, respectively, or in a colloid system. Colloidal dispersion systems include macromolecule complexes, nano-capsules, microspheres, beads, and lipid-based systems, including oil-in-water emulsions, micelles, mixed micelles, and liposomes.

Liposomes for introducing various compositions into cells are known in the art and include, for example, phosphatidylcholine, phosphatidylserine, lipofectin and DOTAP (e.g., U.S. Pat. Nos. 4,844,904, 5,000,959, 4,863,740, and 4,975,282; and GIBCO-BRL, Gaithersburg, Md.). Piperazine based amphilic cationic lipids useful for gene therapy also are known (see, e.g., U.S. Pat. No. 5,861,397). Cationic lipid systems also are known (see, e.g., U.S. Pat. No. 5,459,127). Polymeric substances, microcapsules and colloidal dispersion systems such as liposomes are collectively referred to herein as "vesicles." Accordingly, viral and non-viral vector means delivery into cells are included.

MTB proteins or peptides, or subsequences, portions or modifications thereof can be employed in various methods and uses. Such methods and uses include, for example, use, contact or administration of one or more MTB proteins or peptides, or subsequences, portions or modifications thereof, such as the proteins, peptides and subsequences set forth herein (e.g., Table 1 or Table 5) in vitro and in vivo.

In other embodiments of the present invention, the MTB proteins or peptides described herein, or a subsequence, portion or modification thereof may be used as vaccine antigens or for treatment or diagnosis of a MTB infection or pathology, or one or more physiological conditions, disorders, illness, diseases or symptoms caused by or associated with MTB infection or pathology In one aspect, there is presently provided methods comprising the MTB proteins or peptides, or subsequences, portions or modifications thereof described herein, as tools for identifying biomarkers to provide correlates of risk for, or protection against, one or more physiological conditions, disorders, illness, diseases or symptoms caused by or associated with MTB infection or pathology.

Thus, in one aspect, there is provided a method of diagnosing a subject having or at increased risk of having a MTB infection or pathology, or one or more physiological conditions, disorders, illness, diseases or symptoms caused by or associated with MTB infection or pathology comprising contacting a biological material or sample from a subject with a MTB protein or peptide, or subsequence, portion or modification thereof as described herein and assaying for an immune response in the subject to the MTB protein or peptide, or subsequence, portion or modification thereof, wherein an immune response in the subject indicates that the subject has or is at increased risk of having a MTB infection or pathology, or one or more physiological conditions, disorders, illness, diseases or symptoms caused by or associated with MTB infection or pathology. In particular embodiments of the method, the immune response is T cell reactivity (e.g. CD4+ T cell reactivity, including but not limited to a CXCR3$^+$CCR6$^+$ memory Th1 cell response).

In other embodiments of the present invention, the MTB proteins or peptides described herein, or a subsequence, portion or modification thereof may be used as vaccine antigens or for methods of diagnosis.

Thus, in accordance with the invention, there are provided methods for vaccination and immunization to protect against MTB infection, and methods for treatment of a MTB infection. Such methods are applicable to providing a subject with protection from MTB infection, and also are applicable to providing treatment to a subject having a MTB infection.

In one embodiment, there is provided a method of eliciting, stimulating, inducing, promoting, increasing or enhancing an immune response against M. tuberculosis (MTB) in a subject, the method comprising administering to the subject an amount of a MTB protein or peptide, described herein, or a subsequence, portion or modification thereof sufficient to elicit, stimulate, induce, promote, increase or enhance an immune response against MTB in the subject. Such immune response methods can in turn be used to provide a subject with protection against a MTB infection or pathology, or one or more physiological conditions, disorders, illness, diseases or symptoms caused by or associated with MTB infection or pathology.

In another embodiment, there is provided a method of providing a subject with protection against a M. tuberculosis (MTB) infection or pathology, or one or more physiological conditions, disorders, illnesses, diseases, symptoms or complications caused by or associated with MTB infection or pathology, the method comprising administering to the subject an amount of a MTB protein or peptide, described herein, or a subsequence, portion or modification thereof sufficient to provide the subject with protection against the MTB infection or pathology, or one or more physiological conditions, disorders, illnesses, diseases, symptoms or complications caused by or associated with MTB infection or pathology. In particular embodiments, the presently provided methods of providing a subject with protection against a M. tuberculosis (MTB) infection or pathology, or one or more physiological conditions, disorders, illnesses, diseases, symptoms or complications caused by or associated with MTB infection or pathology may comprise vaccinating the subject against a MTB infection, As used herein, the terms "protection", "protect" and grammatical variations thereof, when used in reference to a MTB infection or pathology, means preventing a MTB infection, or reducing or decreasing susceptibility to a MTB infection, or preventing or reducing one or more symptoms or pathologies caused by or associated with MTB infection or pathology.

In a further embodiment, there is provided a method of treating a subject for a MTB infection, the method comprising administering to the subject an amount of an MTB protein or peptide, described herein, or a subsequence, portion or modification thereof sufficient to treat the subject for the MTB infection. As will be understood by a person skilled in the art, treating a subject for a MTB infection may include decreasing, reducing, inhibiting, suppressing, limiting, controlling or clearing an MTB infection. Thus in certain embodiments, a method of treating a subject for a MTB infection comprises the elimination of an MTB infection from a subject. In other embodiments, a method of treating a subject for a MTB infection comprises reducing the number of MTB mycobacteria or the occurrence, frequency, severity, progression, or duration of MTB infection in the subject. In yet another embodiment, a method of treating a subject for a MTB infection comprises maintaining the level of MTB infection in a subject by preventing an increase in the number of MTB mycobacteria or occurrence, frequency, severity, progression, or duration of MTB infection in the subject. In still further embodiments, a method of treating a subject for a MTB infection comprises eliminating, reducing or maintaining the occurrence, frequency, severity, progression, or duration of physiological conditions, disorders, illnesses, diseases, symptoms or complications caused by or associated with MTB infection or pathology.

In certain embodiments, the subject of the methods provided herein may have been previously exposed to or infected with MTB. Thus, in certain embodiments, the present methods may be used for treating or protecting a subject from a secondary or subsequent MTB infection.

Physiological conditions, disorders, illnesses, diseases, symptoms or complications caused by or associated with MTB infection or pathology include but are not limited to tuberculosis disease, pulmonary tuberculosis, tuberculosis pleuritis, miliary tuberculosis, weight loss, loss of energy, loss of appetite, fever, productive cough, dry cough, night sweats, non-productive cough, chest pain, difficulty breathing, increase in mucus production, MTB infection lung infection, MTB infection lymph node infection, MTB infection genitourinary tract infection, MTB infection bone infection, MTB infection joint infection, MTB infection meninges infection and MTB infection gastrointestinal infection.

In accordance with the present invention, methods of treatment are provided that include therapeutic (following MTB infection) and prophylactic (prior to MTB exposure, infection or pathology) uses and methods. For example, therapeutic and prophylactic methods of treating a subject for a MTB infection include but are not limited to treatment of a subject having or at risk of having a MTB infection or pathology, treating a subject with a MTB infection, and methods of protecting a subject from a MTB infection (e.g., provide the subject with protection against MTB infection), to decrease or reduce the probability of a MTB infection in a subject, to decrease or reduce susceptibility of a subject to a MTB infection, to inhibit or prevent a MTB infection in a subject, and to decrease, reduce, inhibit or suppress transmission of the MTB from an infected host to a subject.

Such methods include, for example, administering a MTB protein or peptide or a subsequence, portion or modification thereof to therapeutically or prophylactically treat (vaccinate or immunize) a subject having or at risk of having a MTB infection or pathology. Accordingly, the presently provided methods can treat MTB infection or pathology, or provide a subject with protection from infection (e.g., prophylactic protection).

As described herein, MTB proteins or peptides, or a subsequence, portion or modification thereof, include T cell epitopes. In one embodiment, a method includes administering an amount of a MTB protein or peptide, or a subsequence, portion or modification thereof (e.g., a T cell epitope) to a subject in need thereof, sufficient to provide the subject with protection against MTB infection or pathology. In another embodiment, a method includes administering an amount of a MTB protein or peptide, or a subsequence, portion or modification thereof (e.g., a T cell epitope) to a subject in need thereof sufficient to treat, vaccinate or immunize the subject against the MTB infection or pathology.

In accordance with the invention, methods of eliciting, stimulating, inducing, promoting, increasing or enhancing anti-MTB activity of T cells, including but not limited to $CD8^+$ T cells or $CD4^+$ T cells, in a subject are provided. In one embodiment, a method includes administering to a subject an amount of MTB protein or peptide, or a subsequence, portion or modification thereof, such as a T cell epitope, sufficient to induce, increase, promote or stimulate anti-MTB activity of $CD4^+$ T cells in the subject.

In methods of the invention, any appropriate MTB protein or peptide, or a subsequence, portion or modification thereof can be used or administered. In particular non-limiting examples, the MTB protein or peptide, or a subsequence, portion or modification thereof includes, comprises or consists of an amino acid sequence of a protein, peptide, subsequence, portion or modification of a MTB intermediary metabolism and respiration protein, cell wall and cell processes protein, lipid metabolism protein, information pathway protein, virulence, detoxification or adaptation protein, regulatory protein, PE/PPE protein, insertion sequence and phage protein, Esx protein, secreted protein, secretion system protein or conserved hypothetical protein.

In particular embodiment, the present methods may comprise a MTB protein or peptide, or a subsequence, portion or modification thereof, that includes, comprises or consists of an amino acid sequence of protein or peptide as set forth in Table 1 or Table 5 or a subsequence, portion or modification thereof. In further particular embodiments, the present methods may comprise a MTB protein or peptide, or a subsequence, portion or modification thereof, that includes, comprises or consists of an amino acid sequence of protein Rv3024c, Rv0289, Rv0290, Rv3330, Rv1788, Rv1791, Rv3125c, Rv0294, Rv2874, Rv3022c, Rv3135, Rv3876, Rv0124, Rv0291, Rv0292, Rv0293c, Rv0297, Rv0299, Rv3012c, Rv3025c, Rv0278c, Rv0279c, Rv0298, Rv0442c, Rv0690c, Rv0985c, Rv0987, Rv1172c, Rv1243c, Rv1317c, Rv1366, Rv1441c, Rv2490c or Rv2853, or a subsequence, portion or modification thereof.

The presently provided methods may comprise MTB protein or peptide, or subsequence, portion or modification thereof, derived from or based upon a sequence from any MTB strain, including but not limited to *Mycobacterium tuberculosis* H37Rv, *Mycobacterium tuberculosis* CDC1551, *Mycobacterium tuberculosis* H37Ra. *Mycobacterium tuberculosis* F11, *Mycobacterium tuberculosis* KZN 1435, *Mycobacterium tuberculosis* KZN 605, *Mycobacterium tuberculosis* C, *Mycobacterium tuberculosis* str. Haarlem, *Mycobacterium tuberculosis* KZN 4207, *Mycobacterium tuberculosis* 94_M4241A, *Mycobacterium tuberculosis* 02_1987, *Mycobacterium tuberculosis* T92, *Mycobacterium tuberculosis* EAS054, *Mycobacterium tuberculosis* T85, *Mycobacterium tuberculosis* GM 1503, *Mycobacterium tuberculosis* T17, *Mycobacterium tuberculosis* '98-R604 INH-RIF-EM', *Mycobacterium tuberculosis* T46, *Mycobacterium tuberculosis* CPHL_A or *Mycobacterium tuberculosis* K85.

In certain embodiments of the presently described methods, two or more MTB proteins or peptides may be administered to the subject. In particular embodiments, two or more of the MTB proteins or peptides set forth in Table 1 or Table 5, or a subsequence, portion or a modification thereof, may be administered to the subject. In certain embodiments of the present methods, a MTB protein or peptide, or subsequence, portion or modification thereof, including, comprising or consisting of an amino acid sequence of MTB protein Rv3024c, Rv0289, Rv0290, Rv3330, Rv1788, Rv1791, Rv3125c, Rv0294, Rv2874, Rv3022c, Rv3135, Rv3876, Rv0124, Rv0291, Rv0292, Rv0293c, Rv0297, Rv0299, Rv3012c, Rv3025c, Rv0278c, Rv0279c, Rv0298, Rv0442c, Rv0690c, Rv0985c, Rv0987, Rv1172c, Rv1243c, Rv1317c, Rv1366, Rv1441c, Rv2490c or Rv2853, or a subsequence, portion or modification thereof, is administered with one or more other MTB protein or peptide, or subsequence, portion or modification thereof. As will be understood by a skilled person two or more MTB proteins or peptides, or a subsequence, portion or modification thereof may be administered as a combination composition, or administered separately, such as concurrently or in series or sequentially. Different MTB proteins or peptides, or a subsequence, portion or modification thereof, may be administered to a subject in the same amount, volume or concentration or different amounts, volumes or concentrations. Thus in certain embodiments, the subject may be administered the same amount of two or more different MTB proteins or peptides, or a subsequence, portion or modification thereof. In other embodiments, the subject may be administered one MTB protein or peptide, or a subsequence, portion or modification thereof in a amount, volume or concentration greater than one or more other MTB protein or peptide, or a subsequence, portion or modification thereof administered to the subject.

In particular embodiments of the methods described herein, one or more disorders, diseases, physiological conditions, pathologies and symptoms associated with or caused by a MTB infection or pathology will respond to treatment. In particular embodiments, methods of treatment reduce, decrease, suppress, limit, control or inhibit MTB bacteria numbers or titer; reduce, decrease, suppress, limit, control or inhibit pathogen proliferation or replication; reduce, decrease, suppress, limit, control or inhibit the amount of a pathogen protein; or reduce, decrease, suppress, limit, control or inhibit the amount of a MTB nucleic acid. In additional particular embodiments of the present invention, methods of treatment include an amount of a MTB protein or peptide, or a subsequence, portion or modification thereof sufficient to elicit, stimulate, induce, promote, increase or enhance or augment an immune response against MTB; elicit, stimulate, induce, promote, increase or enhance or augment MTB clearance or removal; or decrease, reduce, inhibit, suppress, prevent, control, or limit transmission of MTB to a subject (e.g., transmission from an infected host to a subject). In further particular embodiments of the present invention, methods of treatment include an amount of a MTB protein or peptide, or a subsequence, portion or modification thereof sufficient to protect a subject from MTB infection or pathology, or reduce, decrease, limit, control or inhibit susceptibility to MTB infection or pathology.

Methods of the invention include methods of treatment that result in any therapeutic or beneficial effect. In various methods embodiments, MTB infection, proliferation or pathogenesis is reduced, decreased, inhibited, limited, delayed or prevented, or a method decreases, reduces, inhibits, suppresses, prevents, controls or limits one or more adverse (e.g., physical) symptoms, disorders, illnesses, diseases or complications caused by or associated with MTB infection, proliferation or replication, or pathology (e.g., tuberculosis disease, pulmonary tuberculosis, tuberculosis pleuritis, miliary tuberculosis, weight loss, loss of energy, loss of appetite, fever, productive cough, dry cough, night sweats, non-productive cough, chest pain, difficulty breathing, increase in mucus production, MTB infection lung infection, MTB infection lymph node infection, MTB infection genitourinary tract infection, MTB infection bone infection, MTB infection joint infection, MTB infection meninges infection and MTB infection gastrointestinal infection.). In additional various particular embodiments, methods of treatment include reducing, decreasing, inhibiting, delaying or preventing onset, progression, frequency, duration, severity, probability or susceptibility of one or more adverse symptoms, disorders, illnesses, diseases or complications caused by or associated with MTB infection, proliferation or replication, or pathology (e.g. tuberculosis disease, pulmonary tuberculosis, tuberculosis pleuritis, miliary tuberculosis, weight loss, loss of energy, loss of appetite, fever, productive cough, dry cough, night sweats, non-productive cough, chest pain, difficulty breathing, increase in mucus production, MTB infection lung infection, MTB infection lymph node infection, MTB infection genitourinary tract infection, MTB infection bone infection, MTB infection joint infection, MTB infection meninges infection and MTB infection gastrointestinal infection.). In further various particular embodiments, methods of treatment include improving, accelerating, facilitating, enhancing, augmenting, or hastening recovery of a subject from a MTB infection or pathogenesis, or one or more adverse symptoms, disorders, illnesses, diseases or complications caused by or associated with MTB infection, proliferation or replication, or pathology (e.g. tuberculosis disease, pulmonary tuberculosis, tuberculosis pleuritis, miliary tuberculosis, weight loss, loss of energy, loss of appetite, fever, productive cough, dry cough, night sweats, non-productive cough, chest pain, difficulty breathing, increase in mucus production, MTB infection lung infection, MTB infection lymph node infection, MTB infection genitourinary tract infection, MTB infection bone infection, MTB infection joint infection, MTB infection meninges infection and MTB infection gastrointestinal infection.). In yet additional various embodiments, methods of treatment include stabilizing infection, proliferation, replication, pathogenesis, or an adverse symptom, disorder, illness, disease or complication caused by or associated with MTB infection, proliferation or replication, or pathology, or decreasing, reducing, inhibiting, suppressing, limiting or controlling transmission of MTB from an infected host to an uninfected subject.

A therapeutic or beneficial effect of treatment is therefore any objective or subjective measurable or detectable improvement or benefit provided to a particular subject. A therapeutic or beneficial effect can but need not be complete ablation of all or any particular adverse symptom, disorder, illness, disease or complication caused by or associated with MTB infection, proliferation or replication, or pathology (e.g. tuberculosis disease, pulmonary tuberculosis, tuberculosis pleuritis, miliary tuberculosis, weight loss, loss of energy, loss of appetite, fever, productive cough, dry cough, night sweats, non-productive cough, chest pain, difficulty breathing, increase in mucus production, MTB infection lung infection, MTB infection lymph node infection, MTB infection genitourinary tract infection, MTB infection bone infection, MTB infection joint infection, MTB infection meninges infection and MTB infection gastrointestinal infection.) Thus, a satisfactory clinical endpoint is achieved when there is an incremental improvement or a partial reduction in an adverse symptom, disorder, illness, disease or complication caused by or associated with MTB infection, proliferation or replication, or pathology, or an inhibition, decrease, reduction, suppression, prevention, limit or control of worsening or progression of one or more adverse symptoms, disorders, illnesses, diseases or complications caused by or associated with MTB infection, MTB numbers or titers, MTB proliferation or replication, MTB protein or nucleic acid, or MTB pathology, over a short or long duration (hours, days, weeks, months, etc.).

A therapeutic or beneficial effect also includes reducing or eliminating the need, dosage frequency or amount of a second active such as another drug or other agent (e.g., anti-bacterial) used for treating a subject having or at risk of having a MTB infection or pathology. For example, reducing an amount of an adjunct therapy, for example, a reduction or decrease of a treatment for a MTB infection or pathology, or a vaccination or immunization protocol is considered a beneficial effect. In addition, reducing or decreasing an amount of MTB protein or peptide used for vaccination or immunization of a subject to provide protection to the subject is considered a beneficial effect.

Adverse symptoms and complications associated with MTB infection and pathology include, for example, e.g., tuberculosis disease, pulmonary tuberculosis, tuberculosis pleuritis, miliary tuberculosis, weight loss, loss of energy, loss of appetite, fever, productive cough, dry cough, night sweats, non-productive cough, chest pain, difficulty breathing, increase in mucus production, MTB infection lung infection, MTB infection lymph node infection, MTB infection genitourinary tract infection, MTB infection bone infection, MTB infection joint infection, MTB infection meninges infection and MTB infection gastrointestinal infection.) Additional symptoms of MTB infection or pathogenesis are known to one of skill in the art and treatment thereof in accordance with the invention is provided.

Methods and compositions of the invention also include eliciting, stimulating, inducing, promoting, increasing, enhancing or augmenting an anti-MTB T cell response (e.g. $CD4^+$ T cell) in a subject, such as a subject with or at risk of a MTB infection or pathology. In one embodiment, the present methods includes administering to a subject an amount of a MTB protein or peptide, or a subsequence, portion or modification thereof sufficient to elicit, stimulate, induce, promote, increase, enhance or augment an anti-MTB $CD4^+$ T cell response in the subject. In another embodiment, a method includes administering to a subject an amount of a nucleic acid encoding all or a portion (e.g., a T cell epitope) of any a MTB protein or peptide, or a subsequence, portion or modification thereof sufficient to elicit, stimulate, induce, promote, increase, enhance or augment an anti-MTB $CD4^+$ T cell response in the subject.

The present inventors have surprisingly found that the CD4 response to MTB is highly heterogeneous and includes responses by the $CXCR3^+CCR6^+$ memory Th1 cell subset. Thus the methods of the invention additionally include, among other things, eliciting, stimulating, inducing, promoting, increasing, enhancing or augmenting an anti-MTB $CXCR3^+CCR6^+$ memory Th1 cell response. An anti-MTB $CXCR3^+CCR6^+$ memory Th1 cell response may include, among other things, increasing production of Th1 cytokines or other Th1 signalling molecule. Thus, in one embodiment, the present methods include a method of administering to a subject in need thereof an amount of a MTB protein or peptide, or a subsequence, portion or modification thereof sufficient to increase production of a Th1 cytokine or other Th1 signalling molecule in the subject.

Methods and compositions of the invention include administration of a MTB protein or peptide, or a subsequence, portion or modification thereof to a subject prior to contact, exposure or infection by MTB, administration prior to, substantially contemporaneously with or after a subject has been contacted by, exposed to or infected with MTB and administration prior to, substantially contemporaneously with or after MTB pathology or development of one or more adverse symptoms. Methods and compositions of the invention also include administration of a MTB protein or peptide, or a subsequence, portion or modification thereof to a subject prior to, substantially contemporaneously with or following an adverse symptom, disorder, illness or disease caused by or associated with MTB infection, or pathology. A subject infected with MTB may have an infection over a period of 1-5, 5-10, 10-20, 20-30, 30-50, 50-100 hours, days, months, or years.

Invention compositions (e.g., MTB proteins and peptides, or a subsequence, portion or modification thereof, including T cell epitopes) and methods can be combined with any compound, agent, drug, treatment or other therapeutic regimen or protocol having a desired therapeutic, beneficial, additive, synergistic or complementary activity or effect. Exemplary combination compositions and treatments include multiple MTB proteins or peptides or a subsequence, portion or modification thereof such as T cell epitopes as described herein, and second actives, such as anti-MTB compounds, agents, drugs, treatments and therapies, including but not limited to antibiotics, as well as agents that assist, promote, stimulate or enhance efficacy. Such anti-MTB drugs, agents, treatments and therapies can be administered or performed prior to, substantially contemporaneously with or following any method of the invention, for example, a therapeutic use or method of treating a subject for a MTB infection or pathology, or a method of prophylactic treatment of a subject for a MTB infection.

MTB proteins or peptides, or subsequences, portions or modifications thereof can be administered as a combination with a second active, or administered separately, such as concurrently or in series or sequentially (prior to or following) to administering a second active to a subject. The invention therefore provides combinations of one or more MTB proteins or peptides, or subsequences, portions or modifications thereof in combination with a second active, including but not limited to any compound, agent, drug, therapeutic regimen, treatment protocol, process, remedy or composition, such as an anti-bacterial or immune stimulating, enhancing or augmenting protocol, or pathogen vaccination or immunization (e.g., prophylaxis) set forth herein or known in the art. The compound, agent, drug, therapeutic regimen, treatment protocol, process, remedy or composition can be administered or performed prior to, substantially contemporaneously with or following administration of one or more MTB proteins or peptides, or subsequences, portions or modifications thereof, or a nucleic acid encoding all or a portion (e.g., a T cell epitope) of a MTB protein or peptide, or subsequence, portion or modification thereof, to a subject. Specific non-limiting examples of combination embodiments therefore include the foregoing or other compound, agent, drug, therapeutic regimen, treatment protocol, process, remedy or composition.

An exemplary combination is a MTB protein or peptide, or subsequence, portion or modification thereof, and a different MTB protein or peptide, or subsequence, portion or modification thereof, such as a MTB protein or T cell epitope, antigen. Another exemplary combination is a MTB protein or peptide, or subsequence, portion or modification thereof, and a T-cell stimulatory molecule, including for example an OX40 or CD27 agonist.

Such a MTB protein or peptide, or subsequence, portion or modification thereof, described herein forth herein include MTB proteins and peptides, or subsequences, portions or modifications thereof, that elicit, stimulate, induce, promote, increase, enhance or augment a proinflammatory or adaptive immune response, numbers or activation of an immune cell (e.g., T cell, natural killer T (NKT) cell, dendritic cell (DC), B cell, macrophage, neutrophil, eosinophil, mast cell, $CD4^+$ or a $CD8^+$ cell, $B220^+$ cell, $CD14^+$, $CD11b^+$ or $CD11c^+$ cells), an anti-MTB T cell response, production of a Th1 cytokine, a T cell mediated immune response, such as activation or induction of CD4+ T cells, or activation or induction of $CXCR3^+CCR6^+$ memory Th1 cells.

Combination methods of the present invention include, for example, second actives such as anti-pathogen drugs, such as protease inhibitors, reverse transcriptase inhibitors, antibiotics, antibodies to pathogen proteins, live or attenuated pathogen, or a nucleic acid encoding all or a portion (e.g., an epitope) of any protein or proteinaceous pathogen antigen, immune stimulating agents, etc., and include contact with, administration in vitro or in vivo, with another compound, agent, treatment or therapeutic regimen appropriate for pathogen infection, vaccination or immunization Methods of the invention also include, among other things, methods that result in a reduced need or use of another compound, agent, drug, therapeutic regimen, treatment protocol, process, or remedy. For example, for a treatment of MTB infection or pathology, or vaccination or immunization, a method of the invention has a therapeutic benefit if in a given subject a less frequent or reduced dose or elimination of an anti-MTB treatment results. Thus, in accordance with the invention, methods of reducing need or use of a treatment or therapy for a MTB infection or pathology, or vaccination or immunization, are provided.

In invention methods in which there is a desired outcome, such as a therapeutic or prophylactic method that provides a benefit from treatment, vaccination or immunization, a MTB protein or peptide, or subsequence, portion or modification thereof, can be administered in a sufficient or effective amount.

As used herein, a "sufficient amount" or "effective amount" or an "amount sufficient" or an "amount effective" refers to an amount that provides, in single (e.g., primary) or multiple (e.g., booster) doses, alone or in combination with one or more other compounds, treatments, therapeutic regimens or agents (e.g., a drug), a long term or a short term detectable or measurable improvement in a given subject or any objective or subjective benefit to a given subject of any degree or for any time period or duration (e.g., for minutes, hours, days, months, years, or cured).

An amount sufficient or an amount effective can but need not be provided in a single administration and can but need not be achieved by a MTB protein or peptide, or subsequence, portion or modification thereof, alone, optionally in a combination composition or method that includes a second active. In addition, an amount sufficient or an amount effective need not be sufficient or effective if given in single or multiple doses without a second or additional administration or dosage, since additional doses, amounts or duration above and beyond such doses, or additional antigens, compounds, drugs, agents, treatment or therapeutic regimens may be included in order to provide a given subject with a detectable or measurable improvement or benefit to the subject. For example, to increase, enhance, improve or optimize immunization and/or vaccination, after an initial or primary administration of one or more MTB proteins or peptides, or subsequences, portions or modifications thereof, to a subject, the subject can be administered one or more additional "boosters" of one or more MTB proteins or peptides, or subsequences, portions or modifications thereof. Such subsequent "booster" administrations can be of the same or a different formulation, dose or concentration, route, etc.

An amount sufficient or an amount effective need not be therapeutically or prophylactically effective in each and every subject treated, nor a majority of subjects treated in a given group or population. An amount sufficient or an amount effective means sufficiency or effectiveness in a particular subject, not a group of subjects or the general population. As is typical for such methods, different subjects will exhibit varied responses to a method of the invention, such as immunization, vaccination and therapeutic treatments.

The term "subject" refers includes but is not limited to a subject at risk of MTB exposure or infection as well as a subject that has been exposed to or already infected with MTB. Such subjects, include mammalian animals (mammals), such as a non human primate (apes, gibbons, gorillas, chimpanzees, orangutans, macaques), a domestic animal (dogs and cats), a farm animal (poultry such as chickens and ducks, horses, cows, goats, sheep, pigs), experimental animal (mouse, rat, rabbit, guinea pig) and humans. Subjects include animal disease models, for example, mouse and other animal models of pathogen (e.g., MTB) infection known in the art.

Accordingly, subjects appropriate for treatment include those having or at risk of exposure to MTB infection or pathology, also referred to as subjects in need of treatment. Subjects in need of treatment therefore include subjects that have been exposed to or contacted with MTB, or that have an ongoing infection or have developed one or more adverse symptoms caused by or associated with MTB infection or pathology, regardless of the type, timing or degree of onset, progression, severity, frequency, duration of the symptoms.

Target subjects and subjects in need of treatment also include those at risk of MTB exposure, contact, infection or pathology or at risk of having or developing a MTB infection or pathology. The invention methods and compositions are therefore applicable to treating a subject who is at risk of MTB exposure, contact, infection or pathology, but has not yet been exposed to or contacted with MTB. Prophylactic uses and methods are therefore included. Target subjects for prophylaxis may be at increased risk (probability or susceptibility) of exposure, contact, infection or pathology, as set forth herein. Such subjects are considered in need of treatment due to being at risk.

Subjects for prophylaxis need not be at increased risk but may be from the general population in which it is desired to vaccinate or immunize a subject against a MTB infection, for example. Such a subject that is desired to be vaccinated or immunized against MTB infection can be administered a MTB protein or peptide, or subsequence, portion or modification thereof. In another non-limiting example, a subject that is not specifically at risk of exposure to or contact MTB, but nevertheless desires protection against infection or pathology, can be administered a MTB protein or peptide, or subsequence, portion or modification thereof. Such subjects are also considered in need of treatment.

"Prophylaxis" and grammatical variations thereof mean a method in which contact, administration or in vivo delivery to a subject is prior to contact with or exposure to MTB or a MTB infection. In certain situations it may not be known that a subject has been contacted with or exposed to MTB, but administration or in vivo delivery to a subject can be performed prior to infection or manifestation of pathology (or an associated adverse symptom, condition, complication, etc. caused by or associated with a MTB infection. For example, a subject can be immunized or vaccinated with a MTB protein or peptide, or subsequence, portion or modification thereof. In such case, a method can eliminate, prevent, inhibit, suppress, limit, decrease or reduce the probability of or susceptibility towards a MTB infection or pathology, or an adverse symptom, condition or complication associated with or caused by or associated with a MTB infection or pathology.

"Prophylaxis" can also refer to a method in which contact, administration or in vivo delivery to a subject is prior to a secondary or subsequent exposure or infection. In such a situation, a subject may have had a prior MTB infection, or have been contacted with or exposed to MTB. In such subjects, an acute MTB infection may but not need be resolved. Such a subject typically has developed anti-MTB antibodies due to the prior exposure or infection. Immunization or vaccination, by administration or in vivo delivery to such a subject, can be performed prior to a secondary or subsequent MTB infection or exposure. Such a method can eliminate, prevent, inhibit, suppress, limit, decrease or reduce the probability of or susceptibility towards a secondary or subsequent MTB infection or pathology, or an adverse symptom, condition or complication associated with or caused by or associated with a MTB infection or pathology.

Treatment of an infection can be at any time during the infection. A MTB protein or peptide, or subsequence, portion or modification thereof, can be administered as a combination (e.g., with a second active), or separately concurrently or in sequence (sequentially) in accordance with the methods described herein as a single or multiple dose e.g., one or more times hourly, daily, weekly, monthly or annually or between about 1 to 10 weeks, or for as long as appropriate, for example, to achieve a reduction in the onset, progression, severity, frequency, duration of one or more symptoms or complications associated with or caused by MTB infection, pathology, or an adverse symptom, condition or complication associated with or caused by MTB. Thus, a method can be practiced one or more times (e.g., 1-10, 1-5 or 1-3 times) an hour, day, week, month, or year. The skilled artisan will know when it is appropriate to delay or discontinue administration. A non-limiting dosage schedule is 1-7 times per week, for 1, 2, 3, 4, 5, 6, 7, 8, 9, 10, 15, 20 or more weeks, and any numerical value or range or value within such ranges.

Methods of the invention may be practiced by any mode of administration or delivery, or by any route, systemic, regional and local administration or delivery. Exemplary administration and delivery routes include intravenous (i.v.), intraperitoneal (i.p.), intrarterial, intramuscular, parenteral, subcutaneous, intra-pleural, topical, dermal, intradermal, transdermal, transmucosal, intra-cranial, intra-spinal, rectal, oral (alimentary), mucosal, inhalation, respiration, intranasal, intubation, intrapulmonary, intrapulmonary instillation, buccal, sublingual, intravascular, intrathecal, intracavity, iontophoretic, intraocular, ophthalmic, optical, intraglandular, intraorgan, or intralymphatic.

Doses can be based upon current existing protocols, empirically determined, using animal disease models or optionally in human clinical trials. Initial study doses can be based upon animal studies, e.g. a mouse, and the amount of MTB protein or peptide, or subsequence, portion or modification thereof, administered that is determined to be effective. Exemplary non-limiting amounts (doses) are in a range of about 0.1 mg/kg to about 100 mg/kg, and any numerical value or range or value within such ranges. Greater or lesser amounts (doses) can be administered, for example, 0.01-500 mg/kg, and any numerical value or range or value within such ranges. The dose can be adjusted according to the mass of a subject, and will generally be in a range from about 1-10 ug/kg, 10-25 ug/kg, 25-50 ug/kg, 50-100 ug/kg, 100-500 ug/kg, 500-1,000 ug/kg, 1-5 mg/kg, 5-10 mg/kg, 10-20 mg/kg, 20-50 mg/kg, 50-100 mg/kg, 100-250 mg/kg, 250-500 mg/kg, or more, two, three, four, or more times per hour, day, week, month or annually. A typical range will be from about 0.3 mg/kg to about 50 mg/kg, 0-25 mg/kg, or 1.0-10 mg/kg, or any numerical value or range or value within such ranges.

Doses can vary and depend upon whether the treatment is prophylactic or therapeutic, whether a subject has been previously exposed to, infected with our suffered from MTB, the onset, progression, severity, frequency, duration probability of or susceptibility of the symptom, condition, pathology or complication, or vaccination or immunization to which treatment is directed, the clinical endpoint desired, previous or simultaneous treatments, the general health, age, gender, race or immunological competency of the subject and other factors that will be appreciated by the skilled artisan. The skilled artisan will appreciate the factors that may influence the dosage and timing required to provide an amount sufficient for providing a therapeutic or prophylactic benefit.

Typically, for treatment, a MTB protein or peptide, or subsequence, portion or modification thereof, will be administered as soon as practical, typically within 1-2, 2-4, 4-12, 12-24 or 24-72 hours after a subject is exposed to or contacted with MTB, or within 1-2, 2-4, 4-12, 12-24 or 24-48 hours after onset or development of one or more adverse symptoms, conditions, pathologies, complications, etc., associated with or caused by a MTB infection or pathology. For prophylactic treatment in connection with vaccination or immunization, MTB proteins or peptides, or subsequences, portions or modifications thereof can be administered for a duration of 0-4 weeks, e.g., 2-3 weeks, prior to exposure to, contact or infection with MTB or at least within 1-2, 2-4, 4-12, 12-24, 24-48 or 48-72 hours prior to exposure to, contact or infection with MTB. For an acute infection, MTB proteins or peptides, or subsequences, portions or modifications thereof may be administered at any appropriate time.

The dose amount, number, frequency or duration may be proportionally increased or reduced, as indicated by the status of the subject. For example, whether the subject has a pathogen infection, whether the subject has been exposed to, contacted or infected with pathogen or is merely at risk of pathogen contact, exposure or infection, whether the subject is a candidate for or will be vaccinated or immunized. The dose amount, number, frequency or duration may be proportionally increased or reduced, as indicated by any adverse side effects, complications or other risk factors of the treatment or therapy.

In the methods of the invention, the route, dose, number and frequency of administrations, treatments, immunizations or vaccinations, and timing/intervals between treatment, immunization and vaccination, and viral challenge can be modified. Although rapid induction of immune responses is desired for developing protective emergency vaccines against MTB, in certain embodiments, a desirable MTB vaccine will elicit robust, long-lasting immunity. Thus, in certain embodiments, invention methods and compositions provide long-lasting immunity to MTB. Immunization strategies provided may provide long-lived protection against MTB challenge, depending on the level of vaccine-induced T cell response.

In certain embodiments, MTB proteins or peptides, or subsequences, portions or modifications thereof may be pharmaceutical compositions.

As used herein the term "pharmaceutically acceptable" and "physiologically acceptable" mean a biologically acceptable formulation, gaseous, liquid or solid, or mixture thereof, which is suitable for one or more routes of administration, in vivo delivery or contact. Such formulations include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions.

Pharmaceutical compositions can be formulated to be compatible with a particular route of administration. Thus, pharmaceutical compositions include carriers, diluents, or excipients suitable for administration by various routes. Exemplary routes of administration for contact or in vivo delivery which a composition can optionally be formulated include inhalation, respiration, intranasal, intubation, intrapulmonary instillation, oral, buccal, intrapulmonary, intradermal, topical, dermal, parenteral, sublingual, subcutaneous, intravascular, intrathecal, intraarticular, intracavity, transdermal, iontophoretic, intraocular, opthalmic, optical, intravenous (i.v.), intramuscular, intraglandular, intraorgan, or intralymphatic.

Formulations suitable for parenteral administration comprise aqueous and non-aqueous solutions, suspensions or emulsions of the active compound, which preparations are typically sterile and can be isotonic with the blood of the intended recipient. Non-limiting illustrative examples include water, saline, dextrose, fructose, ethanol, animal, vegetable or synthetic oils.

To increase an immune response, immunization or vaccination, MTB proteins or peptides, or subsequences, portions or modifications thereof, can be coupled to another protein such as ovalbumin or keyhole limpet hemocyanin (KLH), thyroglobulin or a toxin such as tetanus or cholera toxin. MTB proteins or peptides, or subsequences, portions or modifications thereof can also be mixed with adjuvants.

Adjuvants include, for example: Oil (mineral or organic) emulsion adjuvants such as Freund's complete (CFA) and incomplete adjuvant (IFA) (WO 95/17210; WO 98/56414; WO 99/12565; WO 99/11241; and U.S. Pat. No. 5,422,109); metal and metallic salts, such as aluminum and aluminum salts, such as aluminum phosphate or aluminum hydroxide, alum (hydrated potassium aluminum sulfate); bacterially derived compounds, such as Monophosphoryl lipid A and derivatives thereof (e.g., 3 De-O-acylated monophosphoryl lipid A, aka 3D-MPL or d3-MPL, to indicate that position 3 of the reducing end glucosamine is de-O-acylated, 3D-MPL consisting of the tri and tetra acyl congeners), and enterobacterial lipopolysaccharides (LPS); plant derived saponins and derivatives thereof, for example Quil A (isolated from the Quilaja Saponaria Molina tree, see, e.g., "Saponin adjuvants", Archiv. fur die gesamte Virusforschung, Vol. 44, Springer Verlag, Berlin, p 243-254; U.S. Pat. No. 5,057,540), and fragments of Quil A which retain adjuvant activity without associated toxicity, for example QS7 and QS21 (also known as QA7 and QA21), as described in WO96/33739, for example; surfactants such as, soya lecithin and oleic acid; sorbitan esters such as sorbitan trioleate; and polyvinylpyrrolidone; oligonucleotides such as CpG (WO 96/02555, and WO 98/16247), polyriboA and polyriboU; block copolymers; and immunostimulatory cytokines such as GM-CSF and IL-1, and Muramyl tripeptide (MTP). Additional examples of adjuvants are described, for example, in "Vaccine Design—the subunit and adjuvant approach" (Edited by Powell, M. F. and Newman, M. J.; 1995, Pharmaceutical Biotechnology (Plenum Press, New York and London, ISBN 0-306-44867-X) entitled "Compendium of vaccine adjuvants and excipients" by Powell, M. F. and Newman M.

Cosolvents may be added to a MTB protein or peptide, or subsequence, portion or modification thereof, composition or formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters.

Supplementary compounds (e.g., preservatives, antioxidants, antimicrobial agents including biocides and biostats such as antibacterial, antiviral and antifungal agents) can also be incorporated into the compositions. Pharmaceutical compositions may therefore include preservatives, anti-oxidants and antimicrobial agents.

Preservatives can be used to inhibit microbial growth or increase stability of ingredients thereby prolonging the shelf life of the pharmaceutical formulation. Suitable preservatives are known in the art and include, for example, EDTA, EGTA, benzalkonium chloride or benzoic acid or benzoates, such as sodium benzoate. Antioxidants include, for example, ascorbic acid, vitamin A, vitamin E, tocopherols, and similar vitamins or provitamins.

An antimicrobial agent or compound directly or indirectly inhibits, reduces, delays, halts, eliminates, arrests, suppresses or prevents contamination by or growth, infectivity, replication, proliferation, reproduction, of a pathogenic or non-pathogenic microbial organism. Classes of antimicrobials include antibacterial, antiviral, antifungal and antiparasitics. Antimicrobials include agents and compounds that kill or destroy (-cidal) or inhibit (-static) contamination by or growth, infectivity, replication, proliferation, reproduction of the microbial organism.

Exemplary antibacterials (antibiotics) include penicillins (e.g., penicillin G, ampicillin, methicillin, oxacillin, and amoxicillin), cephalosporins (e.g., cefadroxil, ceforanid, cefotaxime, and ceftriaxone), tetracyclines (e.g., doxycycline, chlortetracycline, minocycline, and tetracycline), aminoglycosides (e.g., amikacin, gentamycin, kanamycin, neomycin, streptomycin, netilmicin, paromomycin and tobramycin), macrolides (e.g., azithromycin, clarithromycin, and erythromycin), fluoroquinolones (e.g., ciprofloxacin, lomefloxacin, and norfloxacin), and other antibiotics including chloramphenicol, clindamycin, cycloserine, isoniazid, rifampin, vancomycin, aztreonam, clavulanic acid, imipenem, polymyxin, bacitracin, amphotericin and nystatin.

Particular non-limiting classes of anti-virals include reverse transcriptase inhibitors; protease inhibitors; thymidine kinase inhibitors; sugar or glycoprotein synthesis inhibitors; structural protein synthesis inhibitors; nucleoside analogues; and viral maturation inhibitors. Specific non-limiting examples of anti-virals include nevirapine, delavirdine, efavirenz, saquinavir, ritonavir, indinavir, nelfinavir, amprenavir, zidovudine (AZT), stavudine (d4T), larnivudine (3TC), didanosine (DDI), zalcitabine (ddC), abacavir, acyclovir, penciclovir, ribavirin, valacyclovir, ganciclovir, 1,-D-ribofuranosyl-1,2,4-triazole-3 carboxamide, 9→2-hydroxyethoxy methylguanine, adamantanamine, 5-iodo-2'-deoxyuridine, trifluorothymidine, interferon and adenine arabinoside.

Pharmaceutical formulations and delivery systems appropriate for the compositions and methods of the invention are known in the art (see, e.g., *Remington: The Science and Practice of Pharmacy* (2003) 20$^{th}$ ed., Mack Publishing Co., Easton, Pa.; *Remington's Pharmaceutical Sciences* (1990) 18$^{th}$ ed., Mack Publishing Co., Easton, Pa.; *The Merck Index* (1996) 12$^{th}$ ed., Merck Publishing Group, Whitehouse, N.J.; *Pharmaceutical Principles of Solid Dosage Forms* (1993), Technonic Publishing Co., Inc., Lancaster, Pa.; Ansel ad Soklosa, *Pharmaceutical Calculations* (2001) 11$^{th}$ ed., Lippincott Williams & Wilkins, Baltimore, Md.; and Poznansky et al., *Drug Delivery Systems* (1980), R. L. Juliano, ed., Oxford, N.Y., pp. 253-315).

MTB proteins or peptides, or subsequences, portions or modifications thereof, along with any adjunct agent, compound drug, composition, whether active or inactive, etc., can be packaged in unit dosage form (capsules, tablets, troches, cachets, lozenges) for ease of administration and uniformity of dosage. A "unit dosage form" as used herein refers to physically discrete units suited as unitary dosages for the subject to be treated; each unit containing a predetermined quantity of active ingredient optionally in association with a pharmaceutical carrier (excipient, diluent, vehicle or filling agent) which, when administered in one or more doses, is calculated to produce a desired effect (e.g., prophylactic or therapeutic effect). Unit dosage forms also include, for example, ampules and vials, which may include a composition in a freeze-dried or lyophilized state; a sterile liquid carrier, for example, can be added prior to administration or delivery in vivo. Unit dosage forms additionally include, for example, ampules and vials with liquid compositions disposed therein. Individual unit dosage forms can be included in multi-dose kits or containers. Pharmaceutical formulations can be packaged in single or multiple unit dosage form for ease of administration and uniformity of dosage.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All applications, publications, patents and other references, GenBank citations and ATCC citations cited herein are incorporated by reference in their entirety. In case of conflict, the specification, including definitions, will control.

As used herein, the singular forms "a," "and," and "the" include plural referents unless the context clearly indicates otherwise. Thus, for example, reference to a "MTB protein or peptide, or subsequence, portion or modification thereof" or a "MTB infection" includes a plurality of MTB proteins or peptides, or subsequences, portions or modifications thereof, such as CD4$^+$ T cell epitopes, or strains of MTB and reference to an "activity or function" can include reference to one or more activities or functions of a MTB protein or peptide, or subsequence, portion or modification thereof, including function as a T cell epitopes, an ability to elicit, stimulate, induce, promote, increase, enhance or activate a measurable or detectable anti-MTB CD4$^+$ T cell response and so forth.

As used herein, numerical values are often presented in a range format throughout this document. The use of a range format is merely for convenience and brevity and should not be construed as an inflexible limitation on the scope of the invention. Accordingly, the use of a range expressly includes all possible subranges, all individual numerical values within that range, and all numerical values or numerical ranges include integers within such ranges and fractions of the values or the integers within ranges unless the context clearly indicates otherwise. This construction applies regardless of the breadth of the range and in all contexts throughout this patent document. Thus, to illustrate, reference to a range of 90-100% includes 91-99%, 92-98%, 93-95%, 91-98%, 91-97%, 91-96%, 91-95%, 91-94%, 91-93%, and so forth. Reference to a range of 90-100%, includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth. Reference to a range of 1-5 fold therefore includes 1, 2, 3, 4, 5, 6, 7, 8, 9, 10, 11, 12, 13, 14, 15, 16, 17, 18, 19, 20, fold, etc., as well as 1.1, 1.2, 1.3, 1.4, 1.5, fold, etc., 2.1, 2.2, 2.3, 2.4, 2.5, fold, etc., and so forth. Further, for example, reference to a series of ranges of 2-72 hours, 2-48 hours, 4-24 hours, 4-18 hours and 6-12 hours, includes ranges of 2-6 hours, 2, 12 hours, 2-18 hours, 2-24 hours, etc., and 4-27 hours, 4-48 hours, 4-6 hours, etc.

As also used herein a series of range formats are used throughout this document. The use of a series of ranges includes combinations of the upper and lower ranges to provide a range. Accordingly, a series of ranges include ranges which combine the values of the boundaries of different ranges within the series. This construction applies regardless of the breadth of the range and in all contexts throughout this patent document. Thus, for example, reference to a series of ranges such as 5-10, 10-20, 20-30, 30-40, 40-50, 50-75, 75-100, 100-150, and 150-171, includes ranges such as 5-20, 5-30, 5-40, 5-50, 5-75, 5-100, 5-150, 5-171, and 10-30, 10-40, 10-50, 10-75, 10-100, 10-150, 10-171, and 20-40, 20-50, 20-75, 20-100, 20-150, 20-171, and so forth.

The invention is generally disclosed herein using affirmative language to describe the numerous embodiments and aspects. The invention also specifically includes embodiments in which particular subject matter is excluded, in full or in part, such as substances or materials, method steps and conditions, protocols, procedures, assays or analysis. Thus, even though the invention is generally not expressed herein in terms of what is not included, embodiments and aspects that expressly exclude compositions or method steps are nevertheless disclosed and included in the invention.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLES

Materials and Methods
Study Subjects

Leukapheresis samples from 28 adults with LTBI and 28 control donors were obtained from the University of California, San Diego Antiviral Research Center clinic (age range 20-65 years). Subjects had a history of a positive tuberculin skin test (TST). LTBI was confirmed by a positive QuantiFERON-TB Gold In-Tube (Cellestis), as well as a physical exam and/or chest X-ray that was not consistent with active tuberculosis. None of the study subjects endorsed vaccination with BCG, or had laboratory evidence of HIV or Hepatitis B. The control donors had a negative TST, as well as a negative QuantiFERON-TB. Approval for all procedures was obtained from the Institutional Review Board (FWA #00000032) and informed consent was obtained from all donors.

Bioinformatic Analyses

Proteins from the 21 MTB genome projects available from the NCBI Protein database were downloaded into an in-house MySQL database. Of these, 5 were complete (CDC1551, F11, H37Ra, H37Rv, KZN 1435) and 16 were draft assemblies (Table 3). The protein sequences were parsed into all possible 15mer peptides (n=1,568,148), for each of which binding to 22 different HLA class II alleles (Table 4) was predicted using the IEDB HLA class II 'consensus' prediction method (Wang et al., 2010). The sequences of the H37Rv strain were used as a reference sequence. For each H37Rv protein, alignments were made of all orthologs identified in other genomes, as determined by a BLAST search. Because of the overall high sequence conservation among the proteins from all the 21 genomes, 1,220,829 (91.4%) of 15mers were completely conserved among all of the strains. For each protein, the best-predicted binders, as ranked by consensus percentile, were selected for synthesis. In order to ensure coverage of each of the proteins, the number of peptides selected per protein was no less than 2 and no more than 10, depending upon protein length (18,950 peptides). Any variants among the orthologs at the selected positions were also selected (1,660), for a total of 20,610 peptides.

Peptides

Sets of 15-mer peptides synthesized by Mimotopes (Victoria, Australia) and/or A and A (San Diego) as crude material on a small (1 mg) scale were combined into pools of 20 peptides. Peptides utilized for tetramers were synthesized as purified material (>95% by reversed phase HPLC). The IEDB submission number for the peptides is 1000505.

PBMC Isolation

PBMCs were obtained by density gradient centrifugation (Ficoll-Hypaque, Amersham Biosciences) from 100 ml of leukapheresis sample, according to manufacturer's instructions. Cell were suspended in fetal bovine serum (Gemini Bio-products) containing 10% dimethyl sulfoxide, and cryopreserved in liquid nitrogen.

T Cell Library

CD4 T cells were isolated from PBMCs by positive selection with microbeads (Miltenyi Biotec). Memory $CD4_+$ T cell subsets were sorted with a FACSAria (BD Biosciences) to over 98% purity excluding $CD45RA^+$, $CD25^+$, $CD95^+$, $CD8^+$, $CD19^+$, and $CD56^+$ cells. Antibodies used for positive selection were: anti-CCR6-PE or biotinylated (11A9; BD Biosciences) followed by streptavidin-allophycocyanin (APC) (Invitrogen) or streptavidin-APC-cyanine7 (APC-Cy7) (BD Biosciences); anti-CCR10-PE (314305, R&D Systems), anti-CCR4-PE-Cy7 (1G1; BD Pharmingen) and anti-CXCR3-APC (1C6; BD Pharmigen). Cells were cultured in RPMI 1640 medium supplemented with 2 mM glutamine, 1% (vol/vol) nonessential amino acids, 1% (vol/vol) sodium pyruvate, penicillin (50 U/ml), streptomycin (50 µg/ml) (all from Invitrogen) and 5% heat-inactivated human serum (Swiss Red Cross). T cells (1,000 cells/well) were stimulated polyclonally with 1 µg/ml PHA (Remel) in the presence of irradiated (45Gy) allogeneic feeder cells ($1.0\times10^5$ per well) and IL-2 (500 IU/ml) in a 96-well plate format and T cell lines were expanded as previously described (Geiger et al., 2009). Library screening was performed at day 14-21 by culturing extensively washed T cells ($\sim2.5\times10^5$/well) with autologous monocytes ($2.5\times10^4$), either unpulsed or pulsed for 3 h with MTB whole cell lysate (5 µg/ml, BEI Resources) or control antigens. In some experiments, T cells were cultured with peptide pools (2 µg/ml). Proliferation was measured on day 2-3 after 16 h incubation with 1 µCi/ml [methyl-$^3$H]-thymidine (Perkin Elmer). Precursor frequencies were calculated based on numbers of negative wells according to the Poisson distribution and expressed per million cells.

Ex Vivo IFN-γ ELISPOT Assay

PBMCs incubated at a density of $2\times10^5$ cells/well were stimulated with peptide pools (5 µg/ml) or individual peptides (10 µg/ml), PHA (10 µg/ml) or medium containing 0.25% DMSO (corresponding to percent DMSO in the pools/peptides, as a control) in 96-well plates (Immobilon-P; Millipore) coated with 10 µg/ml anti-IFN-γ (AN18; Mabtech). Each peptide or pool was tested in triplicate. After 20 h incubation at 37° C., wells were washed with PBS/ 0.05% Tween 20 and incubated with 2 µg/ml biotinylated anti-IFN-γ (R4-6A2; Mabtech) for 2 h. The spots were developed using Vectastain ABC peroxidase (Vector Laboratories) and 3-amino-9-ethylcarbazole (Sigma-Aldrich) and counted by computer-assisted image analysis (KS-ELISPOT reader, Zeiss). Responses were considered positive if the net spot-forming cells (SFC) per $10^6$ were ≥20, the stimulation index ≥2, and p<0.05 (Student's t-test, mean of triplicate values of the response against relevant pools or peptides vs. the DMSO control). For experiments utilizing depletion of $CD4^+$ or $CD8^+$ T cells, these cells were isolated by positive selection (Miltenyi Biotec) and effluent cells (depleted cells) were used for experiments.

Intracellular Cytokine Staining

PBMCs were cultured in the presence of 5 µg/ml MTB peptide and 4 µl/ml Golgiplug (BD Biosciences) in complete RPMI medium at 37° C. in 5% $CO_2$. Unstimulated PBMCs were used to assess nonspecific/background cytokine production. 6 h, cells were harvested and stained for cell surface antigens CD4 (anti-CD4-PerCPCy5.5, OKT-4) and CD3 (anti-CD3-EFluor450, UCHT1). After washing, cells were fixed and permeabilized, using a Cytofix/Cytoperm kit (BD Biosciences) and then stained for IFN-γ (anti-IFN-γ-APC, 4S.B3), TNFα (anti-TNFα-FITC, MAb11) and IL-2 (anti-IL-2-PE, MQ1-17H12). All antibodies were from eBioscience. Samples were acquired on a BD LSR II flow cytometer. The frequency of $CD4_+$ T cells responding to each MTB peptide was quantified by determining the total number of gated $CD4_+$ and cytokine$_+$ cells and background values subtracted (as determined from the medium alone control) using FlowJo software (Tree Star). A cut-off of 2 times the background was used. Combinations of cytokine producing cells were determined using Boolean gating in FlowJo software.

Tetramer Staining

HLA class II tetramers conjugated using PE labeled streptavidin were provided by the Tetramer Core Laboratory at Benaroya Research Institute. CD4 T cells were purified using the Miltenyi T cell isolation kit II according to manufacturer's instructions. Purified cells (~10×106) were incubated in 0.5 ml PBS containing 0.5% BSA and 2 mM EDTA pH 8.0 (MACS buffer) with a 1:50 dilution of class II tetramer for 2 h at room temperature. Cells were then stained for cell surface antigens using anti-CD4-FITC (OKT-4), anti-CD3-Alexa Fluor 700 (OKT3), anti-CCR7-PerCPEFluor710 (3D12), anti-CD45RA-EFluor450 (HI100) (all from EBioscience) and Live/Dead Yellow (Life Technologies) to exclude dead cells. Tetramer-specific T cell populations were enriched by incubating cells with 50 µl of anti-PE microbeads (Miltenyi Biotech) for 20 min at 4° C.

After washing, cells were resuspended in 5 ml MACS buffer and passed through a magnetized LS column (Miltenyi Biotec). The column was washed three times with 3 ml of MACS buffer, and after removal from the magnetic field, cells were collected with 5 ml of MACS buffer. Samples were acquired on an BD LSR II flow cytometer and analyzed using FlowJo software.

Antigen and IEDB Analysis

The identified epitopes were compared for sequence homology and the weakest epitopes sharing >90% homology were eliminated. The epitopes were mapped to the H37Rv genome allowing 1 substitution per peptide, to identify antigens. IEDB queries utilized criteria matching the experimental study (organism; MTB, host organism; human, latent disease, ex vivo, HLA class II). Epitopes were then mapped as above. To capture the most frequently recognized antigens the response frequency score (no. donors responded−Square root of no. donors responded/no. donors tested), was utilized (Kim et al., 2012).

Example 1

The T Cell Response to MTB is Restricted to a $CXCR3_+$ $CCR6^+$ Memory Subset

To measure frequency and distribution of MTB-specific T cells, the present inventors used the T cell library method (Geiger et al., 2009). CD45RA_CD25_CD4 T cells from donors latently infected with TB (LTBI) were stained with antibodies against chemokine receptors preferentially expressed on functionally distinct memory T cell subsets (Sallusto and Lanzavecchia, 2009). Five Th cell subsets were sorted: 1) $CXCR3_+CCR6_-$; 2) $CXCR3_+CCR6_+$, both enriched in Th1 cells; 3) $CCR4_+CCR6_-$ (Th2); 4) $CCR4_+CCR6_+$ (Th17); and 5) $CCR6_+CCR10_+$ (Th22) (Duhen et al., 2009). MTB-specific T cells were almost exclusively found in the $CXCR3_+CCR6_+$ subset, while Flu-specific T cells were in the $CXCR3_+CCR6_-$ and $CXCR3_+CCR6_+$ subsets, and C. albicans-specific T cells were most prominent in the $CCR4_+CCR6_+$ subset, enriched in Th17 cells, but positive cultures were also detected in libraries from subsets enriched in Th1, Th2 and Th22 cells (FIG. 1, A and B). The narrow distribution of antigen-responding T cells in the $CXCR3_+CCR6_+$ subset was peculiar to MTB since S. pyogenes- or S. aureus-specific T cells were found in both $CXCR3_+CCR6_+$ and $CCR4_+CCR6_+$ subsets.

Figure 2:
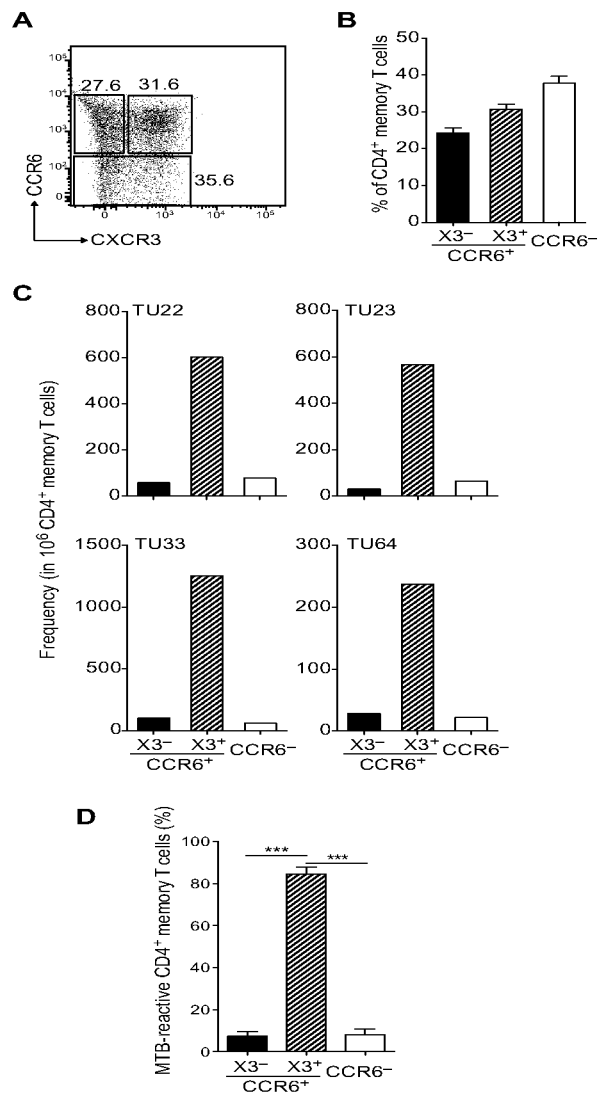

Based on these results, the present inventors sorted three memory CD4 Th cell subsets (FIG. 2, A and B): 1) $CCR6_+CXCR3_-$, accounting for 24.3%±2.7 (mean±SD, n=4) of the memoryCD4$_+$ T cell pool; 2) $CCR6_+CXCR3_+$ (30.8%±2.7) and 3) $CCR6_-$ (37.8%±4.0). For each donor a T cell library of 288 cultures was established. MTB-responding T cells were highly enriched in cultures derived from the $CCR6_+CXCR3_+$ T cell subset, and present at much lower frequency in the $CCR6_+CXCR3_-$ and the $CCR6_-$ subsets (FIG. 2 C). This pattern of distribution was remarkable consistent: in all 4 donors analyzed more than 80% of the MTB-reactive memory CD4 T cell response resided in the $CXCR3_+CCR6_+$ subset (FIG. 2 D).

Example 2

Breadth and Dominance of a Genome-Wide Library of MTB-Derived Predicted HLA Class II Epitopes in LTBI Donors Protein sequences from five complete MTB genomes (CDC1551, F11, H37Ra, H37Rv and KZN 1435) and sixteen draft assemblies from the NCBI Protein database (Table 3) were aligned. The binding capacity of all possible 15-mer peptides (n=1,568,148) was predicted for 22 HLA DR, DP and DQ class II alleles (FIG. 9 and Table 4) most commonly expressed in the general population (Oseroff et al., 2010), to select peptides predicted to bind multiple HLA class II alleles (promiscuous epitopes). This approach identifies the most dominant and prevalent responses, corresponding to approximately 50% of the total overall response (Oseroff et al., 2010).

Figure 9:
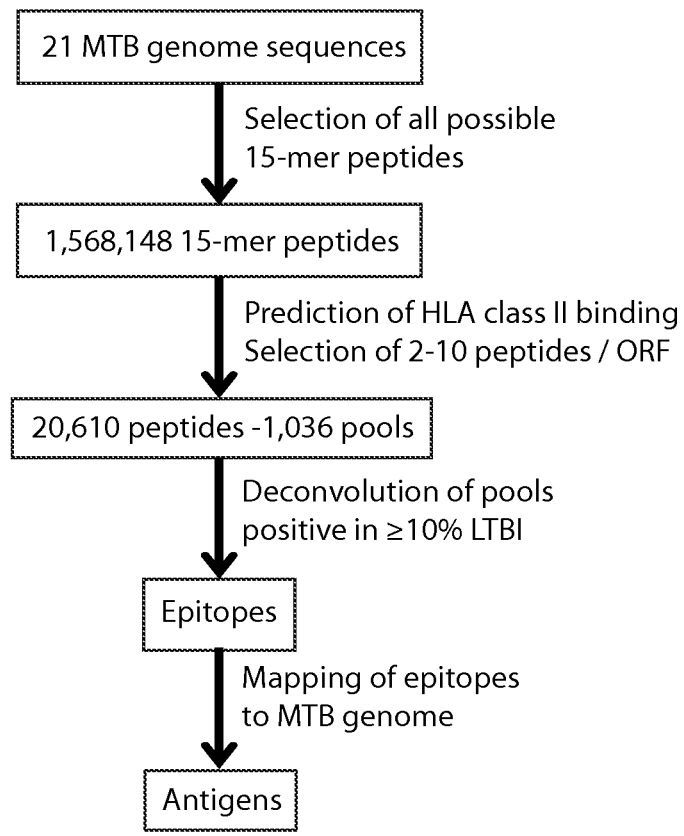

A total of 20,610 peptides (2 to 10 per ORF, average 5), including 1,660 variants not totally conserved amongst the genomes considered in the analysis, were synthesized and arranged into 1,036 peptide pools of 20 peptides (FIG. 9). The ex vivo production of IFN-γ by PBMCs from 28 LTBI donors induced by each of the 1,036 pools was measured utilizing ELISPOT. Pools recognized by >10% of donors were deconvoluted, and 369 individual MTB epitopes were identified (Table 5). Individual donors recognized, on average, 24 epitopes, underlining the large breadth of response to MTB.

Figure 3:
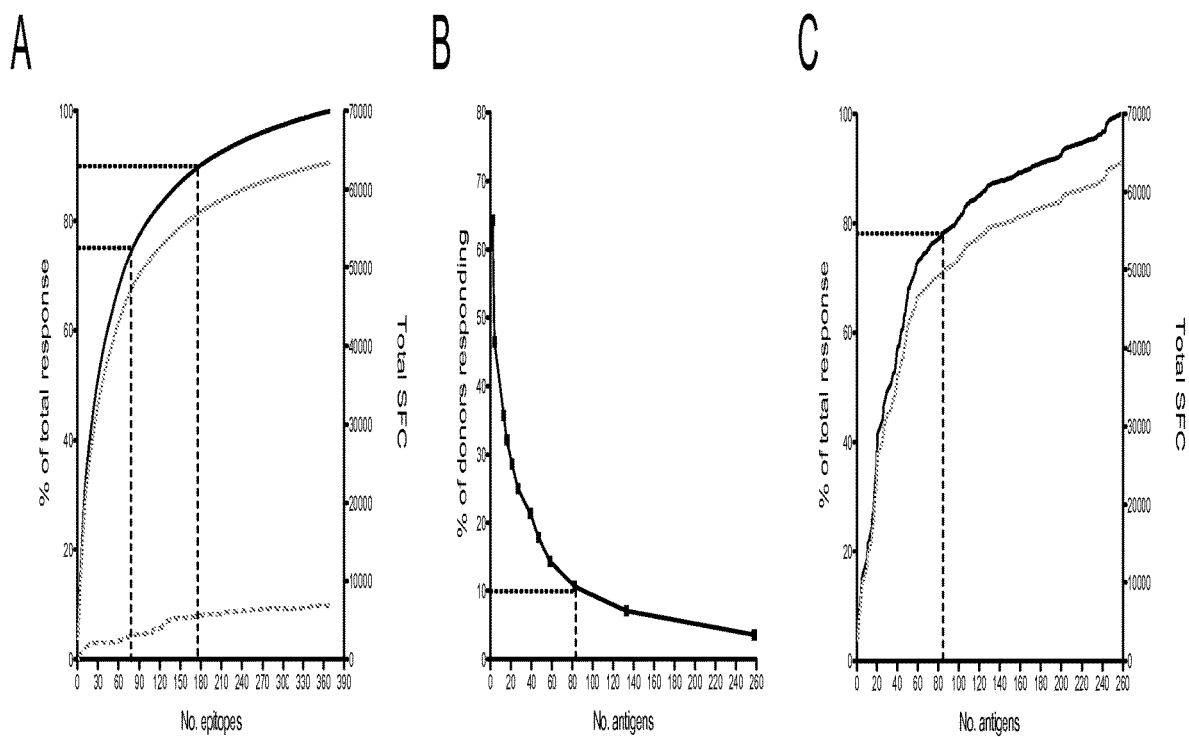

Epitope responses were ranked on the basis of magnitude to assess their relative dominance. The top 80 epitopes accounted for 75% of the total response and the top 175 epitopes accounted for 90% of the total response (FIG. 3A). Only occasional weak responses were detected in 28 TB uninfected/non-BCG vaccinated control donors, thus demonstrating that these responses were LTBI-specific (FIG. 3A). The epitopes were mapped to individual MTB antigens using the H37Rv as a reference genome. A total of 82 antigens were recognized by more than 10% of LTBI donors (FIG. 3 B). These 82 antigens accounted for approximately 80% of the total response in LTBI donors (FIG. 3C). Responses to the epitopes from the most frequently recognized antigens were further characterized utilizing PBMCs depleted of either CD4 or CD8 T cells. The majority (97%) of these epitopes were recognized exclusively by CD4 T cells (Table 5), as expected because of their identification on the basis of predicted HLA class II binding capacity.

Example 3

Novel MTB Antigens and Sources of CD4 T Cell Epitopes Recognized by LTBI Donors

Comparing these 82 most prevalently recognized antigens with antigens for which similar ex vivo epitope reactivity has been described (IEDB), the present inventors found that the majority (61/82 antigens, 74%) was novel. The present inventors performed a literature search for each individual antigen to further categorized them as novel, or as targets of CD4 Tcells, CD8 T cells or undefined T cell type. This revealed that 41% of the antigens identified had not previously been described as T cell targets (FIG. 10 A and Table 1).

Figure 10:
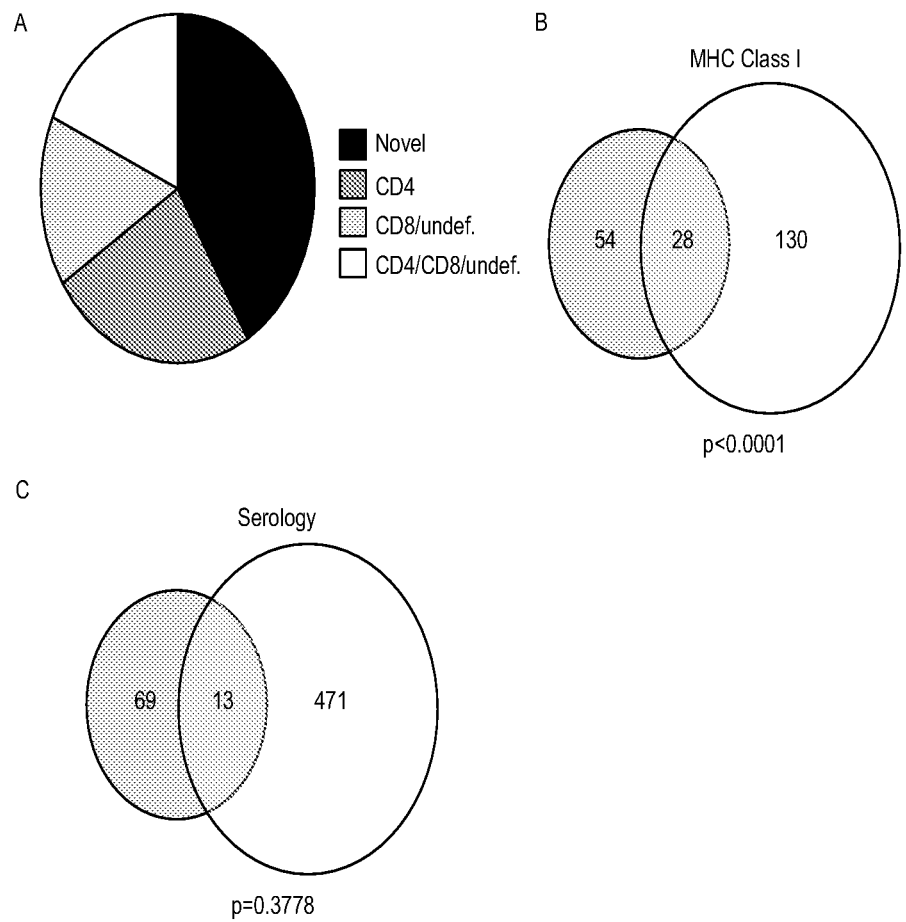

Further analysis of the IEDB data revealed a limited overlap, (18%; 28/158) between antigens identified in this study and antigens known as sources of HLA class Iepitopes (FIG. 10 B). Finally, no significant correlation was found with the antigens recognized by serological responses from the MTB proteome (Kunnath-Velayudhan et al., 2010) (FIG. 10 C).

Example 4

HLA Class II Reactivity is Highly Focalized on MTB Antigenic Islands

Figure 4:
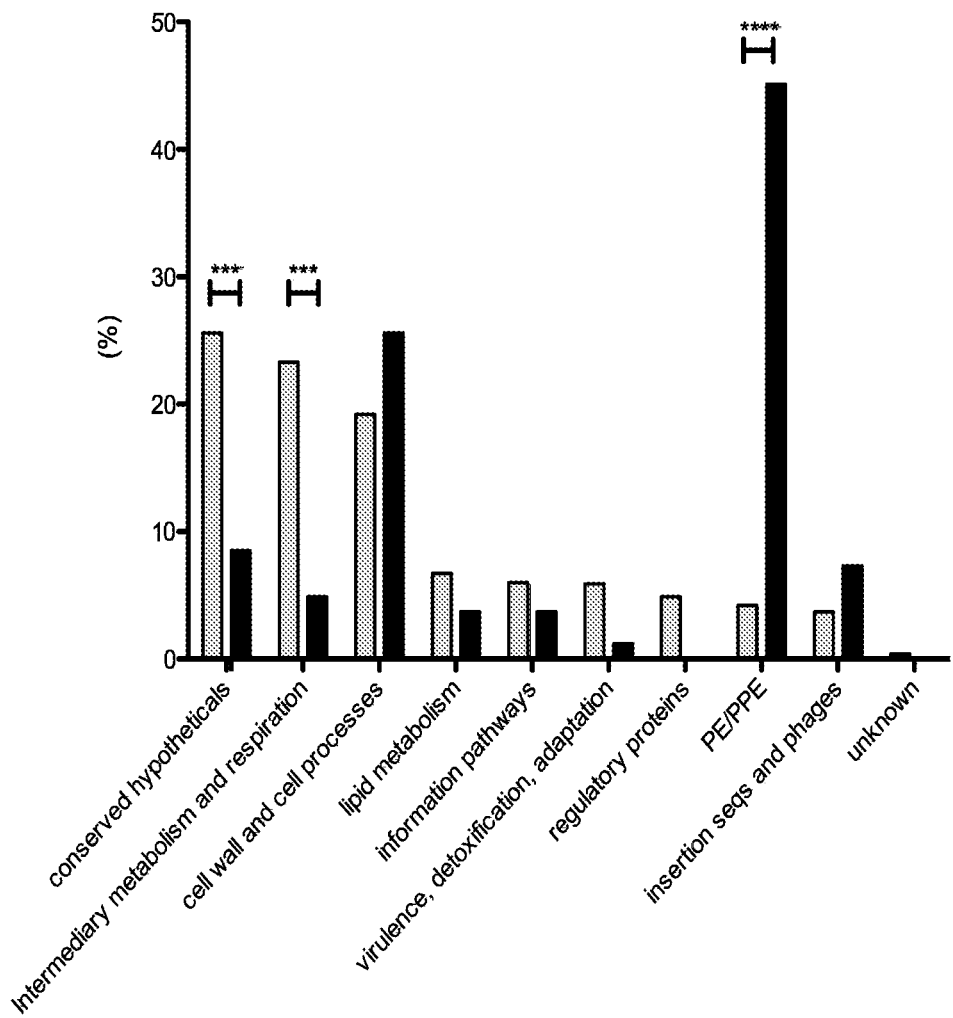

Next, using the TubercuList database (Lew et al., 2011), the present inventors determined the protein category to which the identified antigens belong (FIG. 4). The identified antigens were associated with almost every category, with the exception of regulatory proteins and proteins of unknown function. The significant overrepresentation of PE/PPE proteins was notable, as well as the underrepresentation of proteins in the conserved hypotheticals, cellular metabolism and respiration categories.

Figure 5A:
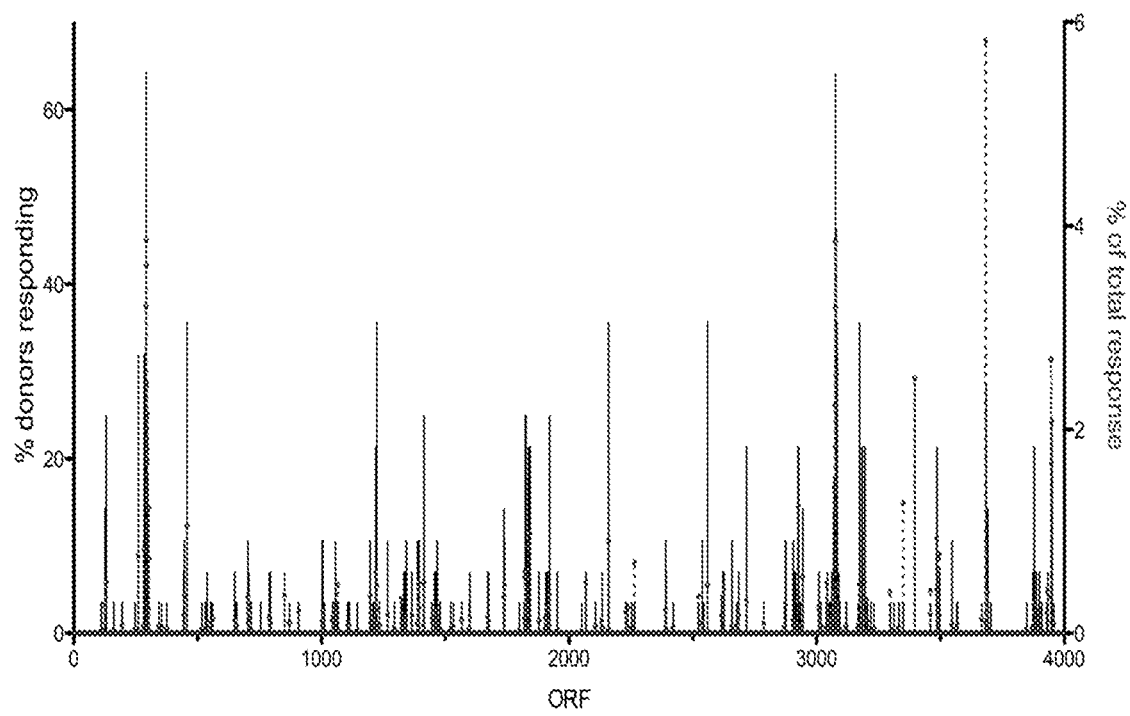
Figure 5B:
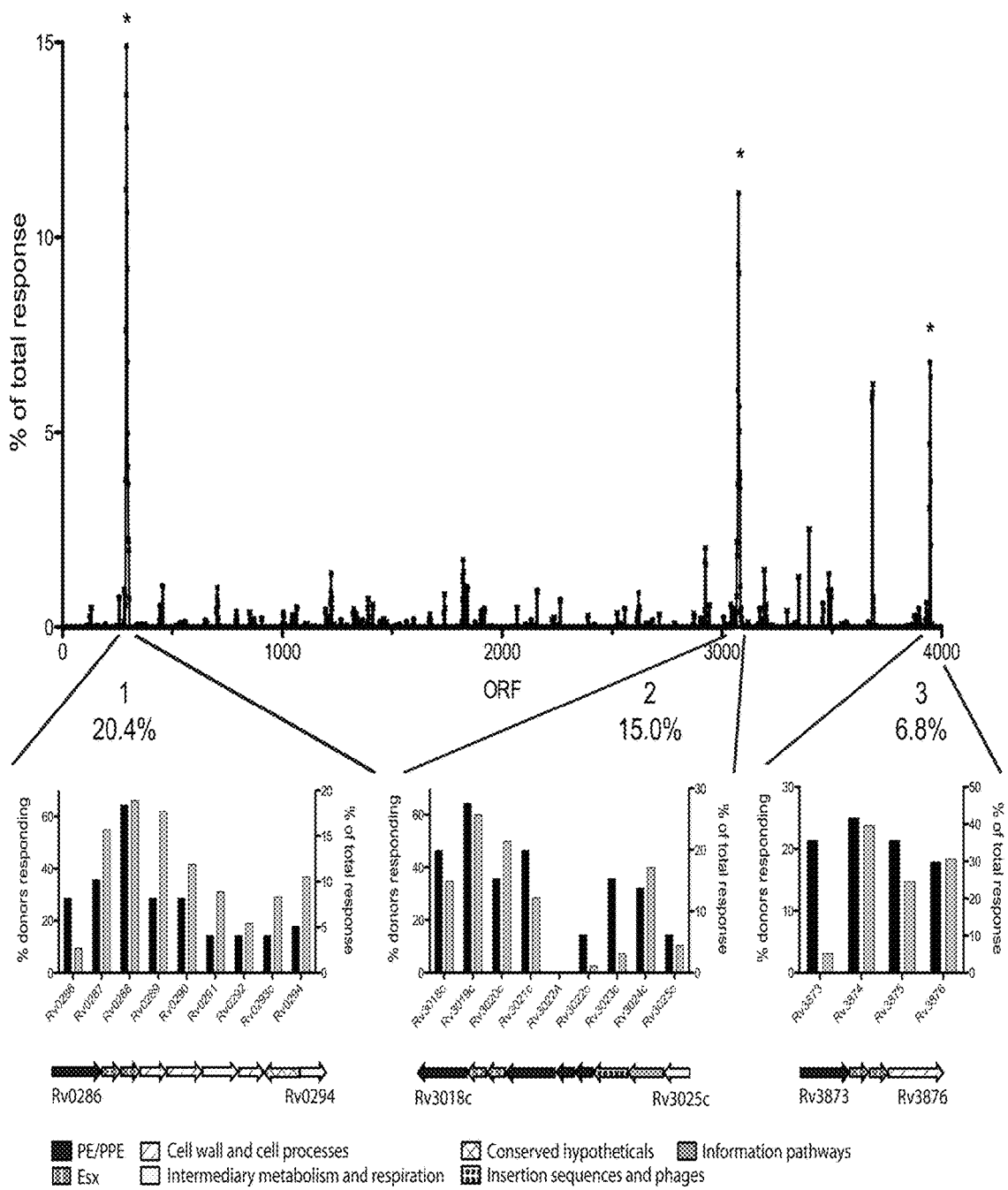

The localization of antigens recognized was next visualized by plotting the recognition data on a linear map of the MTB genome. Analysis of either percent of donors responding or percent of total response revealed striking clusters of reactivity within certain regions of the genome (FIG. 5 A). When the MTB genome was parsed into 5-gene windows, significant antigenic clusters (defined by minimum 4 proteins within the 5-gene window being recognized by 7.1% of LTBI donors) could be identified using binomial distribution probability and Bonferroni correction. Three significant antigenic islands (FIG. 5 B), encoding 0.55% of the total ORFs, accounted for 42% of the total response (Table 2). One of the islands (Island 3) contains Rv3875 and Rv3874 antigens, which is an Esx protein pair secreted via a T7SS. Strikingly, the other two islands also contain Esx protein pairs. Moreover, two of the antigenic islands are part of the known T7SS systems Esx-1 (Island 3) and Esx-3 (Island 1). It is noteworthy that the proteins recognized included not only the proteins believed to be secreted, but also the proteins forming the actual secretion apparatus (Island 1). Indeed, the antigens identified within these islands correspond to proteins from several different protein categories, mostly assigned to the cell wall and cellular processes and the PE/PPE category, which is not surprising since several of these proteins are part of the T7SS.

Additionally, Rv3615c (Millington et al., 2011), which is functionally linked to Esx-1 (Fortune et al., 2005), was also prevalently recognized. However, it stands as a single antigen and not as part of an antigenic island.

Example 5

Antigenic Islands Rather than PE/PPE and Esx Proteins are the Major Determinant of Immunodominance To dissect whether the main determinant of immunodominance was related to a given antigen being contained within an antigenic island or belonging to PE/PPE and Esx proteins families, the present inventors calculated the percentage of the total response for different groups of proteins as well as the percentage of the MTB genome associated with these protein groups (Table 2). To compare different protein groups, the present inventors calculated the ratio between % of response and % genome, as a percent enrichment.

The PE/PPE proteins were responsible for 19% of the total response, and when divided into PE/PPE proteins within an island compared to non-island, the island PE/PPE were more predictive of immunogenicity than the non-island ones (Table 2). Also, in the case of Esx proteins and T7SS, proteins within the antigenic islands were more likely to be immunogenic than those outside the islands. Proteins not in the antigenic islands, and not belonging to PE/PPE and T7SS categories, were responsible for 14% of the total response (Table 2). Thus, these data show that the antigenic islands identified are highly predictive of immunogenicity, and that to be contained within the antigenic islands is the most reliable predictor of the immunodominance of PE/PPE and Esx proteins.

Example 6

Similar Multifunctionality of T cell Responses to Different Categories of MTB Antigens It has been proposed that some of the responses against secreted MTB proteins act as decoys (Baena and Porcelli, 2009), thereby supporting bacterial persistence. It has also been proposed that T cells differing in their degree of multifunctionality might differ in terms of protective potential (Beveridge et al., 2007; Day et al., 2008; Scriba et al., 2010; Sutherland et al., 2009). Definition of dominant antigens allows testing the validity of these hypotheses. To address these issues the present inventors detailed responses against PE/PPE, Esx and other proteins expressed in the three major antigenic islands, or elsewhere, by a variety of approaches, including multiparameter intracellular cytokine staining (ICS) assays, tetramer staining and T cell libraries.

Figure 6E:
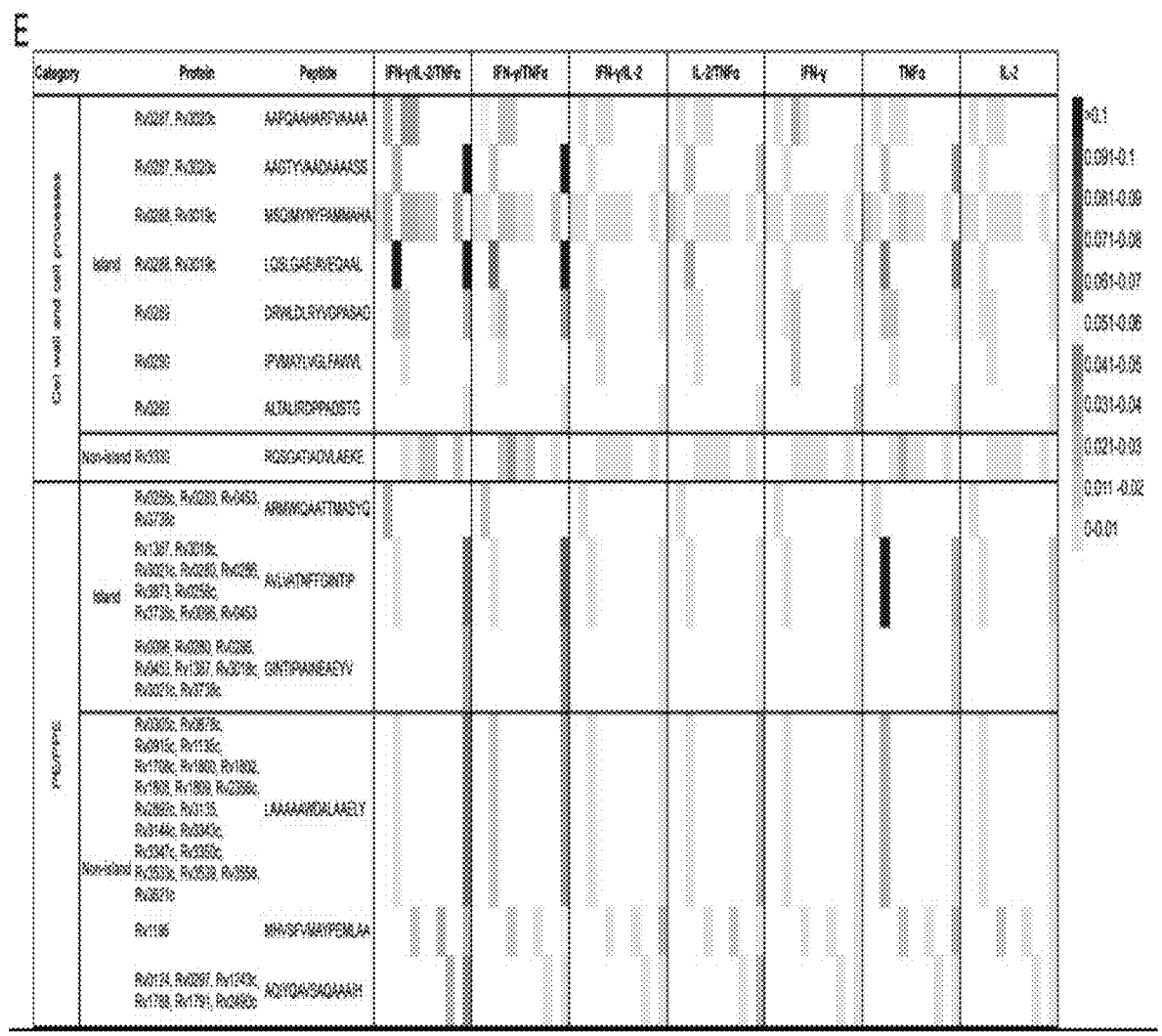
Figure 11:
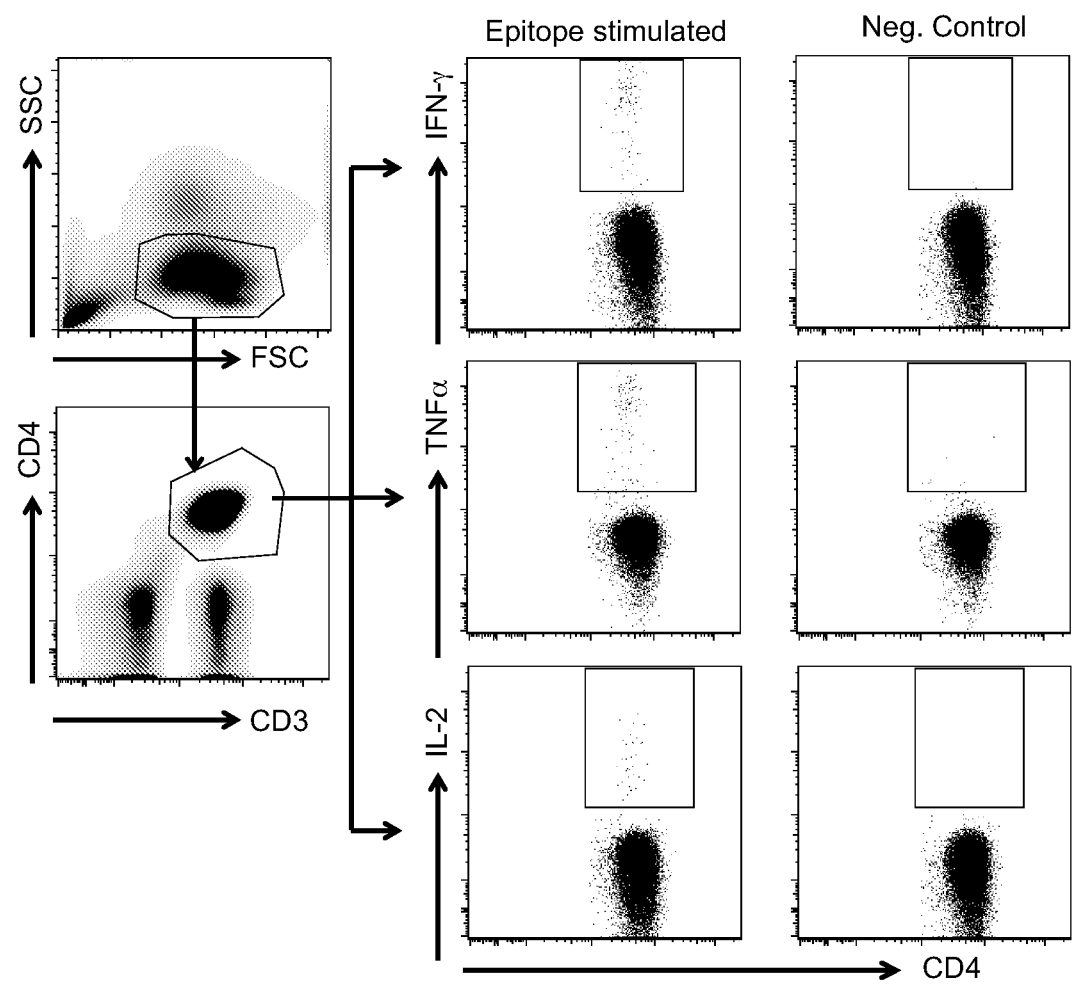

The frequency of IFN-γ, TNFα, and IL-2 expressing CD4 T cells elicited by proteins from the PE/PPE and cell wall and cell processes category, and from within an island versus non-island, induced similar cytokine expression patterns (FIG. 6, A and C; gating strategy in FIG. 11). The vast majority of $CD4_+$ T cells were IFN-$\gamma_+$TNF$\alpha_+$IL-$2_+$ or IFN-$\gamma_+$TNF$\alpha_+$, followed by TNF$\alpha_+$ single producing $CD4_+$ T cells. To a lesser extent, TNF$\alpha_+$IL-$2_+$, single IFN-$\gamma_+$, and single IL-$2_+$ cells were also detected (FIG. 6, A and C).

Triple cytokine producers were found in 27-40% of cytokine-expressing $CD4_+$ T cells, 30-43% expressed any 2 cytokines, and 23-44% produced a single cytokine (FIG. 6, B and D). The present inventors did not observe any donor-, antigen- or epitope-specific pattern of cytokine production (FIG. 6 E).

Example 7

Figure 7:
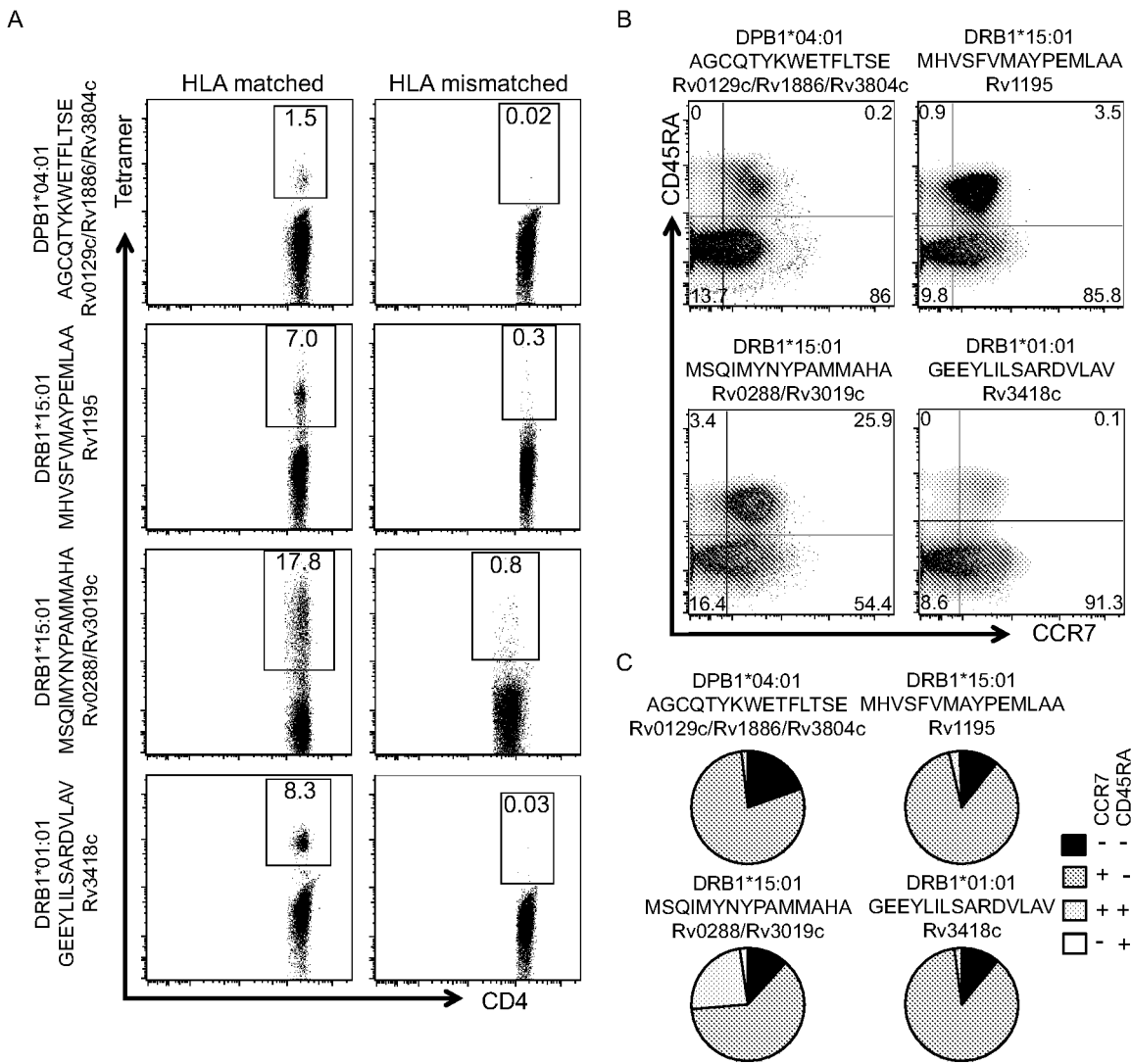
Figure 8A:
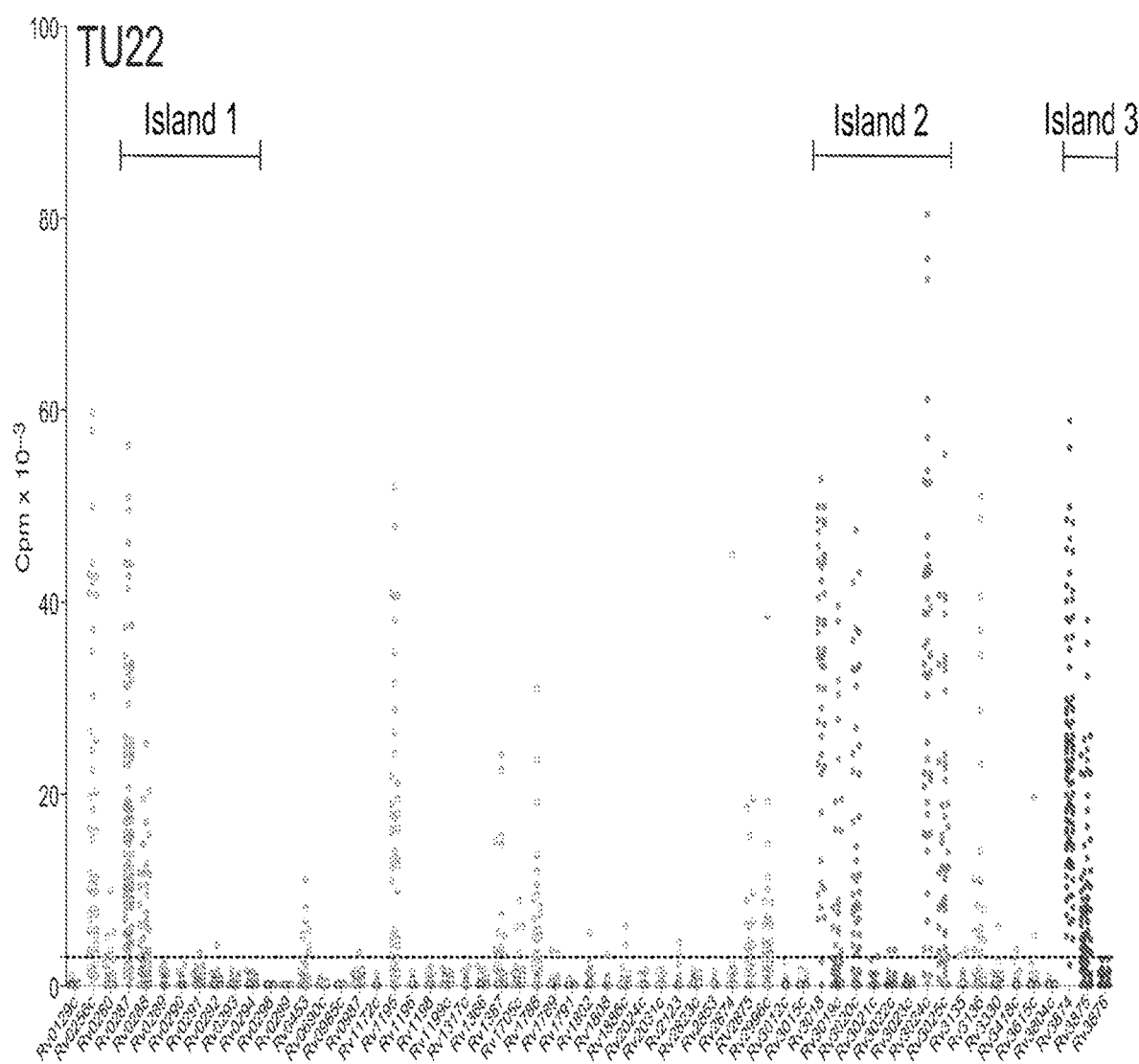
Figure 8B:
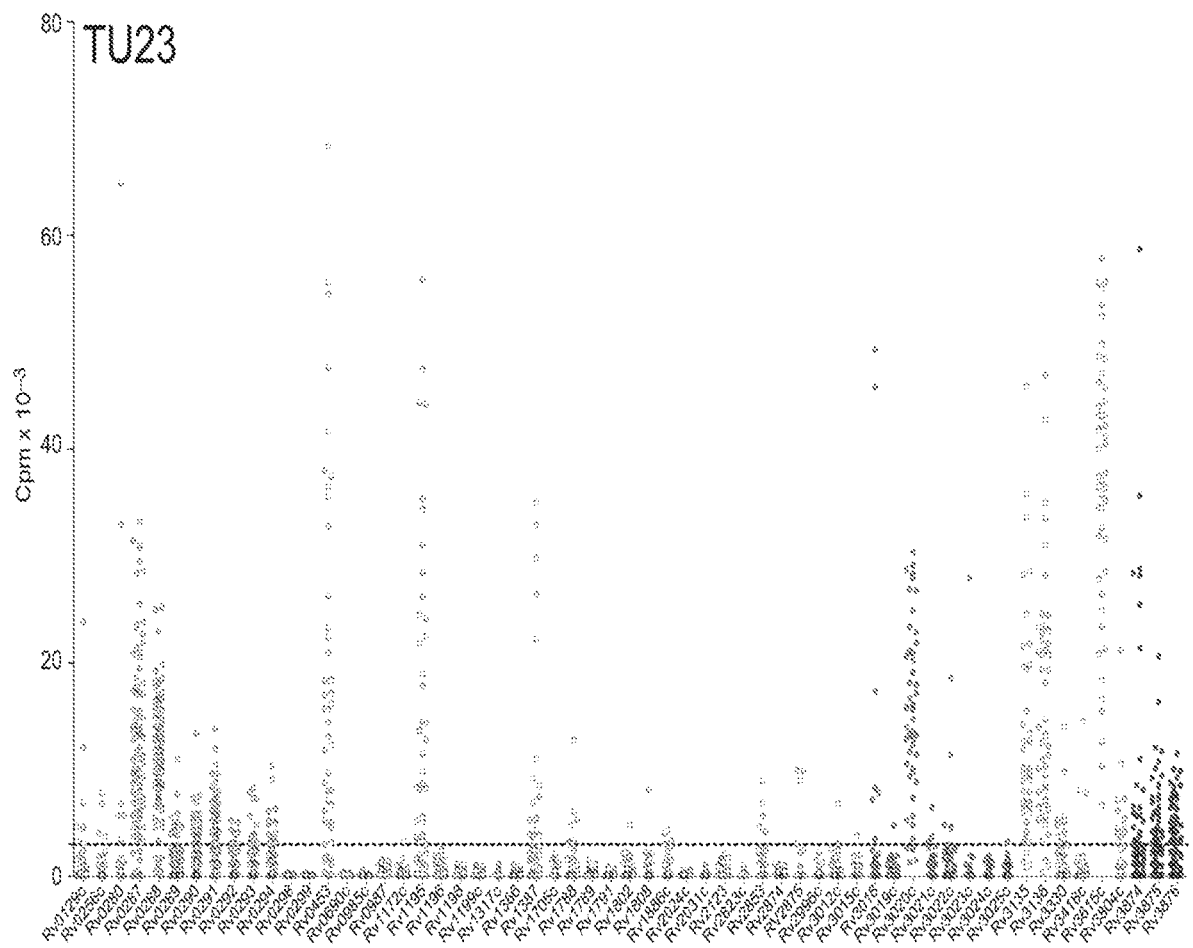
Figure 8C:
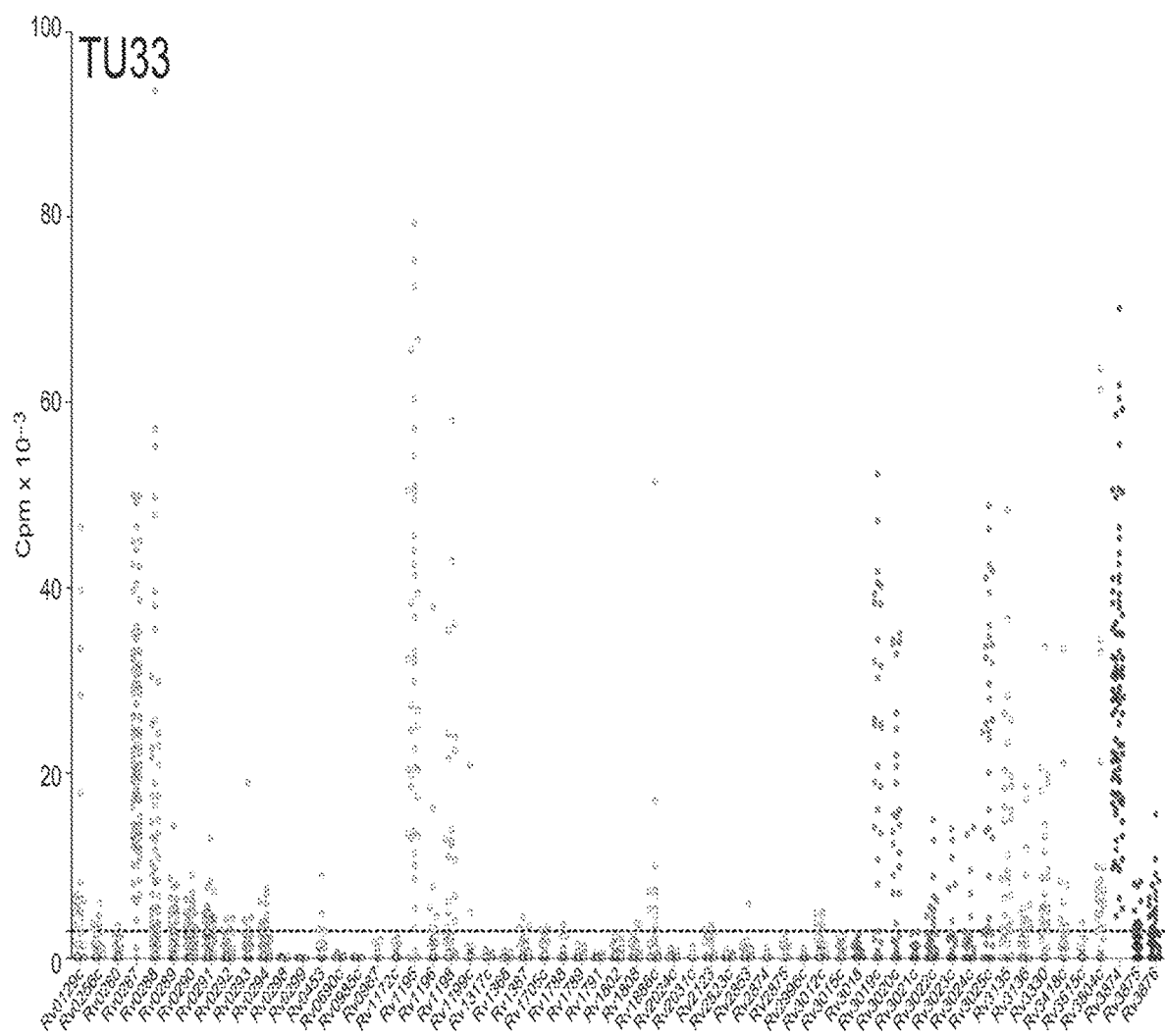
Figure 8D:
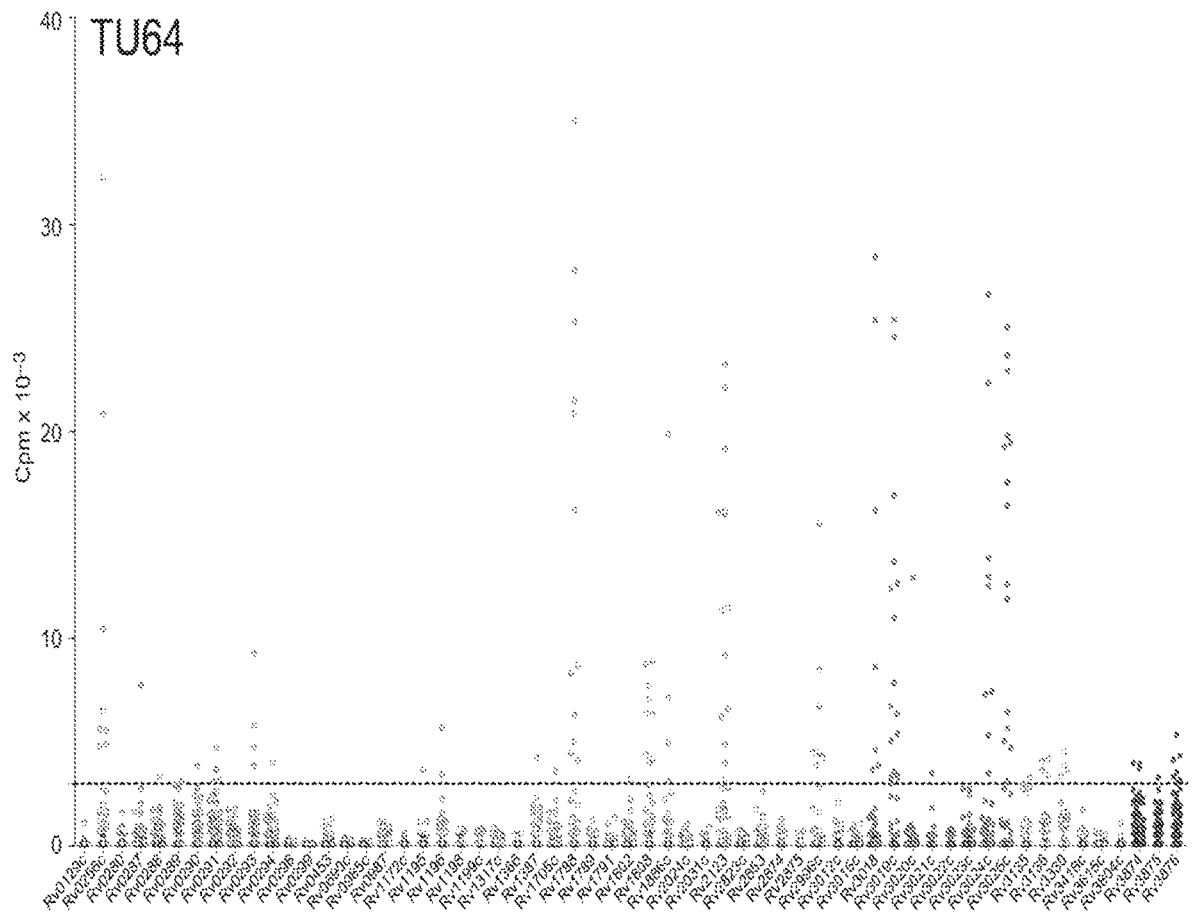

Memory Phenotypes and T Cell Subsets Associated with Different Categories of MTB Antigens $CD4_+$ T cells were stained with selected HLA-epitope tetramer reagents and tetramer$_+$ cells were enriched (Arlehamn et al., 2012; Barnes et al., 2004). Epitope specific T cell responses were detected in 16 donors at frequencies 0.25 to 24.3% (mean of 7.7±8.3 SD) for seven different HLA/T cell epitope tetramer combinations (FIG. 7 A).

Only a small number of tetramer-positive cells were detected with the epitope-specific tetramers in donors with a HLA mismatch (FIG. 7 A), which confirmed that tetramer specificity was derived from the epitope and HLA molecule combination. Memory subset phenotypes were determined using Abs to CD45RA and CCR7. Similar to the multifunctionality phenotype, the present inventors did not observe any differences in memory phenotype when comparing proteins from within an island vs. non-island (FIG. 7, B and C).

Rv0129c/Rv1886/Rv3804, Rv3418c and Rv1195 epitope-specific tetramer$_+$ T cells predominantly consisted of CD45RA_CCR7$_+$ central memory T cells in all donors analyzed, followed by effector memory (CD45RA-CCR7). Percentages ranged between 70.1 and 91.3% (SD ±6.9) for central memory T cells and 8.6-26.8% (SD ±6.4) for effector memory T cells. Only a minor fraction appeared to be naïve (CCR7$_+$CD45RA$_+$) or effector T cells (CCR7_CD45RA$_+$). For Rv0288/Rv3019c the percentages ranged between 49.5 to 84.5% (SD ±13.7) for central memory T cells, 9.8-37.1% (SD ±10.8) for naïve and 4.8-17.2% for effector memory T cells. Again, a minor fraction of the tetramer$_+$ cells appeared to be effector T cells (FIG. 7, B and C).

The data presented in FIGS. 1 and 2 demonstrated that T cells restricted to a CXCR3+CCR6+ memory subset mediate responses to MTB lysate. Here, the present inventors set up T cell libraries from 4 representative donors and the CXCR3+CCR6+ subset were directly stimulated, after expansion, with 59 representative peptide pools. The results of this analysis are shown in FIG. 8 A, B, C and D. Using this approach, the present inventors were able to demonstrate that the results obtained with the MTB lysate also extended to responses specific for the various epitopes, and to confirm with a complementary approach the results of the ex vivo IFN-γ ELISPOT analysis utilizing the library of predicted HLA class II binding epitopes.

Example 8

FIG. 9 shows experimental design for the genome-wide screen of MTB. FIG. 10 shows novelty of the antigens identified as a source of CD4 epitopes in humans. FIG. 11 shows gating strategy for the intracellular cytokine staining assays. Table 3 shows MTB genomes used for peptide predictions. Table 4 shows haplotype and phenotype frequencies of HLA class II alleles used for peptide predictions. Table 5 shows epitopes and their characteristics identified in the genome-wide screen of MTB.

TABLE 1

Summary of characteristics of novel CD4 T cell antigens

| Rv-number | Resp. freq. | Total SFC | Protein category | Location | T7SS |
|---|---|---|---|---|---|
| Rv3024c | 32% | 1630 | Information pathways | Island 2 | — |
| Rv0289 | 29% | 2298 | Cell wall and cell processes | Island 1 | Esx-3 |
| Rv0290 | 29% | 1552 | Cell wall and cell processes | Island 1 | Esx-3 |
| Rv3330 | 29% | 1595 | Cell wall and cell processes | Non-island | — |
| Rv1788 | 25% | 347 | PE/PPE | Non-island | — |
| Rv1791 | 25% | 355 | PE/PPE | Non-island | — |
| Rv3125c | 21% | 125 | PE/PPE | Non-island | — |
| Rv0294 | 18% | 1368 | Intermediary metabolism and respiration | Island 1 | — |
| Rv2874 | 18% | 798 | Intermediary metabolism and respiration | Non-island | — |
| Rv3022c | 18% | 109 | PE/PPE | Island 2 | — |
| Rv3135 | 18% | 317 | PE/PPE | Non-island | — |
| Rv3876 | 18% | 1323 | Cell wall and cell processes | Island 3 | Esx-1 |
| Rv0124 | 14% | 177 | PE/PPE | Non-island | — |
| Rv0291 | 14% | 1153 | Intermediary metabolism and respiration | Island 1 | — |
| Rv0292 | 14% | 708 | Cell wall and cell processes | Island 1 | Esx-3 |
| Rv0293c | 14% | 1073 | Conserved hypotheticals | Island 1 | — |
| Rv0297 | 14% | 154 | PE/PPE | Non-island | — |
| Rv0299 | 14% | 467 | Conserved hypotheticals | Non-island | — |
| Rv3012c | 14% | 233 | Information pathways | Non-island | — |
| Rv3025c | 14% | 423 | Intermediary metabolism and respiration | Island 2 | — |
| Rv0278c | 11% | 45 | PE/PPE | Non-island | — |
| Rv0279c | 11% | 45 | PE/PPE | Non-island | — |
| Rv0298 | 11% | 783 | Conserved hypotheticals | Non-island | — |
| Rv0442c | 11% | 232 | PE/PPE | Non-island | — |
| Rv0690c | 11% | 233 | Conserved hypotheticals | Non-island | — |
| Rv0985c | 11% | 70 | Cell wall and cell processes | Non-island | — |
| Rv0987 | 11% | 133 | Cell wall and cell processes | Non-island | — |
| Rv1172c | 11% | 237 | PE/PPE | Non-island | — |
| Rv1243c | 11% | 114 | PE/PPE | Non-island | — |
| Rv1317c | 11% | 97 | Information pathways | Non-island | — |
| Rv1366 | 11% | 308 | Conserved hypotheticals | Non-island | — |
| Rv1441c | 11% | 86 | PE/PPE | Non-island | — |
| Rv2490c | 11% | 64 | PE/PPE | Non-island | — |
| Rv2853 | 11% | 85 | PE/PPE | Non-island | — |

TABLE 2

Immunodominance of islands, PE/PPE, Esx and T7SS proteins.

| | % donors responding | % of total response | No. proteins | % of total MTB genome | % Enrichment (% response/% genome) |
|---|---|---|---|---|---|
| Islands total | 89 | 42.2 | 22 | 0.55 | 76.7 |
| Island 1 | 79 | 20.4 | 9 | 0.23 | 88.7 |
| Island 2 | 86 | 15.0 | 9 | 0.23 | 65.2 |
| Island 3 | 50 | 6.8 | 4 | 0.10 | 68.0 |
| PE/PPE total | 71 | 19.2 | 38 | 0.95 | 20.2 |
| PE/PPE non-island | 71 | 14.0 | 32 | 0.80 | 17.5 |
| PE/PPE island | 46 | 5.2 | 6 | 0.15 | 34.6 |
| Esx protein[a] total | 75 | 19.6 | 11 | 0.28 | 70.0 |
| Esx proteins non-island | 11 | 1.2 | 5 | 0.13 | 9.2 |
| Esx proteins island | 75 | 18.5 | 6 | 0.15 | 123.3 |
| T7SS[b] total | 79 | 34.7 | 16 | 0.40 | 86.8 |
| T7SS non-island | 39 | 7.0 | 6 | 0.15 | 46.6 |
| T7SS island | 75 | 27.7 | 10 | 0.25 | 110.8 |
| Other | 82 | 14.2 | 23 | 0.58 | 24.5 |

[a]Esx proteins include EsxA-W.
[b]T7SS includes the Esx proteins.

TABLE 3

Summary of MTB genomes used for peptide predictions

| GenBank accession no. | Organism | No. protein sequences[a] | No. unique 15-mer peptides in genome |
|---|---|---|---|
| NC_000962 | *Mycobacterium tuberculosis* H37Rv | 3,988 | 1,258,608 |
| NC_002755 | *Mycobacterium tuberculosis* CDC1551 | 4,189 | 1,252,098 |
| NC_009525 | *Mycobacterium tuberculosis* H37Ra | 4,034 | 1,262,786 |
| NC_009565 | *Mycobacterium tuberculosis* F11 | 3,941 | 1,261,978 |
| NC_012943 | *Mycobacterium tuberculosis* KZN 1435 | 4,059 | 1,265,498 |
| NZ_ABGN00000000 | *Mycobacterium tuberculosis* KZN 605 | 3,972 | 1,097,739 |
| NZ_AAKR00000000 | *Mycobacterium tuberculosis* C | 3,508 | 1,060,472 |
| NZ_AASN00000000 | *Mycobacterium tuberculosis* str. *Haarlem* | 3,596 | 1,108,161 |

TABLE 3-continued

Summary of MTB genomes used for peptide predictions

| GenBank accession no. | Organism | No. protein sequences[a] | No. unique 15-mer peptides in genome |
|---|---|---|---|
| NZ_AAYK00000000 | Mycobacterium tuberculosis H37Ra | 4,438 | 1,133,553 |
| NZ_ABGL00000000 | Mycobacterium tuberculosis KZN 4207 | 4,068 | 1,147,062 |
| NZ_ABLL00000000 | Mycobacterium tuberculosis 94_M4241A | 4,232 | 1,166,312 |
| NZ_ABLM00000000 | Mycobacterium tuberculosis 02_1987 | 4,266 | 1,181,241 |
| NZ_ABLN00000000 | Mycobacterium tuberculosis T92 | 4,254 | 1,085,346 |
| NZ_ABOV00000000 | Mycobacterium tuberculosis EAS054 | 4,101 | 1,167,286 |
| NZ_ABOW00000000 | Mycobacterium tuberculosis T85 | 4,206 | 1,130,366 |
| NZ_ABQG00000000 | Mycobacterium tuberculosis GM 1503 | 4,116 | 1,091,459 |
| NZ_ABQH00000000 | Mycobacterium tuberculosis T17 | 4,254 | 1,116,545 |
| NZ_ABVM00000000 | Mycobacterium tuberculosis '98-R604 INH-RIF-EM' | 4,112 | 1,174,559 |
| NZ_ACHO00000000 | Mycobacterium tuberculosis T46 | 4,134 | 1,155,871 |
| NZ_ACHP00000000 | Mycobacterium tuberculosis CPHL_A | 4,140 | 1,196,800 |
| NZ_ACHQ00000000 | Mycobacterium tuberculosis K85 | 4,196 | 1,201,360 |

[a]Data available in GenBank as of December 2009

TABLE 4

Haplotype and phenotype frequencies of HLA class II alleles used for Predictions

| Locus | Allele | Percent of haplotypes | Phenotype frequency |
|---|---|---|---|
| DRB1 | DRB1*01:01 | 2.8 | 5.4 |
| | DRB1*03:01 | 7.1 | 13.7 |
| | DRB1*04:01 | 2.3 | 4.6 |
| | DRB1*04:05 | 3.1 | 6.2 |
| | DRB1*07:01 | 7.0 | 13.5 |
| | DRB1*08:02 | 2.5 | 4.9 |
| | DRB1*11:01 | 6.1 | 11.8 |
| | DRB1*12:01 | 2.0 | 3.9 |
| | DRB1*13:02 | 3.9 | 7.7 |
| | Total | 36.8 | |
| DRB3/4/5 | DRB3*01:01 | 14.0 | 26.1 |
| | DRB4*01:01 | 23.7 | 41.8 |
| | DRB5*01:01 | 8.3 | 16.0 |
| | Total | 46.0 | |
| DQA1/DQB1 | DQA1*05:01/DQB1*02:01 | 5.8 | 11.3 |
| | DQA1*05:01/DQB1*03:01 | 19.5 | 35.1 |
| | DQA1*03:01/DQB1*03:02 | 10.0 | 19.0 |
| | DQA1*04:01/DQB1*04:02 | 6.6 | 12.8 |
| | DQA1*01:01/DQB1*05:01 | 7.6 | 14.6 |
| | Total | 49.5 | |
| DPB1 | DPA1*02:01/DPB1*01:01 | 8.4 | 16.0 |
| | DPA1*01:03/DPB1*02:01 | 9.2 | 17.5 |
| | DPA1*01:03/DPB1*04:01 | 20.1 | 36.2 |
| | DPA1*03:01/DPB1*04:02 | 23.6 | 41.6 |
| | DPA1*02:01/DPB1*05:01 | 11.5 | 21.7 |
| | Total | 72.8 | |

Average haplotype and phenotype frequencies for individual alleles are based on data available at dbMHC. dbMHC data considers prevalence in Europe, North Africa, North-East Asia, the South Pacific (Australia and Oceania), Hispanic North and South America, American Indian, South-East Asia, South-West Asia, and Sub-Saharan Africa populations. DP, DRB1 and DRB3/4/5 frequencies consider only the beta chain frequency, given that the DR alpha chain is largely monomorphic, and that differences in DPA are not considered to significantly influence binding. Frequency data are not available for DRB3/4/5 alleles, however, because of linkage with DRB1 alleles, coverage for these specificities may be assumed as follows: DRB3 with DR3, DR11, DR12, DR13 and DR14; DRB4 with DR4, DR7 and DR9; DRB5 with DR15 and DR16. Specific allele frequencies at each B3/B4/B5 locus is based on published associations with various DRB1 alleles, and assumes only limited variation at the indicated locus.

TABLE 5

Summary of epitope characteristics
(SEQ ID No: 35 to 403 in order of appearance)

| Category | Rv# | Sequence | Donor | SFC | T cell phenotype | References |
|---|---|---|---|---|---|---|
| Cell wall and cell processes | Rv0110 | AMHLLLNMWALYVVG | TU21 | 21.7 | n.d. | |
| | Rv0192A | SLFAALNIAAVVAVL | TU2 | 48.3 | n.d. | |
| | Rv0287, Rv3020c | AAFQGAHARFVAAAA | TU22 | 245.0 | CD4 | |
| | | | TU23 | 115.0 | CD4 | |
| | | | TU29 | 375.0 | CD4 | |
| | | | TU33 | 420.0 | CD4 | |
| | | | TU35 | 85.0 | CD4 | |
| | | | TU75 | 56.7 | CD4 | |
| | | | TU8 | 480.0 | CD4 | |
| | | | TU81 | 518.3 | CD4 | |
| | | | TU1 | 60.0 | n.d. | |

TABLE 5-continued

Summary of epitope characteristics
(SEQ ID No: 35 to 403 in order of appearance)

| Category | Rv# | Sequence | Donor | SFC | T cell phenotype | References |
|---|---|---|---|---|---|---|
| | | | TU70 | 23.3 | undetectable | |
| | | AAGTYVAADAAAASS | TU22 | 105.0 | CD4 | |
| | | | TU23 | 345.0 | CD4 | |
| | | | TU75 | 28.3 | CD4 | |
| | | | TU8 | 156.7 | CD4 | |
| | | | TU81 | 940.0 | CD4 | |
| | | | TU1 | 36.7 | n.d. | |
| | | | TU33 | 36.7 | undetectable | |
| | | | TU70 | 30.0 | undetectable | |
| | Rv0288, Rv3019c | EDLVRAYHAMSSTHE | TU33 | 21.7 | undetectable | (1) |
| | | | TU8 | 96.7 | undetectable | |
| | | | TU81 | 85.0 | undetectable | |
| | | LQSLGAEIAVEQAAL | TU11 | 60.0 | undetectable | (1) |
| | | | TU22 | 90.0 | CD4 | |
| | | | TU23 | 833.0 | CD4 | |
| | | | TU8 | 333.3 | CD4 | |
| | | | TU81 | 975.0 | CD4 | |
| | | | TU1 | 26.7 | n.d. | |
| | | | TU46 | 61.7 | undetectable | |
| | Rv0288, Rv3019c | MSQIMYNYPAMMAHA | TU11 | 86.7 | CD4 | (1, 2) |
| | | | TU2 | 126.7 | CD4 | |
| | | | TU22 | 96.7 | CD4 | |
| | | | TU29 | 248.3 | CD4 | |
| | | | TU33 | 555.0 | CD4 | |
| | | | TU35 | 75.0 | CD4 | |
| | | | TU36 | 235.0 | CD4 | |
| | | | TU64 | 150.0 | CD4 | |
| | | | TU74 | 123.3 | CD4 | |
| | | | TU78 | 285.0 | CD4 | |
| | | | TU55 | 41.7 | n.d. | |
| | | | TU13 | 126.7 | undetectable | |
| | | | TU40 | 50.0 | undetectable | |
| | Rv0289 | DRWLDLRYVGPASAD | TU22 | 125.0 | CD4 | |
| | | | TU23 | 156.7 | CD4 | |
| | | | TU29 | 150.0 | CD4 | |
| | | | TU33 | 80.0 | CD4 | |
| | | | TU35 | 76.7 | CD4 | |
| | | | TU8 | 335.0 | CD4 | |
| | | | TU81 | 613.3 | CD4 | |
| | | | TU1 | 43.3 | n.d. | |
| | | EVVDYLGIPASARPV | TU23 | 30.0 | CD4 | |
| | | | TU81 | 241.7 | CD4 | |
| | | | TU8 | 21.7 | undetectable | |
| | | GNGVVALRNAQLVTF | TU22 | 33.3 | CD4 | |
| | | | TU23 | 65.0 | CD4 | |
| | | | TU81 | 301.7 | CD4 | |
| | | | TU8 | 25.0 | undetectable | |
| | Rv0290 | AAGAQLLWQLPLLSI | TU23 | 88.3 | CD4 | |
| | | | TU8 | 20.0 | CD4 | |
| | | | TU81 | 355.0 | CD4 | |
| | | | TU46 | 36.7 | undetectable | |
| | | AAGVAAWSLIALMIP | TU23 | 88.3 | CD4 | |
| | | | TU81 | 195.0 | CD4 | |
| | | | TU1 | 31.7 | n.d. | |
| | | | TU22 | 33.3 | undetectable | |
| | | | TU8 | 38.3 | undetectable | |
| | | GWYLVAATAAAATLR | TU81 | 20.0 | undetectable | |
| | Rv0290 | IPVMAYLVGLFAWVL | TU22 | 70.0 | CD4 | |
| | | | TU29 | 55.0 | CD4 | |
| | | | TU35 | 43.3 | CD4 | |
| | | | TU8 | 148.3 | CD4 | |
| | | | TU81 | 238.3 | CD4 | |
| | | | TU23 | 56.7 | undetectable | |
| | | QLSALWARFPLPVIP | TU81 | 33.3 | CD4 | |
| | Rv0292 | AILRRRRRIAEPATC | TU81 | 61.7 | CD4 | |
| | | EIGWEAGTAAPDEIP | TU23 | 138.3 | CD4 | |
| | | | TU8 | 40.0 | CD4 | |
| | | | TU81 | 445.0 | CD4 | |
| | | | TU1 | 23.3 | n.d. | |
| | Rv0522 | ARIVIFFVGSVFLLT | TU40 | 23.3 | n.d. | |
| | Rv0544c | RRPLLVAVSWAIFAL | TU21 | 38.3 | n.d. | |
| | Rv0985c | IDLNVLLSAAINFFL | TU64 | 20.0 | CD4 | |
| | | | TU22 | 21.7 | undetectable | |
| | | | TU46 | 28.3 | undetectable | |

TABLE 5-continued

Summary of epitope characteristics
(SEQ ID No: 35 to 403 in order of appearance)

| Category | Rv# | Sequence | Donor | SFC | T cell phenotype | References |
|---|---|---|---|---|---|---|
| | Rv0987 | CILAWILVRIINVRS | TU40 | 41.7 | undetectable | |
| | | IGLVTQTINDFYFVI | TU78 | 61.7 | undetectable | |
| | | | TU81 | 30.0 | undetectable | |
| | Rv0988 | EPYAVWLDDWYARES | TU40 | 20.0 | n.d. | |
| | | | TU46 | 21.7 | n.d. | |
| | Rv1037c, Rv1198, Rv1793, Rv2346c, Rv3619c | AEHQAIIRDVLTASD | TU29 | 320.8 | CD4 | (3) |
| | | | TU33 | 105.0 | CD4 | |
| | | | TU11 | 37.5 | undetectable | |
| | | AEHQAIVRDVLAAGD | TU11 | 31.7 | n.d. | (3) |
| | | | TU29 | 205.0 | n.d. | |
| | | | TU33 | 33.3 | n.d. | |
| | Rv1038c, Rv1197, Rv2347c, Rv3620c | NQAFRNIVNMLHGVR | TU75 | 65.8 | n.d. | |
| | | NYEQQEQASQQILSS | TU25 | 66.7 | n.d. | |
| | Rv1174c | TCNYGQVVAALNATD | TU29 | 50.0 | n.d. | |
| | Rv1270c | TDAMRKVTGMHVRLA | TU35 | 33.3 | n.d. | |
| | Rv1431 | GDLRVIILEGQPIHV | TU10 | 20.0 | n.d. | |
| | | | TU63 | 70.0 | n.d. | |
| | Rv1565c | AEVIRLIRRLLPALV | TU64 | 25.0 | n.d. | |
| | Rv1639c | LWIWVALTGAAATVL | TU46 | 50.0 | n.d. | |
| | | | TU63 | 51.7 | n.d. | |
| | Rv1877 | AAVALGFFVWLEGRA | TU70 | 23.3 | n.d. | |
| | | AISVTAYALAAEVVP | TU1 | 25.0 | n.d. | |
| | Rv2094c | TPVQSQRVDPSAASG | TU2 | 33.3 | n.d. | |
| | | | TU22 | 45.0 | n.d. | |
| | Rv2376c | NQGGWMLSRASAMEL | TU22 | 38.3 | n.d. | |
| | Rv2575 | FFQVLVTQFGSSGGP | TU11 | 26.7 | n.d. | |
| | Rv2576c | ADSSKYMITLHTPIA | TU23 | 245.0 | n.d. | |
| | | | TU64 | 36.7 | n.d. | |
| | Rv2609c | ALGERRLVRLLRLGG | TU22 | 23.3 | n.d. | |
| | Rv2869c | NLAICLVLIYAIALV | TU75 | 21.7 | n.d. | |
| | Rv2873 | AATIDQLKTDAKLLS | TU33 | 90.0 | n.d. | (4) |
| | Rv2873, Rv2875 | AAFSKLPASTIDELK | TU8 | 90.0 | CD4 | |
| | | ANATVYMIDSVLMPP | TU11 | 70.0 | CD4 | (5-7) |
| | | | TU22 | 55.0 | CD4 | |
| | | | TU24 | 36.7 | CD4 | |
| | | | TU29 | 123.3 | CD4 | |
| | | | TU82 | 26.7 | undetectable | |
| | Rv2963 | AFIFADLLILPILNI | TU10 | 45.0 | n.d. | |
| | Rv2999 | AINGDFILIAPEVQE | TU40 | 48.3 | n.d. | |
| | | EEPRLFYMHYWAVDD | TU40 | 25.0 | n.d. | |
| | Rv3000 | IVVMYLLLAATAVAA | TU40 | 26.7 | n.d. | |
| | | LTAIRYQIVVMYLLL | TU40 | 26.7 | n.d. | |
| | Rv3004 | LLVIPVALSASIIRL | TU40 | 28.3 | n.d. | |
| | Rv3006 | GTVLVNLINTKLTVA | TU2 | 115.0 | n.d. | |
| | | | TU40 | 35.0 | n.d. | |
| | Rv3330 | LENDNQLLYNYPGAL | TU11 | 78.3 | CD4 | |
| | | | TU29 | 163.3 | CD4 | |
| | | | TU33 | 593.3 | CD4 | |
| | | | TU35 | 160.0 | CD4 | |
| | | | TU64 | 133.3 | CD4 | |
| | | | TU74 | 145.0 | CD4 | |
| | | | TU78 | 235.0 | CD4 | |
| | | | TU55 | 58.3 | n.d. | |
| | | MAFLRSVSCLAAAVF | TU64 | 28.3 | n.d. | |
| | Rv3615c | LRIAAKIYSEADEAW | TU2 | 68.3 | CD4 | |
| | | | TU23 | 481.7 | CD4 | |
| | | | TU25 | 628.3 | CD4 | |
| | | | TU70 | 173.3 | CD4 | |
| | | | TU74 | 35.0 | CD4 | |
| | | | TU8 | 158.3 | CD4 | |
| | | | TU81 | 263.3 | CD4 | |
| | | | TU5 | 56.7 | undetectable | |
| | | VDLAKSLRIAAKIYS | TU2 | 81.7 | CD4 | |
| | | | TU23 | 438.3 | CD4 | |
| | | | TU25 | 613.3 | CD4 | |
| | | | TU70 | 180.0 | CD4 | |
| | | | TU74 | 48.3 | CD4 | |
| | | | TU8 | 245.0 | CD4 | |
| | | | TU81 | 215.0 | CD4 | |
| | | | TU5 | 23.3 | undetectable | |
| | Rv3616c | IISDVADIIKGTLGE | TU25 | 73.3 | n.d. | |
| | Rv3823c | ADYNMLLISRLREEA | TU40 | 41.7 | n.d. | |
| | | AITILLLVILLIIYG | TU40 | 23.3 | n.d. | |

TABLE 5-continued

Summary of epitope characteristics
(SEQ ID No: 35 to 403 in order of appearance)

| Category | Rv# | Sequence | Donor | SFC | T cell phenotype | References |
|---|---|---|---|---|---|---|
| | | DRSRIEFAITILLLV | TU40 | 26.7 | n.d. | |
| | | IIPEYLFIQSSTDLR | TU40 | 20.0 | n.d. | |
| | | LVILLIIYRNPITMV | TU40 | 28.3 | n.d. | |
| | Rv3874 | AAVVRFQEAANKQKQ | TU22 | 550.0 | CD4 | (8-10) |
| | | | TU33 | 518.3 | CD4 | |
| | | | TU74 | 381.7 | CD4 | |
| | | | TU78 | 136.7 | CD4 | |
| | | | TU55 | 51.7 | n.d. | |
| | | | TU11 | 20.0 | undetectable | |
| | | | TU29 | 56.7 | undetectable | |
| | Rv3875 | EQQWNFAGIEAAASA | TU22 | 78.3 | CD4 | (9, 11, 12) |
| | | | TU70 | 66.7 | CD4 | |
| | | | TU74 | 216.7 | CD4 | |
| | | | TU75 | 105.0 | CD4 | |
| | | | TU81 | 476.7 | CD4 | |
| | | | TU25 | 118.3 | undetectable | |
| | Rv3876 | RQSGATIADVLAEKE | TU22 | 561.7 | CD4 | |
| | | | TU33 | 503.3 | CD4 | |
| | | | TU74 | 145.0 | CD4 | |
| | | | TU78 | 60.0 | CD4 | |
| | | | TU55 | 53.3 | n.d. | |
| Conserved hypotheticals | Rv0293c | AQAVYDFRSIVDYLR | TU81 | 53.3 | CD4 | |
| | | LDYLRRMTVFLQGLM | TU81 | 36.7 | undetectable | |
| | | LNYRPLLPKDRRMII | TU23 | 176.7 | CD4 | |
| | | | TU8 | 86.7 | CD4 | |
| | | | TU81 | 358.3 | CD4 | |
| | | | TU1 | 23.3 | n.d. | |
| | | RCALHWFPGSHLLHV | TU23 | 61.7 | CD4 | |
| | | | TU81 | 276.7 | CD4 | |
| | Rv0295c | IAYPVLWRHLTAIVA | TU81 | 31.7 | n.d. | |
| | Rv0298 | AYAQRVYQANRAAGS | TU23 | 56.7 | CD4 | |
| | | | TU81 | 196.7 | CD4 | |
| | | VTVDAAVLAAIDADA | TU23 | 171.7 | CD4 | |
| | | | TU81 | 333.3 | CD4 | |
| | | | TU1 | 25.0 | n.d. | |
| | Rv0299 | EHELYVAVLSNALHR | TU81 | 38.3 | undetectable | |
| | | RVPEDLLAMVVAVEQ | TU23 | 93.3 | CD4 | |
| | | | TU81 | 283.3 | CD4 | |
| | | | TU1 | 23.3 | n.d. | |
| | | | TU8 | 28.3 | undetectable | |
| | Rv0371c | ATGIVLMLGDQPQVA | TU81 | 25.0 | n.d. | |
| | Rv0372c | DNGVGYVGLVASTVR | TU81 | 20.0 | n.d. | |
| | Rv0508 | ICVRVAEQLAELSSE | TU23 | 26.7 | n.d. | |
| | Rv0690c | AVPLRLLGGLHRMVL | TU46 | 20.0 | undetectable | |
| | | | TU63 | 71.7 | undetectable | |
| | | MYRELLELVAADVES | TU63 | 90.0 | CD8 | |
| | | | TU46 | 28.3 | undetectable | |
| | | | TU64 | 23.3 | undetectable | |
| | Rv0776c | GDCLVAFDAPLVVAN | TU63 | 81.7 | n.d. | |
| | Rv0854 | SPEEILDVIADFEAM | TU63 | 66.7 | n.d. | |
| | Rv1045 | RRDIELIHEQLADAG | TU75 | 25.0 | n.d. | |
| | Rv1186c | TVRYRIRRIEQLLST | TU22 | 33.3 | n.d. | |
| | Rv1301 | RELIRAFWPGALSLV | TU23 | 23.3 | n.d. | |
| | Rv1339 | ASVHVLLSHLHADHC | TU46 | 20.0 | n.d. | |
| | | LGALTIVPRLVAHPT | TU78 | 93.3 | n.d. | |
| | Rv1366 | AVHVWLRLPAGRVEI | TU63 | 58.3 | CD4 | |
| | | | TU46 | 45.0 | undetectable | |
| | | LQSLWANFYELLADA | TU63 | 101.7 | CD4/CD8 | |
| | | | TU22 | 50.0 | undetectable | |
| | | | TU46 | 53.3 | undetectable | |
| | Rv1367c | ADLILLYLIQHCPDL | TU46 | 38.3 | n.d. | |
| | | HPARRAILIEDLLTH | TU63 | 68.3 | n.d. | |
| | | MVWQREKLLQVNEIG | TU46 | 51.7 | n.d. | |
| | Rv1503c | ELVAAFLWAQFEEAE | TU46 | 45.0 | n.d. | |
| | Rv1535 | HNDVVTVASAPKLRV | TU1 | 88.3 | n.d. | |
| | Rv1765c, Rv2015c | SSTATSGAAVVSPAE | TU23 | 25.0 | n.d. | |
| | Rv1870c | IAGMRLLVIKPEPLA | TU81 | 23.3 | n.d. | |
| | Rv1871c | DYVYNIKANPAVRVR | TU23 | 53.3 | n.d. | |
| | | | TU81 | 45.0 | n.d. | |
| | Rv1873 | LAVRYGISSLEEAQA | TU23 | 40.0 | n.d. | |
| | Rv1879 | AFNEILRRRAATAVA | TU22 | 75.0 | n.d. | |
| | | VDLIAHGTAARIYRL | TU23 | 58.3 | n.d. | |
| | | YLLDFLRQSGNTPIV | TU23 | 30.0 | n.d. | |

TABLE 5-continued

Summary of epitope characteristics
(SEQ ID No: 35 to 403 in order of appearance)

| Category | Rv# | Sequence | Donor | SFC | T cell phenotype | References |
|---|---|---|---|---|---|---|
| | Rv2226 | VVSREHLIQQAIAAN | TU40 | 443.3 | n.d. | |
| | Rv2567 | KAGLDRLRSVVHSLI | TU63 | 61.7 | n.d. | |
| | | NPGLLRFLPQLSERL | TU63 | 46.7 | n.d. | |
| | Rv2574 | PALFVFRPLLNLALR | TU70 | 21.7 | n.d. | |
| | Rv2627c | RRSFYRIFFDSGFTP | TU22 | 25.0 | n.d. | |
| | | RSAFRLSPPVLSGAM | TU22 | 23.3 | n.d. | |
| | Rv2819c | LTLNEIHAFIKDPLG | TU63 | 41.7 | n.d. | |
| | Rv2823c | AAFSRMLSLFFRQHI | TU11 | 38.3 | CD4 | |
| | | FDREFTFGWDELLSK | TU1 | 98.3 | n.d. | |
| | | FYNEKAFLLTTFDVS | TU63 | 96.7 | CD4 | |
| | Rv2868c | VADIHFQPRYIFAAI | TU40 | 33.3 | n.d. | |
| | Rv2955c | DFFVAADSAFSSLND | TU23 | 133.3 | n.d. | |
| | | HRDDRYCYFFIPSRK | TU21 | 28.3 | n.d. | |
| | Rv3015c | AASLLDEDMDALEEA | TU33 | 50.0 | CD4 | |
| | | YRIAARPGAVTRRAA | TU33 | 426.7 | CD4 | |
| | | | TU35 | 76.7 | CD4 | |
| | | | TU64 | 88.3 | CD4 | |
| | | | TU11 | 68.3 | undetectable | |
| | | | TU78 | 200.0 | undetectable | |
| | Rv3026c | LALLLVPGVPLVVMP | TU40 | 33.3 | n.d. | |
| | | | TU64 | 28.3 | n.d. | |
| | Rv3031 | ADQILRETLLTVSSD | TU40 | 23.3 | n.d. | |
| | | EWLYQSWAAAYLPLL | TU33 | 85.0 | n.d. | |
| | Rv3035 | GQLLVFDTRRGMVVG | TU40 | 25.0 | n.d. | |
| | Rv3142c | DDYNELVISVPLQLT | TU63 | 120.0 | n.d. | |
| | | DGLVLNFDDYNELVI | TU63 | 90.0 | n.d. | |
| | Rv3267 | DDGAIDILLVGLDSR | TU40 | 36.7 | n.d. | |
| | Rv3268 | DGLLAILAAGASLVQ | TU1 | 33.3 | n.d. | |
| | Rv3856c | DIGCVFSIDTDAHAP | TU63 | 61.7 | n.d. | |
| | | EPEMLDRLDIVVASV | TU63 | 63.3 | n.d. | |
| Information pathways | Rv0640 | KKVAGLIKLQIVAGQ | TU46 | 28.3 | n.d. | |
| | Rv0703 | EKSYGLLDDNVYTFL | TU46 | 20.0 | n.d. | |
| | Rv1210 | LIILRKRENFRRAFS | TU63 | 50.0 | n.d. | |
| | Rv1297 | NQRQKFNPLVRLDSI | TU13 | 216.7 | n.d. | |
| | Rv1312 | AAFYRLSSLRLWPDR | TU64 | 26.7 | n.d. | |
| | Rv1317c | AQLGYTIRQLERLLQ | TU63 | 50.0 | CD4/CD8 | |
| | | IRQLERLLQAVVGAG | TU64 | 23.3 | CD4 | |
| | | | TU46 | 23.3 | undetectable | |
| | Rv1420 | AAQHRQIVADFCDFL | TU63 | 86.7 | n.d. | |
| | Rv1641 | GHVVRFLEAGSKVKV | TU22 | 33.3 | n.d. | |
| | Rv1642 | GKIVRQKANRRHLLE | TU22 | 53.3 | n.d. | |
| | | | TU64 | 20.0 | n.d. | |
| | Rv2069 | DGDRHARGFEDLVEV | TU36 | 45.0 | n.d. | |
| | Rv2191 | EEIALIARWLAEPGV | TU23 | 130.0 | n.d. | |
| | Rv2572c | DHGGVIFIDLRDASG | TU63 | 46.7 | n.d. | |
| | | FTQLDMEMSFVDAED | TU63 | 75.0 | n.d. | |
| | | FVDAEDIIAISEEVL | TU63 | 76.7 | n.d. | |
| | | MFVLRSHAAGLLREG | TU64 | 25.0 | n.d. | |
| | Rv2736c | ALCLRLLTARSRTRA | TU21 | 63.3 | CD8 | |
| | Rv3012c | AVDGRFAVPQILGDE | TU33 | 126.7 | CD4 | |
| | | | TU78 | 38.3 | CD4 | |
| | | | TU11 | 26.7 | undetectable | |
| | | | TU35 | 41.7 | undetectable | |
| | Rv3014c | QAYLALRAWGLPVSE | TU33 | 58.3 | n.d. | |
| | | | TU78 | 31.7 | n.d. | |
| | | VDHLERMLSLDNAFT | TU33 | 58.3 | n.d. | |
| | | VGGAGFATDFEPVDH | TU33 | 45.0 | n.d. | |
| | | | TU78 | 58.3 | n.d. | |
| | Rv3024c | AEKFKEDVINDFVSS | TU63 | 116.7 | CD4 | |
| | | | TU10 | 26.7 | undetectable | |
| | | AHGETVSAVAELIGD | TU33 | 130.0 | CD4 | |
| | | | TU78 | 35.0 | CD4 | |
| | | | TU35 | 36.7 | undetectable | |
| | | | TU36 | 43.3 | undetectable | |
| | | QQIKFAALSARAVAL | TU11 | 65.0 | CD4 | |
| | | | TU13 | 101.7 | CD4 | |
| | | | TU33 | 560.0 | CD4 | |
| | | | TU35 | 86.7 | CD4 | |
| | | | TU36 | 85.0 | CD4 | |
| | | | TU64 | 123.3 | CD4 | |
| | | | TU78 | 220.0 | CD4 | |

TABLE 5-continued

Summary of epitope characteristics
(SEQ ID No: 35 to 403 in order of appearance)

| Category | Rv# | Sequence | Donor | SFC | T cell phenotype | References |
|---|---|---|---|---|---|---|
| | Rv3062 | ARVQIHRANDQVRIY | TU10 | 35.0 | n.d. | |
| | Rv3598c | GDGTQLQVMISLDKV | TU64 | 36.7 | n.d. | |
| | | LGDIVYVHGAVISSR | TU64 | 48.3 | n.d. | |
| | Rv3834c | SRFYFLTGRGALLQL | TU8 | 30.0 | n.d. | |
| Insertion sequences and phages | Rv0741, Rv1313c, Rv3798 | ESTNTKIRLLTRIAF | TU46 | 21.7 | n.d. | |
| | Rv1036c | ALVAEGIEAIVFRTL | TU75 | 30.0 | n.d. | |
| | Rv1047, Rv1199c, Rv2512c, Rv2666, Rv3023c, Rv3115 | AGWLAFFRDLVARGL | TU29 | 163.3 | CD4 | |
| | | | TU75 | 26.7 | CD4 | |
| | | | TU40 | 30.0 | undetectable | |
| | | | TU63 | 86.7 | undetectable | |
| | | LRGLLSTFIAALMGA | TU29 | 493.3 | CD4 | |
| | | | TU33 | 68.3 | CD4 | |
| | | | TU75 | 35.0 | CD4 | |
| | | | TU11 | 46.7 | undetectable | |
| | | QASPDLLRGLLSTFI | TU11 | 23.3 | CD4 | |
| | | | TU29 | 200.0 | CD4 | |
| | | | TU75 | 48.3 | CD4 | |
| | Rv1047, Rv1199c, Rv2512c, Rv3023c, Rv3115 | ARTDLLAFTAFPKQI | TU63 | 41.7 | undetectable | |
| | | ASIIRLVGAVLAEQH | TU63 | 70.0 | CD4 | |
| | | | TU23 | 30.0 | undetectable | |
| | | FPDRASIIRLVGAVL | TU63 | 48.3 | CD4/CD8 | |
| | | YLGLEVLTRARAALT | TU33 | 181.7 | CD4 | |
| | | | TU36 | 46.7 | CD4 | |
| | | | TU64 | 46.7 | CD4 | |
| | | | TU13 | 20.0 | undetectable | |
| | Rv1313c, Rv3798 | MRNVRLFRALLGVDK | TU46 | 36.7 | n.d. | |
| | | | TU64 | 28.3 | n.d. | |
| | Rv3427c | KPLVLILDDFAMREH | TU63 | 115.0 | n.d. | |
| | Rv3428c | AVWAFVMVLAFSRHL | TU5 | 341.7 | CD4 | |
| | | | TU70 | 151.7 | n.d. | |
| Intermediary metabolism and respiration | Rv0291 | AARLLSIRAMSTKFS | TU23 | 60.0 | CD4 | |
| | | | TU81 | 195.0 | CD4 | |
| | | | TU1 | 20.0 | n.d. | |
| | | ALSVLVGLTAATVAI | TU23 | 143.3 | CD4 | |
| | | | TU8 | 138.3 | CD4 | |
| | | | TU81 | 456.7 | CD4 | |
| | | | TU1 | 33.3 | n.d. | |
| | | ATEVVRRLTATAHRG | TU81 | 93.3 | CD4 | |
| | Rv0291, Rv1796 | AAVDKDAVIVAAAGN | TU81 | 26.7 | undetectable | |
| | Rv0294 | AKLMRDIPFRVGAVV | TU23 | 105.0 | CD4 | |
| | | | TU81 | 368.3 | CD4 | |
| | | | TU8 | 36.7 | undetectable | |
| | | DESWQQFRQELIPLL | TU23 | 50.0 | CD4 | |
| | | | TU81 | 316.7 | CD4 | |
| | | MWDPDVYLAFSGHRN | TU23 | 70.0 | CD4 | |
| | | | TU75 | 60.0 | CD4 | |
| | | | TU81 | 241.7 | CD4 | |
| | | STIFPFRRLFMVADV | TU81 | 80.0 | CD4 | |
| | | | TU22 | 20.0 | undetectable | |
| | | | TU23 | 20.0 | undetectable | |
| | Rv0529 | AYRTTIFAFPVFGFG | TU40 | 30.0 | n.d. | |
| | | FGVIFGAIWAEEAWG | TU22 | 20.0 | n.d. | |
| | | FLLVPVLILLTVSGR | TU40 | 21.7 | n.d. | |
| | Rv0637 | ILAKYVQLDFFRHVD | TU46 | 23.3 | n.d. | |
| | | | TU63 | 58.3 | n.d. | |
| | Rv0693 | DSFFHLAPLGQSGAL | TU63 | 68.3 | n.d. | |
| | | QCKDIIDELERMQVF | TU46 | 20.0 | n.d. | |
| | | | TU63 | 100.0 | n.d. | |
| | Rv0694 | MAEAWFETVAIAQQR | TU46 | 63.3 | n.d. | |
| | | | TU63 | 85.0 | n.d. | |
| | Rv0773c | GIVALIALGILEHFD | TU46 | 26.7 | n.d. | |
| | | | TU63 | 81.7 | n.d. | |
| | Rv0777 | AAQEMMIALRRLREL | TU64 | 23.3 | n.d. | |
| | | LQVVLRGYASMVAEL | TU63 | 40.0 | n.d. | |
| | Rv0853c | KAAIELIADHQLTVL | TU63 | 65.0 | n.d. | |
| | Rv0993 | GKDGVVAHFVEDLVL | TU64 | 23.3 | n.d. | |
| | Rv1122, Rv1844c | GSGHFVKMVHNGIEY | TU40 | 40.0 | n.d. | |
| | Rv1187 | GSPLNLLRWTSARSI | TU29 | 76.7 | n.d. | |
| | Rv1300 | ELVRADVTTPCLLPE | TU13 | 53.3 | n.d. | |
| | Rv1307 | VYLVWRFIVPLVGRL | TU46 | 40.0 | n.d. | |
| | Rv1308 | AMDYTTIVAAAASES | TU22 | 26.7 | n.d. | |
| | | GKHVLIIFDDLTKQA | TU46 | 40.0 | n.d. | |

TABLE 5-continued

Summary of epitope characteristics
(SEQ ID No: 35 to 403 in order of appearance)

| Category | Rv# | Sequence | Donor | SFC | T cell phenotype | References |
|---|---|---|---|---|---|---|
| | Rv1310 | DNLVRTISLQPTDGL | TU64 | 33.3 | n.d. | |
| | | FDHVPEQAFFLIGGL | TU64 | 30.0 | n.d. | |
| | | KDLQDIIAILGIDEL | TU64 | 26.7 | n.d. | |
| | Rv1311 | EGVSILAESAEFESE | TU64 | 20.0 | n.d. | |
| | Rv1436 | GRLKGILKYYDAPIV | TU36 | 25.0 | n.d. | |
| | | IGRNFYRALLAQQEQ | TU63 | 106.7 | n.d. | |
| | Rv1568 | CRRYEVLLIFDEIAT | TU35 | 41.7 | n.d. | |
| | | | TU78 | 65.0 | n.d. | |
| | Rv1785c | CLGSHLARLELTLLV | TU46 | 91.7 | n.d. | |
| | Rv1844c | DLDSYLVEITAEVLR | TU64 | 23.3 | n.d. | |
| | | EPGDIIIDGGNALYT | TU40 | 35.0 | n.d. | |
| | Rv1872c | AAFDYADGAAEDELS | TU23 | 21.7 | n.d. | |
| | | RARQGFRDIEFHPTI | TU23 | 45.0 | n.d. | |
| | | | TU81 | 28.3 | n.d. | |
| | Rv1876 | AVLLEKIVADEEEHI | TU22 | 26.7 | n.d. | |
| | | | TU23 | 28.3 | n.d. | |
| | Rv1885c | AVSIGILLSLIAPLG | TU63 | 55.0 | n.d. | |
| | Rv2096c | LLSTRGYITAEKIRS | TU22 | 35.0 | n.d. | |
| | Rv2122c | SLAVKTFEDLFAELG | TU46 | 23.3 | n.d. | |
| | Rv2200c | DVIHAFWVPEFLFKR | TU23 | 158.3 | n.d. | |
| | Rv2215 | DMTKIVGLRARAKAA | TU82 | 35.0 | n.d. | |
| | Rv2476c | APPNLIRAILRAPVD | TU40 | 30.0 | n.d. | |
| | | EVNIKILIDSLVSAG | TU40 | 201.7 | n.d. | |
| | Rv2495c | LRLLVIALKHNVILN | TU40 | 31.7 | n.d. | |
| | Rv2855 | DTQSMIVTDHRYVPA | TU23 | 33.3 | n.d. | |
| | | VDVEDGRVIVDEYQR | TU78 | 20.0 | n.d. | |
| | Rv2861c | DSTVITDGDIVNIDV | TU40 | 31.7 | n.d. | |
| | | EKMRVAGRIAAGALA | TU78 | 20.0 | n.d. | |
| | Rv2867c | AAVIVGSGRIASLYV | TU40 | 23.3 | n.d. | |
| | | AHESLCFAGANLIPL | TU40 | 25.0 | n.d. | |
| | Rv2874 | AALPLLFFALAGQRI | TU11 | 81.7 | CD4 | |
| | | | TU24 | 36.7 | CD4 | |
| | | | TU82 | 33.3 | CD4 | |
| | | | TU29 | 143.3 | undetectable | |
| | | | TU40 | 45.0 | undetectable | |
| | | GTVVLTATFALGAAL | TU24 | 33.3 | n.d. | |
| | | | TU29 | 128.3 | CD4 | |
| | | | TU11 | 71.7 | undetectable | |
| | | | TU82 | 30.0 | undetectable | |
| | | LALVGFLGGLITGIS | TU29 | 65.0 | CD4 | |
| | | | TU11 | 65.0 | undetectable | |
| | | | TU40 | 36.7 | undetectable | |
| | | | TU82 | 25.0 | undetectable | |
| | | RGKVVLIDFWAYPCI | TU11 | 35.0 | undetectable | |
| | Rv2984 | ARVFLDSVLPALGEE | TU40 | 38.3 | n.d. | |
| | Rv2987c | FRVVISSRFGDIFRG | TU40 | 20.0 | n.d. | |
| | Rv2988c | AVDAVFVGSCTNGRI | TU40 | 46.7 | n.d. | |
| | | DTEVYLDAASLSPFV | TU33 | 266.7 | n.d. | |
| | Rv2996c | INLIIHYVDRPGALG | TU40 | 31.7 | undetectable | |
| | | IVQINGRHFDLRAQG | TU40 | 26.7 | undetectable | |
| | Rv3001c | AGYPAELAYFEVLHE | TU40 | 23.3 | n.d. | |
| | | ALEMFYDDDADLSII | TU40 | 25.0 | n.d. | |
| | Rv3002c | SQVIEAVNLFRANVI | TU40 | 33.3 | n.d. | |
| | Rv3003c | AVITELIAMLRHHHI | TU81 | 40.0 | n.d. | |
| | | DDIPRVLAEAFHIAA | TU81 | 31.7 | n.d. | |
| | | QAARGIRPLFDDITE | TU81 | 21.7 | n.d. | |
| | Rv3007c | CSEDLLYLSDLDFDV | TU10 | 33.3 | n.d. | |
| | Rv3010c | AAHAGEYGQMVTLRG | TU40 | 23.3 | n.d. | |
| | Rv3025c | ALQSHDDVALVSVMW | TU33 | 28.3 | CD4 | |
| | | | TU63 | 61.7 | undetectable | |
| | | ILPIAEMSVVAMEFG | TU63 | 111.7 | CD4 | |
| | | | TU10 | 26.7 | undetectable | |
| | | | TU64 | 33.3 | undetectable | |
| | | SARLRLLRDRLVEGV | TU63 | 138.3 | CD4 | |
| | | | TU64 | 23.3 | undetectable | |
| | Rv3028c | GSAENFSVVEALADS | TU33 | 138.3 | n.d. | |
| | | | TU64 | 20.0 | n.d. | |
| | Rv3029c | EGGNQIVQYLVAQKI | TU40 | 25.0 | n.d. | |
| | Rv3032 | LVAQEAAAAGTPLVT | TU35 | 23.3 | n.d. | |
| | Rv3109 | ELADLIEFARTVNEE | TU64 | 43.3 | n.d. | |
| | Rv3146 | KMAPVLRQIYDQMAE | TU63 | 66.7 | n.d. | |
| | Rv3161c | AQTSQFVMAMINYED | TU40 | 26.7 | n.d. | |
| | Rv3232c | AELFRLQTEFVKLQE | TU21 | 85.0 | n.d. | |
| | | EQMLIDDGILLRKYW | TU21 | 178.3 | n.d. | |

TABLE 5-continued

Summary of epitope characteristics
(SEQ ID No: 35 to 403 in order of appearance)

| Category | Rv# | Sequence | Donor | SFC | T cell phenotype | References |
|---|---|---|---|---|---|---|
| | Rv3247c | CRGYDVVILDRYVAS | TU64 | 21.7 | n.d. | |
| | Rv3393 | ALPRLLRRLVIMGGM | TU63 | 128.3 | n.d. | |
| | | RVIEDALRFYFESHE | TU63 | 141.7 | n.d. | |
| | Rv3419c | ADVLTMKAVRAATAL | TU63 | 41.7 | n.d. | |
| | | TDNGAMIAAFAAQLV | TU63 | 203.3 | n.d. | |
| | | | TU81 | 30.0 | n.d. | |
| | Rv3634c | EIYLNTFRHLYGLDC | TU22 | 25.0 | n.d. | |
| | Rv3775 | LYRPGLVHIYHALTW | TU1 | 28.3 | n.d. | |
| | Rv3859c | ENFFMFIAEEVREYL | TU40 | 23.3 | n.d. | |
| | | | TU63 | 65.0 | n.d. | |
| | | QRPRMLYDYFHQLFA | TU63 | 141.7 | n.d. | |
| | | QTLVYKGMLTTPQLK | TU63 | 40.0 | n.d. | |
| | Rv3883c | AQIIHRITATARHPG | TU29 | 53.3 | n.d. | |
| Lipid metabolism | Rv0129c | GQNYTYKWETFLTRE | TU75 | 26.7 | CD4 | |
| | | | TU23 | 66.7 | undetectable | |
| | | | TU33 | 50.0 | undetectable | |
| | | | TU70 | 33.3 | undetectable | |
| | | | TU8 | 50.0 | undetectable | |
| | Rv0129c, Rv1886c | DPMVQIPRLVANNTR | TU2 | 60.0 | undetectable | |
| | Rv0129c, Rv1886c, Rv3804c | AGCQTYKWETFLTSE | TU2 | 60.0 | CD4 | (11, 13-15) |
| | | | TU23 | 55.8 | CD4 | |
| | | | TU75 | 36.7 | CD4 | |
| | | | TU8 | 51.7 | CD4 | |
| | | | TU33 | 36.7 | undetectable | |
| | | PSPSMGRDIKVQFQS | TU1 | 45.0 | n.d. | (11, 13-17) |
| | | | TU33 | 46.7 | undetectable | |
| | | QVPSASMGRDIKVQF | TU1 | 53.3 | n.d. | |
| | | | TU33 | 48.3 | undetectable | |
| | Rv0244c | FLMSVGALIIGWLLQ | TU40 | 26.7 | n.d. | |
| | Rv0551c | AGISSLIIDPNPMFV | TU35 | 88.3 | n.d. | |
| | Rv0644c, Rv3392c | RVLLAGWEQFDEPVD | TU63 | 101.7 | n.d. | |
| | Rv1185c | EHIHRPNTNNVGPII | TU8 | 65.0 | n.d. | |
| | Rv1493 | SILDMRQLFDGIDLS | TU46 | 26.7 | n.d. | |
| | Rv1886c | HPQQFIYAGSLSALL | TU64 | 35.0 | n.d. | (6, 11, 15, 17, 18) |
| | Rv2881c | IGLVLIAVLVFVPRV | TU40 | 38.3 | n.d. | |
| | Rv3061c | SEFNEVFFNDVFVPD | TU10 | 41.7 | n.d. | |
| | Rv3285 | DPVKGADEVVAFAEE | TU8 | 813.3 | n.d. | |
| | Rv3392c | EHFGHERYDAFFSLA | TU63 | 66.7 | n.d. | |
| | Rv3824c | FSLVNFFDAQVGPLS | TU40 | 43.3 | n.d. | |
| | Rv3825c | AVVVLKRLPDALADG | TU40 | 25.0 | n.d. | |
| | | ESVFAATVAELESLI | TU10 | 36.7 | n.d. | |
| | | ITPDEGAYAFEALLR | TU10 | 28.3 | n.d. | |
| | | LDWFCLFSSAAALTG | TU40 | 23.3 | n.d. | |
| PE/PPE | Rv0109, Rv0124, Rv0278c, Rv0279c, Rv0297, Rv0834c, Rv1243c, Rv1788, Rv2490c | AQEYQALSAQAAAFH | TU22 | 41.7 | n.d. | |
| | Rv0124, Rv0278c, Rv0279c, Rv0297, Rv0834c, Rv1243c, Rv2490c | GQQYQAMSAQAAAFH | TU81 | 50.0 | n.d. | |
| | Rv0124, Rv0297, Rv1243c, Rv1788, Rv1791, Rv2490c | AQIYQAVSAQAAAIH | TU75 | 225.0 | CD4 | |
| | | | TU81 | 86.7 | CD4 | |
| | Rv0124, Rv2634c | GSTINAANAAAALPT | TU23 | 36.7 | n.d. | |
| | | | TU81 | 190.0 | n.d. | |
| | Rv0159c | ERYVGLYLPFLDMSF | TU33 | 23.3 | n.d. | |
| | Rv0256c | AEAPAAAAAPEEQVQ | TU22 | 20.0 | CD4 | |
| | Rv0256c, Rv0280, Rv0286, Rv0453, Rv1387, Rv2123, Rv3018c, Rv3021c | GAMVATNFFGINTIP | TU63 | 90.0 | CD4 | |
| | | | TU81 | 393.3 | CD4 | |
| | | | TU21 | 28.3 | undetectable | |
| | Rv0256c, Rv0280, Rv0286, Rv0453, Rv1387, Rv3018c, Rv3021c, Rv3873 | AVLVATNFFGINTIP | TU70 | 102.5 | CD4 | |
| | | | TU81 | 458.3 | CD4 | |
| | | | TU1 | 33.3 | n.d. | |
| | | | TU21 | 35.0 | undetectable | |
| | | | TU23 | 36.7 | undetectable | |
| | | HTVLVATNFFGINTI | TU81 | 331.7 | n.d. | |
| | Rv0256c, Rv0280, Rv0286, Rv1387, Rv3018c, Rv3021c, Rv3873 | QAVLTATNFFGINTI | TU81 | 341.7 | n.d. | |

TABLE 5-continued

Summary of epitope characteristics
(SEQ ID No: 35 to 403 in order of appearance)

| Category | Rv# | Sequence | Donor | SFC | T cell phenotype | References |
|---|---|---|---|---|---|---|
| | Rv0256c, Rv0280, Rv0453 | ARMWIQAATTMASYQ | TU22 | 428.3 | CD4 | |
| | | | TU46 | 158.3 | CD4 | |
| | | | TU78 | 31.7 | CD4 | |
| | Rv0256c, Rv3018c | LAWLVQASANSAAMA | TU46 | 25.0 | undetectable | |
| | Rv0278c, Rv0279c | DPINEFFLANTGRPL | TU63 | 66.7 | n.d. | |
| | Rv0280, Rv0286, Rv0453, Rv1387, Rv3018c, Rv3021c | GINTIPIAINEAEYV | TU70 | 120.0 | CD4 | |
| | | | TU81 | 201.7 | CD4 | |
| | | | TU20 | 20.0 | n.d. | |
| | | | TU23 | 118.3 | undetectable | |
| | Rv0286 | QLSAEYASTAAELSG | TU22 | 26.7 | n.d. | |
| | Rv0286, Rv0453 | YAAALVAMPTLAELA | TU40 | 25.0 | undetectable | |
| | Rv0297 | LTVDAGAYASAEAAN | TU11 | 31.7 | n.d. | |
| | | | TU22 | 58.3 | n.d. | |
| | Rv0442c | APWQQVLRNLGIDIG | TU63 | 96.7 | n.d. | |
| | Rv0442c, Rv1789 | AWMSAAAAQAEQAAT | TU81 | 25.0 | undetectable | |
| | | YLAWLSTAAAQAEQA | TU29 | 145.0 | n.d. | |
| | | | TU63 | 100.0 | n.d. | |
| | Rv0453 | GWSSLGREYAAVAEE | TU23 | 185.0 | CD4 | |
| | Rv0834c | AGAMGAYAAAEAANA | TU22 | 111.7 | n.d. | |
| | | AGGFGGAGAGIANFL | TU81 | 20.0 | n.d. | |
| | Rv0834c, Rv1087, Rv1091 | GAYAAAEAANVSAAQ | TU22 | 176.7 | n.d. | |
| | Rv0834c, Rv1243c, Rv1441c | SAAGSYAAAEAANAS | TU22 | 91.7 | n.d. | |
| | | | TU81 | 21.7 | n.d. | |
| | Rv1172c | ALLPRAGAAAAAALP | TU22 | 45.0 | CD4 | |
| | | | TU74 | 26.7 | CD4 | |
| | | ALSRVHSMFLGTGGS | TU22 | 71.7 | CD4 | |
| | | | TU74 | 43.3 | CD4 | |
| | | APQINFFYYLGEPIV | TU40 | 20.0 | undetectable | |
| | Rv1172c, Rv1788, Rv1791, Rv3812 | MSFVTTQPEALAAAA | TU22 | 121.7 | CD4 | |
| | Rv1195 | MHVSFVMAYPEMLAA* | TU22 | 165.0 | CD4 | |
| | | | TU33 | 290.0 | CD4 | |
| | | | TU74 | 181.7 | CD4 | |
| | | | TU81 | 283.3 | CD4 | |
| | Rv1195, Rv1788, Rv1791 | SSYAATEVANAAAAS | TU81 | 60.0 | CD4 | |
| | Rv1196 | LGGLWTAVSPHLSPL | TU22 | 38.3 | CD4 | |
| | | | TU74 | 25.0 | CD4 | |
| | | LSPISNMVSMANNHM | TU22 | 70.0 | CD4 | |
| | | | TU29 | 115.0 | undetectable | |
| | | | TU40 | 43.3 | undetectable | |
| | | | TU75 | 28.3 | undetectable | |
| | Rv1196, Rv1361c, Rv3478 | AELMILIATNLLGQN | TU78 | 33.3 | CD4 | (19) |
| | | | TU40 | 90.0 | undetectable | |
| | | AQNGVQAMSSLGSSL | TU22 | 46.7 | CD4 | |
| | Rv1243c, Rv1441c, Rv1791 | ASVGSYAAAEAANAS | TU22 | 38.3 | n.d. | |
| | Rv1386 | ESGASYAARDALAAA | TU33 | 45.0 | n.d. | |
| | Rv1441c | ARFHQQFVQALTASV | TU82 | 35.0 | n.d. | |
| | Rv1450c | IGSSIGAANAAAAGS | TU23 | 45.0 | n.d. | |
| | Rv1705c | APYVAWMRATAIQAE | TU29 | 41.7 | undetectable | |
| | | WFINWYLPISQLFYN | TU40 | 40.0 | undetectable | |
| | Rv1705c, Rv1706c, Rv1789, Rv1802 | AAAQASAAAAAYEAA | TU81 | 20.0 | n.d. | |
| | Rv1705c, Rv1706c, Rv1789, Rv1802, Rv3125c, Rv3135 | AATQARAAAAAFEAA | TU81 | 25.0 | undetectable | |
| | Rv1705c, Rv1789, Rv1802, Rv1808, Rv2892c, Rv3136, Rv3621c | FGQNTSAIAAAEAQY | TU70 | 161.7 | CD4 | |
| | | | TU81 | 176.7 | CD4 | |
| | Rv1705c, Rv1789, Rv1808, Rv2892c, Rv3136, Rv3621c | FFGQNTAAIAATEAQ | TU70 | 193.3 | CD4 | |
| | | | TU81 | 165.0 | CD4 | |
| | | FGQNTASIAATEAQY | TU70 | 110.0 | CD4 | |
| | | | TU81 | 26.7 | CD4 | |
| | Rv1706c, Rv1800, Rv1802, Rv1808, Rv2892c, Rv3135, Rv3621c | LAAAAAWDALAAELY | TU23 | 170.0 | CD4 | |
| | | | TU8 | 78.3 | CD4 | |
| | | | TU81 | 411.7 | CD4 | |
| | Rv1706c, Rv1808, Rv3135, Rv3136 | AAASWDALAAELASA | TU23 | 217.5 | CD4 | |
| | | | TU8 | 130.0 | CD4 | |
| | | | TU81 | 440.8 | CD4 | |

TABLE 5-continued

Summary of epitope characteristics
(SEQ ID No: 35 to 403 in order of appearance)

| Category | Rv# | Sequence | Donor | SFC | T cell phenotype | References |
|---|---|---|---|---|---|---|
| | Rv1788, Rv1791 | AAIHEMFVNTLQMSS | TU29 | 25.0 | CD8 | |
| | | | TU55 | 165.0 | n.d. | |
| | | AAIHEMFVNTLVASS | TU29 | 41.7 | CD8 | |
| | | | TU55 | 160.0 | n.d. | |
| | | | TU40 | 26.7 | undetectable | |
| | | | TU64 | 61.7 | undetectable | |
| | Rv1789 | NRASLMQLISTNVFG | TU55 | 21.7 | n.d. | |
| | Rv1789, Rv1802, Rv1808, Rv2892c, Rv3136 | FGQNTGAIAAAEARY | TU70 | 108.3 | CD4 | |
| | | | TU81 | 276.7 | CD4 | |
| | Rv1800, Rv2608, Rv3125c | PPEVNSARVFAGAGS | TU70 | 38.3 | n.d. | |
| | | | TU74 | 31.7 | n.d. | |
| | Rv1802 | YVAWMSATAALAREA | TU29 | 150.0 | CD4 | |
| | | | TU8 | 83.3 | CD4 | |
| | | | TU81 | 58.3 | CD4 | |
| | | | TU40 | 25.0 | undetectable | |
| | Rv1806 | AMNEAFVAMLGASAD | TU40 | 31.7 | n.d. | |
| | Rv1808 | AQLSQLISLLPSTLQ | TU40 | 50.0 | undetectable | |
| | | | TU64 | 51.7 | undetectable | |
| | | | TU81 | 23.3 | undetectable | |
| | Rv1917c, Rv2892c | FFGQNAPAIAAIEAA | TU70 | 20.0 | n.d. | |
| | | | TU8 | 21.7 | n.d. | |
| | Rv2123, Rv3018c, Rv3021c | ADYLRMWIQAATVMS | TU22 | 375.0 | CD4 | |
| | | | TU24 | 35.0 | CD4 | |
| | | | TU46 | 128.3 | CD4 | |
| | | | TU64 | 48.3 | CD4 | |
| | | | TU78 | 26.7 | CD4 | |
| | | | TU40 | 75.0 | undetectable | |
| | | DYVRMWVQAATVMSA | TU22 | 343.3 | CD4 | |
| | | | TU64 | 38.3 | CD4 | |
| | | | TU78 | 31.7 | CD4 | |
| | | | TU46 | 81.7 | CD4/CD8 | |
| | | | TU40 | 28.3 | undetectable | |
| | Rv2608 | LPLLVPLRAIPLLGN | TU64 | 20.0 | n.d. | |
| | Rv2853 | FVQALTTAAASYASV | TU40 | 26.7 | undetectable | |
| | | | TU78 | 23.3 | undetectable | |
| | | YASVEAANASPLQVA | TU23 | 35.0 | undetectable | |
| | Rv3018c | EIVQFLEETFAAYDQ | TU22 | 103.3 | CD4 | |
| | | | TU64 | 105.0 | CD4 | |
| | | | TU81 | 25.0 | CD4 | |
| | | | TU46 | 80.0 | undetectable | |
| | Rv3018c, Rv3021c | AAVPAVGAAAGAPAA | TU22 | 203.3 | CD4 | |
| | | | TU46 | 28.3 | CD4 | |
| | | | TU70 | 20.0 | undetectable | |
| | | | TU81 | 30.0 | undetectable | |
| | Rv3018c, Rv3021c, Rv3022c | ALSAEYAAVAQELSV | TU81 | 31.7 | CD4 | |
| | | | TU64 | 46.7 | n.d. | |
| | Rv3018c, Rv3022c | ELFVAAYVPYVAWLV | TU8 | 25.0 | n.d. | (20) |
| | | | TU40 | 20.0 | undetectable | |
| | | | TU46 | 30.0 | undetectable | |
| | | | TU64 | 21.7 | undetectable | |
| | | | TU81 | 28.3 | undetectable | |
| | Rv3021c | GWIISNIFGAIPVLG | TU22 | 195.0 | CD4 | |
| | | | TU46 | 41.7 | undetectable | |
| | | | TU8 | 58.3 | undetectable | |
| | | | TU81 | 26.7 | undetectable | |
| | | LLEFAVVLELAILSI | TU46 | 26.7 | undetectable | |
| | Rv3125c | ASMSMAAAASPYVGW | TU29 | 78.3 | n.d. | |
| | Rv3125c, Rv3135, Rv3136 | IQARAAALAFEQAYA | TU22 | 23.3 | CD4 | |
| | | | TU25 | 33.3 | CD4 | |
| | Rv3136 | AAGGWDSLAAELATT | TU23 | 130.0 | CD4 | |
| | | | TU8 | 31.7 | undetectable | |
| | Rv3812 | AGTLSTFFGVPLVLT | TU75 | 21.7 | n.d. | |
| | | NPFPFLRQIIANQQV | TU75 | 26.7 | n.d. | |
| | Rv3873 | MDYFIRMWNQAALAM | TU22 | 46.7 | n.d. | (21, 22) |
| Regulatory proteins | Rv0339c | EMLSMLRAMLAPESL | TU21 | 40.0 | n.d. | |
| | Rv0691c | TVAWTMLGVALSAYE | TU40 | 50.0 | n.d. | |
| | | | TU46 | 25.0 | n.d. | |
| | Rv0890c | GFTIANHNAAAVGEI | TU2 | 140.0 | n.d. | |
| | Rv1027c | LVLVIDDEPQILRAL | TU63 | 81.7 | n.d. | |
| | Rv1028c | ALLWLADQVDAALEK | TU63 | 48.3 | n.d. | |
| | | ESALFFIGVLIVALL | TU63 | 55.0 | n.d. | |

TABLE 5-continued

Summary of epitope characteristics
(SEQ ID No: 35 to 403 in order of appearance)

| Category | Rv# | Sequence | Donor | SFC | T cell phenotype | References |
|---|---|---|---|---|---|---|
| | Rv1453 | AHLIHFAAANLRNPG | TU23 | 30.0 | n.d. | |
| | Rv3143 | ALRILVYSDNVQTRE | TU63 | 91.7 | n.d. | |
| | Rv3173c | ALVEEYLRGLRQAAG | TU40 | 30.0 | n.d. | |
| Virulence, | Rv0350 | ADKNPLFLDEQLTRA | TU33 | 45.0 | n.d. | |
| detoxification | Rv0440 | AVLEDPYILLVSSKV | TU1 | 21.7 | n.d. | (23, 24) |
| adaptation | | MAKTIAYDEEARRGL | TU1 | 38.3 | n.d. | (16, 25, 26) |
| | | | TU25 | 56.7 | n.d. | |
| | Rv2031c | AYGSFVRTVSLPVGA | TU63 | 271.7 | CD4 | (27-30) |
| | | | TU75 | 45.0 | CD4 | |
| | Rv2865 | ETLYWLAQPGIRESI | TU26 | 31.7 | n.d. | |
| | Rv3418c | GEEYLILSARDVLAV | TU2 | 136.7 | CD4 | (31-34) |
| | | | TU22 | 60.0 | CD4 | |
| | | | TU40 | 145.0 | CD4 | |
| | | | TU81 | 151.7 | CD4 | |
| | | | TU23 | 45.0 | undetectable | |
| | | | TU82 | 53.3 | undetectable | |
| | Rv3497c | TGIFGLVLVICVVLI | TU40 | 35.0 | n.d. | |
| | Rv3500c | DVTIRFRRFFSRLQR | TU40 | 50.0 | n.d. | |
| | Rv3617 | APVVILAHGFPELAY | TU23 | 23.3 | n.d. | |
| | | QAFRSRFGENFFYIL | TU75 | 31.7 | n.d. | | n.d. indicates assay not done

REFERENCES

Aagaard, C., T. Hoang, J. Dietrich, P.-J. Cardona, A. Izzo, G. Dolganov, G. K. Schoolnik, J. P. Cassidy, R. Billeskov, and P. Andersen. 2011. A multistage tuberculosis vaccine that confers efficient protection before and after exposure. Nat Med 17:189-194.

Abdallah, A. M., N. C. Gey van Pittius, P. A. DiGiuseppe Champion, J. Cox, J. Luirink, C. M. J. E. Vandenbroucke-Grauls, B. J. Appelmelk, and W. Bitter. 2007. Type VII secretion—mycobacteria show the way. Nat Rev Micro 5:883-891.

Abel, B., M. Tameris, N. Mansoor, S. Gelderbloem, J. Hughes, D. Abrahams, L. Makhethe, M. Erasmus, M. d. Kock, L. van der Merwe, A. Hawkridge, A. Veldsman, M. Hatherill, G. Schirru, M. G. Pau, J. Hendriks, G. J. Weverling, J. Goudsmit, D. Sizemore, J. B. McClain, M. Goetz, J. Gearhart, H. Mahomed, G. D. Hussey, J. C. Sadoff, and W. A. Hanekom. 2010. The Novel Tuberculosis Vaccine, AERAS-402, Induces Robust and Polyfunctional CD4+ and CD8+ T Cells in Adults. Am. J. Respir. Crit. Care Med. 181:1407-1417.

Acosta-Rodriguez, E. V., L. Rivino, J. Geginat, D. Jarrossay, M. Gattorno, A. Lanzavecchia, F. Sallusto, and G. Napolitani. 2007. Surface phenotype and antigenic specificity of human interleukin 17-producing T helper memory cells. Nat. Immunol. 8:639-646.

Arlehamn, C. S., J. Sidney, R. Henderson, J. A. Greenbaum, E. A. James, M. Moutaftsi, R. Coler, D. M. McKinney, D. Park, R. Taplitz, W. W. Kwok, H. Grey, B. Peters, and A. Sette. 2012. Dissecting mechanisms of immunodominance to the common tuberculosis antigens ESAT-6, CFP10, Rv2031c (hspX), Rv2654c (TB7.7), and Rv1038c (EsxJ). J Immunol 188:5020-5031.

Baena, A., and S. A. Porcelli. 2009. Evasion and subversion of antigen presentation by *Mycobacterium tuberculosis*. Tissue Antigens 74:189-204.

Barnes, E., S. M. Ward, V. O. Kasprowicz, G. Dusheiko, P. Klenerman, and M. Lucas. 2004. Ultra-sensitive class I tetramer analysis reveals previously undetectable populations of antiviral CD8+ T cells. Eur J Immunol 34:1570-1577.

Barnes, P. F., A. B. Bloch, P. T. Davidson, and D. E. Snider, Jr. 1991. Tuberculosis in patients with human immunodeficiency virus infection. N Engl J Med 324:1644-1650.

Bertholet, S., G. C. Ireton, M. Kahn, J. Guderian, R. Mohamath, N. Stride, E. M. Laughlin, S. L. Baldwin, T. S. Vedvick, R. N. Coler, and S. G. Reed. 2008. Identification of Human T Cell Antigens for the Development of Vaccines against *Mycobacterium tuberculosis*. J Immunol 181:7948-7957.

Bertholet, S., G. C. Ireton, D. J. Ordway, H. P. Windish, S. O. Pine, M. Kahn, T. Phan, I. M. Orme, T. S. Vedvick, S. L. Baldwin, R. N. Coler, and S. G. Reed. 2010. A Defined Tuberculosis Vaccine Candidate Boosts BCG and Protects Against Multidrug-Resistant *Mycobacterium tuberculosis*. Sci. Transl. Med. 2:53ra74.

Beveridge, N. E., D. A. Price, J. P. Casazza, A. Pathan, C. R. Sander, T. E. Asher, D. R. Ambrozak, M. L. Precopio, P. Scheinberg, N. C. Alder, M. Roederer, R. A. Koup, D. C. Douek, A. V. Hill, and H. McShane. 2007. Immunisation with BCG and recombinant MVA85A induces long-lasting, polyfunctional *Mycobacterium tuberculosis*-specific CD4+ memory T lymphocyte populations. Eur J Immunol 37:3089-3100.

Blythe, M., Q. Zhang, K. Vaughan, R. de Castro, N. Salimi, H.-H. Bui, D. Lewinsohn, J. Ernst, B. Peters, and A. Sette. 2007. An analysis of the epitope knowledge related to Mycobacteria. Immunome Research 3:10.

Boesen, H., B. Jensen, T. Wilcke, and P. Andersen. 1995. Human T-cell responses to secreted antigen fractions of *Mycobacterium tuberculosis*. Infect. Immun. 63:1491-1497.

Chegou, N., G. Black, A. Loxton, K. Stanley, P. Essone, M. Klein, S. Parida, S. Kaufmann, T. M. Doherty, A. Friggen, K. Franken, T. Ottenhoff, and G. Walzl. 2012. Potential of novel *Mycobacterium tuberculosis* infection phase-dependent antigens in the diagnosis of TB disease in a high burden setting. BMC Infectious Diseases 12:10.

Cole, S., R. Brosch, J. Parkhill, T. Garnier, C. Churcher, D. Harris, S. Gordon, K. Eiglmeier, S. Gas, C. Barry, F. Tekaia, K. Badcock, D. Basham, D. Brown, T. Chillingworth, R. Connor, R. Davies, K. Devlin, T. Feltwell, S.

Gentles, N. Hamlin, S. Holroyd, T. Hornsby, K. Jagels, A. Krogh, J. McLean, S. Moule, L. Murphy, K. Oliver, J. Osborne, M. Quail, M. Rajandream, J. Rogers, S. Rutter, K. Seeger, J. Skelton, R. Squares, S. Squares, J. Sulston, K. Taylor, S. Whitehead, and B. Barrell. 1998. Deciphering the biology of *Mycobacterium tuberculosis* from the complete genome sequence. Nature 393:537-544.

Covert, B. A., J. S. Spencer, I. M. Orme, and J. T. Belisle. 2001. The application of proteomics in defining the T cell antigens of *Mycobacterium tuberculosis*. PROTEOMICS 1:574-586.

Day, Cheryl L., N. Mkhwanazi, S. Reddy, Z. Mncube, M. van der Stok, P. Klenerman, and Bruce D. Walker. 2008. Detection of Polyfunctional *Mycobacterium tuberculosis*—Specific T Cells and Association with Viral Load in HIV-1—Infected Persons. J Infect Dis 197:990-999.

Del Prete, G. F., M. De Carli, C. Mastromauro, R. Biagiotti, D. Macchia, P. Falagiani, M. Ricci, and S. Romagnani. 1991. Purified protein derivative of *Mycobacterium tuberculosis* and excretory-secretory antigen(s) of *Toxocara canis* expand in vitro human T cells with stable and opposite (type 1 T helper or type 2 T helper) profile of cytokine production. J Clin Invest 88:346-350.

Duhen, T., R. Geiger, D. Jarrossay, A. Lanzavecchia, and F. Sallusto. 2009. Production of interleukin 22 but not interleukin 17 by a subset of human skin-homing memory T cells. Nat Immunol 10:857-863.

Fortune, S., A. Jaeger, D. Sarracino, M. Chase, C. Sassetti, D. Sherman, B. Bloom, and E. Rubin. 2005. Mutually dependent secretion of proteins required for mycobacterialbvirulence. Proc Natl Acad Sci USA 102:10676-10681.

Garton, N. J., S. J. Waddell, A. L. Sherratt, S.-M. Lee, R. J. Smith, C. Senner, J. Hinds, K. Rajakumar, R. A. Adegbola, G. S. Besra, P. D. Butcher, and M. R. Barer. 2008. Cytological and Transcript Analyses Reveal Fat and Lazy Persister-Like Bacilli in Tuberculous Sputum. PLoS Med 5:e75.

Geiger, R., T. Duhen, A. Lanzavecchia, and F. Sallusto. 2009. Human naive and memory $CD4_+$ T cell repertoires specific for naturally processed antigens analyzed using libraries of amplified T cells. J Exp Med 206:1525-1534.

Gey van Pittius, N., J. Gamieldien, W. Hide, G. Brown, R. Siezen, and A. Beyers. 2001. The ESAT-6 gene cluster of *Mycobacterium tuberculosis* and other high G+C Grampositive bacteria. Genome Biology 2:research0044.0041-research0044.0018.

Gey van Pittius, N., S. Sampson, H. Lee, Y. Kim, P. van Helden, and R. Warren. 2006. Evolution and expansion of the *Mycobacterium tuberculosis* PE and PPE multigene families and their association with the duplication of the ESAT-6 (esx) gene cluster regions. BMC Evolutionary Biology 6:95.

Gideon, H. P., K. A. Wilkinson, T. R. Rustad, T. Oni, H. Guio, R. A. Kozak, D. R. Sherman, G. Meintjes, M. A. Behr, H. M. Vordermeier, D. B. Young, and R. J. Wilkinson. 2010. Hypoxia Induces an Immunodominant Target of Tuberculosis Specific T Cells Absent from Common BCG Vaccines. PLoS Pathog 6:e1001237.

Havlir, D. V., R. S. Wallis, W. H. Boom, T. M. Daniel, K. Chervenak, and J. J. Ellner. 1991. Human immune response to *Mycobacterium tuberculosis* antigens. Infect. Immun. 59:665-670.

Kaech, S. M., E. J. Wherry, and R. Ahmed. 2002. Effector and memory T-cell differentiation: implications for vaccine development. Nat Rev Immunol 2:251-262.

Kim, Y., K. Vaughan, J. Greenbaum, B. Peters, M. Law, and A. Sette. 2012. A Meta-Analysis of the Existing Knowledge of Immunoreactivity against Hepatitis C Virus (HCV). PLoS ONE 7:e38028.

Kunnath-Velayudhan, S., H. Salamon, H.-Y. Wang, A. L. Davidow, D. M. Molina, V. T. Huynh, D. M. Cirillo, G. Michel, E. A. Talbot, M. D. Perkins, P. L. Felgner, X. Liang, and M. L. Gennaro. 2010. Dynamic antibody responses to the *Mycobacterium tuberculosis* proteome. Proc Natl Acad Sci USA 107:14703-14708.

Lalvani, A., P. Nagvenkar, Z. Udwadia, A. A. Pathan, K. A. Wilkinson, J. S. Shastri, K. Ewer, A. V. S. Hill, A. Mehta, and C. Rodrigues. 2001. Enumeration of T Cells Specific for RD1-Encoded Antigens Suggests a High Prevalence of Latent *Mycobacterium tuberculosis* Infection in Healthy Urban Indians. J. Infect. Dis. 183:469-477.

Lew, J. M., A. Kapopoulou, L. M. Jones, and S. T. Cole. 2011. TubercuList—10 years after. Tuberculosis 91:1-7.

Leyten, E. M. S., M. Y. Lin, K. L. M. C. Franken, A. H. Friggen, C. Prins, K. E. van Meijgaarden, M. I. Voskuil, K. Weldingh, P. Andersen, G. K. Schoolnik, S. M. Arend, T. H. M. Ottenhoff, and M. R. Klein. 2006. Human T-cell responses to 25 novel antigens encoded by genes of the dormancy regulon of *Mycobacterium tuberculosis*. Microbes and Infection 8:2052-2060.

Maciąg, E. Dainese, G. M. Rodriguez, A. Milano, R. Provvedi, M. R. Pasca, I. Smith, G. Palù, G. Riccardi, and R. Manganelli. 2007. Global Analysis of the *Mycobacterium tuberculosis* Zur (FurB) Regulon. J Bacteriol 189:730-740.

MUlen, H., F. S. Berven, K. E. Fladmark, and H. G. Wiker. 2007. Comprehensive analysis of exported proteins from *Mycobacterium tuberculosis* H37Rv. PROTEOMICS 7:1702-1718.

Miao, E. A., D. P. Mao, N. Yudkovsky, R. Bonneau, C. G. Lorang, S. E. Warren, I. A. Leaf, and A. Aderem. 2010. Innate immune detection of the type III secretion apparatus through the NLRC4 inflammasome. Proc Natl Acad Sci USA 107:3076-3080.

Millington, K. A., S. M. Fortune, J. Low, A. Garces, S. M. Hingley-Wilson, M. Wickremasinghe, O. M. Kon, and A. Lalvani. 2011. Rv3615c is a highly immunodominant RD1 (Region of Difference 1)-dependent secreted antigen specific for *Mycobacterium tuberculosis* infection. Proc Natl Acad Sci USA Newport, M. J., C. M. Huxley, S. Huston, C. M. Hawrylowicz, B. A. Oostra, R. Williamson, and M. Levin. 1996. A Mutation in the Interferon-γ-Receptor Gene and Susceptibility to Mycobacterial Infection. N Engl J Med 335:1941-1949.

O'Shea, J. J., and W. E. Paul. 2010. Mechanisms underlying lineage commitment and plasticity of helper $CD4_+$ T cells. Science 327:1098-1102.

Okkels, L., and P. Andersen. 2004. Protein-protein interactions of proteins from the ESAT-6 family of *Mycobacterium tuberculosis*. J Bacteriol 186:2487-2491.

Oseroff, C., F. Kos, H. H. Bui, B. Peters, V. Pasquetto, J. Glenn, T. Palmore, J. Sidney, D. C. Tscharke, J. R. Bennink, S Southwood, H. M. Grey, J. W. Yewdell, and A. Sette. 2005. HLA class I-restricted responses to vaccinia recognize a broad array of proteins mainly involved in virulence and viral gene regulation. Proc Natl Acad Sci USA 102:13980-13985.

Oseroff, C., J. Sidney, M. F. Kotturi, R. Kolla, R. Alam, D. H. Broide, S. I. Wasserman, D. Weiskopf, D. M. McKinney, J. L. Chung, A. Petersen, H. Grey, B. Peters, and A.

Sette. 2010. Molecular determinants of T cell epitope recognition to the common Timothy grass allergen. J Immunol 185:943-955.

Pasquetto, V., H. H. Bui, R. Giannino, C. Banh, F. Mirza, J. Sidney, C. Oseroff, D. C. Tscharke, K. Irvine, J. R. Bennink, B. Peters, S. Southwood, V. Cerundolo, H. Grey, J. W. Yewdell, and A. Sette. 2005. HLA-A*0201, HLA-A*1101, and HLAB*0702 transgenic mice recognize numerous poxvirus determinants from a wide variety of viral gene products. J Immunol 175:5504-5515.

Pathan, A. A., A. M. Minassian, C. R. Sander, R. Rowland, D. W. Porter, I. D. Poulton, A. V. Hill, H. A. Fletcher, and H. McShane. 2012. Effect of vaccine dose on the safety and immunogenicity of a candidate TB vaccine, MVA85A, in BCG vaccinated UK adults. Vaccine 30:5616-5624.

Pathan, A. A., K. A. Wilkinson, P. Klenerman, H. McShane, R. N. Davidson, G. Pasvol, A. V. S. Hill, and A. Lalvani. 2001. Direct Ex Vivo Analysis of Antigen-Specific IFN-γ-Secreting CD4 T Cells in *Mycobacterium tuberculosis*-Infected Individuals: Associations with Clinical Disease State and Effect of Treatment. J Immunol 167:5217-5225.

Pheiffer, C., J. Betts, P. Lukey, and v. Helden Paul. 2002. Protein Expression in *Mycobacterium tuberculosis* Differs with Growth Stage and Strain Type. Clinical Chemistry and Laboratory Medicine 40:869.

Rodriguez, G., M. Voskuil, B. Gold, G. Schoolnik, and I. Smith. 2002. ideR, An essential gene in *Mycobacterium tuberculosis*: role of IdeR in iron-dependent gene expression, iron metabolism, and oxidative stress response. Infect Immun 70:3371-3381.

Rogerson, B. J., Y. J. Jung, R. LaCourse, L. Ryan, N. Enright, and R. J. North. 2006. Expression levels of *Mycobacterium tuberculosis* antigen-encoding genes versus production levels of antigen-specific T cells during stationary level lung infection in mice. Immunology 118:195-201.

Sallusto, F., and A. Lanzavecchia. 2009. Heterogeneity of CD4+ memory T cells: Functional modules for tailored immunity. Eur J Immunol 39:2076-2082.

Sallusto, F., D. Lenig, C. R. Mackay, and A. Lanzavecchia. 1998. Flexible programs of chemokine receptor expression on human polarized T helper 1 and 2 lymphocytes. J Exp Med 187:875-883.

Sampson, S. L. 2011. Mycobacterial PE/PPE Proteins at the Host-Pathogen Interface. Clinical and Developmental Immunology 2011:

Sani, M., E. N. G. Houben, J. Geurtsen, J. Pierson, K. de Punder, M. van Zon, B. Wever, S. R. Piersma, C. R. Jiménez, M. Daffé, B. J. Appelmelk, W. Bitter, N. van der Wel, and P. J. Peters. 2010. Direct Visualization by Cryo-EM of the Mycobacterial Capsular Layer: A Labile Structure Containing ESX-1-Secreted Proteins. PLoS Pathog 6:e1000794.

Sassetti, C. M., and E. J. Rubin. 2003. Genetic requirements for mycobacterial survival during infection. Proc Natl Acad Sci USA 100:12989-12994.

Schuck, S. D., H. Mueller, F. Kunitz, A. Neher, H. Hoffmann, K. L. C. M. Franken, D. Repsilber, T. H. M. Ottenhoff, S. H. E. Kaufmann, and M. Jacobsen. 2009. Identification of T-Cell Antigens Specific for Latent *Mycobacterium Tuberculosis* Infection. PLoS ONE 4:e5590.

Scriba, T. J., M. Tameris, N. Mansoor, E. Smit, L. van der Merwe, F. Isaacs, A. Keyser, S. Moyo, N. Brittain, A. Lawrie, S. Gelderbloem, A. Veldsman, M. Hatherill, A. Hawkridge, A. V. Hill, G. D. Hussey, H. Mahomed, H. McShane, and W. A. Hanekom. 2010. Modified vaccinia Ankara-expressing Ag85A, a novel tuberculosis vaccine, is safe in adolescents and children, and induces polyfunctional $CD4_+$ T cells. Eur J Immunol 40:279-290.

Simeone, R., D. Bottai, and R. Brosch. 2009. ESX/type VII secretion systems and their role in host-pathogen interaction. Curr Opinion Microbiol 12:4-10.

Skeiky, Y. A., J. Dietrich, T. M. Lasco, K. Stagliano, V. Dheenadhayalan, M. A. Goetz, L. Cantarero, R. J. Basaraba, P. Bang, I. Kromann, J. B. McMclain, J. C. Sadoff, and P. Andersen. 2010. Non-clinical efficacy and safety of HyVac4:IC31 vaccine administered in a BCG prime-boost regimen. Vaccine 28:1084-1093.

Skjot, R. L. V., T. Oettinger, I. Rosenkrands, P. Ravn, I. Brock, S. Jacobsen, and P. Andersen. 2000. Comparative Evaluation of Low-Molecular-Mass Proteins from *Mycobacterium tuberculosis* Identifies Members of the ESAT-6 Family as Immunodominant T-Cell Antigens. Infect. Immun. 68:214-220.

Sun, Y. H., H. G. Rolan, and R. M. Tsolis. 2007. Injection of flagellin into the host cell cytosol by *Salmonella enterica* serotype *Typhimurium*. J Biol Chem 282:33897-33901.

Sutherland, J. S., I. M. Adetifa, P. C. Hill, R. A. Adegbola, and M. O. C. Ota. 2009. Pattern and diversity of cytokine production differentiates between *Mycobacterium tuberculosis* infection and disease. Eur J Immunol 39:723-729.

Sweeney, K. A., D. N. Dao, M. F. Goldberg, T. Hsu, M. M. Venkataswamy, M. Henao-Tamayo, D. Ordway, R. S. Sellers, P. Jain, B. Chen, M. Chen, J. Kim, R. Lukose, J. Chan, I. M. Orme, S. A. Porcelli, and W. R. Jacobs. 2011. A recombinant *Mycobacterium smegmatis* induces potent bactericidal immunity against *Mycobacterium tuberculosis*. Nat Med 17:1261-1268.

van Dissel, J. T., D. Soonawala, S. A. Joosten, C. Prins, S. M. Arend, P. Bang, P. N. Tingskov, K. Lingnau, J. Nouta, S. T. Hoff, I. Rosenkrands, I. Kromann, T. H. Ottenhoff, T. M. Doherty, and P. Andersen. 2011. Ag85B-ESAT-6 adjuvanted with IC31(R) promotes strong and long-lived *Mycobacterium tuberculosis* specific T cell responses in volunteers with previous BCG vaccination or tuberculosis infection. Vaccine 29:2100-2109.

Von Eschen, K., R. Morrison, M. Braun, O. Ofori-Anyinam, E. De Kock, P. Pavithran, M. Koutsoukos, P. Moris, D. Cain, M. C. Dubois, J. Cohen, and W. R. Ballou. 2009. The candidate tuberculosis vaccine Mtb72F/AS02A: Tolerability and immunogenicity in humans. Hum Vaccin 5:475-482.

Wang, Y. H., K. S. Voo, B. Liu, C. Y. Chen, B. Uygungil, W. Spoede, J. A. Bernstein, D. P. Huston, and Y. J. Liu. 2010. A novel subset of CD4(+) T(H)2 memory/effector cells that produce inflammatory IL-17 cytokine and promote the exacerbation of chronic allergic asthma. J Exp Med 207:2479-2491.

What is claimed is:

1. A pharmaceutical composition comprising a peptide consisting of an amino acid sequence having a length of 15-50 residues which has a sequence therein that is identical to any of SEQ ID NOs 35-36, 42-57, 63-94, 97-395, 398-403 and 405, wherein the peptide, elicits, stimulates, induces, promotes, increases or enhances an anti-MTB immune response and a pharmaceutically acceptable adjuvant or excipient.

2. The pharmaceutical composition of claim 1,
further comprising one or more additional peptides consisting of an amino acid sequence having a length of 15-50 residues which has a sequence therein that is identical to any of SEQ ID NOs 35-36, 42-57, 63-94, 97-395, 398-403 and 405.

3. The pharmaceutical composition of claim 1, further comprising one or more additional peptides of SEQ ID Nos 35-405, or a subsequence, portion, or modification thereof, wherein the one or more additional peptides, subsequence, portion, or modification thereof elicit, stimulate, induce, promote, increase or enhance an anti-MTB immune response.

4. The pharmaceutical composition of claim 1, wherein the pharmaceutically acceptable adjuvant consists of an oil emulsion adjuvant.

5. The pharmaceutical composition of claim 1, further comprising an anti-microbial agent.

6. The pharmaceutical composition of claim 1, wherein the peptide further comprises a detectable label.

* * * * *

SEQUENCE LISTING

<160> NUMBER OF SEQ ID NOS: 405

<210> SEQ ID NO 1
<211> LENGTH: 367
<212> TYPE: PRT
<213> ORGANISM: Mycobacterium tuberculosis

<400> SEQUENCE: 1

```
Met Lys Val Leu Ala Ala Met Ser Gly Gly Val Asp Ser Ser Val Ala
1               5                   10                  15

Ala Ala Arg Met Val Asp Ala Gly His Glu Val Val Gly Val His Met
            20                  25                  30

Ala Leu Ser Thr Ala Pro Gly Thr Leu Arg Thr Gly Ser Arg Gly Cys
        35                  40                  45

Cys Ser Lys Glu Asp Ala Ala Asp Ala Arg Arg Val Ala Asp Val Leu
    50                  55                  60

Gly Ile Pro Phe Tyr Val Trp Asp Phe Ala Glu Lys Phe Lys Glu Asp
65                  70                  75                  80

Val Ile Asn Asp Phe Val Ser Ser Tyr Ala Arg Gly Glu Thr Pro Asn
                85                  90                  95

Pro Cys Val Arg Cys Asn Gln Gln Ile Lys Phe Ala Ala Leu Ser Ala
            100                 105                 110

Arg Ala Val Ala Leu Gly Phe Asp Thr Val Ala Thr Gly His Tyr Ala
        115                 120                 125

Arg Leu Ser Gly Gly Arg Leu Arg Arg Ala Val Asp Arg Asp Lys Asp
    130                 135                 140

Gln Ser Tyr Val Leu Ala Val Leu Thr Ala Gln Gln Leu Arg His Ala
145                 150                 155                 160

Ala Phe Pro Ile Gly Asp Thr Pro Lys Arg Gln Ile Arg Ala Glu Ala
                165                 170                 175

Ala Arg Arg Gly Leu Ala Val Ala Asn Lys Pro Asp Ser His Asp Ile
            180                 185                 190

Cys Phe Ile Pro Ser Gly Asn Thr Lys Ala Phe Leu Gly Glu Arg Ile
        195                 200                 205

Gly Val Arg Arg Gly Val Val Val Asp Ala Asp Gly Val Val Leu Ala
    210                 215                 220

Ser His Asp Gly Val His Gly Phe Thr Ile Gly Gln Arg Arg Gly Leu
225                 230                 235                 240

Gly Ile Ala Gly Pro Gly Pro Asn Gly Arg Pro Arg Tyr Val Thr Ala
                245                 250                 255

Ile Asp Ala Asp Thr Ala Thr Val His Val Gly Asp Val Thr Asp Leu
            260                 265                 270

Asp Val Gln Thr Leu Thr Gly Arg Ala Pro Val Phe Thr Ala Gly Ala
        275                 280                 285

Ala Pro Ser Gly Pro Val Asp Cys Val Val Gln Val Arg Ala His Gly
    290                 295                 300

Glu Thr Val Ser Ala Val Ala Glu Leu Ile Gly Asp Ala Leu Phe Val
305                 310                 315                 320

Gln Leu His Ala Pro Leu Arg Gly Val Ala Arg Gly Gln Thr Leu Val
                325                 330                 335

Leu Tyr Arg Pro Asp Pro Ala Gly Asp Glu Val Leu Gly Ser Ala Thr
            340                 345                 350

Ile Ala Gly Ala Ser Gly Leu Ser Thr Gly Gly Asn Pro Gly Ala
        355                 360                 365
```

<210> SEQ ID NO 2
<211> LENGTH: 295
<212> TYPE: PRT
<213> ORGANISM: Mycobacterium tuberculosis

<400> SEQUENCE: 2

Met Asp Ala Thr Pro Asn Ala Val Glu Leu Thr Val Asp Asn Ala Trp
1               5                   10                  15

Phe Ile Ala Glu Thr Ile Gly Ala Gly Thr Phe Pro Trp Val Leu Ala
            20                  25                  30

Ile Thr Met Pro Tyr Ser Asp Ala Ala Gln Arg Gly Ala Phe Val Asp
        35                  40                  45

Arg Gln Arg Asp Glu Leu Thr Arg Met Gly Leu Leu Ser Pro Gln Gly
    50                  55                  60

Val Ile Asn Pro Ala Val Ala Asp Trp Ile Lys Val Val Cys Phe Pro
65                  70                  75                  80

Asp Arg Trp Leu Asp Leu Arg Tyr Val Gly Pro Ala Ser Ala Asp Gly
                85                  90                  95

Ala Cys Glu Leu Leu Arg Gly Ile Val Ala Leu Arg Thr Gly Thr Gly
            100                 105                 110

Lys Thr Ser Asn Lys Thr Gly Asn Gly Val Val Ala Leu Arg Asn Ala
        115                 120                 125

Gln Leu Val Thr Phe Thr Ala Met Asp Ile Asp Pro Arg Ala Leu
    130                 135                 140

Val Pro Ile Leu Gly Val Gly Leu Ala His Arg Pro Ala Arg Phe
145                 150                 155                 160

Asp Glu Phe Ser Leu Pro Thr Arg Val Gly Ala Arg Ala Asp Glu Arg
                165                 170                 175

Leu Arg Ser Gly Val Pro Leu Gly Glu Val Val Asp Tyr Leu Gly Ile
            180                 185                 190

Pro Ala Ser Ala Arg Pro Val Val Glu Ser Val Phe Ser Gly Pro Arg
        195                 200                 205

Ser Tyr Val Glu Ile Val Ala Gly Cys Asn Arg Asp Gly Arg His Thr
    210                 215                 220

Thr Thr Glu Val Gly Leu Ser Ile Val Asp Thr Ser Ala Gly Arg Val
225                 230                 235                 240

Leu Val Ser Pro Ser Arg Ala Phe Asp Gly Glu Trp Val Ser Thr Phe
                245                 250                 255

Ser Pro Gly Thr Pro Phe Ala Ile Ala Val Ala Ile Gln Thr Leu Thr
            260                 265                 270

Ala Cys Leu Pro Asp Gly Gln Trp Phe Pro Gly Gln Arg Val Ser Arg
        275                 280                 285

Asp Phe Ser Thr Gln Ser Ser
    290                 295

<210> SEQ ID NO 3
<211> LENGTH: 472
<212> TYPE: PRT
<213> ORGANISM: Mycobacterium tuberculosis

<400> SEQUENCE: 3

Met Ser Gly Thr Val Met Gln Ile Val Arg Val Ala Ile Leu Ala Asp
1               5                   10                  15

Ser Arg Leu Thr Glu Met Ala Leu Pro Ala Glu Leu Pro Leu Arg Glu
            20                  25                  30

-continued

```
Ile Leu Pro Ala Val Gln Arg Leu Val Val Pro Ser Ala Gln Asn Gly
            35                  40                  45

Asp Gly Gly Gln Ala Asp Ser Gly Ala Ala Val Gln Leu Ser Leu Ala
 50                  55                  60

Pro Val Gly Gly Gln Pro Phe Ser Leu Asp Ala Ser Leu Asp Thr Val
 65                  70                  75                  80

Gly Val Val Asp Gly Asp Leu Leu Val Leu Gln Pro Val Pro Ala Gly
                    85                  90                  95

Pro Ala Ala Pro Gly Ile Val Glu Asp Ile Ala Asp Ala Ala Met Ile
                100                 105                 110

Phe Ser Thr Ser Arg Leu Lys Pro Trp Gly Ile Ala His Ile Gln Arg
            115                 120                 125

Gly Ala Leu Ala Ala Val Ile Ala Val Ala Leu Leu Ala Thr Gly Leu
130                 135                 140

Thr Val Thr Tyr Arg Val Ala Thr Gly Val Leu Ala Gly Leu Leu Ala
145                 150                 155                 160

Val Ala Gly Ile Ala Val Ala Ser Ala Leu Ala Gly Leu Leu Ile Thr
                    165                 170                 175

Ile Arg Ser Pro Arg Ser Gly Ile Ala Leu Ser Ile Ala Ala Leu Val
                180                 185                 190

Pro Ile Gly Ala Ala Leu Ala Leu Ala Val Pro Gly Lys Phe Gly Pro
            195                 200                 205

Ala Gln Val Leu Leu Gly Ala Ala Gly Val Ala Ala Trp Ser Leu Ile
            210                 215                 220

Ala Leu Met Ile Pro Ser Ala Glu Arg Glu Arg Val Val Ala Phe Phe
225                 230                 235                 240

Thr Ala Ala Ala Val Gly Ala Ser Val Leu Ala Ala Gly Ala
                    245                 250                 255

Gln Leu Leu Trp Gln Leu Pro Leu Leu Ser Ile Gly Cys Gly Leu Ile
            260                 265                 270

Val Ala Ala Leu Leu Val Thr Ile Gln Ala Ala Gln Leu Ser Ala Leu
            275                 280                 285

Trp Ala Arg Phe Pro Leu Pro Val Ile Pro Ala Pro Gly Asp Pro Thr
            290                 295                 300

Pro Ser Ala Pro Pro Leu Arg Leu Leu Glu Asp Leu Pro Arg Arg Val
305                 310                 315                 320

Arg Val Ser Asp Ala His Gln Ser Gly Phe Ile Ala Ala Ala Val Leu
                    325                 330                 335

Leu Ser Val Leu Gly Ser Val Ala Ile Ala Val Arg Pro Glu Ala Leu
                340                 345                 350

Ser Val Val Gly Trp Tyr Leu Val Ala Ala Thr Ala Ala Ala Thr
            355                 360                 365

Leu Arg Ala Arg Val Trp Asp Ser Ala Ala Cys Lys Ala Trp Leu Leu
            370                 375                 380

Ala Gln Pro Tyr Leu Val Ala Gly Val Leu Leu Val Phe Tyr Thr Ala
385                 390                 395                 400

Thr Gly Arg Tyr Val Ala Ala Phe Gly Ala Val Leu Val Leu Ala Val
                    405                 410                 415

Leu Met Leu Ala Trp Val Val Ala Leu Asn Pro Gly Ile Ala Ser
                420                 425                 430

Pro Glu Ser Tyr Ser Leu Pro Leu Arg Arg Leu Leu Gly Leu Val Ala
            435                 440                 445

Ala Gly Leu Asp Val Ser Leu Ile Pro Val Met Ala Tyr Leu Val Gly
```

```
                    450                 455                 460
Leu Phe Ala Trp Val Leu Asn Arg
465                 470

<210> SEQ ID NO 4
<211> LENGTH: 405
<212> TYPE: PRT
<213> ORGANISM: Mycobacterium tuberculosis

<400> SEQUENCE: 4

Met Ala Phe Leu Arg Ser Val Ser Cys Leu Ala Ala Val Phe Ala
1               5                   10                  15

Val Gly Thr Gly Ile Gly Leu Pro Thr Ala Ala Gly Glu Pro Asn Ala
                20                  25                  30

Ala Pro Ala Ala Cys Pro Tyr Lys Val Ser Thr Pro Pro Ala Val Asp
            35                  40                  45

Ser Ser Glu Val Pro Ala Ala Gly Glu Pro Pro Leu Pro Leu Val Val
        50                  55                  60

Pro Pro Thr Pro Val Gly Gly Asn Ala Leu Gly Gly Cys Gly Ile Ile
65                  70                  75                  80

Thr Ala Pro Gly Ser Ala Pro Ala Pro Gly Asp Val Ser Ala Glu Ala
                85                  90                  95

Trp Leu Val Ala Asp Leu Asp Ser Gly Ala Val Ile Ala Ala Arg Asp
            100                 105                 110

Pro His Gly Arg His Arg Pro Ala Ser Val Ile Lys Val Leu Val Ala
        115                 120                 125

Met Ala Ser Ile Asn Thr Thr Leu Asn Lys Ser Val Ala Gly Thr
            130                 135                 140

Ala Asp Asp Ala Ala Val Glu Gly Thr Lys Val Gly Val Asn Thr Gly
145                 150                 155                 160

Gly Thr Tyr Thr Val Asn Gln Leu Leu His Gly Leu Leu Met His Ser
                165                 170                 175

Gly Asn Asp Ala Ala Tyr Ala Leu Ala Arg Gln Leu Gly Gly Met Pro
            180                 185                 190

Ala Ala Leu Glu Lys Ile Asn Leu Leu Ala Ala Lys Leu Gly Gly Arg
        195                 200                 205

Asp Thr Arg Val Ala Thr Pro Ser Gly Leu Asp Gly Pro Gly Met Ser
    210                 215                 220

Thr Ser Ala Tyr Asp Ile Gly Leu Phe Tyr Arg Tyr Ala Trp Gln Asn
225                 230                 235                 240

Pro Val Phe Ala Asp Ile Val Ala Thr Arg Thr Phe Asp Phe Pro Gly
                245                 250                 255

His Gly Asp His Pro Gly Tyr Glu Leu Glu Asn Asp Asn Gln Leu Leu
            260                 265                 270

Tyr Asn Tyr Pro Gly Ala Leu Gly Gly Lys Thr Gly Tyr Thr Asp Asp
        275                 280                 285

Ala Gly Gln Thr Phe Val Gly Ala Ala Asn Arg Asp Gly Arg Arg Leu
    290                 295                 300

Met Thr Val Leu Leu His Gly Thr Arg Gln Pro Ile Pro Pro Trp Glu
305                 310                 315                 320

Gln Ala Ala His Leu Leu Asp Tyr Gly Phe Asn Thr Pro Ala Gly Thr
                325                 330                 335

Gln Ile Gly Thr Leu Ile Glu Pro Asp Pro Ser Leu Met Ser Thr Asp
            340                 345                 350
```

```
Arg Asn Pro Ala Asp Arg Gln Arg Val Asp Pro Gln Ala Ala Ala Arg
            355                 360                 365

Ile Ser Ala Ala Asp Ala Leu Pro Val Arg Val Gly Val Ala Val Ile
    370                 375                 380

Gly Ala Leu Ile Val Phe Gly Leu Ile Met Val Ala Arg Ala Met Asn
385                 390                 395                 400

Arg Arg Pro Gln His
                405
```

<210> SEQ ID NO 5
<211> LENGTH: 99
<212> TYPE: PRT
<213> ORGANISM: Mycobacterium tuberculosis

<400> SEQUENCE: 5

```
Met Ser Phe Val Thr Thr Gln Pro Glu Ala Leu Ala Ala Ala Ala Gly
1               5                   10                  15

Ser Leu Gln Gly Ile Gly Ser Ala Leu Asn Ala Gln Asn Ala Ala Ala
            20                  25                  30

Ala Thr Pro Thr Thr Gly Val Val Pro Ala Ala Ala Asp Glu Val Ser
        35                  40                  45

Ala Leu Thr Ala Ala Gln Phe Ala His Ala Gln Ile Tyr Gln Ala
    50                  55                  60

Val Ser Ala Gln Ala Ala Ala Ile His Glu Met Phe Val Asn Thr Leu
65                  70                  75                  80

Gln Met Ser Ser Gly Ser Tyr Ala Ala Thr Glu Ala Ala Asn Ala Ala
                85                  90                  95

Ala Ala Gly
```

<210> SEQ ID NO 6
<211> LENGTH: 99
<212> TYPE: PRT
<213> ORGANISM: Mycobacterium tuberculosis

<400> SEQUENCE: 6

```
Met Ser Phe Val Thr Thr Gln Pro Glu Ala Leu Ala Ala Ala Ala Ala
1               5                   10                  15

Asn Leu Gln Gly Ile Gly Thr Thr Met Asn Ala Gln Asn Ala Ala Ala
            20                  25                  30

Ala Ala Pro Thr Thr Gly Val Val Pro Ala Ala Ala Asp Glu Val Ser
        35                  40                  45

Ala Leu Thr Ala Ala Gln Phe Ala Ala His Ala Gln Met Tyr Gln Thr
    50                  55                  60

Val Ser Ala Gln Ala Ala Ala Ile His Glu Met Phe Val Asn Thr Leu
65                  70                  75                  80

Val Ala Ser Ser Gly Ser Tyr Ala Ala Thr Glu Ala Ala Asn Ala Ala
                85                  90                  95

Ala Ala Gly
```

<210> SEQ ID NO 7
<211> LENGTH: 391
<212> TYPE: PRT
<213> ORGANISM: Mycobacterium tuberculosis

<400> SEQUENCE: 7

```
Met Val Leu Gly Phe Ser Trp Leu Pro Pro Glu Ile Asn Ser Ala Arg
1               5                   10                  15
```

```
Met Phe Ala Gly Ala Gly Ser Gly Pro Leu Phe Ala Ala Ser Ala
             20                  25                  30

Trp Glu Gly Leu Ala Ala Asp Leu Trp Ala Ser Ala Ser Phe Glu
         35                  40                  45

Ser Val Leu Ala Ala Leu Thr Thr Gly Pro Trp Thr Gly Pro Ala Ser
 50                      55                  60

Met Ser Met Ala Ala Ala Ser Pro Tyr Val Gly Trp Leu Ser Thr
 65                  70                  75                  80

Val Ala Ser Gln Ala Gln Leu Ala Ala Ile Gln Ala Arg Ala Ala
                 85                  90                  95

Thr Ala Phe Glu Ala Ala Leu Ala Ala Thr Val His Pro Thr Ala Val
                100                 105                 110

Thr Ala Asn Arg Val Ser Leu Ala Ser Leu Ile Ala Ala Asn Val Leu
            115                 120                 125

Gly Gln Asn Thr Pro Ala Ile Ala Ala Thr Glu Phe Asp Tyr Leu Glu
        130                 135                 140

Met Trp Ala Gln Asp Val Ala Ala Met Val Gly Tyr His Ala Gly Ala
145                 150                 155                 160

Lys Ser Val Ala Ala Thr Leu Ala Pro Phe Ser Leu Pro Val Ser
                165                 170                 175

Leu Ala Gly Leu Ala Ala Gln Val Gly Thr Gln Val Ala Gly Met Ala
            180                 185                 190

Thr Thr Ala Ser Ala Ala Val Thr Pro Val Val Glu Gly Ala Met Ala
        195                 200                 205

Ser Val Pro Thr Val Met Ser Gly Met Gln Ser Leu Val Ser Gln Leu
    210                 215                 220

Pro Leu Gln His Ala Ser Met Leu Phe Leu Pro Val Arg Ile Leu Thr
225                 230                 235                 240

Ser Pro Ile Thr Thr Leu Ala Ser Met Ala Arg Glu Ser Ala Thr Arg
                245                 250                 255

Leu Gly Pro Pro Ala Gly Gly Leu Ala Ala Ala Asn Thr Pro Asn Pro
            260                 265                 270

Ser Gly Ala Ala Ile Pro Ala Phe Lys Pro Leu Gly Gly Arg Glu Leu
        275                 280                 285

Gly Ala Gly Met Ser Ala Gly Leu Gly Gln Ala Gln Leu Val Gly Ser
    290                 295                 300

Met Ser Val Pro Pro Thr Trp Gln Gly Ser Ile Pro Ile Ser Met Ala
305                 310                 315                 320

Ser Ser Ala Met Ser Gly Leu Gly Val Pro Pro Asn Pro Val Ala Leu
                325                 330                 335

Thr Gln Ala Ala Gly Ala Gly Gly Met Pro Met Met Leu Met
            340                 345                 350

Pro Met Ser Ile Ser Gly Ala Gly Ala Gly Met Pro Gly Gly Leu Met
        355                 360                 365

Asp Arg Asp Gly Ala Gly Trp His Val Thr Gln Ala Arg Leu Thr Val
    370                 375                 380

Ile Pro Arg Thr Gly Val Gly
385                 390

<210> SEQ ID NO 8
<211> LENGTH: 261
<212> TYPE: PRT
<213> ORGANISM: Mycobacterium tuberculosis

<400> SEQUENCE: 8
```

```
Met Trp Asp Pro Asp Val Tyr Leu Ala Phe Ser Gly His Arg Asn Arg
1               5                   10                  15

Pro Phe Tyr Glu Leu Val Ser Arg Val Gly Leu Glu Arg Ala Arg Arg
            20                  25                  30

Val Val Asp Leu Gly Cys Gly Pro Gly His Leu Thr Arg Tyr Leu Ala
        35                  40                  45

Arg Arg Trp Pro Gly Ala Val Ile Glu Ala Leu Asp Ser Ser Pro Glu
    50                  55                  60

Met Val Ala Ala Ala Glu Arg Gly Ile Asp Ala Thr Thr Gly Asp
65                  70                  75                  80

Leu Arg Asp Trp Lys Pro Lys Pro Asp Thr Asp Val Val Val Ser Asn
                85                  90                  95

Ala Ala Leu His Trp Val Pro Glu His Ser Asp Leu Leu Val Arg Trp
            100                 105                 110

Val Asp Glu Leu Ala Pro Gly Ser Trp Ile Ala Val Gln Ile Pro Gly
        115                 120                 125

Asn Phe Glu Thr Pro Ser His Ala Ala Val Arg Ala Leu Ala Arg Arg
    130                 135                 140

Glu Pro Tyr Ala Lys Leu Met Arg Asp Ile Pro Phe Arg Val Gly Ala
145                 150                 155                 160

Val Val Gln Ser Pro Ala Tyr Tyr Ala Glu Leu Leu Met Asp Thr Gly
                165                 170                 175

Cys Lys Val Asp Val Trp Glu Thr Thr Tyr Leu His Gln Leu Thr Gly
            180                 185                 190

Glu His Pro Val Leu Asp Trp Ile Thr Gly Ser Ala Leu Val Pro Val
        195                 200                 205

Arg Glu Arg Leu Ser Asp Glu Ser Trp Gln Gln Phe Arg Gln Glu Leu
    210                 215                 220

Ile Pro Leu Leu Asn Asp Ala Tyr Pro Pro Arg Ala Asp Gly Ser Thr
225                 230                 235                 240

Ile Phe Pro Phe Arg Arg Leu Phe Met Val Ala Glu Val Gly Gly Ala
                245                 250                 255

Arg Arg Ser Gly Gly
            260

<210> SEQ ID NO 9
<211> LENGTH: 695
<212> TYPE: PRT
<213> ORGANISM: Mycobacterium tuberculosis

<400> SEQUENCE: 9

Met Val Glu Ser Arg Arg Ala Ala Ala Ala Ser Ala Tyr Ala Ser
1               5                   10                  15

Arg Cys Gly Ile Ala Pro Ala Thr Ser Gln Arg Ser Leu Ala Thr Pro
            20                  25                  30

Pro Thr Ile Ser Val Pro Ser Gly Glu Gly Arg Cys Arg Cys His Val
        35                  40                  45

Ala Arg Gly Ala Gly Arg Asp Pro Arg Arg Leu Arg Arg Arg
    50                  55                  60

Trp Cys Gly Arg Cys Gly Tyr His Ser His Leu Thr Gly Gly Glu Phe
65                  70                  75                  80

Asp Val Asn Arg Leu Cys Gln Gln Arg Ser Arg Glu Arg Ser Cys Gln
                85                  90                  95

Leu Val Ala Val Pro Ala Asp Pro Arg Pro Lys Arg Gln Arg Ile Thr
```

-continued

```
            100                 105                 110
Asp Val Leu Thr Leu Ala Leu Val Gly Phe Leu Gly Leu Ile Thr
            115                 120                 125
Gly Ile Ser Pro Cys Ile Leu Pro Val Leu Pro Val Ile Phe Phe Ser
            130                 135             140
Gly Ala Gln Ser Val Asp Ala Ala Gln Val Ala Lys Pro Glu Gly Ala
145                 150                 155                 160
Val Ala Val Arg Arg Lys Arg Ala Leu Ser Ala Thr Leu Arg Pro Tyr
                165                 170                 175
Arg Val Ile Gly Gly Leu Val Leu Ser Phe Gly Met Val Thr Leu Leu
            180                 185                 190
Gly Ser Ala Leu Leu Ser Val Leu His Leu Pro Gln Asp Ala Ile Arg
            195                 200                 205
Trp Ala Ala Leu Val Ala Leu Val Ala Ile Gly Ala Gly Leu Ile Phe
            210                 215                 220
Pro Arg Phe Glu Gln Leu Leu Glu Lys Pro Phe Ser Arg Ile Pro Gln
225                 230                 235                 240
Lys Gln Ile Val Thr Arg Ser Asn Gly Phe Gly Leu Gly Leu Ala Leu
                245                 250                 255
Gly Val Leu Tyr Val Pro Cys Ala Gly Pro Ile Leu Ala Ala Ile Val
            260                 265                 270
Val Ala Gly Ala Thr Ala Thr Ile Gly Leu Gly Thr Val Val Leu Thr
            275                 280                 285
Ala Thr Phe Ala Leu Gly Ala Ala Leu Pro Leu Leu Phe Phe Ala Leu
            290                 295                 300
Ala Gly Gln Arg Ile Ala Glu Arg Val Gly Ala Phe Arg Arg Arg Gln
305                 310                 315                 320
Arg Glu Ile Arg Ile Ala Thr Gly Ser Val Thr Ile Leu Leu Ala Val
                325                 330                 335
Ala Leu Val Phe Asp Leu Pro Ala Ala Leu Gln Arg Ala Ile Pro Asp
            340                 345                 350
Tyr Thr Ala Ser Leu Gln Gln Gln Ile Ser Thr Gly Thr Glu Ile Arg
            355                 360                 365
Glu Gln Leu Asn Leu Gly Gly Ile Val Asn Ala Gln Asn Ala Gln Leu
            370                 375                 380
Ser Asn Cys Ser Asp Gly Ala Ala Gln Leu Glu Ser Cys Gly Thr Ala
385                 390                 395                 400
Pro Asp Leu Lys Gly Ile Thr Gly Trp Leu Asn Thr Pro Gly Asn Lys
                405                 410                 415
Pro Ile Asp Leu Lys Ser Leu Arg Gly Lys Val Val Leu Ile Asp Phe
            420                 425                 430
Trp Ala Tyr Ser Cys Ile Asn Cys Gln Arg Ala Ile Pro His Val Val
            435                 440                 445
Gly Trp Tyr Gln Ala Tyr Lys Asp Ser Gly Leu Ala Val Ile Gly Val
            450                 455                 460
His Thr Pro Glu Tyr Ala Phe Glu Lys Val Pro Gly Asn Val Ala Lys
465                 470                 475                 480
Gly Ala Ala Asn Leu Gly Ile Ser Tyr Pro Ile Ala Leu Asp Asn Asn
                485                 490                 495
Tyr Ala Thr Trp Thr Asn Tyr Arg Asn Arg Tyr Trp Pro Ala Glu Tyr
            500                 505                 510
Leu Ile Asp Ala Thr Gly Thr Val Arg His Ile Lys Phe Gly Glu Gly
            515                 520                 525
```

-continued

Asp Tyr Asn Val Thr Glu Thr Leu Val Arg Gln Leu Leu Asn Asp Ala
            530                 535                 540
Lys Pro Gly Val Lys Leu Pro Gln Pro Ser Ser Thr Thr Thr Pro Asp
545                 550                 555                 560
Leu Thr Pro Arg Ala Ala Leu Thr Pro Glu Thr Tyr Phe Gly Val Gly
            565                 570                 575
Lys Val Val Asn Tyr Gly Gly Gly Ala Tyr Asp Glu Gly Ser Ala
            580                 585                 590
Val Phe Asp Tyr Pro Pro Ser Leu Ala Ala Asn Ser Phe Ala Leu Arg
            595                 600                 605
Gly Arg Trp Ala Leu Asp Tyr Gln Gly Ala Thr Ser Asp Gly Asn Asp
            610                 615                 620
Ala Ala Ile Lys Leu Asn Tyr His Ala Lys Asp Val Tyr Ile Val Val
625                 630                 635                 640
Gly Gly Thr Gly Thr Leu Thr Val Val Arg Asp Gly Lys Pro Ala Thr
            645                 650                 655
Leu Pro Ile Ser Gly Pro Pro Thr Thr His Gln Val Val Ala Gly Tyr
            660                 665                 670
Arg Leu Ala Ser Glu Thr Leu Glu Val Arg Pro Ser Lys Gly Leu Gln
            675                 680                 685
Val Phe Ser Phe Thr Tyr Gly
            690                 695

<210> SEQ ID NO 10
<211> LENGTH: 81
<212> TYPE: PRT
<213> ORGANISM: Mycobacterium tuberculosis

<400> SEQUENCE: 10

Val Thr Ala Pro Val Trp Leu Ala Ser Pro Pro Glu Val His Ser Ala
1               5                   10                  15
Leu Leu Ser Ala Gly Pro Gly Pro Gly Ser Leu Gln Ala Ala Ala Ala
            20                  25                  30
Gly Trp Ser Ala Leu Ser Ala Glu Tyr Ala Ala Val Ala Gln Glu Leu
            35                  40                  45
Ser Val Val Ala Ala Val Gly Ala Gly Val Trp Gln Gly Pro Ser
            50                  55                  60
Ala Glu Leu Phe Val Ala Ala Tyr Val Pro Tyr Val Ala Trp Leu Val
65                  70                  75                  80
Gln

<210> SEQ ID NO 11
<211> LENGTH: 391
<212> TYPE: PRT
<213> ORGANISM: Mycobacterium tuberculosis

<400> SEQUENCE: 11

Met Val Leu Gly Phe Ser Trp Leu Pro Pro Glu Ile Asn Ser Ala Arg
1               5                   10                  15
Met Phe Ala Gly Ala Gly Ser Gly Pro Leu Phe Ala Ala Ala Ser Ala
            20                  25                  30
Trp Glu Gly Leu Ala Ala Asp Leu Trp Ala Ser Ala Ser Ser Phe Glu
            35                  40                  45
Ser Val Leu Ala Ala Leu Thr Thr Gly Pro Trp Thr Gly Pro Ala Ser
            50                  55                  60

```
Met Ser Met Ala Ala Ala Ser Pro Tyr Val Gly Trp Leu Ser Thr
 65                  70                  75                  80

Val Ala Ser Gln Ala Gln Leu Ala Ala Ile Gln Ala Arg Ala Ala Ala
                 85                  90                  95

Thr Ala Phe Glu Ala Ala Leu Ala Ala Thr Val His Pro Thr Ala Val
            100                 105                 110

Thr Ala Asn Arg Val Ser Leu Ala Ser Leu Ile Ala Ala Asn Val Leu
        115                 120                 125

Gly Gln Asn Thr Pro Ala Ile Ala Ala Thr Glu Phe Asp Tyr Leu Glu
    130                 135                 140

Met Trp Ala Gln Asp Val Ala Ala Met Val Gly Tyr His Ala Gly Ala
145                 150                 155                 160

Lys Ser Val Ala Ala Thr Leu Ala Pro Phe Ser Leu Pro Pro Val Ser
                165                 170                 175

Leu Ala Gly Leu Ala Ala Gln Val Gly Thr Gln Val Ala Gly Met Ala
            180                 185                 190

Thr Thr Ala Ser Ala Ala Val Thr Pro Val Val Glu Gly Ala Met Ala
        195                 200                 205

Ser Val Pro Thr Val Met Ser Gly Met Gln Ser Leu Val Ser Gln Leu
    210                 215                 220

Pro Leu Gln His Ala Ser Met Leu Phe Leu Pro Val Arg Ile Leu Thr
225                 230                 235                 240

Ser Pro Ile Thr Thr Leu Ala Ser Met Ala Arg Glu Ser Ala Thr Arg
                245                 250                 255

Leu Gly Pro Pro Ala Gly Gly Leu Ala Ala Ala Asn Thr Pro Asn Pro
            260                 265                 270

Ser Gly Ala Ala Ile Pro Ala Phe Lys Pro Leu Gly Gly Arg Glu Leu
        275                 280                 285

Gly Ala Gly Met Ser Ala Gly Leu Gly Gln Ala Gln Leu Val Gly Ser
    290                 295                 300

Met Ser Val Pro Pro Thr Trp Gln Gly Ser Ile Pro Ile Ser Met Ala
305                 310                 315                 320

Ser Ser Ala Met Ser Gly Leu Gly Val Pro Pro Asn Pro Val Ala Leu
                325                 330                 335

Thr Gln Ala Ala Gly Ala Ala Gly Gly Met Pro Met Met Leu Met
            340                 345                 350

Pro Met Ser Ile Ser Gly Ala Gly Ala Gly Met Pro Gly Gly Leu Met
            355                 360                 365

Asp Arg Asp Gly Ala Gly Trp His Val Thr Gln Ala Arg Leu Thr Val
    370                 375                 380

Ile Pro Arg Thr Gly Val Gly
385                 390

<210> SEQ ID NO 12
<211> LENGTH: 666
<212> TYPE: PRT
<213> ORGANISM: Mycobacterium tuberculosis

<400> SEQUENCE: 12

Met Ala Ala Asp Tyr Asp Lys Leu Phe Arg Pro His Glu Gly Met Glu
1               5                   10                  15

Ala Pro Asp Asp Met Ala Ala Gln Pro Phe Phe Asp Pro Ser Ala Ser
            20                  25                  30

Phe Pro Pro Ala Pro Ala Ser Ala Asn Leu Pro Lys Pro Asn Gly Gln
        35                  40                  45
```

```
Thr Pro Pro Pro Thr Ser Asp Asp Leu Ser Glu Arg Phe Val Ser Ala
    50              55                  60
Pro Pro Pro Pro Pro Pro Pro Pro Pro Pro Pro Thr Pro Met
65              70                  75                  80
Pro Ile Ala Ala Gly Glu Pro Pro Ser Pro Glu Pro Ala Ala Ser Lys
                85                  90                  95
Pro Pro Thr Pro Pro Met Pro Ile Ala Gly Pro Glu Pro Ala Pro Pro
            100                 105                 110
Lys Pro Pro Thr Pro Pro Met Pro Ile Ala Gly Pro Glu Pro Ala Pro
        115                 120                 125
Pro Lys Pro Pro Thr Pro Pro Met Pro Ile Ala Gly Pro Ala Pro Thr
    130                 135                 140
Pro Thr Glu Ser Gln Leu Ala Pro Pro Arg Pro Pro Thr Pro Gln Thr
145                 150                 155                 160
Pro Thr Gly Ala Pro Gln Gln Pro Glu Ser Pro Ala Pro His Val Pro
                165                 170                 175
Ser His Gly Pro His Gln Pro Arg Arg Thr Ala Pro Ala Pro Pro Trp
            180                 185                 190
Ala Lys Met Pro Ile Gly Glu Pro Pro Ala Pro Ser Arg Pro Ser
        195                 200                 205
Ala Ser Pro Ala Glu Pro Pro Thr Arg Pro Ala Pro Gln His Ser Arg
    210                 215                 220
Arg Ala Arg Arg Gly His Arg Tyr Arg Thr Asp Thr Glu Arg Asn Val
225                 230                 235                 240
Gly Lys Val Ala Thr Gly Pro Ser Ile Gln Ala Arg Leu Arg Ala Glu
                245                 250                 255
Glu Ala Ser Gly Ala Gln Leu Ala Pro Gly Thr Glu Pro Ser Pro Ala
            260                 265                 270
Pro Leu Gly Gln Pro Arg Ser Tyr Leu Ala Pro Pro Thr Arg Pro Ala
        275                 280                 285
Pro Thr Glu Pro Pro Pro Ser Pro Ser Pro Gln Arg Asn Ser Gly Arg
    290                 295                 300
Arg Ala Glu Arg Arg Val His Pro Asp Leu Ala Ala Gln His Ala Ala
305                 310                 315                 320
Ala Gln Pro Asp Ser Ile Thr Ala Ala Thr Thr Gly Arg Arg
                325                 330                 335
Lys Arg Ala Ala Pro Asp Leu Asp Ala Thr Gln Lys Ser Leu Arg Pro
            340                 345                 350
Ala Ala Lys Gly Pro Lys Val Lys Val Lys Pro Gln Lys Pro Lys
        355                 360                 365
Ala Thr Lys Pro Pro Lys Val Val Ser Gln Arg Gly Trp Arg His Trp
    370                 375                 380
Val His Ala Leu Thr Arg Ile Asn Leu Gly Leu Ser Pro Asp Glu Lys
385                 390                 395                 400
Tyr Glu Leu Asp Leu His Ala Arg Val Arg Arg Asn Pro Arg Gly Ser
                405                 410                 415
Tyr Gln Ile Ala Val Val Gly Leu Lys Gly Gly Ala Gly Lys Thr Thr
            420                 425                 430
Leu Thr Ala Ala Leu Gly Ser Thr Leu Ala Gln Val Arg Ala Asp Arg
        435                 440                 445
Ile Leu Ala Leu Asp Ala Asp Pro Gly Ala Gly Asn Leu Ala Asp Arg
    450                 455                 460
```

```
Val Gly Arg Gln Ser Gly Ala Thr Ile Ala Asp Val Leu Ala Glu Lys
465                 470                 475                 480

Glu Leu Ser His Tyr Asn Asp Ile Arg Ala His Thr Ser Val Asn Ala
            485                 490                 495

Val Asn Leu Glu Val Leu Pro Ala Pro Glu Tyr Ser Ser Ala Gln Arg
        500                 505                 510

Ala Leu Ser Asp Ala Asp Trp His Phe Ile Ala Asp Pro Ala Ser Arg
    515                 520                 525

Phe Tyr Asn Leu Val Leu Ala Asp Cys Gly Ala Gly Phe Phe Asp Pro
530                 535                 540

Leu Thr Arg Gly Val Leu Ser Thr Val Ser Gly Val Val Val Val Ala
545                 550                 555                 560

Ser Val Ser Ile Asp Gly Ala Gln Gln Ala Ser Val Ala Leu Asp Trp
                565                 570                 575

Leu Arg Asn Asn Gly Tyr Gln Asp Leu Ala Ser Arg Ala Cys Val Val
            580                 585                 590

Ile Asn His Ile Met Pro Gly Glu Pro Asn Val Ala Val Lys Asp Leu
        595                 600                 605

Val Arg His Phe Glu Gln Gln Val Gln Pro Gly Arg Val Val Val Met
    610                 615                 620

Pro Trp Asp Arg His Ile Ala Ala Gly Thr Glu Ile Ser Leu Asp Leu
625                 630                 635                 640

Leu Asp Pro Ile Tyr Lys Arg Lys Val Leu Glu Leu Ala Ala Ala Leu
                645                 650                 655

Ser Asp Asp Phe Glu Arg Ala Gly Arg Arg
            660                 665

<210> SEQ ID NO 13
<211> LENGTH: 486
<212> TYPE: PRT
<213> ORGANISM: Mycobacterium tuberculosis

<400> SEQUENCE: 13

Met Ser Phe Val Ser Val Ala Pro Glu Ile Val Val Ala Ala Ala Thr
1               5                   10                  15

Asp Leu Ala Gly Ile Gly Ser Ala Ile Ser Ala Ala Asn Ala Ala Ala
            20                  25                  30

Ala Ala Pro Thr Thr Ala Val Leu Ala Ala Gly Ala Asp Glu Val Ser
        35                  40                  45

Ala Ala Ile Ala Ala Leu Ser Gly His Ala Gln Ala Tyr Gln Ala Leu
    50                  55                  60

Ser Ala Gln Ala Ala Ala Phe His Gln Gln Phe Val Gln Thr Leu Ala
65                  70                  75                  80

Gly Gly Ala Gly Ala Tyr Ala Ala Ala Glu Ala Gln Val Glu Gln Gln
                85                  90                  95

Leu Leu Ala Ala Ile Asn Ala Pro Thr Gln Ala Leu Leu Gly Arg Pro
            100                 105                 110

Leu Ile Gly Asn Gly Ala Asp Gly Ala Pro Gly Thr Gly Gln Ala Gly
        115                 120                 125

Gly Ala Gly Gly Ile Leu Tyr Gly Asn Gly Gly Asn Gly Gly Ser Gly
    130                 135                 140

Ala Ala Gly Gln Ala Gly Gly Ala Gly Gly Pro Ala Gly Leu Ile Gly
145                 150                 155                 160

His Gly Gly Ser Gly Gly Ala Gly Gly Ser Gly Ala Ala Gly Gly Ala
                165                 170                 175
```

```
Gly Gly His Gly Gly Trp Leu Trp Gly Asn Gly Gly Val Gly Gly Ser
            180                 185                 190

Gly Gly Ala Gly Val Gly Ala Gly Val Ala Gly Gly His Gly Gly Ala
        195                 200                 205

Gly Gly Ala Ala Gly Leu Trp Gly Ala Gly Gly Gly Gly Asn Gly
    210                 215                 220

Gly Asn Gly Ala Asp Ala Asn Ile Val Ser Gly Gly Asp Gly Gly Leu
225                 230                 235                 240

Gly Gly Ala Gly Gly Gly Gly Trp Leu Tyr Gly Asp Gly Ala
                245                 250                 255

Gly Gly His Gly Gly Gln Gly Ala Ile Gly Leu Gly Gly Ala Gly
            260                 265                 270

Gly Asp Gly Gly Gln Gly Gly Ala Gly Arg Gly Leu Trp Gly Thr Gly
        275                 280                 285

Gly Ala Gly Gly His Gly Gly Gln Gly Gly Thr Gly Gly Pro Pro
    290                 295                 300

Leu Pro Gly Gln Ala Gly Met Gly Ala Ala Gly Gly Ala Gly Gly Leu
305                 310                 315                 320

Ile Gly Asn Gly Gly Ala Gly Gly Asp Gly Gly Val Gly Ala Ser Gly
                325                 330                 335

Gly Val Ala Gly Val Gly Gly Ala Gly Gly Asn Ala Met Leu Ile Gly
            340                 345                 350

His Gly Gly Ala Gly Gly Ala Gly Gly Asp Ser Ser Phe Ala Asn Gly
        355                 360                 365

Ala Ala Gly Gly Ala Gly Gly Ala Gly Gly His Leu Phe Gly Asn Gly
    370                 375                 380

Gly Ser Gly Gly His Gly Gly Ala Val Thr Ala Gly Asn Thr Gly Ile
385                 390                 395                 400

Gly Gly Ala Gly Gly Val Gly Gly Asp Ala Arg Leu Ile Gly His Gly
                405                 410                 415

Gly Ala Gly Gly Ala Gly Gly Asp Arg Ala Gly Ala Leu Val Gly Arg
            420                 425                 430

Asp Gly Gly Pro Gly Gly Asn Gly Gly Ala Gly Gly Gln Leu Tyr Gly
        435                 440                 445

Asn Gly Gly Asp Gly Ala Pro Gly Thr Gly Gly Thr Leu Gln Ala Ala
    450                 455                 460

Val Ser Gly Leu Val Thr Ala Leu Phe Gly Ala Pro Gly Gln Pro Gly
465                 470                 475                 480

Asp Thr Gly Gln Pro Gly
                485

<210> SEQ ID NO 14
<211> LENGTH: 461
<212> TYPE: PRT
<213> ORGANISM: Mycobacterium tuberculosis

<400> SEQUENCE: 14

Met Ile Arg Ala Ala Phe Ala Cys Leu Ala Ala Thr Val Val Ala
1               5                   10                  15

Gly Trp Trp Thr Pro Pro Ala Trp Ala Ile Gly Pro Pro Val Val Asp
                20                  25                  30

Ala Ala Ala Gln Pro Pro Ser Gly Asp Pro Gly Pro Val Ala Pro Met
            35                  40                  45

Glu Gln Arg Gly Ala Cys Ser Val Ser Gly Val Ile Pro Gly Thr Asp
```

```
                50                  55                  60
Ala Gly Val Pro Thr Pro Ser Gln Thr Met Leu Asn Leu Pro Ala Ala
 65                  70                  75                  80

Trp Gln Phe Ser Arg Gly Glu Gly Gln Leu Val Ala Ile Ile Asp Thr
                     85                  90                  95

Gly Val Gln Pro Gly Pro Arg Leu Pro Asn Val Asp Ala Gly Gly Asp
                100                 105                 110

Phe Val Glu Ser Thr Asp Gly Leu Thr Asp Cys Asp Gly His Gly Thr
                115                 120                 125

Leu Val Ala Gly Ile Val Ala Gly Gln Pro Gly Asn Asp Gly Phe Ser
130                 135                 140

Gly Val Ala Pro Ala Ala Arg Leu Leu Ser Ile Arg Ala Met Ser Thr
145                 150                 155                 160

Lys Phe Ser Pro Arg Thr Ser Gly Gly Asp Pro Gln Leu Ala Gln Ala
                165                 170                 175

Thr Leu Asp Val Ala Val Leu Ala Gly Ala Ile Val His Ala Ala Asp
                180                 185                 190

Leu Gly Ala Lys Val Ile Asn Val Ser Thr Ile Thr Cys Leu Pro Ala
                195                 200                 205

Asp Arg Met Val Asp Gln Ala Ala Leu Gly Ala Ala Ile Arg Tyr Ala
210                 215                 220

Ala Val Asp Lys Asp Ala Val Ile Val Ala Ala Gly Asn Thr Gly
225                 230                 235                 240

Ala Ser Gly Ser Val Ser Ala Ser Cys Asp Ser Asn Pro Leu Thr Asp
                245                 250                 255

Leu Ser Arg Pro Asp Asp Pro Arg Asn Trp Ala Gly Val Thr Ser Val
                260                 265                 270

Ser Ile Pro Ser Trp Trp Gln Pro Tyr Val Leu Ser Val Ala Ser Leu
                275                 280                 285

Thr Ser Ala Gly Gln Pro Ser Lys Phe Ser Met Pro Gly Pro Trp Val
                290                 295                 300

Gly Ile Ala Ala Pro Gly Glu Asn Ile Ala Ser Val Ser Asn Ser Gly
305                 310                 315                 320

Asp Gly Ala Leu Ala Asn Gly Leu Pro Asp Ala His Gln Lys Leu Val
                325                 330                 335

Ala Leu Ser Gly Thr Ser Tyr Ala Ala Gly Tyr Val Ser Gly Val Ala
                340                 345                 350

Ala Leu Val Arg Ser Arg Tyr Pro Gly Leu Asn Ala Thr Glu Val Val
                355                 360                 365

Arg Arg Leu Thr Ala Thr Ala His Arg Gly Ala Arg Glu Ser Ser Asn
370                 375                 380

Ile Val Gly Ala Gly Asn Leu Asp Ala Val Ala Ala Leu Thr Trp Gln
385                 390                 395                 400

Leu Pro Ala Glu Pro Gly Gly Ala Ala Pro Ala Lys Pro Val Ala
                405                 410                 415

Asp Pro Pro Val Pro Ala Pro Lys Asp Thr Thr Pro Arg Asn Val Ala
                420                 425                 430

Phe Ala Gly Ala Ala Leu Ser Val Leu Val Gly Leu Thr Ala Ala
                435                 440                 445

Thr Val Ala Ile Ala Arg Arg Arg Glu Pro Thr Glu
450                 455                 460
```

<210> SEQ ID NO 15

-continued

<211> LENGTH: 331
<212> TYPE: PRT
<213> ORGANISM: Mycobacterium tuberculosis

<400> SEQUENCE: 15

Met Asn Pro Ile Pro Ser Trp Pro Gly Arg Gly Arg Val Thr Leu Val
1               5                   10                  15

Leu Leu Ala Val Val Pro Val Ala Leu Ala Tyr Pro Trp Gln Ser Thr
            20                  25                  30

Arg Asp Tyr Val Leu Leu Gly Val Ala Ala Val Val Ile Gly Leu
        35                  40                  45

Phe Gly Phe Trp Arg Gly Leu Tyr Phe Thr Thr Ile Ala Arg Arg Gly
50                  55                  60

Leu Ala Ile Leu Arg Arg Arg Arg Ile Ala Glu Pro Ala Thr Cys
65                  70                  75                  80

Thr Arg Thr Thr Val Leu Val Trp Val Gly Pro Pro Ala Ser Asp Thr
                85                  90                  95

Asn Val Leu Pro Leu Thr Leu Ile Ala Arg Tyr Leu Asp Arg Tyr Gly
            100                 105                 110

Ile Arg Ala Asp Thr Ile Arg Ile Thr Ser Arg Val Thr Ala Ser Gly
        115                 120                 125

Asp Cys Arg Thr Trp Val Gly Leu Thr Val Val Ala Asp Asp Asn Leu
130                 135                 140

Ala Ala Leu Gln Ala Arg Ser Ala Arg Ile Pro Leu Gln Glu Thr Ala
145                 150                 155                 160

Gln Val Ala Ala Arg Leu Ala Asp His Leu Arg Glu Ile Gly Trp
                165                 170                 175

Glu Ala Gly Thr Ala Ala Pro Asp Glu Ile Pro Ala Leu Val Ala Ala
            180                 185                 190

Asp Ser Arg Glu Thr Trp Arg Gly Met Arg His Thr Asp Ser Asp Tyr
        195                 200                 205

Val Ala Ala Tyr Arg Val Ser Ala Asn Ala Glu Leu Pro Asp Thr Leu
210                 215                 220

Pro Ala Ile Arg Ser Arg Pro Ala Gln Glu Thr Trp Ile Ala Leu Glu
225                 230                 235                 240

Ile Ala Tyr Ala Ala Gly Ser Ser Thr Arg Tyr Thr Val Ala Ala Ala
                245                 250                 255

Cys Ala Leu Arg Thr Asp Trp Arg Pro Gly Gly Thr Ala Pro Val Ala
            260                 265                 270

Gly Leu Leu Pro Gln His Gly Asn His Val Pro Ala Leu Thr Ala Leu
        275                 280                 285

Asp Pro Arg Ser Thr Arg Arg Leu Asp Gly His Thr Asp Ala Pro Ala
290                 295                 300

Asp Leu Leu Thr Arg Leu His Trp Pro Thr Pro Thr Ala Gly Ala His
305                 310                 315                 320

Arg Ala Pro Leu Thr Asn Ala Val Ser Arg Thr
                325                 330

<210> SEQ ID NO 16
<211> LENGTH: 400
<212> TYPE: PRT
<213> ORGANISM: Mycobacterium tuberculosis

<400> SEQUENCE: 16

Met Ser Gly Thr Phe Thr Ala Asp Ala Ile Gly Pro Pro Val Pro Ile
1               5                   10                  15

Pro Asp Val Pro Gly Ala Asp Ala Glu Gly Leu Pro Ser Arg
            20                  25                  30

Ser Val Leu Ser Ala Arg Gln Arg Ile Leu Val Glu Ser Ala Ile
        35                  40                  45

Ala Asp Val Ala Leu Arg Thr Ala Val Ala Ser Val Leu Ser Ala Thr
50                  55                  60

Val Thr Pro Ala Val Val Ala Asn Ala Leu Arg His Val Asn Glu Gly
65                  70                  75                  80

Ser Glu Arg Ser Asn Leu Asn Phe Tyr Ala Glu Leu Ala Ala His
                85                  90                  95

Asp Pro Ala Lys Ser Phe Pro Ala Pro Thr Glu Leu Pro Lys Val Thr
            100                 105                 110

Ser Arg Pro Ala Ser Pro Leu Thr Glu Trp Val Ala Arg Gly Thr Val
        115                 120                 125

Asp Asn Ile Ala Phe Ala Ser Gly Phe Arg Ala Ile Asn Pro Thr Met
130                 135                 140

Arg Gln Arg Trp Ser Ala Leu Thr Ala Asn Asn Ile Val His Ala Gln
145                 150                 155                 160

His Trp Arg His Arg Asp Gly Pro Arg Pro Thr Leu Cys Val Ile His
            165                 170                 175

Gly Phe Met Gly Ser Ser Tyr Leu Leu Asn Gly Leu Phe Phe Ser Leu
            180                 185                 190

Pro Trp Tyr Tyr Arg Ser Gly Tyr Asp Val Leu Leu Tyr Thr Leu Pro
        195                 200                 205

Phe His Gly Gln Arg Ala Glu Lys Phe Ser Pro Phe Ser Gly Phe Gly
210                 215                 220

Tyr Phe Thr Ser Gly Leu Ser Gly Phe Ala Glu Ala Met Ala Gln Ala
225                 230                 235                 240

Val Tyr Asp Phe Arg Ser Ile Val Asp Tyr Leu Arg His Ile Gly Val
            245                 250                 255

Asp Arg Ile Ala Leu Thr Gly Ile Ser Leu Gly Gly Tyr Thr Ser Ala
            260                 265                 270

Leu Leu Ala Ser Val Glu Ser Arg Leu Glu Ala Val Ile Pro Asn Cys
        275                 280                 285

Pro Val Val Met Pro Ala Lys Leu Phe Asp Glu Trp Phe Pro Ala Asn
290                 295                 300

Lys Leu Val Lys Leu Gly Leu Arg Leu Thr Asn Ile Ser Arg Asp Glu
305                 310                 315                 320

Leu Ile Ala Gly Leu Ala Tyr His Gly Pro Leu Asn Tyr Arg Pro Leu
            325                 330                 335

Leu Pro Lys Asp Arg Arg Met Ile Ile Thr Gly Leu Asp Arg Met
            340                 345                 350

Ala Pro Pro Glu His Ala Val Thr Leu Trp Lys Gln Trp Asp Arg Cys
        355                 360                 365

Ala Leu His Trp Phe Pro Gly Ser His Leu Leu His Val Ser Gln Leu
370                 375                 380

Asp Tyr Leu Arg Arg Met Thr Val Phe Leu Gln Gly Leu Met Phe Asp
385                 390                 395                 400

<210> SEQ ID NO 17
<211> LENGTH: 591
<212> TYPE: PRT
<213> ORGANISM: Mycobacterium tuberculosis

```
<400> SEQUENCE: 17

Met Ser Phe Val Ile Ala Gln Pro Glu Met Ile Ala Ala Ala Gly
1               5                   10                  15

Glu Leu Ala Ser Ile Arg Ser Ala Ile Asn Ala Ala Asn Ala Ala
            20                  25                  30

Ala Ala Gln Thr Thr Gly Val Met Ser Ala Ala Asp Glu Val Ser
        35                  40                  45

Thr Ala Val Ala Ala Leu Phe Ser Ser His Ala Gln Ala Tyr Gln Ala
50                      55                  60

Ala Ser Ala Gln Ala Ala Ala Phe His Ala Gln Val Val Arg Thr Leu
65                  70                  75                  80

Thr Val Asp Ala Gly Ala Tyr Ala Ser Ala Glu Ala Ala Asn Ala Gly
                85                  90                  95

Pro Asn Met Leu Ala Ala Val Asn Ala Pro Ala Gln Ala Leu Leu Gly
            100                 105                 110

Arg Pro Leu Ile Gly Asn Gly Ala Asn Gly Ala Pro Gly Thr Gly Gln
            115                 120                 125

Ala Gly Gly Asp Gly Gly Leu Leu Phe Gly Asn Gly Gly Asn Gly Gly
130                 135                 140

Ser Gly Ala Pro Gly Gln Ala Gly Gly Ala Gly Gly Ala Ala Gly Phe
145                 150                 155                 160

Phe Gly Asn Gly Gly Asn Gly Gly Asp Gly Gly Ala Gly Ala Asn Gly
                165                 170                 175

Gly Ala Gly Gly Thr Ala Gly Trp Phe Phe Gly Phe Gly Gly Asn Gly
                180                 185                 190

Gly Ala Gly Gly Ile Gly Val Ala Gly Ile Asn Gly Gly Leu Gly Gly
                195                 200                 205

Ala Gly Gly Asp Gly Gly Asn Ala Gly Phe Phe Gly Asn Gly Gly Asn
210                 215                 220

Gly Gly Met Gly Gly Ala Gly Ala Ala Gly Val Asn Ala Val Asn Pro
225                 230                 235                 240

Gly Leu Ala Thr Pro Val Thr Pro Ala Ala Asn Gly Gly Asn Gly Leu
                245                 250                 255

Asn Leu Val Gly Val Pro Gly Thr Ala Gly Gly Ala Gly Asp Gly Ala
                260                 265                 270

Asn Gly Ser Ala Ile Gly Gln Ala Gly Gly Ala Gly Gly Asp Gly Gly
                275                 280                 285

Asn Ala Ser Thr Ser Gly Gly Ile Gly Ile Ala Gln Thr Gly Gly Ala
                290                 295                 300

Gly Gly Ala Gly Gly Ala Gly Gly Asp Gly Ala Pro Gly Gly Asn Gly
305                 310                 315                 320

Gly Asn Gly Gly Ser Val Glu His Thr Gly Ala Thr Gly Ser Ser Ala
                325                 330                 335

Ser Gly Gly Asn Gly Ala Thr Gly Gly Asn Gly Gly Val Gly Ala Pro
                340                 345                 350

Gly Gly Ala Gly Gly Asn Gly Gly His Val Ser Gly Gly Ser Val Asn
                355                 360                 365

Thr Ala Gly Ala Gly Gly Lys Gly Gly Asn Gly Gly Thr Gly Gly Ala
                370                 375                 380

Gly Gly Pro Gly Gly His Gly Gly Ser Val Leu Ser Gly Pro Val Gly
385                 390                 395                 400

Asp Ser Gly Asn Gly Gly Ala Gly Gly Asp Gly Gly Ala Gly Val Ser
                405                 410                 415
```

-continued

```
Ala Thr Asp Ile Ala Gly Thr Gly Arg Gly Gly Asn Gly Gly His
            420                 425                 430

Gly Gly Leu Trp Ile Gly Asn Gly Gly Asp Gly Gly Ala Gly Gly Val
            435                 440                 445

Gly Gly Val Gly Gly Ala Gly Ala Ala Gly Ala Ile Gly Gly His Gly
            450                 455                 460

Gly Asp Gly Gly Ser Val Asn Thr Pro Ile Gly Gly Ser Glu Ala Gly
465                 470                 475                 480

Asp Gly Gly Lys Gly Gly Leu Gly Gly Asp Gly Gly Arg Gly Ile
                485                 490                 495

Phe Gly Gln Phe Gly Ala Gly Ala Gly Gly Ala Gly Val Gly
            500                 505                 510

Gly Ala Gly Gly Ala Gly Gly Thr Gly Gly Gly Gly Asn Gly Gly
            515                 520                 525

Ala Ile Phe Asn Ala Gly Thr Pro Gly Ala Gly Thr Gly Gly Asp
            530                 535                 540

Gly Gly Val Gly Gly Thr Gly Ala Ala Gly Gly Lys Gly Gly Ala Gly
545                 550                 555                 560

Gly Ser Gly Gly Val Asn Gly Ala Thr Gly Ala Asp Gly Ala Lys Gly
                565                 570                 575

Leu Asp Gly Ala Thr Gly Gly Lys Gly Asn Asn Gly Asn Pro Gly
            580                 585                 590

<210> SEQ ID NO 18
<211> LENGTH: 100
<212> TYPE: PRT
<213> ORGANISM: Mycobacterium tuberculosis

<400> SEQUENCE: 18

Met Ile Ala Pro Gly Asp Ile Ala Pro Arg Arg Asp Ser Glu His Glu
1               5                   10                  15

Leu Tyr Val Ala Val Leu Ser Asn Ala Leu His Arg Ala Ala Asp Thr
            20                  25                  30

Gly Arg Val Ile Thr Cys Pro Phe Ile Pro Gly Arg Val Pro Glu Asp
        35                  40                  45

Leu Leu Ala Met Val Val Ala Val Glu Gln Pro Asn Gly Thr Leu Leu
    50                  55                  60

Pro Glu Leu Val Gln Trp Leu His Val Ala Ala Leu Gly Ala Pro Leu
65                  70                  75                  80

Gly Asn Ala Gly Val Ala Ala Leu Arg Glu Ala Ala Ser Val Val Thr
                85                  90                  95

Ala Leu Leu Cys
            100

<210> SEQ ID NO 19
<211> LENGTH: 99
<212> TYPE: PRT
<213> ORGANISM: Mycobacterium tuberculosis

<400> SEQUENCE: 19

Met Ser Gln Ile Ser Arg Asp Glu Val Ala His Leu Ala Arg Leu Ala
1               5                   10                  15

Arg Leu Ala Leu Thr Glu Thr Glu Leu Asp Ser Phe Ala Gly Gln Leu
            20                  25                  30

Asp Ala Ile Leu Thr His Val Ser Gln Ile Gln Ala Val Asp Val Thr
        35                  40                  45
```

-continued

```
Gly Val Gln Ala Thr Asp Asn Pro Leu Lys Asp Val Asn Val Thr Arg
        50                  55                  60

Pro Asp Glu Thr Val Pro Cys Leu Thr Gln Arg Gln Val Leu Asp Gln
 65                  70                  75                  80

Ala Pro Asp Ala Val Asp Gly Arg Phe Ala Val Pro Gln Ile Leu Gly
                 85                  90                  95

Asp Glu Gln

<210> SEQ ID NO 20
<211> LENGTH: 393
<212> TYPE: PRT
<213> ORGANISM: Mycobacterium tuberculosis

<400> SEQUENCE: 20

Met Ala Tyr Leu Asp His Ala Thr Thr Pro Met His Pro Ala Ala
 1               5                  10                  15

Ile Glu Ala Met Ala Ala Val Gln Arg Thr Ile Gly Asn Ala Ser Ser
                20                  25                  30

Leu His Thr Ser Gly Arg Ser Ala Arg Arg Ile Glu Glu Ala Arg
                35                  40                  45

Glu Leu Ile Ala Asp Lys Leu Gly Ala Arg Pro Ser Glu Val Ile Phe
 50                  55                  60

Thr Ala Gly Gly Thr Glu Ser Asp Asn Leu Ala Val Lys Gly Ile Tyr
 65                  70                  75                  80

Trp Ala Arg Arg Asp Ala Glu Pro His Arg Arg Ile Val Thr Thr
                 85                  90                  95

Glu Val Glu His His Ala Val Leu Asp Ser Val Asn Trp Leu Val Glu
                100                 105                 110

His Glu Gly Ala His Val Thr Trp Leu Pro Thr Ala Ala Asp Gly Ser
                115                 120                 125

Val Ser Ala Thr Ala Leu Arg Glu Ala Leu Gln Ser His Asp Asp Val
                130                 135                 140

Ala Leu Val Ser Val Met Trp Ala Asn Asn Glu Val Gly Thr Ile Leu
145                 150                 155                 160

Pro Ile Ala Glu Met Ser Val Val Ala Met Glu Phe Gly Val Pro Met
                165                 170                 175

His Ser Asp Ala Ile Gln Ala Val Gly Gln Leu Pro Leu Asp Phe Gly
                180                 185                 190

Ala Ser Gly Leu Ser Ala Met Ser Val Ala Gly His Lys Phe Gly Gly
                195                 200                 205

Pro Pro Gly Val Gly Ala Leu Leu Arg Arg Asp Val Thr Cys Val
210                 215                 220

Pro Leu Met His Gly Gly Gly Gln Glu Arg Asp Ile Arg Ser Gly Thr
225                 230                 235                 240

Pro Asp Val Ala Ser Ala Val Gly Met Ala Thr Ala Ala Gln Ile Ala
                245                 250                 255

Val Asp Gly Leu Glu Glu Asn Ser Ala Arg Leu Arg Leu Leu Arg Asp
                260                 265                 270

Arg Leu Val Glu Gly Val Leu Ala Glu Ile Asp Val Cys Leu Asn
                275                 280                 285

Gly Ala Asp Asp Pro Met Arg Leu Ala Gly Asn Ala His Phe Thr Phe
                290                 295                 300

Arg Gly Cys Glu Gly Asp Ala Leu Leu Met Leu Leu Asp Ala Asn Gly
305                 310                 315                 320
```

```
Ile Glu Cys Ser Thr Gly Ser Ala Cys Thr Ala Gly Val Ala Gln Pro
                325                 330                 335

Ser His Val Leu Ile Ala Met Gly Val Asp Ala Ala Ser Ala Arg Gly
            340                 345                 350

Ser Leu Arg Leu Ser Leu Gly His Thr Ser Val Glu Ala Asp Val Asp
        355                 360                 365

Ala Ala Leu Glu Val Leu Pro Gly Ala Val Ala Arg Ala Arg Arg Ala
370                 375                 380

Ala Leu Ala Ala Ala Gly Ala Ser Arg
385                 390

<210> SEQ ID NO 21
<211> LENGTH: 957
<212> TYPE: PRT
<213> ORGANISM: Mycobacterium tuberculosis

<400> SEQUENCE: 21

Met Ser Phe Val Ile Ala Ala Pro Glu Val Ile Ala Ala Ala Ala Thr
1               5                   10                  15

Asp Leu Ala Ser Leu Gly Ser Ser Ile Ser Ala Ala Asn Ala Ala Ala
            20                  25                  30

Ala Ala Asn Thr Thr Ala Leu Met Ala Ala Gly Ala Asp Glu Val Ser
        35                  40                  45

Thr Ala Ile Ala Ala Leu Phe Gly Ala His Gly Gln Ala Tyr Gln Ala
    50                  55                  60

Leu Ser Ala Gln Ala Gln Ala Phe His Ala Gln Phe Val Gln Ala Leu
65                  70                  75                  80

Thr Ser Gly Gly Gly Ala Tyr Ala Ala Ala Glu Ala Ala Ala Val Ser
                85                  90                  95

Pro Leu Leu Asp Pro Ile Asn Glu Phe Phe Leu Ala Asn Thr Gly Arg
            100                 105                 110

Pro Leu Ile Gly Asn Gly Ala Asn Gly Ala Pro Gly Thr Gly Ala Asn
        115                 120                 125

Gly Gly Asp Gly Gly Trp Leu Ile Gly Asn Gly Ala Gly Gly Ser
    130                 135                 140

Gly Ala Ala Gly Val Asn Gly Ala Gly Gly Asn Gly Gly Ala Gly
145                 150                 155                 160

Gly Asn Gly Gly Ala Gly Gly Leu Ile Gly Asn Gly Ala Gly Gly
                165                 170                 175

Ala Gly Gly Val Ala Ser Ser Gly Ile Gly Gly Ser Gly Gly Ala Gly
            180                 185                 190

Gly Asn Ala Met Leu Phe Gly Ala Gly Gly Ala Gly Gly Ala Gly Gly
        195                 200                 205

Gly Val Val Ala Leu Thr Gly Gly Ala Gly Gly Ala Gly Gly Ala Gly
    210                 215                 220

Gly Asn Ala Gly Leu Leu Phe Gly Ala Ala Gly Val Gly Gly Ala Gly
225                 230                 235                 240

Gly Phe Thr Asn Gly Ser Ala Leu Gly Gly Ala Gly Gly Ala Gly Gly
                245                 250                 255

Ala Gly Gly Leu Phe Ala Thr Gly Gly Val Gly Gly Ser Gly Gly Ala
            260                 265                 270

Gly Ser Ser Gly Gly Ala Gly Gly Ala Gly Gly Ala Gly Gly Leu Phe
        275                 280                 285

Gly Ala Gly Gly Thr Gly Gly His Gly Gly Phe Ala Asp Ser Ser Phe
```

```
              290                 295                 300
Gly Gly Val Gly Gly Ala Gly Ala Gly Gly Leu Phe Gly Ala Gly
305                 310                 315                 320

Gly Glu Gly Gly Ser Gly Gly His Ser Leu Val Ala Gly Gly Asp Gly
                325                 330                 335

Gly Ala Gly Gly Asn Ala Gly Met Leu Ala Leu Gly Ala Ala Gly Gly
                340                 345                 350

Ala Gly Gly Ile Gly Gly Asp Gly Gly Thr Leu Thr Ala Gly Gly Ile
            355                 360                 365

Gly Gly Ala Gly Gly Ala Gly Gly Asn Ala Gly Leu Leu Phe Gly Ser
        370                 375                 380

Gly Gly Ser Gly Gly Ala Gly Gly Phe Gly Phe Ala Asp Gly Gly Gln
385                 390                 395                 400

Gly Gly Pro Gly Gly Asn Ala Gly Thr Val Phe Gly Ser Gly Gly Ala
                405                 410                 415

Gly Gly Asn Gly Gly Val Gly Gln Gly Phe Ala Gly Gly Ile Gly Gly
                420                 425                 430

Ala Gly Gly Thr Pro Gly Leu Ile Gly Asn Gly Gly Asn Gly Gly Asn
            435                 440                 445

Gly Gly Ala Ser Ala Val Thr Gly Gly Asn Gly Gly Ile Gly Gly Thr
        450                 455                 460

Gly Val Leu Ile Gly Asn Gly Gly Asn Gly Gly Ser Gly Gly Ile Gly
465                 470                 475                 480

Ala Gly Lys Ala Gly Val Gly Gly Val Ser Gly Leu Leu Gly Leu
                485                 490                 495

Asp Gly Phe Asn Ala Pro Ala Ser Thr Ser Pro Leu His Thr Leu Gln
                500                 505                 510

Gln Asn Val Leu Asn Val Val Asn Glu Pro Phe Gln Thr Leu Thr Gly
                515                 520                 525

Arg Pro Leu Ile Gly Asn Gly Ala Asn Gly Thr Pro Gly Thr Gly Ala
            530                 535                 540

Asp Gly Gly Ala Gly Gly Trp Leu Phe Gly Asn Gly Ala Asn Gly Thr
545                 550                 555                 560

Pro Gly Thr Gly Ala Ala Gly Ala Gly Gly Trp Leu Phe Gly Asn
                565                 570                 575

Gly Gly Asn Gly Gly His Gly Ala Thr Asn Thr Ala Ala Thr Ala Thr
                580                 585                 590

Gly Gly Ala Gly Gly Ala Gly Gly Ile Leu Phe Gly Thr Gly Gly Asn
            595                 600                 605

Gly Gly Thr Gly Gly Ile Ala Thr Gly Ala Gly Gly Ile Gly Gly Ala
        610                 615                 620

Gly Gly Ala Gly Gly Val Ser Leu Leu Ile Gly Ser Gly Gly Thr Gly
625                 630                 635                 640

Gly Asn Gly Gly Asn Ser Ile Gly Val Ala Gly Ile Gly Gly Ala Gly
                645                 650                 655

Gly Arg Gly Gly Asp Ala Gly Leu Leu Phe Gly Ala Ala Gly Thr Gly
                660                 665                 670

Gly His Gly Ala Ala Gly Gly Val Pro Ala Gly Val Gly Gly Ala Gly
            675                 680                 685

Gly Asn Gly Gly Leu Phe Ala Asn Gly Gly Ala Gly Gly Ala Gly Gly
        690                 695                 700

Phe Asn Ala Ala Gly Gly Asn Gly Gly Asn Gly Gly Leu Phe Gly Thr
705                 710                 715                 720
```

```
Gly Gly Thr Gly Gly Ala Gly Thr Asn Phe Gly Ala Gly Gly Asn Gly
            725                 730                 735

Gly Asn Gly Gly Leu Phe Gly Ala Gly Gly Thr Gly Gly Ala Ala Gly
            740                 745                 750

Ser Gly Gly Ser Gly Ile Thr Thr Gly Gly Gly His Gly Gly Asn
            755                 760                 765

Ala Gly Leu Leu Ser Leu Gly Ala Ser Gly Gly Ala Gly Gly Ser Gly
            770                 775                 780

Gly Ala Ser Ser Leu Ala Gly Ala Gly Gly Thr Gly Gly Asn Gly
785                 790                 795                 800

Ala Leu Leu Phe Gly Phe Arg Gly Ala Gly Gly Ala Gly His Gly
            805                 810                 815

Gly Ala Ala Leu Thr Ser Ile Gln Gln Gly Gly Ala Gly Gly Ala Gly
            820                 825                 830

Gly Asn Gly Gly Leu Leu Phe Gly Ser Ala Gly Ala Gly Gly Ala Gly
            835                 840                 845

Gly Ser Gly Ala Asn Ala Leu Gly Ala Gly Thr Gly Gly Thr Gly Gly
            850                 855                 860

Asp Gly Gly His Ala Gly Val Phe Gly Asn Gly Gly Asp Gly Gly Cys
865                 870                 875                 880

Arg Arg Val Trp Arg Arg Tyr Arg Arg Gln Arg Trp Cys Arg Arg Gln
            885                 890                 895

Arg Arg Ala Asp Arg Gln Arg Gln Arg Arg Gln Arg Arg Gln Ser
            900                 905                 910

Arg Gly His Ala Arg Cys Arg Arg His Arg Arg Ala Ala Arg Arg
            915                 920                 925

Glu Arg Thr Gln Arg Leu Ala Ile Ala Gly Arg Pro Ala Thr Thr Arg
930                 935                 940

Gly Val Glu Gly Ile Ser Cys Ser Pro Gln Met Met Pro
945                 950                 955

<210> SEQ ID NO 22
<211> LENGTH: 837
<212> TYPE: PRT
<213> ORGANISM: Mycobacterium tuberculosis

<400> SEQUENCE: 22

Met Ser Phe Val Ile Ala Ala Pro Glu Val Ile Ala Ala Ala Ala Thr
1               5                   10                  15

Asp Leu Ala Ser Leu Glu Ser Ser Ile Ala Ala Asn Ala Ala Ala
            20                  25                  30

Ala Ala Asn Thr Thr Ala Leu Leu Ala Ala Gly Ala Asp Glu Val Ser
            35                  40                  45

Thr Ala Val Ala Ala Leu Phe Gly Ala His Gly Gln Ala Tyr Gln Ala
        50                  55                  60

Leu Ser Ala Gln Ala Gln Ala Phe His Ala Gln Phe Val Gln Ala Leu
65                  70                  75                  80

Thr Ser Gly Gly Gly Ala Tyr Ala Ala Ala Glu Ala Ala Ala Thr Ser
            85                  90                  95

Pro Leu Leu Ala Pro Ile Asn Glu Phe Phe Leu Ala Asn Thr Gly Arg
            100                 105                 110

Pro Leu Ile Gly Asn Gly Thr Asn Gly Ala Pro Gly Thr Gly Ala Asn
            115                 120                 125

Gly Gly Asp Gly Gly Trp Leu Ile Gly Asn Gly Gly Ala Gly Gly Ser
```

-continued

```
                130                 135                 140
Gly Ala Ala Gly Val Asn Gly Ala Gly Asn Gly Gly Ala Gly
145                 150                 155                 160

Gly Leu Ile Gly Asn Gly Gly Ala Gly Gly Gly Arg Ala Ser
                165                 170                 175

Thr Gly Thr Gly Gly Ala Gly Gly Ala Gly Ala Ala Gly Met Leu
                180                 185                 190

Phe Gly Ala Ala Gly Val Gly Gly Pro Gly Gly Phe Ala Ala Phe
                195                 200                 205

Gly Ala Thr Gly Gly Ala Gly Gly Ala Gly Gly Asn Gly Gly Leu Phe
                210                 215                 220

Ala Asp Gly Gly Val Gly Gly Ala Gly Gly Ala Thr Asp Ala Gly Thr
225                 230                 235                 240

Gly Gly Ala Gly Gly Ser Gly Gly Asn Gly Gly Leu Phe Gly Ala Gly
                245                 250                 255

Gly Thr Gly Gly Pro Gly Gly Phe Gly Ile Phe Gly Gly Ala Gly
                260                 265                 270

Gly Asp Gly Gly Ser Gly Gly Leu Phe Gly Ala Gly Gly Thr Gly Gly
                275                 280                 285

Ser Gly Gly Thr Ser Ile Ile Asn Val Gly Gly Asn Gly Gly Ala Gly
                290                 295                 300

Gly Asp Ala Gly Met Leu Ser Leu Gly Ala Ala Gly Ala Gly Gly
305                 310                 315                 320

Ser Gly Gly Ser Asn Pro Asp Gly Gly Gly Ala Gly Gly Ile Gly
                325                 330                 335

Gly Asp Gly Gly Thr Leu Phe Gly Ser Gly Gly Ala Gly Gly Val Cys
                340                 345                 350

Gly Leu Gly Phe Asp Ala Gly Gly Ala Gly Gly Ala Gly Gly Lys Ala
                355                 360                 365

Gly Leu Leu Ile Gly Ala Gly Gly Ala Gly Gly Ala Gly Gly Ser
                370                 375                 380

Phe Ala Gly Ala Gly Gly Thr Gly Gly Ala Gly Gly Ala Pro Gly Leu
385                 390                 395                 400

Val Gly Asn Ala Gly Asn Gly Gly Asn Gly Gly Ala Ser Ala Asn Gly
                405                 410                 415

Ala Gly Ala Ala Gly Gly Ala Gly Gly Ser Gly Val Leu Ile Gly Asn
                420                 425                 430

Gly Gly Asn Gly Gly Ser Gly Gly Thr Gly Ala Pro Ala Gly Thr Ala
                435                 440                 445

Gly Ala Gly Gly Leu Gly Gly Gln Leu Leu Gly Arg Asp Gly Phe Asn
450                 455                 460

Ala Pro Ala Ser Thr Pro Leu His Thr Leu Gln Gln Ile Leu Asn
465                 470                 475                 480

Ala Ile Asn Glu Pro Thr Gln Ala Leu Thr Gly Arg Pro Leu Ile Gly
                485                 490                 495

Asn Gly Ala Asn Gly Thr Pro Gly Thr Gly Ala Asp Gly Gly Ala Gly
                500                 505                 510

Gly Trp Leu Phe Gly Asn Gly Gly Asn Gly Gly His Gly Ala Thr Gly
                515                 520                 525

Ala Asp Gly Gly Asp Gly Gly Ser Gly Gly Ala Gly Gly Ile Leu Ser
                530                 535                 540

Gly Ile Gly Gly Thr Gly Gly Ser Gly Gly Ile Gly Thr Thr Gly Gln
545                 550                 555                 560
```

```
Gly Gly Thr Gly Gly Thr Gly Ala Ala Leu Leu Ile Gly Ser Gly
            565                 570                 575

Gly Thr Gly Gly Ser Gly Gly Phe Gly Leu Asp Thr Gly Gly Ala Gly
            580                 585                 590

Gly Arg Gly Gly Asp Ala Gly Leu Phe Leu Gly Ala Ala Gly Thr Gly
        595                 600                 605

Gly Gln Ala Ala Leu Ser Gln Asn Phe Ile Gly Ala Gly Gly Thr Ala
    610                 615                 620

Gly Ala Gly Gly Thr Gly Gly Leu Phe Ala Asn Gly Gly Ala Gly Gly
625                 630                 635                 640

Ala Gly Gly Phe Gly Ala Asn Gly Gly Thr Gly Asn Gly Leu Leu
            645                 650                 655

Phe Gly Ala Gly Gly Thr Gly Gly Ala Gly Thr Leu Gly Ala Asp Gly
            660                 665                 670

Gly Ala Gly Gly His Gly Gly Leu Phe Gly Ala Gly Gly Thr Gly Gly
        675                 680                 685

Ala Gly Gly Ser Ser Gly Gly Thr Phe Gly Gly Asn Gly Gly Ser Gly
    690                 695                 700

Gly Asn Ala Gly Leu Leu Ala Leu Gly Ala Ser Gly Gly Ala Gly Gly
705                 710                 715                 720

Ser Gly Gly Ser Ala Leu Asn Val Gly Gly Thr Gly Gly Val Gly Gly
            725                 730                 735

Asn Gly Gly Ser Gly Gly Ser Leu Phe Gly Phe Gly Gly Ala Gly Gly
            740                 745                 750

Thr Gly Gly Ser Ser Gly Ile Gly Ser Ser Gly Gly Thr Gly Gly Asp
        755                 760                 765

Gly Gly Thr Ala Gly Val Phe Gly Asn Gly Gly Asp Gly Gly Ala Gly
    770                 775                 780

Gly Phe Gly Ala Asp Thr Gly Gly Asn Ser Ser Val Pro Asn Ala
785                 790                 795                 800

Val Leu Ile Gly Asn Gly Gly Asn Gly Gly Asn Gly Gly Lys Ala Gly
            805                 810                 815

Gly Thr Pro Gly Ala Gly Gly Thr Ser Gly Leu Ile Ile Gly Glu Asn
            820                 825                 830

Gly Leu Asn Gly Leu
        835

<210> SEQ ID NO 23
<211> LENGTH: 75
<212> TYPE: PRT
<213> ORGANISM: Mycobacterium tuberculosis

<400> SEQUENCE: 23

Met Thr Lys Glu Lys Ile Ser Val Thr Val Asp Ala Ala Val Leu Ala
1               5                   10                  15

Ala Ile Asp Ala Asp Ala Arg Ala Ala Gly Leu Asn Arg Ser Glu Met
            20                  25                  30

Ile Glu Gln Ala Leu Arg Asn Glu His Leu Arg Val Ala Leu Arg Asp
        35                  40                  45

Tyr Thr Ala Lys Thr Val Pro Ala Leu Asp Ile Asp Ala Tyr Ala Gln
    50                  55                  60

Arg Val Tyr Gln Ala Asn Arg Ala Ala Gly Ser
65                  70                  75
```

<210> SEQ ID NO 24
<211> LENGTH: 487
<212> TYPE: PRT
<213> ORGANISM: Mycobacterium tuberculosis

<400> SEQUENCE: 24

```
Met Thr Ser Pro His Phe Ala Trp Leu Pro Pro Glu Ile Asn Ser Ala
 1               5                  10                  15
Leu Met Phe Ala Gly Pro Gly Ser Gly Pro Leu Ile Ala Ala Ala Thr
            20                  25                  30
Ala Trp Gly Glu Leu Ala Glu Lys Leu Leu Ala Ser Ile Ala Ser Leu
        35                  40                  45
Gly Ser Val Thr Ser Glu Leu Thr Ser Gly Ala Trp Leu Gly Pro Ser
    50                  55                  60
Ala Ala Met Met Ala Val Ala Thr Gln Tyr Leu Ala Trp Leu Ser
65                  70                  75                  80
Thr Ala Ala Gln Ala Glu Gln Ala Ala Gln Ala Met Ala Ile
                85                  90                  95
Ala Thr Ala Phe Glu Ala Ala Leu Ala Ala Thr Val Gln Pro Ala Val
            100                 105                 110
Val Ala Ala Asn Arg Gly Leu Met Gln Leu Leu Ala Ala Thr Asn Trp
        115                 120                 125
Phe Gly Gln Asn Ala Pro Ala Leu Met Asp Val Glu Ala Ala Tyr Glu
    130                 135                 140
Gln Met Trp Ala Leu Asp Val Ala Ala Met Ala Gly Tyr His Phe Asp
145                 150                 155                 160
Ala Ser Ala Ala Val Ala Gln Leu Ala Pro Trp Gln Gln Val Leu Arg
                165                 170                 175
Asn Leu Gly Ile Asp Ile Gly Lys Asn Gly Gln Ile Asn Leu Gly Phe
            180                 185                 190
Gly Asn Thr Gly Ser Gly Asn Ile Gly Asn Asn Ile Gly Asn Asn
        195                 200                 205
Asn Ile Gly Ser Gly Asn Thr Gly Thr Gly Asn Ile Gly Ser Gly Asn
    210                 215                 220
Thr Gly Ser Gly Asn Leu Gly Leu Gly Asn Leu Gly Asp Gly Asn Ile
225                 230                 235                 240
Gly Phe Gly Asn Thr Gly Ser Gly Asn Ile Gly Phe Gly Ile Thr Gly
                245                 250                 255
Asp His Gln Met Gly Phe Gly Phe Asn Ser Gly Ser Gly Asn Ile
            260                 265                 270
Gly Phe Gly Asn Ser Gly Thr Gly Asn Val Gly Leu Phe Asn Ser Gly
        275                 280                 285
Ser Gly Asn Ile Gly Ile Gly Asn Ser Gly Ser Leu Asn Ser Gly Ile
    290                 295                 300
Gly Thr Ser Gly Thr Ile Asn Ala Gly Leu Gly Ser Ala Gly Ser Leu
305                 310                 315                 320
Asn Thr Ser Phe Trp Asn Ala Gly Met Gln Asn Ala Ala Leu Gly Ser
                325                 330                 335
Ala Ala Gly Ser Glu Ala Ala Leu Val Ser Ser Ala Gly Tyr Ala Thr
            340                 345                 350
Gly Gly Met Ser Thr Ala Ala Leu Ser Ser Gly Ile Leu Ala Ser Ala
        355                 360                 365
Leu Gly Ser Thr Gly Gly Leu Gln His Gly Leu Ala Asn Val Leu Asn
    370                 375                 380
```

```
Ser Gly Leu Thr Asn Thr Pro Val Ala Ala Pro Ala Ser Ala Pro Val
385                 390                 395                 400

Gly Gly Leu Asp Ser Gly Asn Pro Asn Pro Gly Ser Gly Ser Ala Ala
            405                 410                 415

Ala Gly Ser Gly Ala Asn Pro Gly Leu Arg Ser Pro Gly Thr Ser Tyr
        420                 425                 430

Pro Ser Phe Val Asn Ser Gly Ser Asn Asp Ser Gly Leu Arg Asn Thr
    435                 440                 445

Ala Val Arg Glu Pro Ser Thr Pro Gly Ser Gly Ile Pro Lys Ser Asn
450                 455                 460

Phe Tyr Pro Ser Pro Asp Arg Glu Ser Ala Tyr Ala Ser Pro Arg Ile
465                 470                 475                 480

Gly Gln Pro Val Gly Ser Glu
                485

<210> SEQ ID NO 25
<211> LENGTH: 349
<212> TYPE: PRT
<213> ORGANISM: Mycobacterium tuberculosis

<400> SEQUENCE: 25

Met Thr Gly Thr Glu His Leu Val His Thr Leu Arg Ser Gln Gly Arg
1               5                   10                  15

Val Cys Thr Ser Ser Gly Ser Pro Met Tyr Arg Glu Leu Leu Glu Leu
            20                  25                  30

Val Ala Ala Asp Val Glu Ser Gly Gly Val Phe Ala Ser Ile Leu Ala
        35                  40                  45

Asp Gln Lys Gly Ala Pro Glu Gly Gln Ala Val Pro Leu Arg Leu Leu
    50                  55                  60

Gly Gly Leu His Arg Met Val Leu Asp Gly Arg Ala Pro Val Leu Arg
65                  70                  75                  80

Arg Trp Tyr Pro Ser Thr Gly Gly Thr Trp Gln Ala Glu Ala Ala Trp
                85                  90                  95

Pro Asp Ile Val Arg Thr Ala Thr Asp Gln Pro Glu Ser Leu Arg Ala
            100                 105                 110

Ala Leu Asp Arg Pro Gln Thr Asn Glu Val Gly Arg Ser Ala Ala
        115                 120                 125

Leu Ile Gly Gly Leu Leu Ile Ala Cys Leu Gln Phe Asp Leu Pro Ile
    130                 135                 140

Arg Leu Phe Glu Ile Gly Ser Ser Ala Gly Leu Asn Leu Arg Pro Asp
145                 150                 155                 160

Arg Tyr Arg Tyr Arg Tyr Leu Gly Gly Glu Trp Gly Leu Ala Asp Ser
                165                 170                 175

Pro Val Arg Ile Asp Asn Ala Trp Leu Gly Glu Leu Pro Pro Thr Ala
            180                 185                 190

Thr Val Arg Ile Val Glu Arg His Gly Tyr Asp Ile Ala Pro Ile Asp
        195                 200                 205

Val Thr Ser Pro Asp Gly Glu Leu Asn Ala Leu Ser Tyr Ile Trp Pro
    210                 215                 220

Asp Gln Thr Asp Arg Leu Glu Arg Leu Arg Gly Ala Ile Ala Val Ala
225                 230                 235                 240

Arg Asn Ile Pro Ala Asp Leu His Arg Gln Ala Ala His Ala Ala Val
                245                 250                 255

Ala Gly Met Thr Leu Thr Asp Asp Ala Leu Thr Val Leu Trp His Ser
            260                 265                 270
```

```
Ile Thr Trp Gln Tyr Leu Pro Ala Asp Glu Arg Ala Ala Ile Arg Ala
            275                 280                 285

Gly Ile Asp Ala Leu Ala Ala Gln Ala Asp Ala His Cys Pro Phe Val
        290                 295                 300

His Leu Thr Leu Glu Pro Ala His Gln Arg Pro Gly Ala Gln Ile Lys
305                 310                 315                 320

Tyr Leu Val Arg Met Arg Ser Trp Pro Gly His Ala Arg Val Leu
                325                 330                 335

Gly Glu Cys His Pro His Gly Pro Pro Val Thr Trp Gln
                340                 345

<210> SEQ ID NO 26
<211> LENGTH: 151
<212> TYPE: PRT
<213> ORGANISM: Mycobacterium tuberculosis

<400> SEQUENCE: 26

Met Leu Lys Gly Phe Lys Glu Phe Leu Ala Arg Gly Asn Ile Val Asp
1               5                   10                  15

Leu Ala Val Ala Val Val Ile Gly Thr Ala Phe Thr Ala Leu Val Thr
            20                  25                  30

Lys Phe Thr Asp Ser Ile Ile Thr Pro Leu Ile Asn Arg Ile Gly Val
        35                  40                  45

Asn Ala Gln Ser Asp Val Gly Ile Leu Arg Ile Gly Ile Gly Gly Gly
    50                  55                  60

Gln Thr Ile Asp Leu Asn Val Leu Leu Ser Ala Ala Ile Asn Phe Phe
65                  70                  75                  80

Leu Ile Ala Phe Ala Val Tyr Phe Leu Val Val Leu Pro Tyr Asn Thr
                85                  90                  95

Leu Arg Lys Lys Gly Glu Val Glu Gln Pro Gly Asp Thr Gln Val Val
            100                 105                 110

Leu Leu Thr Glu Ile Arg Asp Leu Leu Ala Gln Thr Asn Gly Asp Ser
        115                 120                 125

Pro Gly Arg His Gly Arg Gly Thr Pro Ser Pro Thr Asp Gly Pro
    130                 135                 140

Arg Ala Ser Thr Glu Ser Gln
145                 150

<210> SEQ ID NO 27
<211> LENGTH: 855
<212> TYPE: PRT
<213> ORGANISM: Mycobacterium tuberculosis

<400> SEQUENCE: 27

Met Asn Asp Gln Ala Pro Val Ala Tyr Ala Pro Leu Trp Arg Thr Ala
1               5                   10                  15

Trp Arg Arg Leu Arg Gln Arg Pro Phe Gln Tyr Ile Leu Leu Val Leu
            20                  25                  30

Gly Ile Ala Leu Gly Val Ala Met Ile Val Ala Ile Asp Val Ser Ser
        35                  40                  45

Asn Ser Ala Gln Arg Ala Phe Asp Leu Ser Ala Ala Ile Thr Gly
    50                  55                  60

Lys Ser Thr His Arg Leu Val Ser Gly Pro Ala Gly Val Asp Gln Gln
65                  70                  75                  80

Leu Tyr Val Asp Leu Arg Arg His Gly Tyr Asp Phe Ser Ala Pro Val
                85                  90                  95
```

-continued

```
Ile Glu Gly Tyr Val Leu Ala Arg Gly Leu Gly Asn Arg Ala Met Gln
                100                 105                 110
Phe Met Gly Thr Asp Pro Phe Ala Glu Ser Ala Phe Arg Ser Pro Leu
            115                 120                 125
Trp Ser Asn Gln Asn Ile Ala Glu Leu Gly Gly Phe Leu Thr Arg Pro
        130                 135                 140
Asn Gly Val Val Leu Ser Arg Gln Val Ala Gln Lys Tyr Gly Leu Ala
145                 150                 155                 160
Val Gly Asp Arg Ile Ala Leu Gln Val Lys Gly Ala Pro Thr Thr Val
                165                 170                 175
Thr Leu Val Gly Leu Leu Thr Pro Ala Asp Glu Val Ser Asn Gln Lys
            180                 185                 190
Leu Ser Asp Leu Ile Ile Ala Asp Ile Ser Thr Ala Gln Glu Leu Phe
        195                 200                 205
His Met Pro Gly Arg Leu Ser His Ile Asp Leu Ile Ile Lys Asp Glu
    210                 215                 220
Ala Thr Ala Thr Arg Ile Gln Gln Arg Leu Pro Ala Gly Val Arg Met
225                 230                 235                 240
Glu Thr Ser Asp Thr Gln Arg Asp Thr Val Lys Gln Met Thr Asp Ala
                245                 250                 255
Phe Thr Val Asn Leu Thr Ala Leu Ser Leu Ile Ala Leu Leu Val Gly
            260                 265                 270
Ile Phe Leu Ile Tyr Asn Thr Val Thr Phe Asn Val Val Gln Arg Arg
        275                 280                 285
Pro Phe Phe Ala Ile Leu Arg Cys Leu Gly Val Thr Arg Glu Gln Leu
    290                 295                 300
Phe Trp Leu Ile Met Thr Glu Ser Leu Val Ala Gly Leu Ile Gly Thr
305                 310                 315                 320
Gly Leu Gly Leu Leu Ile Gly Ile Trp Leu Gly Glu Gly Leu Ile Gly
                325                 330                 335
Leu Val Thr Gln Thr Ile Asn Asp Phe Tyr Phe Val Ile Asn Val Arg
            340                 345                 350
Asn Val Ser Val Ser Ala Glu Ser Leu Leu Lys Gly Leu Ile Ile Gly
        355                 360                 365
Ile Phe Ala Ala Met Leu Ala Thr Leu Pro Pro Ala Ile Glu Ala Met
    370                 375                 380
Arg Thr Val Pro Ala Ser Thr Leu Arg Arg Ser Ser Leu Glu Ser Lys
385                 390                 395                 400
Ile Thr Lys Leu Met Pro Trp Leu Trp Val Ala Trp Phe Gly Leu Gly
                405                 410                 415
Ser Phe Gly Val Leu Met Leu Trp Leu Pro Gly Asn Asn Leu Val Val
            420                 425                 430
Ala Phe Val Gly Leu Phe Ser Val Leu Ile Ala Leu Ala Leu Ile Ala
        435                 440                 445
Pro Pro Leu Thr Arg Phe Val Met Leu Arg Leu Ala Pro Gly Leu Gly
    450                 455                 460
Arg Leu Leu Gly Pro Ile Gly Arg Met Ala Pro Arg Asn Ile Val Arg
465                 470                 475                 480
Ser Leu Ser Arg Thr Ser Ile Ala Ile Ala Ala Leu Met Met Ala Val
                485                 490                 495
Ser Leu Met Val Gly Val Ser Ile Ser Val Gly Ser Phe Arg Gln Thr
            500                 505                 510
```

```
Leu Ala Asn Trp Leu Glu Val Thr Leu Lys Ser Asp Val Tyr Val Ser
            515                 520                 525

Pro Pro Thr Leu Thr Ser Gly Arg Pro Ser Gly Asn Leu Pro Val Asp
        530                 535                 540

Ala Val Arg Asn Ile Ser Lys Trp Pro Gly Val Arg Asp Ala Val Met
545                 550                 555                 560

Ala Arg Tyr Ser Ser Val Phe Ala Pro Asp Trp Gly Arg Glu Val Glu
                565                 570                 575

Leu Met Ala Val Ser Gly Asp Ile Ser Asp Gly Lys Arg Pro Tyr Arg
            580                 585                 590

Trp Ile Asp Gly Asn Lys Asp Thr Leu Trp Pro Arg Phe Leu Ala Gly
        595                 600                 605

Lys Gly Val Met Leu Ser Glu Pro Met Val Ser Arg Gln His Leu Gln
610                 615                 620

Met Pro Pro Arg Pro Ile Thr Leu Met Thr Asp Ser Gly Pro Gln Thr
625                 630                 635                 640

Phe Pro Val Leu Ala Val Phe Ser Asp Tyr Thr Ser Asp Gln Gly Val
                645                 650                 655

Ile Leu Met Asp Arg Ala Ser Tyr Arg Ala His Trp Gln Asp Asp
            660                 665                 670

Val Thr Thr Met Phe Leu Phe Leu Ala Ser Gly Ala Asn Ser Gly Ala
        675                 680                 685

Leu Ile Asp Gln Leu Gln Ala Ala Phe Ala Gly Arg Glu Asp Ile Val
            690                 695                 700

Ile Gln Ser Thr His Ser Val Arg Glu Ala Ser Met Phe Ile Phe Asp
705                 710                 715                 720

Arg Ser Phe Thr Ile Thr Ile Ala Leu Gln Leu Val Ala Thr Val Val
                725                 730                 735

Ala Phe Ile Gly Val Leu Ser Ala Leu Met Ser Leu Glu Leu Asp Arg
            740                 745                 750

Ala His Glu Leu Gly Val Phe Arg Ala Ile Gly Met Thr Thr Arg Gln
        755                 760                 765

Leu Trp Lys Leu Met Phe Ile Glu Thr Gly Leu Met Gly Gly Met Ala
770                 775                 780

Gly Leu Met Ala Leu Pro Thr Gly Cys Ile Leu Ala Trp Ile Leu Val
785                 790                 795                 800

Arg Ile Ile Asn Val Arg Ser Phe Gly Trp Thr Leu Gln Met His Phe
                805                 810                 815

Glu Ser Ala His Phe Leu Arg Ala Leu Leu Val Ala Val Ala Ala
            820                 825                 830

Leu Ala Ala Gly Met Tyr Pro Ala Trp Arg Leu Gly Arg Met Thr Ile
        835                 840                 845

Arg Thr Ala Ile Arg Glu Glu
850                 855

<210> SEQ ID NO 28
<211> LENGTH: 308
<212> TYPE: PRT
<213> ORGANISM: Mycobacterium tuberculosis

<400> SEQUENCE: 28

Met Ser Phe Val Phe Ala Ala Pro Glu Ala Leu Ala Ala Ala Ala
1               5                   10                  15

Asp Met Ala Gly Ile Gly Ser Thr Leu Asn Ala Ala Asn Val Val Ala
                20                  25                  30
```

```
Ala Val Pro Thr Thr Gly Val Leu Ala Ala Ala Asp Glu Val Ser
         35                  40                  45

Thr Gln Val Ala Ala Leu Leu Ser Ala His Ala Gln Gly Tyr Gln Gln
 50                  55                  60

Leu Ser Arg Gln Met Met Thr Ala Phe His Asp Gln Phe Val Gln Ala
 65                  70                  75                  80

Leu Arg Ala Ser Ala Asp Ala Tyr Ala Thr Ala Glu Ala Ser Ala Ala
                 85                  90                  95

Gln Thr Met Val Asn Ala Val Asn Ala Pro Ala Arg Ala Leu Leu Gly
                100                 105                 110

His Pro Leu Ile Ser Ala Asp Ala Ser Thr Gly Gly Ser Asn Ala
                115                 120                 125

Leu Ser Arg Val Gln Ser Met Phe Leu Gly Thr Gly Gly Ser Ser Ala
130                 135                 140

Leu Gly Gly Ser Ala Ala Asn Ala Ala Ser Gly Ala Leu Gln
145                 150                 155                 160

Leu Gln Pro Thr Gly Gly Ala Ser Gly Leu Ser Ala Val Gly Ala Leu
                165                 170                 175

Leu Pro Arg Ala Gly Ala Ala Ala Ala Ala Leu Pro Ala Leu Ala
                180                 185                 190

Ala Glu Ser Ile Gly Asn Ala Ile Lys Asn Leu Tyr Asn Ala Val Glu
                195                 200                 205

Pro Trp Val Gln Tyr Gly Phe Asn Leu Thr Ala Trp Ala Val Gly Trp
                210                 215                 220

Leu Pro Tyr Ile Gly Ile Leu Ala Pro Gln Ile Asn Phe Phe Tyr Tyr
225                 230                 235                 240

Leu Gly Glu Pro Ile Val Gln Ala Val Leu Phe Asn Ala Ile Asp Phe
                245                 250                 255

Val Asp Gly Thr Val Thr Phe Ser Gln Ala Leu Thr Asn Ile Glu Thr
                260                 265                 270

Ala Thr Ala Ala Ser Ile Asn Gln Phe Ile Asn Thr Glu Ile Asn Trp
                275                 280                 285

Ile Arg Gly Phe Leu Pro Pro Leu Pro Pro Ile Ser Pro Gly Phe
                290                 295                 300

Pro Ser Leu Pro
305

<210> SEQ ID NO 29
<211> LENGTH: 562
<212> TYPE: PRT
<213> ORGANISM: Mycobacterium tuberculosis

<400> SEQUENCE: 29

Met Glu Tyr Leu Ile Ala Ala Gln Asp Val Leu Val Ala Ala Ala
 1               5                  10                  15

Asp Leu Glu Gly Ile Gly Ser Ala Leu Ala Ala Asn Arg Ala Ala
                 20                  25                  30

Glu Ala Pro Thr Thr Gly Leu Leu Ala Ala Gly Ala Asp Glu Val Ser
                 35                  40                  45

Ala Ala Ile Ala Ser Leu Phe Ser Gly Asn Ala Gln Ala Tyr Gln Ala
 50                  55                  60

Leu Ser Ala Gln Ala Ala Ala Phe His Gln Gln Phe Val Arg Ala Leu
 65                  70                  75                  80

Ser Ser Ala Ala Gly Ser Tyr Ala Ala Ala Glu Ala Ala Asn Ala Ser
```

```
                    85                  90                  95
Pro Met Gln Ala Val Leu Asp Val Val Asn Gly Pro Thr Gln Leu Leu
            100                 105                 110

Leu Gly Arg Pro Leu Ile Gly Asp Gly Ala Asn Gly Gly Pro Gly Gln
            115                 120                 125

Asn Gly Gly Asp Gly Gly Leu Leu Tyr Gly Asn Gly Asn Gly Gly
            130                 135                 140

Ser Ser Ser Thr Pro Gly Gln Pro Gly Gly Arg Gly Gly Ala Ala Gly
145                 150                 155                 160

Leu Ile Gly Asn Gly Gly Ala Gly Gly Ala Gly Gly Pro Gly Ala Asn
                165                 170                 175

Gly Gly Ala Gly Gly Asn Gly Gly Trp Leu Tyr Gly Asn Gly Gly Leu
            180                 185                 190

Gly Gly Asn Gly Gly Ala Ala Thr Gln Ile Gly Asn Gly Gly Asn
            195                 200                 205

Gly Gly His Gly Gly Asn Ala Gly Leu Trp Gly Asn Gly Gly Ala Gly
            210                 215                 220

Gly Ala Gly Ala Ala Gly Ala Ala Gly Ala Asn Gly Gln Asn Pro Val
225                 230                 235                 240

Ser His Gln Val Thr His Ala Thr Asp Gly Ala Asp Gly Thr Thr Gly
                245                 250                 255

Pro Asp Gly Asn Gly Thr Asp Ala Gly Ser Gly Ser Asn Ala Val Asn
            260                 265                 270

Pro Gly Val Gly Gly Gly Ala Gly Gly Ile Gly Gly Asp Gly Thr Asn
            275                 280                 285

Leu Gly Gln Thr Asp Val Ser Gly Ala Gly Gly Asp Gly Gly Asp
            290                 295                 300

Gly Ala Asn Phe Ala Ser Gly Gly Ala Gly Gly Asn Gly Gly Ala Ala
305                 310                 315                 320

Gln Ser Gly Phe Gly Asp Ala Val Gly Gly Asn Gly Gly Ala Gly Gly
            325                 330                 335

Asn Gly Gly Ala Gly Gly Gly Gly Leu Gly Gly Ala Gly Gly Ser
            340                 345                 350

Ala Asn Val Ala Asn Ala Gly Asn Ser Ile Gly Gly Asn Gly Gly Ala
            355                 360                 365

Gly Gly Asn Gly Gly Ile Gly Ala Pro Gly Gly Ala Gly Gly Ala Gly
            370                 375                 380

Gly Asn Ala Asn Gln Asp Asn Pro Pro Gly Gly Asn Ser Thr Gly Gly
385                 390                 395                 400

Asn Gly Gly Ala Gly Gly Asp Gly Gly Val Gly Ala Ser Ala Asp Val
            405                 410                 415

Gly Gly Ala Gly Gly Phe Gly Gly Ser Gly Gly Arg Gly Gly Leu Leu
            420                 425                 430

Leu Gly Thr Gly Gly Ala Gly Gly Asp Gly Gly Val Gly Gly Asp Gly
            435                 440                 445

Gly Ile Gly Ala Gln Gly Gly Ser Gly Gly Asn Gly Gly Asn Gly Gly
            450                 455                 460

Ile Gly Ala Asp Gly Met Ala Asn Gln Asp Gly Asp Gly Gly Asp Gly
465                 470                 475                 480

Gly Asn Gly Gly Asp Gly Gly Ala Gly Ala Gly Gly Val Gly Gly
            485                 490                 495

Asn Gly Gly Thr Gly Gly Ala Gly Gly Leu Phe Gly Gln Ser Gly Ser
            500                 505                 510
```

-continued

Pro Gly Ser Gly Ala Ala Gly Leu Gly Ala Gly Gly Asn Gly
                515                 520                 525

Gly Ala Gly Gly Gly Gly Thr Gly Phe Asn Pro Gly Ala Pro Gly
    530                 535                 540

Asp Pro Gly Thr Gln Gly Ala Thr Gly Ala Asn Gly Gln His Gly Leu
545                 550                 555                 560

Asn Gly

<210> SEQ ID NO 30
<211> LENGTH: 496
<212> TYPE: PRT
<213> ORGANISM: Mycobacterium tuberculosis

<400> SEQUENCE: 30

Met His Asp Asp Phe Glu Arg Cys Tyr Arg Ala Ile Gln Ser Lys Asp
1               5                   10                  15

Ala Arg Phe Asp Gly Trp Phe Val Val Ala Val Leu Thr Thr Gly Val
                20                  25                  30

Tyr Cys Arg Pro Ser Cys Pro Val Arg Pro Phe Ala Arg Asn Val
            35                  40                  45

Arg Phe Leu Pro Thr Ala Ala Ala Gln Gly Glu Gly Phe Arg Ala
    50                  55                  60

Cys Lys Arg Cys Arg Pro Asp Ala Ser Pro Gly Ser Pro Glu Trp Asn
65                  70                  75                  80

Val Arg Ser Asp Val Val Ala Arg Ala Met Arg Leu Ile Ala Asp Gly
                85                  90                  95

Thr Val Asp Arg Asp Gly Val Ser Gly Leu Ala Ala Gln Leu Gly Tyr
            100                 105                 110

Thr Ile Arg Gln Leu Glu Arg Leu Leu Gln Ala Val Val Gly Ala Gly
        115                 120                 125

Pro Leu Ala Leu Ala Arg Ala Gln Arg Met Gln Thr Ala Arg Val Leu
    130                 135                 140

Ile Glu Thr Thr Asn Leu Pro Phe Gly Asp Val Ala Phe Ala Ala Gly
145                 150                 155                 160

Phe Ser Ser Ile Arg Gln Phe Asn Asp Thr Val Arg Leu Ala Cys Asp
                165                 170                 175

Gly Thr Pro Thr Ala Leu Arg Ala Arg Ala Ala Arg Phe Glu Ser
            180                 185                 190

Ala Thr Ala Ser Ala Gly Thr Val Ser Leu Arg Leu Pro Val Arg Ala
        195                 200                 205

Pro Phe Ala Phe Glu Gly Val Phe Gly His Leu Ala Ala Thr Ala Val
    210                 215                 220

Pro Gly Cys Glu Glu Val Arg Asp Gly Ala Tyr Arg Arg Thr Leu Arg
225                 230                 235                 240

Leu Pro Trp Gly Asn Gly Ile Val Ser Leu Thr Pro Ala Pro Asp His
                245                 250                 255

Val Arg Cys Leu Leu Val Leu Asp Asp Phe Arg Asp Leu Met Thr Ala
            260                 265                 270

Thr Ala Arg Cys Arg Arg Leu Leu Asp Leu Asp Ala Asp Pro Glu Ala
        275                 280                 285

Ile Val Glu Ala Leu Gly Ala Asp Pro Asp Leu Arg Ala Val Val Gly
    290                 295                 300

Lys Ala Pro Gly Gln Arg Ile Pro Arg Thr Val Asp Glu Ala Glu Phe
305                 310                 315                 320

```
Ala Val Arg Ala Val Leu Ala Gln Gln Val Ser Thr Lys Ala Ala Ser
                325                 330                 335

Thr His Ala Gly Arg Leu Val Ala Ala Tyr Gly Arg Pro Val His Asp
            340                 345                 350

Arg His Gly Ala Leu Thr His Thr Phe Pro Ser Ile Glu Gln Leu Ala
        355                 360                 365

Glu Ile Asp Pro Gly His Leu Ala Val Pro Lys Ala Arg Gln Arg Thr
    370                 375                 380

Ile Asn Ala Leu Val Ala Ser Leu Ala Asp Lys Ser Leu Val Leu Asp
385                 390                 395                 400

Ala Gly Cys Asp Trp Gln Arg Ala Arg Gly Gln Leu Leu Ala Leu Pro
                405                 410                 415

Gly Val Gly Pro Trp Thr Ala Glu Val Ile Ala Met Arg Gly Leu Gly
            420                 425                 430

Asp Pro Asp Ala Phe Pro Ala Ser Asp Leu Gly Leu Arg Leu Ala Ala
        435                 440                 445

Lys Lys Leu Gly Leu Pro Ala Gln Arg Arg Ala Leu Thr Val His Ser
    450                 455                 460

Ala Arg Trp Arg Pro Trp Arg Ser Tyr Ala Thr Gln His Leu Trp Thr
465                 470                 475                 480

Thr Leu Glu His Pro Val Asn Gln Trp Pro Pro Gln Glu Lys Ile Ala
                485                 490                 495

<210> SEQ ID NO 31
<211> LENGTH: 273
<212> TYPE: PRT
<213> ORGANISM: Mycobacterium tuberculosis

<400> SEQUENCE: 31

Met Val Val Ala Leu Val Gly Ser Ala Ile Val Asp Leu His Ser Arg
1               5                   10                  15

Pro Pro Trp Ser Asn Asn Ala Val Arg Arg Leu Gly Val Ala Leu Arg
            20                  25                  30

Asp Gly Val Asp Pro Pro Val Asp Cys Pro Ser Tyr Ala Glu Val Met
        35                  40                  45

Leu Trp His Ala Asp Leu Ala Ala Glu Val Gln Asp Arg Ile Glu Gly
    50                  55                  60

Arg Ser Trp Ser Ala Ser Glu Leu Leu Val Thr Ser Arg Ala Lys Ser
65                  70                  75                  80

Gln Asp Thr Leu Leu Ala Lys Leu Arg Arg Arg Pro Tyr Leu Gln Leu
                85                  90                  95

Asn Thr Ile Gln Asp Ile Ala Gly Val Arg Ile Asp Ala Asp Leu Leu
            100                 105                 110

Leu Gly Glu Gln Thr Arg Leu Ala Arg Glu Ile Ala Asp His Phe Gly
        115                 120                 125

Ala Asp Gln Pro Ala Ile His Asp Leu Arg Asp His Pro His Ala Gly
    130                 135                 140

Tyr Arg Ala Val His Val Trp Leu Arg Leu Pro Ala Gly Arg Val Glu
145                 150                 155                 160

Ile Gln Ile Arg Thr Ile Leu Gln Ser Leu Trp Ala Asn Phe Tyr Glu
                165                 170                 175

Leu Leu Ala Asp Ala Tyr Gly Arg Gly Ile Arg Tyr Asp Glu Arg Pro
            180                 185                 190

Glu Gln Leu Ala Ala Gly Val Val Pro Ala Gln Leu Gln Glu Leu Val
```

```
                195                 200                 205
Gly Val Met Gln Asp Ala Ser Ala Asp Leu Ala Met His Glu Ala Glu
    210                 215                 220

Trp Gln His Cys Ala Glu Ile Glu Tyr Pro Gly Gln Arg Ala Met Ala
225                 230                 235                 240

Leu Gly Glu Ala Ser Lys Asn Lys Ala Thr Val Leu Ala Thr Thr Lys
                245                 250                 255

Phe Arg Leu Glu Arg Ala Ile Asn Glu Ala Glu Ser Ala Gly Gly Gly
                260                 265                 270

Gly

<210> SEQ ID NO 32
<211> LENGTH: 491
<212> TYPE: PRT
<213> ORGANISM: Mycobacterium tuberculosis

<400> SEQUENCE: 32

Met Ser Asn Val Met Val Val Pro Gly Met Leu Ser Ala Ala Ala Ala
1               5                   10                  15

Asp Val Ala Ser Ile Gly Ala Ala Leu Ser Ala Ala Asn Gly Ala Ala
                20                  25                  30

Ala Pro Thr Thr Ala Gly Val Leu Ala Ala Gly Ala Asp Glu Val Ser
            35                  40                  45

Ala Ala Ile Ala Ser Leu Phe Ser Gly Tyr Ala Arg Asp Tyr Gln Ala
        50                  55                  60

Leu Ser Ala Gln Met Ala Arg Phe His Gln Gln Phe Val Gln Ala Leu
65                  70                  75                  80

Thr Ala Ser Val Gly Ser Tyr Ala Ala Ala Glu Ala Ala Asn Ala Ser
                85                  90                  95

Pro Leu Gln Ala Leu Glu Gln Gln Val Leu Ala Ala Ile Asn Ala Pro
                100                 105                 110

Thr Gln Thr Leu Leu Gly Arg Pro Leu Ile Gly Asn Gly Ala Asp Gly
            115                 120                 125

Leu Pro Gly Gln Asn Gly Ala Gly Gly Leu Leu Trp Gly Asn Gly
        130                 135                 140

Gly Asn Gly Gly Ala Gly Asp Ala Ala His Pro Asn Gly Gly Asn Gly
145                 150                 155                 160

Gly Asp Ala Gly Met Phe Gly Asn Gly Gly Ala Gly Gly Ala Gly Tyr
                165                 170                 175

Ser Pro Ala Gly Thr Gly Ala Ala Gly Gly Ala Gly Gly Ala Gly
            180                 185                 190

Gly Ala Gly Gly Trp Leu Ser Gly Asn Gly Gly Ala Gly Gly Asn Gly
            195                 200                 205

Gly Thr Gly Ala Ser Gly Ala Asp Gly Gly Gly Gly Leu Pro Pro Val
    210                 215                 220

Pro Ala Ser Pro Gly Gly Asn Gly Gly Gly Gly Asp Ala Gly Gly Ala
225                 230                 235                 240

Ala Gly Met Phe Gly Thr Gly Gly Ala Gly Gly Thr Gly Gly Asp Gly
                245                 250                 255

Gly Ala Gly Gly Ala Gly Asp Ser Pro Asn Ser Gly Ala Asn Gly Ala
                260                 265                 270

Arg Gly Gly Asp Gly Gly Asn Gly Ala Ala Gly Gly Ala Gly Gly Arg
            275                 280                 285

Leu Phe Gly Asn Gly Gly Ala Gly Gly Asn Gly Gly Thr Ala Gly Gln
```

```
                    290                 295                 300
Gly Gly Asp Gly Gly Thr Ala Leu Gly Ala Gly Ile Gly Asp
305                 310                 315                 320

Gly Gly Thr Gly Gly Ala Gly Thr Gly Thr Ala Gly Ile Gly
                325                 330                 335

Gly Ser Ser Ala Gly Ala Gly Ala Gly Gly Asp Gly Gly Ala Gly
                340                 345                 350

Gly Thr Gly Gly Ser Ser Met Ile Gly Gly Lys Gly Gly Thr Gly
                355                 360                 365

Gly Asn Gly Gly Val Gly Gly Thr Gly Gly Ala Ser Ala Leu Thr Ile
    370                 375                 380

Gly Asn Gly Ser Ser Ala Gly Ala Gly Gly Ala Gly Gly Ala Gly Gly
385                 390                 395                 400

Thr Gly Gly Thr Gly Gly Tyr Ile Glu Ser Leu Asp Gly Lys Gly Gln
                405                 410                 415

Ala Gly Asn Gly Gly Asn Gly Gly Asn Gly Ala Ala Gly Gly Ala Gly
                420                 425                 430

Gly Gly Gly Thr Gly Ala Gly Gly Asn Gly Ala Gly Gly Asn Gly
                435                 440                 445

Gly Asp Gly Gly Pro Ser Gln Gly Gly Asn Pro Gly Phe Gly Gly
    450                 455                 460

Asp Gly Gly Thr Gly Gly Pro Gly Gly Val Gly Val Pro Asp Gly Ile
465                 470                 475                 480

Gly Gly Ala Asn Gly Ala Gln Gly Lys His Gly
                485                 490

<210> SEQ ID NO 33
<211> LENGTH: 111
<212> TYPE: PRT
<213> ORGANISM: Mycobacterium tuberculosis

<400> SEQUENCE: 33

Met Gln Ser Met Ser Phe Asp Pro Ala Val Ala Asp Ile Gly Ser Gln
1               5                   10                  15

Val Val Asn Asn Ala Phe Gln Gly Leu Gln Ala Gly Ala Val Ala Trp
            20                  25                  30

Val Ser Leu Ser Ser Leu Leu Pro Ala Gly Ala Glu Glu Val Ser Ala
        35                  40                  45

Trp Ala Val Thr Ala Phe Thr Thr Ala Thr Gly Leu Leu Ala Leu
    50                  55                  60

Asn Gln Ala Ala Gln Glu Glu Leu Arg Lys Ala Gly Glu Val Phe Thr
65                  70                  75                  80

Ala Ile Ala Arg Met Tyr Ser Asp Ala Asp Val Arg Ala Ala Ala Cys
                85                  90                  95

Leu Leu Glu Ala Ile Pro Arg Pro Gly Gln Thr Leu Ala Arg Glu
            100                 105                 110

<210> SEQ ID NO 34
<211> LENGTH: 615
<212> TYPE: PRT
<213> ORGANISM: Mycobacterium tuberculosis

<400> SEQUENCE: 34

Met Leu Tyr Val Val Ala Ser Pro Asp Leu Met Thr Ala Ala Ala Thr
1               5                   10                  15

Asn Leu Ala Glu Ile Gly Ser Ala Ile Ser Thr Ala Asn Gly Ala Ala
```

```
                20                  25                  30
Ala Leu Pro Thr Val Glu Val Ala Ala Ala Asp Glu Val Ser
            35                  40                  45
Thr Gln Ile Ala Ala Leu Phe Gly Ala His Ala Arg Ser Tyr Gln Thr
    50                  55                  60
Leu Ser Thr Gln Ala Ala Phe His Ser Arg Phe Val Gln Ala Leu
65                  70                  75                  80
Thr Thr Ala Ala Ala Ser Tyr Ala Ser Val Glu Ala Ala Asn Ala Ser
                85                  90                  95
Pro Leu Gln Val Ala Leu Asp Val Ile Asn Ala Pro Ala Gln Thr Leu
            100                 105                 110
Leu Gly Arg Pro Leu Ile Gly Asn Gly Ala Asp Gly Ser Thr Pro Gly
            115                 120                 125
Gln Ala Gly Gly Pro Gly Gly Leu Leu Tyr Gly Asn Gly Gly Asn Gly
        130                 135                 140
Ala Ala Gly Gly Pro Asn Gln Ala Gly Gly Ala Gly Gly Asn Ala Gly
145                 150                 155                 160
Leu Ile Gly Asn Gly Gly Ala Gly Gly Ala Gly Gly Val Gly Ala Val
                165                 170                 175
Gly Gly Lys Arg Gly Thr Gly Gly Leu Leu Phe Gly Asn Gly Gly Ala
            180                 185                 190
Gly Gly Gln Gly Gly Leu Gly Leu Ala Gly Ile Asn Gly Gly Ser Gly
        195                 200                 205
Gly Gln Gly Gly His Gly Gly Asn Ala Ile Leu Phe Gly Gln Gly Gly
    210                 215                 220
Ala Gly Gly Pro Gly Gly Thr Gly Ala Met Gly Val Ala Gly Thr Asn
225                 230                 235                 240
Pro Thr Pro Ile Gly Thr Ala Ala Pro Gly Ser Asp Gly Val Asn Gln
                245                 250                 255
Ile Gly Asn Gly Gly Asn Thr Asp Leu Thr Gly Gly Ala Gly Gly Asp
            260                 265                 270
Gly Asn Ala Gly Ser Thr Thr Val Asn Gly Gly Asn Gly Gly Thr Gly
        275                 280                 285
Gly Ala Ala Arg Asn Ser Ser Gly Gly Thr Gly Asn Ser Phe Gly Gly
    290                 295                 300
Ala Gly Gly Ala Gly Gly Asp Gly Ala Asn Gly Gly Asp Gly Gly Ala
305                 310                 315                 320
Gly Gly Glu Ala Leu Thr Glu Gly Gly Ala Thr Ala Val Ser Gly Ala
                325                 330                 335
Gly Gly Lys Gly Gly Asn Ala Glu Ala Ser Gly Gly Ala Gly Gly Asn
            340                 345                 350
Gly Gly Lys Gly Gly Phe Ala Gln Ala Thr Thr Ser Val Thr Gly Gly
        355                 360                 365
Asn Gly Gly Asn Gly Gly Asn Gly His Asp Ser Asn Ala Pro Gly Gly
    370                 375                 380
Ala Gly Gly Ser Gly Gly Val Gly Gly Asp Gly Gly Arg Gly Gly Leu
385                 390                 395                 400
Leu Ala Gly Asn Gly Gly Thr Gly Gly Ala Gly Gly Asn Gly Gly Thr
                405                 410                 415
Gly Gly Ala Gly Ala Pro Gly Gly Ala Gly Gly Ala Gly Gly Lys Ala
            420                 425                 430
Asp Ile Ala Asn Ser Leu Gly Asp Asn Ala Thr Val Thr Gly Gly Asn
        435                 440                 445
```

-continued

```
Gly Gly Thr Gly Gly Asp Gly Ser Ala Leu Gly Thr Gly Gly Ala
    450                 455                 460
Gly Gly Ala Gly Gly Leu Gly His Gly Ala Gly Gly Leu Leu
465                 470                 475                 480
Ile Gly Asn Gly Gly Ala Gly Gly Ala Gly Leu Gly Gly Ala Gly
                485                 490                 495
Gly Ala Gly Gly Ala Gly Gly Glu Gly Ala Gly Gly Ala Gly Gly
            500                 505                 510
Glu Ala Ile Pro Gly Gly Ala Ser Thr Asn Ser Ala Gly Asp Gly
        515                 520                 525
Gly Ala Gly Gly Thr Gly Gly Asn Gly Gly Asp Gly Ala Gly Gly
    530                 535                 540
Ala Pro Gly Leu Gly Gly Ala Gly Gly Ala Gly Gly Trp Leu Ile Gly
545                 550                 555                 560
Gln Ser Gly Ser Thr Gly Gly Gly Ala Gly Gly Ala Gly Gly Ala
                565                 570                 575
Gly Gly Ala Gly Gly Ala Gly Gly Ser Gly Gly Ala Gly Gly His Gly
            580                 585                 590
Asp Thr Thr Ser Gly Lys Asn Gly Ser Ser Gly Thr Ala Gly Phe Asp
        595                 600                 605
Gly Asn Pro Gly Gln Pro Gly
    610                 615

<210> SEQ ID NO 35
<211> LENGTH: 15
<212> TYPE: PRT
<213> ORGANISM: Mycobacterium tuberculosis

<400> SEQUENCE: 35

Ala Met His Leu Leu Leu Asn Met Trp Ala Leu Tyr Val Val Gly
1               5                   10                  15

<210> SEQ ID NO 36
<211> LENGTH: 15
<212> TYPE: PRT
<213> ORGANISM: Mycobacterium tuberculosis

<400> SEQUENCE: 36

Ser Leu Phe Ala Ala Leu Asn Ile Ala Ala Val Val Ala Val Leu
1               5                   10                  15

<210> SEQ ID NO 37
<211> LENGTH: 15
<212> TYPE: PRT
<213> ORGANISM: Mycobacterium tuberculosis

<400> SEQUENCE: 37

Ala Ala Phe Gln Gly Ala His Ala Arg Phe Val Ala Ala Ala Ala
1               5                   10                  15

<210> SEQ ID NO 38
<211> LENGTH: 15
<212> TYPE: PRT
<213> ORGANISM: Mycobacterium tuberculosis

<400> SEQUENCE: 38

Ala Ala Gly Thr Tyr Val Ala Ala Asp Ala Ala Ala Ala Ser Ser
1               5                   10                  15
```

<210> SEQ ID NO 39
<211> LENGTH: 15
<212> TYPE: PRT
<213> ORGANISM: Mycobacterium tuberculosis

<400> SEQUENCE: 39

Glu Asp Leu Val Arg Ala Tyr His Ala Met Ser Ser Thr His Glu
1 5 10 15

<210> SEQ ID NO 40
<211> LENGTH: 15
<212> TYPE: PRT
<213> ORGANISM: Mycobacterium tuberculosis

<400> SEQUENCE: 40

Leu Gln Ser Leu Gly Ala Glu Ile Ala Val Glu Gln Ala Ala Leu
1 5 10 15

<210> SEQ ID NO 41
<211> LENGTH: 15
<212> TYPE: PRT
<213> ORGANISM: Mycobacterium tuberculosis

<400> SEQUENCE: 41

Met Ser Gln Ile Met Tyr Asn Tyr Pro Ala Met Met Ala His Ala
1 5 10 15

<210> SEQ ID NO 42
<211> LENGTH: 15
<212> TYPE: PRT
<213> ORGANISM: Mycobacterium tuberculosis

<400> SEQUENCE: 42

Asp Arg Trp Leu Asp Leu Arg Tyr Val Gly Pro Ala Ser Ala Asp
1 5 10 15

<210> SEQ ID NO 43
<211> LENGTH: 15
<212> TYPE: PRT
<213> ORGANISM: Mycobacterium tuberculosis

<400> SEQUENCE: 43

Glu Val Val Asp Tyr Leu Gly Ile Pro Ala Ser Ala Arg Pro Val
1 5 10 15

<210> SEQ ID NO 44
<211> LENGTH: 15
<212> TYPE: PRT
<213> ORGANISM: Mycobacterium tuberculosis

<400> SEQUENCE: 44

Gly Asn Gly Val Val Ala Leu Arg Asn Ala Gln Leu Val Thr Phe
1 5 10 15

<210> SEQ ID NO 45
<211> LENGTH: 15
<212> TYPE: PRT
<213> ORGANISM: Mycobacterium tuberculosis

<400> SEQUENCE: 45

Ala Ala Gly Ala Gln Leu Leu Trp Gln Leu Pro Leu Leu Ser Ile
1 5 10 15

<210> SEQ ID NO 46
<211> LENGTH: 15

```
<212> TYPE: PRT
<213> ORGANISM: Mycobacterium tuberculosis

<400> SEQUENCE: 46

Ala Ala Gly Val Ala Ala Trp Ser Leu Ile Ala Leu Met Ile Pro
1               5                   10                  15

<210> SEQ ID NO 47
<211> LENGTH: 15
<212> TYPE: PRT
<213> ORGANISM: Mycobacterium tuberculosis

<400> SEQUENCE: 47

Gly Trp Tyr Leu Val Ala Ala Thr Ala Ala Ala Thr Leu Arg
1               5                   10                  15

<210> SEQ ID NO 48
<211> LENGTH: 15
<212> TYPE: PRT
<213> ORGANISM: Mycobacterium tuberculosis

<400> SEQUENCE: 48

Ile Pro Val Met Ala Tyr Leu Val Gly Leu Phe Ala Trp Val Leu
1               5                   10                  15

<210> SEQ ID NO 49
<211> LENGTH: 15
<212> TYPE: PRT
<213> ORGANISM: Mycobacterium tuberculosis

<400> SEQUENCE: 49

Gln Leu Ser Ala Leu Trp Ala Arg Phe Pro Leu Pro Val Ile Pro
1               5                   10                  15

<210> SEQ ID NO 50
<211> LENGTH: 15
<212> TYPE: PRT
<213> ORGANISM: Mycobacterium tuberculosis

<400> SEQUENCE: 50

Ala Ile Leu Arg Arg Arg Arg Arg Ile Ala Glu Pro Ala Thr Cys
1               5                   10                  15

<210> SEQ ID NO 51
<211> LENGTH: 15
<212> TYPE: PRT
<213> ORGANISM: Mycobacterium tuberculosis

<400> SEQUENCE: 51

Glu Ile Gly Trp Glu Ala Gly Thr Ala Ala Pro Asp Glu Ile Pro
1               5                   10                  15

<210> SEQ ID NO 52
<211> LENGTH: 15
<212> TYPE: PRT
<213> ORGANISM: Mycobacterium tuberculosis

<400> SEQUENCE: 52

Ala Arg Ile Val Ile Phe Phe Val Gly Ser Val Phe Leu Leu Thr
1               5                   10                  15

<210> SEQ ID NO 53
<211> LENGTH: 15
<212> TYPE: PRT
<213> ORGANISM: Mycobacterium tuberculosis
```

<400> SEQUENCE: 53

Arg Arg Pro Leu Leu Val Ala Val Ser Trp Ala Ile Phe Ala Leu
1               5                   10                  15

<210> SEQ ID NO 54
<211> LENGTH: 15
<212> TYPE: PRT
<213> ORGANISM: Mycobacterium tuberculosis

<400> SEQUENCE: 54

Ile Asp Leu Asn Val Leu Leu Ser Ala Ala Ile Asn Phe Phe Leu
1               5                   10                  15

<210> SEQ ID NO 55
<211> LENGTH: 15
<212> TYPE: PRT
<213> ORGANISM: Mycobacterium tuberculosis

<400> SEQUENCE: 55

Cys Ile Leu Ala Trp Ile Leu Val Arg Ile Ile Asn Val Arg Ser
1               5                   10                  15

<210> SEQ ID NO 56
<211> LENGTH: 15
<212> TYPE: PRT
<213> ORGANISM: Mycobacterium tuberculosis

<400> SEQUENCE: 56

Ile Gly Leu Val Thr Gln Thr Ile Asn Asp Phe Tyr Phe Val Ile
1               5                   10                  15

<210> SEQ ID NO 57
<211> LENGTH: 15
<212> TYPE: PRT
<213> ORGANISM: Mycobacterium tuberculosis

<400> SEQUENCE: 57

Glu Pro Tyr Ala Val Trp Leu Asp Asp Trp Tyr Ala Arg Glu Ser
1               5                   10                  15

<210> SEQ ID NO 58
<211> LENGTH: 15
<212> TYPE: PRT
<213> ORGANISM: Mycobacterium tuberculosis

<400> SEQUENCE: 58

Ala Glu His Gln Ala Ile Ile Arg Asp Val Leu Thr Ala Ser Asp
1               5                   10                  15

<210> SEQ ID NO 59
<211> LENGTH: 15
<212> TYPE: PRT
<213> ORGANISM: Mycobacterium tuberculosis

<400> SEQUENCE: 59

Ala Glu His Gln Ala Ile Val Arg Asp Val Leu Ala Ala Gly Asp
1               5                   10                  15

<210> SEQ ID NO 60
<211> LENGTH: 15
<212> TYPE: PRT
<213> ORGANISM: Mycobacterium tuberculosis

<400> SEQUENCE: 60

Asn Gln Ala Phe Arg Asn Ile Val Asn Met Leu His Gly Val Arg
1               5                   10                  15

<210> SEQ ID NO 61
<211> LENGTH: 15
<212> TYPE: PRT
<213> ORGANISM: Mycobacterium tuberculosis

<400> SEQUENCE: 61

Asn Tyr Glu Gln Gln Glu Gln Ala Ser Gln Gln Ile Leu Ser Ser
1               5                   10                  15

<210> SEQ ID NO 62
<211> LENGTH: 15
<212> TYPE: PRT
<213> ORGANISM: Mycobacterium tuberculosis

<400> SEQUENCE: 62

Thr Cys Asn Tyr Gly Gln Val Val Ala Ala Leu Asn Ala Thr Asp
1               5                   10                  15

<210> SEQ ID NO 63
<211> LENGTH: 15
<212> TYPE: PRT
<213> ORGANISM: Mycobacterium tuberculosis

<400> SEQUENCE: 63

Thr Asp Ala Met Arg Lys Val Thr Gly Met His Val Arg Leu Ala
1               5                   10                  15

<210> SEQ ID NO 64
<211> LENGTH: 15
<212> TYPE: PRT
<213> ORGANISM: Mycobacterium tuberculosis

<400> SEQUENCE: 64

Gly Asp Leu Arg Val Ile Ile Leu Glu Gly Gln Pro Ile His Val
1               5                   10                  15

<210> SEQ ID NO 65
<211> LENGTH: 15
<212> TYPE: PRT
<213> ORGANISM: Mycobacterium tuberculosis

<400> SEQUENCE: 65

Ala Glu Val Ile Arg Leu Ile Arg Arg Leu Leu Pro Ala Leu Val
1               5                   10                  15

<210> SEQ ID NO 66
<211> LENGTH: 15
<212> TYPE: PRT
<213> ORGANISM: Mycobacterium tuberculosis

<400> SEQUENCE: 66

Leu Trp Ile Trp Val Ala Leu Thr Gly Ala Ala Ala Thr Val Leu
1               5                   10                  15

<210> SEQ ID NO 67
<211> LENGTH: 15
<212> TYPE: PRT
<213> ORGANISM: Mycobacterium tuberculosis

<400> SEQUENCE: 67

Ala Ala Val Ala Leu Gly Phe Phe Val Trp Leu Glu Gly Arg Ala

<210> SEQ ID NO 68
<211> LENGTH: 15
<212> TYPE: PRT
<213> ORGANISM: Mycobacterium tuberculosis

<400> SEQUENCE: 68

Ala Ile Ser Val Thr Ala Tyr Ala Leu Ala Ala Glu Val Val Pro
1               5                   10                  15

<210> SEQ ID NO 69
<211> LENGTH: 15
<212> TYPE: PRT
<213> ORGANISM: Mycobacterium tuberculosis

<400> SEQUENCE: 69

Thr Pro Val Gln Ser Gln Arg Val Asp Pro Ser Ala Ala Ser Gly
1               5                   10                  15

<210> SEQ ID NO 70
<211> LENGTH: 15
<212> TYPE: PRT
<213> ORGANISM: Mycobacterium tuberculosis

<400> SEQUENCE: 70

Asn Gln Gly Gly Trp Met Leu Ser Arg Ala Ser Ala Met Glu Leu
1               5                   10                  15

<210> SEQ ID NO 71
<211> LENGTH: 15
<212> TYPE: PRT
<213> ORGANISM: Mycobacterium tuberculosis

<400> SEQUENCE: 71

Phe Phe Gln Val Leu Val Thr Gln Phe Gly Ser Ser Gly Gly Pro
1               5                   10                  15

<210> SEQ ID NO 72
<211> LENGTH: 15
<212> TYPE: PRT
<213> ORGANISM: Mycobacterium tuberculosis

<400> SEQUENCE: 72

Ala Asp Ser Ser Lys Tyr Met Ile Thr Leu His Thr Pro Ile Ala
1               5                   10                  15

<210> SEQ ID NO 73
<211> LENGTH: 15
<212> TYPE: PRT
<213> ORGANISM: Mycobacterium tuberculosis

<400> SEQUENCE: 73

Ala Leu Gly Glu Arg Arg Leu Val Arg Leu Leu Arg Leu Gly Gly
1               5                   10                  15

<210> SEQ ID NO 74
<211> LENGTH: 15
<212> TYPE: PRT
<213> ORGANISM: Mycobacterium tuberculosis

<400> SEQUENCE: 74

Asn Leu Ala Ile Cys Leu Val Leu Ile Tyr Ala Ile Ala Leu Val
1               5                   10                  15

```
<210> SEQ ID NO 75
<211> LENGTH: 15
<212> TYPE: PRT
<213> ORGANISM: Mycobacterium tuberculosis

<400> SEQUENCE: 75

Ala Ala Thr Ile Asp Gln Leu Lys Thr Asp Ala Lys Leu Leu Ser
1               5                   10                  15

<210> SEQ ID NO 76
<211> LENGTH: 15
<212> TYPE: PRT
<213> ORGANISM: Mycobacterium tuberculosis

<400> SEQUENCE: 76

Ala Ala Phe Ser Lys Leu Pro Ala Ser Thr Ile Asp Glu Leu Lys
1               5                   10                  15

<210> SEQ ID NO 77
<211> LENGTH: 15
<212> TYPE: PRT
<213> ORGANISM: Mycobacterium tuberculosis

<400> SEQUENCE: 77

Ala Asn Ala Thr Val Tyr Met Ile Asp Ser Val Leu Met Pro Pro
1               5                   10                  15

<210> SEQ ID NO 78
<211> LENGTH: 15
<212> TYPE: PRT
<213> ORGANISM: Mycobacterium tuberculosis

<400> SEQUENCE: 78

Ala Phe Ile Phe Ala Asp Leu Leu Ile Leu Pro Ile Leu Asn Ile
1               5                   10                  15

<210> SEQ ID NO 79
<211> LENGTH: 15
<212> TYPE: PRT
<213> ORGANISM: Mycobacterium tuberculosis

<400> SEQUENCE: 79

Ala Ile Asn Gly Asp Phe Ile Leu Ile Ala Pro Glu Val Gln Glu
1               5                   10                  15

<210> SEQ ID NO 80
<211> LENGTH: 15
<212> TYPE: PRT
<213> ORGANISM: Mycobacterium tuberculosis

<400> SEQUENCE: 80

Glu Glu Pro Arg Leu Phe Tyr Met His Tyr Trp Ala Val Asp Asp
1               5                   10                  15

<210> SEQ ID NO 81
<211> LENGTH: 15
<212> TYPE: PRT
<213> ORGANISM: Mycobacterium tuberculosis

<400> SEQUENCE: 81

Ile Val Val Met Tyr Leu Leu Leu Ala Ala Thr Ala Val Ala Ala
1               5                   10                  15

<210> SEQ ID NO 82
```

```
<211> LENGTH: 15
<212> TYPE: PRT
<213> ORGANISM: Mycobacterium tuberculosis

<400> SEQUENCE: 82

Leu Thr Ala Ile Arg Tyr Gln Ile Val Val Met Tyr Leu Leu Leu
1               5                   10                  15

<210> SEQ ID NO 83
<211> LENGTH: 15
<212> TYPE: PRT
<213> ORGANISM: Mycobacterium tuberculosis

<400> SEQUENCE: 83

Leu Leu Val Ile Pro Val Ala Leu Ser Ala Ser Ile Ile Arg Leu
1               5                   10                  15

<210> SEQ ID NO 84
<211> LENGTH: 15
<212> TYPE: PRT
<213> ORGANISM: Mycobacterium tuberculosis

<400> SEQUENCE: 84

Gly Thr Val Leu Val Asn Leu Ile Asn Thr Lys Leu Thr Val Ala
1               5                   10                  15

<210> SEQ ID NO 85
<211> LENGTH: 15
<212> TYPE: PRT
<213> ORGANISM: Mycobacterium tuberculosis

<400> SEQUENCE: 85

Leu Glu Asn Asp Asn Gln Leu Leu Tyr Asn Tyr Pro Gly Ala Leu
1               5                   10                  15

<210> SEQ ID NO 86
<211> LENGTH: 15
<212> TYPE: PRT
<213> ORGANISM: Mycobacterium tuberculosis

<400> SEQUENCE: 86

Met Ala Phe Leu Arg Ser Val Ser Cys Leu Ala Ala Ala Val Phe
1               5                   10                  15

<210> SEQ ID NO 87
<211> LENGTH: 15
<212> TYPE: PRT
<213> ORGANISM: Mycobacterium tuberculosis

<400> SEQUENCE: 87

Leu Arg Ile Ala Ala Lys Ile Tyr Ser Glu Asp Glu Ala Trp
1               5                   10                  15

<210> SEQ ID NO 88
<211> LENGTH: 15
<212> TYPE: PRT
<213> ORGANISM: Mycobacterium tuberculosis

<400> SEQUENCE: 88

Val Asp Leu Ala Lys Ser Leu Arg Ile Ala Ala Lys Ile Tyr Ser
1               5                   10                  15

<210> SEQ ID NO 89
<211> LENGTH: 15
<212> TYPE: PRT
```

-continued

<213> ORGANISM: Mycobacterium tuberculosis

<400> SEQUENCE: 89

Ile Ile Ser Asp Val Ala Asp Ile Ile Lys Gly Thr Leu Gly Glu
1               5                   10                  15

<210> SEQ ID NO 90
<211> LENGTH: 15
<212> TYPE: PRT
<213> ORGANISM: Mycobacterium tuberculosis

<400> SEQUENCE: 90

Ala Asp Tyr Asn Met Leu Leu Ile Ser Arg Leu Arg Glu Glu Ala
1               5                   10                  15

<210> SEQ ID NO 91
<211> LENGTH: 15
<212> TYPE: PRT
<213> ORGANISM: Mycobacterium tuberculosis

<400> SEQUENCE: 91

Ala Ile Thr Ile Leu Leu Leu Val Ile Leu Leu Ile Ile Tyr Gly
1               5                   10                  15

<210> SEQ ID NO 92
<211> LENGTH: 15
<212> TYPE: PRT
<213> ORGANISM: Mycobacterium tuberculosis

<400> SEQUENCE: 92

Asp Arg Ser Arg Ile Glu Phe Ala Ile Thr Ile Leu Leu Leu Val
1               5                   10                  15

<210> SEQ ID NO 93
<211> LENGTH: 15
<212> TYPE: PRT
<213> ORGANISM: Mycobacterium tuberculosis

<400> SEQUENCE: 93

Ile Ile Pro Glu Tyr Leu Phe Ile Gln Ser Ser Thr Asp Leu Arg
1               5                   10                  15

<210> SEQ ID NO 94
<211> LENGTH: 15
<212> TYPE: PRT
<213> ORGANISM: Mycobacterium tuberculosis

<400> SEQUENCE: 94

Leu Val Ile Leu Leu Ile Ile Tyr Arg Asn Pro Ile Thr Met Val
1               5                   10                  15

<210> SEQ ID NO 95
<211> LENGTH: 15
<212> TYPE: PRT
<213> ORGANISM: Mycobacterium tuberculosis

<400> SEQUENCE: 95

Ala Ala Val Val Arg Phe Gln Glu Ala Ala Asn Lys Gln Lys Gln
1               5                   10                  15

<210> SEQ ID NO 96
<211> LENGTH: 15
<212> TYPE: PRT
<213> ORGANISM: Mycobacterium tuberculosis

```
<400> SEQUENCE: 96

Glu Gln Gln Trp Asn Phe Ala Gly Ile Glu Ala Ala Ala Ser Ala
1               5                   10                  15

<210> SEQ ID NO 97
<211> LENGTH: 15
<212> TYPE: PRT
<213> ORGANISM: Mycobacterium tuberculosis

<400> SEQUENCE: 97

Arg Gln Ser Gly Ala Thr Ile Ala Asp Val Leu Ala Glu Lys Glu
1               5                   10                  15

<210> SEQ ID NO 98
<211> LENGTH: 15
<212> TYPE: PRT
<213> ORGANISM: Mycobacterium tuberculosis

<400> SEQUENCE: 98

Ala Gln Ala Val Tyr Asp Phe Arg Ser Ile Val Asp Tyr Leu Arg
1               5                   10                  15

<210> SEQ ID NO 99
<211> LENGTH: 15
<212> TYPE: PRT
<213> ORGANISM: Mycobacterium tuberculosis

<400> SEQUENCE: 99

Leu Asp Tyr Leu Arg Arg Met Thr Val Phe Leu Gln Gly Leu Met
1               5                   10                  15

<210> SEQ ID NO 100
<211> LENGTH: 15
<212> TYPE: PRT
<213> ORGANISM: Mycobacterium tuberculosis

<400> SEQUENCE: 100

Leu Asn Tyr Arg Pro Leu Leu Pro Lys Asp Arg Arg Met Ile Ile
1               5                   10                  15

<210> SEQ ID NO 101
<211> LENGTH: 15
<212> TYPE: PRT
<213> ORGANISM: Mycobacterium tuberculosis

<400> SEQUENCE: 101

Arg Cys Ala Leu His Trp Phe Pro Gly Ser His Leu Leu His Val
1               5                   10                  15

<210> SEQ ID NO 102
<211> LENGTH: 15
<212> TYPE: PRT
<213> ORGANISM: Mycobacterium tuberculosis

<400> SEQUENCE: 102

Ile Ala Tyr Pro Val Leu Trp Arg His Leu Thr Ala Ile Val Ala
1               5                   10                  15

<210> SEQ ID NO 103
<211> LENGTH: 15
<212> TYPE: PRT
<213> ORGANISM: Mycobacterium tuberculosis

<400> SEQUENCE: 103
```

Ala Tyr Ala Gln Arg Val Tyr Gln Ala Asn Arg Ala Ala Gly Ser
1               5                   10                  15

<210> SEQ ID NO 104
<211> LENGTH: 15
<212> TYPE: PRT
<213> ORGANISM: Mycobacterium tuberculosis

<400> SEQUENCE: 104

Val Thr Val Asp Ala Ala Val Leu Ala Ala Ile Asp Ala Asp Ala
1               5                   10                  15

<210> SEQ ID NO 105
<211> LENGTH: 15
<212> TYPE: PRT
<213> ORGANISM: Mycobacterium tuberculosis

<400> SEQUENCE: 105

Glu His Glu Leu Tyr Val Ala Val Leu Ser Asn Ala Leu His Arg
1               5                   10                  15

<210> SEQ ID NO 106
<211> LENGTH: 15
<212> TYPE: PRT
<213> ORGANISM: Mycobacterium tuberculosis

<400> SEQUENCE: 106

Arg Val Pro Glu Asp Leu Leu Ala Met Val Val Ala Val Glu Gln
1               5                   10                  15

<210> SEQ ID NO 107
<211> LENGTH: 15
<212> TYPE: PRT
<213> ORGANISM: Mycobacterium tuberculosis

<400> SEQUENCE: 107

Ala Thr Gly Ile Val Leu Met Leu Gly Asp Gln Pro Gln Val Ala
1               5                   10                  15

<210> SEQ ID NO 108
<211> LENGTH: 15
<212> TYPE: PRT
<213> ORGANISM: Mycobacterium tuberculosis

<400> SEQUENCE: 108

Asp Asn Gly Val Gly Tyr Val Gly Leu Val Ala Ser Thr Val Arg
1               5                   10                  15

<210> SEQ ID NO 109
<211> LENGTH: 15
<212> TYPE: PRT
<213> ORGANISM: Mycobacterium tuberculosis

<400> SEQUENCE: 109

Ile Cys Val Arg Val Ala Glu Gln Leu Ala Glu Leu Ser Ser Glu
1               5                   10                  15

<210> SEQ ID NO 110
<211> LENGTH: 15
<212> TYPE: PRT
<213> ORGANISM: Mycobacterium tuberculosis

<400> SEQUENCE: 110

Ala Val Pro Leu Arg Leu Leu Gly Gly Leu His Arg Met Val Leu
1               5                   10                  15

<210> SEQ ID NO 111
<211> LENGTH: 15
<212> TYPE: PRT
<213> ORGANISM: Mycobacterium tuberculosis

<400> SEQUENCE: 111

Met Tyr Arg Glu Leu Leu Glu Leu Val Ala Ala Asp Val Glu Ser
1 5 10 15

<210> SEQ ID NO 112
<211> LENGTH: 15
<212> TYPE: PRT
<213> ORGANISM: Mycobacterium tuberculosis

<400> SEQUENCE: 112

Gly Asp Cys Leu Val Ala Phe Asp Ala Pro Leu Val Val Ala Asn
1 5 10 15

<210> SEQ ID NO 113
<211> LENGTH: 15
<212> TYPE: PRT
<213> ORGANISM: Mycobacterium tuberculosis

<400> SEQUENCE: 113

Ser Pro Glu Glu Ile Leu Asp Val Ile Ala Asp Phe Glu Ala Met
1 5 10 15

<210> SEQ ID NO 114
<211> LENGTH: 15
<212> TYPE: PRT
<213> ORGANISM: Mycobacterium tuberculosis

<400> SEQUENCE: 114

Arg Arg Asp Ile Glu Leu Ile His Glu Gln Leu Ala Asp Ala Gly
1 5 10 15

<210> SEQ ID NO 115
<211> LENGTH: 15
<212> TYPE: PRT
<213> ORGANISM: Mycobacterium tuberculosis

<400> SEQUENCE: 115

Thr Val Arg Tyr Arg Ile Arg Arg Ile Glu Gln Leu Leu Ser Thr
1 5 10 15

<210> SEQ ID NO 116
<211> LENGTH: 15
<212> TYPE: PRT
<213> ORGANISM: Mycobacterium tuberculosis

<400> SEQUENCE: 116

Arg Glu Leu Ile Arg Ala Phe Trp Pro Gly Ala Leu Ser Leu Val
1 5 10 15

<210> SEQ ID NO 117
<211> LENGTH: 15
<212> TYPE: PRT
<213> ORGANISM: Mycobacterium tuberculosis

<400> SEQUENCE: 117

Ala Ser Val His Val Leu Leu Ser His Leu His Ala Asp His Cys
1 5 10 15

<210> SEQ ID NO 118
<211> LENGTH: 15
<212> TYPE: PRT
<213> ORGANISM: Mycobacterium tuberculosis

<400> SEQUENCE: 118

Leu Gly Ala Leu Thr Ile Val Pro Arg Leu Val Ala His Pro Thr
1 5 10 15

<210> SEQ ID NO 119
<211> LENGTH: 15
<212> TYPE: PRT
<213> ORGANISM: Mycobacterium tuberculosis

<400> SEQUENCE: 119

Ala Val His Val Trp Leu Arg Leu Pro Ala Gly Arg Val Glu Ile
1 5 10 15

<210> SEQ ID NO 120
<211> LENGTH: 15
<212> TYPE: PRT
<213> ORGANISM: Mycobacterium tuberculosis

<400> SEQUENCE: 120

Leu Gln Ser Leu Trp Ala Asn Phe Tyr Glu Leu Leu Ala Asp Ala
1 5 10 15

<210> SEQ ID NO 121
<211> LENGTH: 15
<212> TYPE: PRT
<213> ORGANISM: Mycobacterium tuberculosis

<400> SEQUENCE: 121

Ala Asp Leu Ile Leu Leu Tyr Leu Ile Gln His Cys Pro Asp Leu
1 5 10 15

<210> SEQ ID NO 122
<211> LENGTH: 15
<212> TYPE: PRT
<213> ORGANISM: Mycobacterium tuberculosis

<400> SEQUENCE: 122

His Pro Ala Arg Arg Ala Ile Leu Ile Glu Asp Leu Leu Thr His
1 5 10 15

<210> SEQ ID NO 123
<211> LENGTH: 15
<212> TYPE: PRT
<213> ORGANISM: Mycobacterium tuberculosis

<400> SEQUENCE: 123

Met Val Trp Gln Arg Glu Lys Leu Leu Gln Val Asn Glu Ile Gly
1 5 10 15

<210> SEQ ID NO 124
<211> LENGTH: 15
<212> TYPE: PRT
<213> ORGANISM: Mycobacterium tuberculosis

<400> SEQUENCE: 124

Glu Leu Val Ala Ala Phe Leu Trp Ala Gln Phe Glu Glu Ala Glu
1 5 10 15

<210> SEQ ID NO 125
<211> LENGTH: 15

```
<212> TYPE: PRT
<213> ORGANISM: Mycobacterium tuberculosis

<400> SEQUENCE: 125

His Asn Asp Val Val Thr Val Ala Ser Ala Pro Lys Leu Arg Val
1               5                   10                  15

<210> SEQ ID NO 126
<211> LENGTH: 15
<212> TYPE: PRT
<213> ORGANISM: Mycobacterium tuberculosis

<400> SEQUENCE: 126

Ser Ser Thr Ala Thr Ser Gly Ala Ala Val Val Ser Pro Ala Glu
1               5                   10                  15

<210> SEQ ID NO 127
<211> LENGTH: 15
<212> TYPE: PRT
<213> ORGANISM: Mycobacterium tuberculosis

<400> SEQUENCE: 127

Ile Ala Gly Met Arg Leu Leu Val Ile Lys Pro Glu Pro Leu Ala
1               5                   10                  15

<210> SEQ ID NO 128
<211> LENGTH: 15
<212> TYPE: PRT
<213> ORGANISM: Mycobacterium tuberculosis

<400> SEQUENCE: 128

Asp Tyr Val Tyr Asn Ile Lys Ala Asn Pro Ala Val Arg Val Arg
1               5                   10                  15

<210> SEQ ID NO 129
<211> LENGTH: 15
<212> TYPE: PRT
<213> ORGANISM: Mycobacterium tuberculosis

<400> SEQUENCE: 129

Leu Ala Val Arg Tyr Gly Ile Ser Ser Leu Glu Glu Ala Gln Ala
1               5                   10                  15

<210> SEQ ID NO 130
<211> LENGTH: 15
<212> TYPE: PRT
<213> ORGANISM: Mycobacterium tuberculosis

<400> SEQUENCE: 130

Ala Phe Asn Glu Ile Leu Arg Arg Arg Ala Ala Thr Ala Val Ala
1               5                   10                  15

<210> SEQ ID NO 131
<211> LENGTH: 15
<212> TYPE: PRT
<213> ORGANISM: Mycobacterium tuberculosis

<400> SEQUENCE: 131

Val Asp Leu Ile Ala His Gly Thr Ala Ala Arg Ile Tyr Arg Leu
1               5                   10                  15

<210> SEQ ID NO 132
<211> LENGTH: 15
<212> TYPE: PRT
<213> ORGANISM: Mycobacterium tuberculosis
```

<400> SEQUENCE: 132

Tyr Leu Leu Asp Phe Leu Arg Gln Ser Gly Asn Thr Pro Ile Val
1               5                   10                  15

<210> SEQ ID NO 133
<211> LENGTH: 15
<212> TYPE: PRT
<213> ORGANISM: Mycobacterium tuberculosis

<400> SEQUENCE: 133

Val Val Ser Arg Glu His Leu Ile Gln Gln Ala Ile Ala Ala Asn
1               5                   10                  15

<210> SEQ ID NO 134
<211> LENGTH: 15
<212> TYPE: PRT
<213> ORGANISM: Mycobacterium tuberculosis

<400> SEQUENCE: 134

Lys Ala Gly Leu Asp Arg Leu Arg Ser Val Val His Ser Leu Ile
1               5                   10                  15

<210> SEQ ID NO 135
<211> LENGTH: 15
<212> TYPE: PRT
<213> ORGANISM: Mycobacterium tuberculosis

<400> SEQUENCE: 135

Asn Pro Gly Leu Leu Arg Phe Leu Pro Gln Leu Ser Glu Arg Leu
1               5                   10                  15

<210> SEQ ID NO 136
<211> LENGTH: 15
<212> TYPE: PRT
<213> ORGANISM: Mycobacterium tuberculosis

<400> SEQUENCE: 136

Pro Ala Leu Phe Val Phe Arg Pro Leu Leu Asn Leu Ala Leu Arg
1               5                   10                  15

<210> SEQ ID NO 137
<211> LENGTH: 15
<212> TYPE: PRT
<213> ORGANISM: Mycobacterium tuberculosis

<400> SEQUENCE: 137

Arg Arg Ser Phe Tyr Arg Ile Phe Phe Asp Ser Gly Phe Thr Pro
1               5                   10                  15

<210> SEQ ID NO 138
<211> LENGTH: 15
<212> TYPE: PRT
<213> ORGANISM: Mycobacterium tuberculosis

<400> SEQUENCE: 138

Arg Ser Ala Phe Arg Leu Ser Pro Pro Val Leu Ser Gly Ala Met
1               5                   10                  15

<210> SEQ ID NO 139
<211> LENGTH: 15
<212> TYPE: PRT
<213> ORGANISM: Mycobacterium tuberculosis

<400> SEQUENCE: 139

```
Leu Thr Leu Asn Glu Ile His Ala Phe Ile Lys Asp Pro Leu Gly
1               5                   10                  15
```

<210> SEQ ID NO 140
<211> LENGTH: 15
<212> TYPE: PRT
<213> ORGANISM: Mycobacterium tuberculosis

<400> SEQUENCE: 140

```
Ala Ala Phe Ser Arg Met Leu Ser Leu Phe Phe Arg Gln His Ile
1               5                   10                  15
```

<210> SEQ ID NO 141
<211> LENGTH: 15
<212> TYPE: PRT
<213> ORGANISM: Mycobacterium tuberculosis

<400> SEQUENCE: 141

```
Phe Asp Arg Glu Phe Thr Phe Gly Trp Asp Glu Leu Leu Ser Lys
1               5                   10                  15
```

<210> SEQ ID NO 142
<211> LENGTH: 15
<212> TYPE: PRT
<213> ORGANISM: Mycobacterium tuberculosis

<400> SEQUENCE: 142

```
Phe Tyr Asn Glu Lys Ala Phe Leu Leu Thr Thr Phe Asp Val Ser
1               5                   10                  15
```

<210> SEQ ID NO 143
<211> LENGTH: 15
<212> TYPE: PRT
<213> ORGANISM: Mycobacterium tuberculosis

<400> SEQUENCE: 143

```
Val Ala Asp Ile His Phe Gln Pro Arg Tyr Ile Phe Ala Ala Ile
1               5                   10                  15
```

<210> SEQ ID NO 144
<211> LENGTH: 15
<212> TYPE: PRT
<213> ORGANISM: Mycobacterium tuberculosis

<400> SEQUENCE: 144

```
Asp Phe Phe Val Ala Ala Asp Ser Ala Phe Ser Ser Leu Asn Asp
1               5                   10                  15
```

<210> SEQ ID NO 145
<211> LENGTH: 15
<212> TYPE: PRT
<213> ORGANISM: Mycobacterium tuberculosis

<400> SEQUENCE: 145

```
His Arg Asp Asp Arg Tyr Cys Tyr Phe Phe Ile Pro Ser Arg Lys
1               5                   10                  15
```

<210> SEQ ID NO 146
<211> LENGTH: 15
<212> TYPE: PRT
<213> ORGANISM: Mycobacterium tuberculosis

<400> SEQUENCE: 146

```
Ala Ala Ser Leu Leu Asp Glu Asp Met Asp Ala Leu Glu Glu Ala
```

```
1               5                   10                  15

<210> SEQ ID NO 147
<211> LENGTH: 15
<212> TYPE: PRT
<213> ORGANISM: Mycobacterium tuberculosis

<400> SEQUENCE: 147

Tyr Arg Ile Ala Ala Arg Pro Gly Ala Val Thr Arg Arg Ala Ala
1               5                   10                  15

<210> SEQ ID NO 148
<211> LENGTH: 15
<212> TYPE: PRT
<213> ORGANISM: Mycobacterium tuberculosis

<400> SEQUENCE: 148

Leu Ala Leu Leu Leu Val Pro Gly Val Pro Leu Val Val Met Pro
1               5                   10                  15

<210> SEQ ID NO 149
<211> LENGTH: 15
<212> TYPE: PRT
<213> ORGANISM: Mycobacterium tuberculosis

<400> SEQUENCE: 149

Ala Asp Gln Ile Leu Arg Glu Thr Leu Leu Thr Val Ser Ser Asp
1               5                   10                  15

<210> SEQ ID NO 150
<211> LENGTH: 15
<212> TYPE: PRT
<213> ORGANISM: Mycobacterium tuberculosis

<400> SEQUENCE: 150

Glu Trp Leu Tyr Gln Ser Trp Ala Ala Ala Tyr Leu Pro Leu Leu
1               5                   10                  15

<210> SEQ ID NO 151
<211> LENGTH: 15
<212> TYPE: PRT
<213> ORGANISM: Mycobacterium tuberculosis

<400> SEQUENCE: 151

Gly Gln Leu Leu Val Phe Asp Thr Arg Arg Gly Met Val Val Gly
1               5                   10                  15

<210> SEQ ID NO 152
<211> LENGTH: 15
<212> TYPE: PRT
<213> ORGANISM: Mycobacterium tuberculosis

<400> SEQUENCE: 152

Asp Asp Tyr Asn Glu Leu Val Ile Ser Val Pro Leu Gln Leu Thr
1               5                   10                  15

<210> SEQ ID NO 153
<211> LENGTH: 15
<212> TYPE: PRT
<213> ORGANISM: Mycobacterium tuberculosis

<400> SEQUENCE: 153

Asp Gly Leu Val Leu Asn Phe Asp Asp Tyr Asn Glu Leu Val Ile
1               5                   10                  15
```

<210> SEQ ID NO 154
<211> LENGTH: 15
<212> TYPE: PRT
<213> ORGANISM: Mycobacterium tuberculosis

<400> SEQUENCE: 154

Asp Asp Gly Ala Ile Asp Ile Leu Leu Val Gly Leu Asp Ser Arg
1               5                   10                  15

<210> SEQ ID NO 155
<211> LENGTH: 15
<212> TYPE: PRT
<213> ORGANISM: Mycobacterium tuberculosis

<400> SEQUENCE: 155

Asp Gly Leu Leu Ala Ile Leu Ala Ala Gly Ala Ser Leu Val Gln
1               5                   10                  15

<210> SEQ ID NO 156
<211> LENGTH: 15
<212> TYPE: PRT
<213> ORGANISM: Mycobacterium tuberculosis

<400> SEQUENCE: 156

Asp Ile Gly Cys Val Phe Ser Ile Asp Thr Asp Ala His Ala Pro
1               5                   10                  15

<210> SEQ ID NO 157
<211> LENGTH: 15
<212> TYPE: PRT
<213> ORGANISM: Mycobacterium tuberculosis

<400> SEQUENCE: 157

Glu Pro Glu Met Leu Asp Arg Leu Asp Ile Val Val Ala Ser Val
1               5                   10                  15

<210> SEQ ID NO 158
<211> LENGTH: 15
<212> TYPE: PRT
<213> ORGANISM: Mycobacterium tuberculosis

<400> SEQUENCE: 158

Lys Lys Val Ala Gly Leu Ile Lys Leu Gln Ile Val Ala Gly Gln
1               5                   10                  15

<210> SEQ ID NO 159
<211> LENGTH: 15
<212> TYPE: PRT
<213> ORGANISM: Mycobacterium tuberculosis

<400> SEQUENCE: 159

Glu Lys Ser Tyr Gly Leu Leu Asp Asp Asn Val Tyr Thr Phe Leu
1               5                   10                  15

<210> SEQ ID NO 160
<211> LENGTH: 15
<212> TYPE: PRT
<213> ORGANISM: Mycobacterium tuberculosis

<400> SEQUENCE: 160

Leu Ile Ile Leu Arg Lys Arg Glu Asn Phe Arg Arg Ala Phe Ser
1               5                   10                  15

<210> SEQ ID NO 161

```
<211> LENGTH: 15
<212> TYPE: PRT
<213> ORGANISM: Mycobacterium tuberculosis

<400> SEQUENCE: 161

Asn Gln Arg Gln Lys Phe Asn Pro Leu Val Arg Leu Asp Ser Ile
1               5                   10                  15

<210> SEQ ID NO 162
<211> LENGTH: 15
<212> TYPE: PRT
<213> ORGANISM: Mycobacterium tuberculosis

<400> SEQUENCE: 162

Ala Ala Phe Tyr Arg Leu Ser Ser Leu Arg Leu Trp Pro Asp Arg
1               5                   10                  15

<210> SEQ ID NO 163
<211> LENGTH: 15
<212> TYPE: PRT
<213> ORGANISM: Mycobacterium tuberculosis

<400> SEQUENCE: 163

Ala Gln Leu Gly Tyr Thr Ile Arg Gln Leu Glu Arg Leu Leu Gln
1               5                   10                  15

<210> SEQ ID NO 164
<211> LENGTH: 15
<212> TYPE: PRT
<213> ORGANISM: Mycobacterium tuberculosis

<400> SEQUENCE: 164

Ile Arg Gln Leu Glu Arg Leu Leu Gln Ala Val Val Gly Ala Gly
1               5                   10                  15

<210> SEQ ID NO 165
<211> LENGTH: 15
<212> TYPE: PRT
<213> ORGANISM: Mycobacterium tuberculosis

<400> SEQUENCE: 165

Ala Ala Gln His Arg Gln Ile Val Ala Asp Phe Cys Asp Phe Leu
1               5                   10                  15

<210> SEQ ID NO 166
<211> LENGTH: 15
<212> TYPE: PRT
<213> ORGANISM: Mycobacterium tuberculosis

<400> SEQUENCE: 166

Gly His Val Val Arg Phe Leu Glu Ala Gly Ser Lys Val Lys Val
1               5                   10                  15

<210> SEQ ID NO 167
<211> LENGTH: 15
<212> TYPE: PRT
<213> ORGANISM: Mycobacterium tuberculosis

<400> SEQUENCE: 167

Gly Lys Ile Val Arg Gln Lys Ala Asn Arg Arg His Leu Leu Glu
1               5                   10                  15

<210> SEQ ID NO 168
<211> LENGTH: 15
<212> TYPE: PRT
```

<213> ORGANISM: Mycobacterium tuberculosis

<400> SEQUENCE: 168

Asp Gly Asp Arg His Ala Arg Gly Phe Glu Asp Leu Val Glu Val
1 5 10 15

<210> SEQ ID NO 169
<211> LENGTH: 15
<212> TYPE: PRT
<213> ORGANISM: Mycobacterium tuberculosis

<400> SEQUENCE: 169

Glu Glu Ile Ala Leu Ile Ala Arg Trp Leu Ala Glu Pro Gly Val
1 5 10 15

<210> SEQ ID NO 170
<211> LENGTH: 15
<212> TYPE: PRT
<213> ORGANISM: Mycobacterium tuberculosis

<400> SEQUENCE: 170

Asp His Gly Gly Val Ile Phe Ile Asp Leu Arg Asp Ala Ser Gly
1 5 10 15

<210> SEQ ID NO 171
<211> LENGTH: 15
<212> TYPE: PRT
<213> ORGANISM: Mycobacterium tuberculosis

<400> SEQUENCE: 171

Phe Thr Gln Leu Asp Met Glu Met Ser Phe Val Asp Ala Glu Asp
1 5 10 15

<210> SEQ ID NO 172
<211> LENGTH: 15
<212> TYPE: PRT
<213> ORGANISM: Mycobacterium tuberculosis

<400> SEQUENCE: 172

Phe Val Asp Ala Glu Asp Ile Ile Ala Ile Ser Glu Glu Val Leu
1 5 10 15

<210> SEQ ID NO 173
<211> LENGTH: 15
<212> TYPE: PRT
<213> ORGANISM: Mycobacterium tuberculosis

<400> SEQUENCE: 173

Met Phe Val Leu Arg Ser His Ala Ala Gly Leu Leu Arg Glu Gly
1 5 10 15

<210> SEQ ID NO 174
<211> LENGTH: 15
<212> TYPE: PRT
<213> ORGANISM: Mycobacterium tuberculosis

<400> SEQUENCE: 174

Ala Leu Cys Leu Arg Leu Leu Thr Ala Arg Ser Arg Thr Arg Ala
1 5 10 15

<210> SEQ ID NO 175
<211> LENGTH: 15
<212> TYPE: PRT
<213> ORGANISM: Mycobacterium tuberculosis

<400> SEQUENCE: 175

Ala Val Asp Gly Arg Phe Ala Val Pro Gln Ile Leu Gly Asp Glu
1               5                   10                  15

<210> SEQ ID NO 176
<211> LENGTH: 15
<212> TYPE: PRT
<213> ORGANISM: Mycobacterium tuberculosis

<400> SEQUENCE: 176

Gln Ala Tyr Leu Ala Leu Arg Ala Trp Gly Leu Pro Val Ser Glu
1               5                   10                  15

<210> SEQ ID NO 177
<211> LENGTH: 15
<212> TYPE: PRT
<213> ORGANISM: Mycobacterium tuberculosis

<400> SEQUENCE: 177

Val Asp His Leu Glu Arg Met Leu Ser Leu Asp Asn Ala Phe Thr
1               5                   10                  15

<210> SEQ ID NO 178
<211> LENGTH: 15
<212> TYPE: PRT
<213> ORGANISM: Mycobacterium tuberculosis

<400> SEQUENCE: 178

Val Gly Gly Ala Gly Phe Ala Thr Asp Phe Glu Pro Val Asp His
1               5                   10                  15

<210> SEQ ID NO 179
<211> LENGTH: 15
<212> TYPE: PRT
<213> ORGANISM: Mycobacterium tuberculosis

<400> SEQUENCE: 179

Ala Glu Lys Phe Lys Glu Asp Val Ile Asn Asp Phe Val Ser Ser
1               5                   10                  15

<210> SEQ ID NO 180
<211> LENGTH: 15
<212> TYPE: PRT
<213> ORGANISM: Mycobacterium tuberculosis

<400> SEQUENCE: 180

Ala His Gly Glu Thr Val Ser Ala Val Ala Glu Leu Ile Gly Asp
1               5                   10                  15

<210> SEQ ID NO 181
<211> LENGTH: 15
<212> TYPE: PRT
<213> ORGANISM: Mycobacterium tuberculosis

<400> SEQUENCE: 181

Gln Gln Ile Lys Phe Ala Ala Leu Ser Ala Arg Ala Val Ala Leu
1               5                   10                  15

<210> SEQ ID NO 182
<211> LENGTH: 15
<212> TYPE: PRT
<213> ORGANISM: Mycobacterium tuberculosis

<400> SEQUENCE: 182

Ala Arg Val Gln Ile His Arg Ala Asn Asp Gln Val Arg Ile Tyr
1               5                   10                  15

<210> SEQ ID NO 183
<211> LENGTH: 15
<212> TYPE: PRT
<213> ORGANISM: Mycobacterium tuberculosis

<400> SEQUENCE: 183

Gly Asp Gly Thr Gln Leu Gln Val Met Ile Ser Leu Asp Lys Val
1               5                   10                  15

<210> SEQ ID NO 184
<211> LENGTH: 15
<212> TYPE: PRT
<213> ORGANISM: Mycobacterium tuberculosis

<400> SEQUENCE: 184

Leu Gly Asp Ile Val Tyr Val His Gly Ala Val Ile Ser Ser Arg
1               5                   10                  15

<210> SEQ ID NO 185
<211> LENGTH: 15
<212> TYPE: PRT
<213> ORGANISM: Mycobacterium tuberculosis

<400> SEQUENCE: 185

Ser Arg Phe Tyr Phe Leu Thr Gly Arg Gly Ala Leu Leu Gln Leu
1               5                   10                  15

<210> SEQ ID NO 186
<211> LENGTH: 15
<212> TYPE: PRT
<213> ORGANISM: Mycobacterium tuberculosis

<400> SEQUENCE: 186

Glu Ser Thr Asn Thr Lys Ile Arg Leu Leu Thr Arg Ile Ala Phe
1               5                   10                  15

<210> SEQ ID NO 187
<211> LENGTH: 15
<212> TYPE: PRT
<213> ORGANISM: Mycobacterium tuberculosis

<400> SEQUENCE: 187

Ala Leu Val Ala Glu Gly Ile Glu Ala Ile Val Phe Arg Thr Leu
1               5                   10                  15

<210> SEQ ID NO 188
<211> LENGTH: 15
<212> TYPE: PRT
<213> ORGANISM: Mycobacterium tuberculosis

<400> SEQUENCE: 188

Ala Gly Trp Leu Ala Phe Phe Arg Asp Leu Val Ala Arg Gly Leu
1               5                   10                  15

<210> SEQ ID NO 189
<211> LENGTH: 15
<212> TYPE: PRT
<213> ORGANISM: Mycobacterium tuberculosis

<400> SEQUENCE: 189

Leu Arg Gly Leu Leu Ser Thr Phe Ile Ala Ala Leu Met Gly Ala
1               5                   10                  15

<210> SEQ ID NO 190
<211> LENGTH: 15
<212> TYPE: PRT
<213> ORGANISM: Mycobacterium tuberculosis

<400> SEQUENCE: 190

Gln Ala Ser Pro Asp Leu Leu Arg Gly Leu Leu Ser Thr Phe Ile
1               5                   10                  15

<210> SEQ ID NO 191
<211> LENGTH: 15
<212> TYPE: PRT
<213> ORGANISM: Mycobacterium tuberculosis

<400> SEQUENCE: 191

Ala Arg Thr Asp Leu Leu Ala Phe Thr Ala Phe Pro Lys Gln Ile
1               5                   10                  15

<210> SEQ ID NO 192
<211> LENGTH: 15
<212> TYPE: PRT
<213> ORGANISM: Mycobacterium tuberculosis

<400> SEQUENCE: 192

Ala Ser Ile Ile Arg Leu Val Gly Ala Val Leu Ala Glu Gln His
1               5                   10                  15

<210> SEQ ID NO 193
<211> LENGTH: 15
<212> TYPE: PRT
<213> ORGANISM: Mycobacterium tuberculosis

<400> SEQUENCE: 193

Phe Pro Asp Arg Ala Ser Ile Ile Arg Leu Val Gly Ala Val Leu
1               5                   10                  15

<210> SEQ ID NO 194
<211> LENGTH: 15
<212> TYPE: PRT
<213> ORGANISM: Mycobacterium tuberculosis

<400> SEQUENCE: 194

Tyr Leu Gly Leu Glu Val Leu Thr Arg Ala Arg Ala Ala Leu Thr
1               5                   10                  15

<210> SEQ ID NO 195
<211> LENGTH: 15
<212> TYPE: PRT
<213> ORGANISM: Mycobacterium tuberculosis

<400> SEQUENCE: 195

Met Arg Asn Val Arg Leu Phe Arg Ala Leu Leu Gly Val Asp Lys
1               5                   10                  15

<210> SEQ ID NO 196
<211> LENGTH: 15
<212> TYPE: PRT
<213> ORGANISM: Mycobacterium tuberculosis

<400> SEQUENCE: 196

Lys Pro Leu Val Leu Ile Leu Asp Asp Phe Ala Met Arg Glu His
1               5                   10                  15

-continued

<210> SEQ ID NO 197
<211> LENGTH: 15
<212> TYPE: PRT
<213> ORGANISM: Mycobacterium tuberculosis

<400> SEQUENCE: 197

Ala Val Trp Ala Phe Val Met Val Leu Ala Phe Ser Arg His Leu
1               5                   10                  15

<210> SEQ ID NO 198
<211> LENGTH: 15
<212> TYPE: PRT
<213> ORGANISM: Mycobacterium tuberculosis

<400> SEQUENCE: 198

Ala Ala Arg Leu Leu Ser Ile Arg Ala Met Ser Thr Lys Phe Ser
1               5                   10                  15

<210> SEQ ID NO 199
<211> LENGTH: 15
<212> TYPE: PRT
<213> ORGANISM: Mycobacterium tuberculosis

<400> SEQUENCE: 199

Ala Leu Ser Val Leu Val Gly Leu Thr Ala Ala Thr Val Ala Ile
1               5                   10                  15

<210> SEQ ID NO 200
<211> LENGTH: 15
<212> TYPE: PRT
<213> ORGANISM: Mycobacterium tuberculosis

<400> SEQUENCE: 200

Ala Thr Glu Val Val Arg Arg Leu Thr Ala Thr Ala His Arg Gly
1               5                   10                  15

<210> SEQ ID NO 201
<211> LENGTH: 15
<212> TYPE: PRT
<213> ORGANISM: Mycobacterium tuberculosis

<400> SEQUENCE: 201

Ala Ala Val Asp Lys Asp Ala Val Ile Val Ala Ala Ala Gly Asn
1               5                   10                  15

<210> SEQ ID NO 202
<211> LENGTH: 15
<212> TYPE: PRT
<213> ORGANISM: Mycobacterium tuberculosis

<400> SEQUENCE: 202

Ala Lys Leu Met Arg Asp Ile Pro Phe Arg Val Gly Ala Val Val
1               5                   10                  15

<210> SEQ ID NO 203
<211> LENGTH: 15
<212> TYPE: PRT
<213> ORGANISM: Mycobacterium tuberculosis

<400> SEQUENCE: 203

Asp Glu Ser Trp Gln Gln Phe Arg Gln Glu Leu Ile Pro Leu Leu
1               5                   10                  15

<210> SEQ ID NO 204
<211> LENGTH: 15

-continued

```
<212> TYPE: PRT
<213> ORGANISM: Mycobacterium tuberculosis

<400> SEQUENCE: 204

Met Trp Asp Pro Asp Val Tyr Leu Ala Phe Ser Gly His Arg Asn
1               5                   10                  15

<210> SEQ ID NO 205
<211> LENGTH: 15
<212> TYPE: PRT
<213> ORGANISM: Mycobacterium tuberculosis

<400> SEQUENCE: 205

Ser Thr Ile Phe Pro Phe Arg Arg Leu Phe Met Val Ala Asp Val
1               5                   10                  15

<210> SEQ ID NO 206
<211> LENGTH: 15
<212> TYPE: PRT
<213> ORGANISM: Mycobacterium tuberculosis

<400> SEQUENCE: 206

Ala Tyr Arg Thr Thr Ile Phe Ala Phe Pro Val Phe Gly Phe Gly
1               5                   10                  15

<210> SEQ ID NO 207
<211> LENGTH: 15
<212> TYPE: PRT
<213> ORGANISM: Mycobacterium tuberculosis

<400> SEQUENCE: 207

Phe Gly Val Ile Phe Gly Ala Ile Trp Ala Glu Ala Trp Gly
1               5                   10                  15

<210> SEQ ID NO 208
<211> LENGTH: 15
<212> TYPE: PRT
<213> ORGANISM: Mycobacterium tuberculosis

<400> SEQUENCE: 208

Phe Leu Leu Val Pro Val Leu Ile Leu Leu Thr Val Ser Gly Arg
1               5                   10                  15

<210> SEQ ID NO 209
<211> LENGTH: 15
<212> TYPE: PRT
<213> ORGANISM: Mycobacterium tuberculosis

<400> SEQUENCE: 209

Ile Leu Ala Lys Tyr Val Gln Leu Asp Phe Phe Arg His Val Asp
1               5                   10                  15

<210> SEQ ID NO 210
<211> LENGTH: 15
<212> TYPE: PRT
<213> ORGANISM: Mycobacterium tuberculosis

<400> SEQUENCE: 210

Asp Ser Phe Phe His Leu Ala Pro Leu Gly Gln Ser Gly Ala Leu
1               5                   10                  15

<210> SEQ ID NO 211
<211> LENGTH: 15
<212> TYPE: PRT
<213> ORGANISM: Mycobacterium tuberculosis
```

<400> SEQUENCE: 211

Gln Cys Lys Asp Ile Ile Asp Glu Leu Glu Arg Met Gln Val Phe
1               5                   10                  15

<210> SEQ ID NO 212
<211> LENGTH: 15
<212> TYPE: PRT
<213> ORGANISM: Mycobacterium tuberculosis

<400> SEQUENCE: 212

Met Ala Glu Ala Trp Phe Glu Thr Val Ala Ile Ala Gln Gln Arg
1               5                   10                  15

<210> SEQ ID NO 213
<211> LENGTH: 15
<212> TYPE: PRT
<213> ORGANISM: Mycobacterium tuberculosis

<400> SEQUENCE: 213

Gly Ile Val Ala Leu Ile Ala Leu Gly Ile Leu Glu His Phe Asp
1               5                   10                  15

<210> SEQ ID NO 214
<211> LENGTH: 15
<212> TYPE: PRT
<213> ORGANISM: Mycobacterium tuberculosis

<400> SEQUENCE: 214

Ala Ala Gln Glu Met Met Ile Ala Leu Arg Arg Leu Arg Glu Leu
1               5                   10                  15

<210> SEQ ID NO 215
<211> LENGTH: 15
<212> TYPE: PRT
<213> ORGANISM: Mycobacterium tuberculosis

<400> SEQUENCE: 215

Leu Gln Val Val Leu Arg Gly Tyr Ala Ser Met Val Ala Glu Leu
1               5                   10                  15

<210> SEQ ID NO 216
<211> LENGTH: 15
<212> TYPE: PRT
<213> ORGANISM: Mycobacterium tuberculosis

<400> SEQUENCE: 216

Lys Ala Ala Ile Glu Leu Ile Ala Asp His Gln Leu Thr Val Leu
1               5                   10                  15

<210> SEQ ID NO 217
<211> LENGTH: 15
<212> TYPE: PRT
<213> ORGANISM: Mycobacterium tuberculosis

<400> SEQUENCE: 217

Gly Lys Asp Gly Val Val Ala His Phe Val Glu Asp Leu Val Leu
1               5                   10                  15

<210> SEQ ID NO 218
<211> LENGTH: 15
<212> TYPE: PRT
<213> ORGANISM: Mycobacterium tuberculosis

<400> SEQUENCE: 218

Gly Ser Gly His Phe Val Lys Met Val His Asn Gly Ile Glu Tyr
1               5                   10                  15

<210> SEQ ID NO 219
<211> LENGTH: 15
<212> TYPE: PRT
<213> ORGANISM: Mycobacterium tuberculosis

<400> SEQUENCE: 219

Gly Ser Pro Leu Asn Leu Leu Arg Trp Thr Ser Ala Arg Ser Ile
1               5                   10                  15

<210> SEQ ID NO 220
<211> LENGTH: 15
<212> TYPE: PRT
<213> ORGANISM: Mycobacterium tuberculosis

<400> SEQUENCE: 220

Glu Leu Val Arg Ala Asp Val Thr Thr Pro Cys Leu Leu Pro Glu
1               5                   10                  15

<210> SEQ ID NO 221
<211> LENGTH: 15
<212> TYPE: PRT
<213> ORGANISM: Mycobacterium tuberculosis

<400> SEQUENCE: 221

Val Tyr Leu Val Trp Arg Phe Ile Val Pro Leu Val Gly Arg Leu
1               5                   10                  15

<210> SEQ ID NO 222
<211> LENGTH: 15
<212> TYPE: PRT
<213> ORGANISM: Mycobacterium tuberculosis

<400> SEQUENCE: 222

Ala Met Asp Tyr Thr Thr Ile Val Ala Ala Ala Ser Glu Ser
1               5                   10                  15

<210> SEQ ID NO 223
<211> LENGTH: 15
<212> TYPE: PRT
<213> ORGANISM: Mycobacterium tuberculosis

<400> SEQUENCE: 223

Gly Lys His Val Leu Ile Ile Phe Asp Asp Leu Thr Lys Gln Ala
1               5                   10                  15

<210> SEQ ID NO 224
<211> LENGTH: 15
<212> TYPE: PRT
<213> ORGANISM: Mycobacterium tuberculosis

<400> SEQUENCE: 224

Asp Asn Leu Val Arg Thr Ile Ser Leu Gln Pro Thr Asp Gly Leu
1               5                   10                  15

<210> SEQ ID NO 225
<211> LENGTH: 15
<212> TYPE: PRT
<213> ORGANISM: Mycobacterium tuberculosis

<400> SEQUENCE: 225

Phe Asp His Val Pro Glu Gln Ala Phe Phe Leu Ile Gly Gly Leu

```
<210> SEQ ID NO 226
<211> LENGTH: 15
<212> TYPE: PRT
<213> ORGANISM: Mycobacterium tuberculosis

<400> SEQUENCE: 226

Lys Asp Leu Gln Asp Ile Ile Ala Ile Leu Gly Ile Asp Glu Leu
1               5                   10                  15

<210> SEQ ID NO 227
<211> LENGTH: 15
<212> TYPE: PRT
<213> ORGANISM: Mycobacterium tuberculosis

<400> SEQUENCE: 227

Glu Gly Val Ser Ile Leu Ala Glu Ser Ala Glu Phe Glu Ser Glu
1               5                   10                  15

<210> SEQ ID NO 228
<211> LENGTH: 15
<212> TYPE: PRT
<213> ORGANISM: Mycobacterium tuberculosis

<400> SEQUENCE: 228

Gly Arg Leu Lys Gly Ile Leu Lys Tyr Tyr Asp Ala Pro Ile Val
1               5                   10                  15

<210> SEQ ID NO 229
<211> LENGTH: 15
<212> TYPE: PRT
<213> ORGANISM: Mycobacterium tuberculosis

<400> SEQUENCE: 229

Ile Gly Arg Asn Phe Tyr Arg Ala Leu Leu Ala Gln Gln Glu Gln
1               5                   10                  15

<210> SEQ ID NO 230
<211> LENGTH: 15
<212> TYPE: PRT
<213> ORGANISM: Mycobacterium tuberculosis

<400> SEQUENCE: 230

Cys Arg Arg Tyr Glu Val Leu Leu Ile Phe Asp Glu Ile Ala Thr
1               5                   10                  15

<210> SEQ ID NO 231
<211> LENGTH: 15
<212> TYPE: PRT
<213> ORGANISM: Mycobacterium tuberculosis

<400> SEQUENCE: 231

Cys Leu Gly Ser His Leu Ala Arg Leu Glu Leu Thr Leu Leu Val
1               5                   10                  15

<210> SEQ ID NO 232
<211> LENGTH: 15
<212> TYPE: PRT
<213> ORGANISM: Mycobacterium tuberculosis

<400> SEQUENCE: 232

Asp Leu Asp Ser Tyr Leu Val Glu Ile Thr Ala Glu Val Leu Arg
1               5                   10                  15
```

<210> SEQ ID NO 233
<211> LENGTH: 15
<212> TYPE: PRT
<213> ORGANISM: Mycobacterium tuberculosis

<400> SEQUENCE: 233

Glu Pro Gly Asp Ile Ile Ile Asp Gly Gly Asn Ala Leu Tyr Thr
1               5                   10                  15

<210> SEQ ID NO 234
<211> LENGTH: 15
<212> TYPE: PRT
<213> ORGANISM: Mycobacterium tuberculosis

<400> SEQUENCE: 234

Ala Ala Phe Asp Tyr Ala Asp Gly Ala Ala Glu Asp Glu Leu Ser
1               5                   10                  15

<210> SEQ ID NO 235
<211> LENGTH: 15
<212> TYPE: PRT
<213> ORGANISM: Mycobacterium tuberculosis

<400> SEQUENCE: 235

Arg Ala Arg Gln Gly Phe Arg Asp Ile Glu Phe His Pro Thr Ile
1               5                   10                  15

<210> SEQ ID NO 236
<211> LENGTH: 15
<212> TYPE: PRT
<213> ORGANISM: Mycobacterium tuberculosis

<400> SEQUENCE: 236

Ala Val Leu Leu Glu Lys Ile Val Ala Asp Glu Glu Glu His Ile
1               5                   10                  15

<210> SEQ ID NO 237
<211> LENGTH: 15
<212> TYPE: PRT
<213> ORGANISM: Mycobacterium tuberculosis

<400> SEQUENCE: 237

Ala Val Ser Ile Gly Ile Leu Leu Ser Leu Ile Ala Pro Leu Gly
1               5                   10                  15

<210> SEQ ID NO 238
<211> LENGTH: 15
<212> TYPE: PRT
<213> ORGANISM: Mycobacterium tuberculosis

<400> SEQUENCE: 238

Leu Leu Ser Thr Arg Gly Tyr Ile Thr Ala Glu Lys Ile Arg Ser
1               5                   10                  15

<210> SEQ ID NO 239
<211> LENGTH: 15
<212> TYPE: PRT
<213> ORGANISM: Mycobacterium tuberculosis

<400> SEQUENCE: 239

Ser Leu Ala Val Lys Thr Phe Glu Asp Leu Phe Ala Glu Leu Gly
1               5                   10                  15

<210> SEQ ID NO 240

```
<211> LENGTH: 15
<212> TYPE: PRT
<213> ORGANISM: Mycobacterium tuberculosis

<400> SEQUENCE: 240

Asp Val Ile His Ala Phe Trp Val Pro Glu Phe Leu Phe Lys Arg
1               5                   10                  15

<210> SEQ ID NO 241
<211> LENGTH: 15
<212> TYPE: PRT
<213> ORGANISM: Mycobacterium tuberculosis

<400> SEQUENCE: 241

Asp Met Thr Lys Ile Val Gly Leu Arg Ala Arg Ala Lys Ala Ala
1               5                   10                  15

<210> SEQ ID NO 242
<211> LENGTH: 15
<212> TYPE: PRT
<213> ORGANISM: Mycobacterium tuberculosis

<400> SEQUENCE: 242

Ala Pro Pro Asn Leu Ile Arg Ala Ile Leu Arg Ala Pro Val Asp
1               5                   10                  15

<210> SEQ ID NO 243
<211> LENGTH: 15
<212> TYPE: PRT
<213> ORGANISM: Mycobacterium tuberculosis

<400> SEQUENCE: 243

Glu Val Asn Ile Lys Ile Leu Ile Asp Ser Leu Val Ser Ala Gly
1               5                   10                  15

<210> SEQ ID NO 244
<211> LENGTH: 15
<212> TYPE: PRT
<213> ORGANISM: Mycobacterium tuberculosis

<400> SEQUENCE: 244

Leu Arg Leu Leu Val Ile Ala Leu Lys His Asn Val Ile Leu Asn
1               5                   10                  15

<210> SEQ ID NO 245
<211> LENGTH: 15
<212> TYPE: PRT
<213> ORGANISM: Mycobacterium tuberculosis

<400> SEQUENCE: 245

Asp Thr Gln Ser Met Ile Val Thr Asp His Arg Tyr Val Pro Ala
1               5                   10                  15

<210> SEQ ID NO 246
<211> LENGTH: 15
<212> TYPE: PRT
<213> ORGANISM: Mycobacterium tuberculosis

<400> SEQUENCE: 246

Val Asp Val Glu Asp Gly Arg Val Ile Val Asp Glu Tyr Gln Arg
1               5                   10                  15

<210> SEQ ID NO 247
<211> LENGTH: 15
<212> TYPE: PRT
```

<213> ORGANISM: Mycobacterium tuberculosis

<400> SEQUENCE: 247

Asp Ser Thr Val Ile Thr Asp Gly Asp Ile Val Asn Ile Asp Val
1               5                   10                  15

<210> SEQ ID NO 248
<211> LENGTH: 15
<212> TYPE: PRT
<213> ORGANISM: Mycobacterium tuberculosis

<400> SEQUENCE: 248

Glu Lys Met Arg Val Ala Gly Arg Ile Ala Ala Gly Ala Leu Ala
1               5                   10                  15

<210> SEQ ID NO 249
<211> LENGTH: 15
<212> TYPE: PRT
<213> ORGANISM: Mycobacterium tuberculosis

<400> SEQUENCE: 249

Ala Ala Val Ile Val Gly Ser Gly Arg Ile Ala Ser Leu Tyr Val
1               5                   10                  15

<210> SEQ ID NO 250
<211> LENGTH: 15
<212> TYPE: PRT
<213> ORGANISM: Mycobacterium tuberculosis

<400> SEQUENCE: 250

Ala His Glu Ser Leu Cys Phe Ala Gly Ala Asn Leu Ile Pro Leu
1               5                   10                  15

<210> SEQ ID NO 251
<211> LENGTH: 15
<212> TYPE: PRT
<213> ORGANISM: Mycobacterium tuberculosis

<400> SEQUENCE: 251

Ala Ala Leu Pro Leu Leu Phe Phe Ala Leu Ala Gly Gln Arg Ile
1               5                   10                  15

<210> SEQ ID NO 252
<211> LENGTH: 15
<212> TYPE: PRT
<213> ORGANISM: Mycobacterium tuberculosis

<400> SEQUENCE: 252

Gly Thr Val Val Leu Thr Ala Thr Phe Ala Leu Gly Ala Ala Leu
1               5                   10                  15

<210> SEQ ID NO 253
<211> LENGTH: 15
<212> TYPE: PRT
<213> ORGANISM: Mycobacterium tuberculosis

<400> SEQUENCE: 253

Leu Ala Leu Val Gly Phe Leu Gly Gly Leu Ile Thr Gly Ile Ser
1               5                   10                  15

<210> SEQ ID NO 254
<211> LENGTH: 15
<212> TYPE: PRT
<213> ORGANISM: Mycobacterium tuberculosis

<400> SEQUENCE: 254

Arg Gly Lys Val Val Leu Ile Asp Phe Trp Ala Tyr Pro Cys Ile
1               5                   10                  15

<210> SEQ ID NO 255
<211> LENGTH: 15
<212> TYPE: PRT
<213> ORGANISM: Mycobacterium tuberculosis

<400> SEQUENCE: 255

Ala Arg Val Phe Leu Asp Ser Val Leu Pro Ala Leu Gly Glu Glu
1               5                   10                  15

<210> SEQ ID NO 256
<211> LENGTH: 15
<212> TYPE: PRT
<213> ORGANISM: Mycobacterium tuberculosis

<400> SEQUENCE: 256

Phe Arg Val Val Ile Ser Ser Arg Phe Gly Asp Ile Phe Arg Gly
1               5                   10                  15

<210> SEQ ID NO 257
<211> LENGTH: 15
<212> TYPE: PRT
<213> ORGANISM: Mycobacterium tuberculosis

<400> SEQUENCE: 257

Ala Val Asp Ala Val Phe Val Gly Ser Cys Thr Asn Gly Arg Ile
1               5                   10                  15

<210> SEQ ID NO 258
<211> LENGTH: 15
<212> TYPE: PRT
<213> ORGANISM: Mycobacterium tuberculosis

<400> SEQUENCE: 258

Asp Thr Glu Val Tyr Leu Asp Ala Ala Ser Leu Ser Pro Phe Val
1               5                   10                  15

<210> SEQ ID NO 259
<211> LENGTH: 15
<212> TYPE: PRT
<213> ORGANISM: Mycobacterium tuberculosis

<400> SEQUENCE: 259

Ile Asn Leu Ile Ile His Tyr Val Asp Arg Pro Gly Ala Leu Gly
1               5                   10                  15

<210> SEQ ID NO 260
<211> LENGTH: 15
<212> TYPE: PRT
<213> ORGANISM: Mycobacterium tuberculosis

<400> SEQUENCE: 260

Ile Val Gln Ile Asn Gly Arg His Phe Asp Leu Arg Ala Gln Gly
1               5                   10                  15

<210> SEQ ID NO 261
<211> LENGTH: 15
<212> TYPE: PRT
<213> ORGANISM: Mycobacterium tuberculosis

<400> SEQUENCE: 261

Ala Gly Tyr Pro Ala Glu Leu Ala Tyr Phe Glu Val Leu His Glu
1               5                   10                  15

<210> SEQ ID NO 262
<211> LENGTH: 15
<212> TYPE: PRT
<213> ORGANISM: Mycobacterium tuberculosis

<400> SEQUENCE: 262

Ala Leu Glu Met Phe Tyr Asp Asp Ala Asp Leu Ser Ile Ile
1               5                   10              15

<210> SEQ ID NO 263
<211> LENGTH: 15
<212> TYPE: PRT
<213> ORGANISM: Mycobacterium tuberculosis

<400> SEQUENCE: 263

Ser Gln Val Ile Glu Ala Val Asn Leu Phe Arg Ala Asn Val Ile
1               5                   10                  15

<210> SEQ ID NO 264
<211> LENGTH: 15
<212> TYPE: PRT
<213> ORGANISM: Mycobacterium tuberculosis

<400> SEQUENCE: 264

Ala Val Ile Thr Glu Leu Ile Ala Met Leu Arg His His His Ile
1               5                   10                  15

<210> SEQ ID NO 265
<211> LENGTH: 15
<212> TYPE: PRT
<213> ORGANISM: Mycobacterium tuberculosis

<400> SEQUENCE: 265

Asp Asp Ile Pro Arg Val Leu Ala Glu Ala Phe His Ile Ala Ala
1               5                   10                  15

<210> SEQ ID NO 266
<211> LENGTH: 15
<212> TYPE: PRT
<213> ORGANISM: Mycobacterium tuberculosis

<400> SEQUENCE: 266

Gln Ala Ala Arg Gly Ile Arg Pro Leu Phe Asp Asp Ile Thr Glu
1               5                   10                  15

<210> SEQ ID NO 267
<211> LENGTH: 15
<212> TYPE: PRT
<213> ORGANISM: Mycobacterium tuberculosis

<400> SEQUENCE: 267

Cys Ser Glu Asp Leu Leu Tyr Leu Ser Asp Leu Asp Phe Asp Val
1               5                   10                  15

<210> SEQ ID NO 268
<211> LENGTH: 15
<212> TYPE: PRT
<213> ORGANISM: Mycobacterium tuberculosis

<400> SEQUENCE: 268

Ala Ala His Ala Gly Glu Tyr Gly Gln Met Val Thr Leu Arg Gly
1               5                   10                  15

```
<210> SEQ ID NO 269
<211> LENGTH: 15
<212> TYPE: PRT
<213> ORGANISM: Mycobacterium tuberculosis

<400> SEQUENCE: 269

Ala Leu Gln Ser His Asp Asp Val Ala Leu Val Ser Val Met Trp
1               5                   10                  15

<210> SEQ ID NO 270
<211> LENGTH: 15
<212> TYPE: PRT
<213> ORGANISM: Mycobacterium tuberculosis

<400> SEQUENCE: 270

Ile Leu Pro Ile Ala Glu Met Ser Val Val Ala Met Glu Phe Gly
1               5                   10                  15

<210> SEQ ID NO 271
<211> LENGTH: 15
<212> TYPE: PRT
<213> ORGANISM: Mycobacterium tuberculosis

<400> SEQUENCE: 271

Ser Ala Arg Leu Arg Leu Leu Arg Asp Arg Leu Val Glu Gly Val
1               5                   10                  15

<210> SEQ ID NO 272
<211> LENGTH: 15
<212> TYPE: PRT
<213> ORGANISM: Mycobacterium tuberculosis

<400> SEQUENCE: 272

Gly Ser Ala Glu Asn Phe Ser Val Val Glu Ala Leu Ala Asp Ser
1               5                   10                  15

<210> SEQ ID NO 273
<211> LENGTH: 15
<212> TYPE: PRT
<213> ORGANISM: Mycobacterium tuberculosis

<400> SEQUENCE: 273

Glu Gly Gly Asn Gln Ile Val Gln Tyr Leu Val Ala Gln Lys Ile
1               5                   10                  15

<210> SEQ ID NO 274
<211> LENGTH: 15
<212> TYPE: PRT
<213> ORGANISM: Mycobacterium tuberculosis

<400> SEQUENCE: 274

Leu Val Ala Gln Glu Ala Ala Ala Ala Gly Thr Pro Leu Val Thr
1               5                   10                  15

<210> SEQ ID NO 275
<211> LENGTH: 15
<212> TYPE: PRT
<213> ORGANISM: Mycobacterium tuberculosis

<400> SEQUENCE: 275

Glu Leu Ala Asp Leu Ile Glu Phe Ala Arg Thr Val Asn Glu Glu
1               5                   10                  15
```

-continued

```
<210> SEQ ID NO 276
<211> LENGTH: 15
<212> TYPE: PRT
<213> ORGANISM: Mycobacterium tuberculosis

<400> SEQUENCE: 276

Lys Met Ala Pro Val Leu Arg Gln Ile Tyr Asp Gln Met Ala Glu
1               5                   10                  15

<210> SEQ ID NO 277
<211> LENGTH: 15
<212> TYPE: PRT
<213> ORGANISM: Mycobacterium tuberculosis

<400> SEQUENCE: 277

Ala Gln Thr Ser Gln Phe Val Met Ala Met Ile Asn Tyr Glu Asp
1               5                   10                  15

<210> SEQ ID NO 278
<211> LENGTH: 15
<212> TYPE: PRT
<213> ORGANISM: Mycobacterium tuberculosis

<400> SEQUENCE: 278

Ala Glu Leu Phe Arg Leu Gln Thr Glu Phe Val Lys Leu Gln Glu
1               5                   10                  15

<210> SEQ ID NO 279
<211> LENGTH: 15
<212> TYPE: PRT
<213> ORGANISM: Mycobacterium tuberculosis

<400> SEQUENCE: 279

Glu Gln Met Leu Ile Asp Asp Gly Ile Leu Leu Arg Lys Tyr Trp
1               5                   10                  15

<210> SEQ ID NO 280
<211> LENGTH: 15
<212> TYPE: PRT
<213> ORGANISM: Mycobacterium tuberculosis

<400> SEQUENCE: 280

Cys Arg Gly Tyr Asp Val Val Ile Leu Asp Arg Tyr Val Ala Ser
1               5                   10                  15

<210> SEQ ID NO 281
<211> LENGTH: 15
<212> TYPE: PRT
<213> ORGANISM: Mycobacterium tuberculosis

<400> SEQUENCE: 281

Ala Leu Pro Arg Leu Leu Arg Arg Leu Val Ile Met Gly Gly Met
1               5                   10                  15

<210> SEQ ID NO 282
<211> LENGTH: 15
<212> TYPE: PRT
<213> ORGANISM: Mycobacterium tuberculosis

<400> SEQUENCE: 282

Arg Val Ile Glu Asp Ala Leu Arg Phe Tyr Phe Glu Ser His Glu
1               5                   10                  15

<210> SEQ ID NO 283
<211> LENGTH: 15
```

```
<212> TYPE: PRT
<213> ORGANISM: Mycobacterium tuberculosis

<400> SEQUENCE: 283

Ala Asp Val Leu Thr Met Lys Ala Val Arg Ala Ala Thr Ala Leu
1               5                   10                  15

<210> SEQ ID NO 284
<211> LENGTH: 15
<212> TYPE: PRT
<213> ORGANISM: Mycobacterium tuberculosis

<400> SEQUENCE: 284

Thr Asp Asn Gly Ala Met Ile Ala Ala Phe Ala Ala Gln Leu Val
1               5                   10                  15

<210> SEQ ID NO 285
<211> LENGTH: 15
<212> TYPE: PRT
<213> ORGANISM: Mycobacterium tuberculosis

<400> SEQUENCE: 285

Glu Ile Tyr Leu Asn Thr Phe Arg His Leu Tyr Gly Leu Asp Cys
1               5                   10                  15

<210> SEQ ID NO 286
<211> LENGTH: 15
<212> TYPE: PRT
<213> ORGANISM: Mycobacterium tuberculosis

<400> SEQUENCE: 286

Leu Tyr Arg Pro Gly Leu Val His Ile Tyr His Ala Leu Thr Trp
1               5                   10                  15

<210> SEQ ID NO 287
<211> LENGTH: 15
<212> TYPE: PRT
<213> ORGANISM: Mycobacterium tuberculosis

<400> SEQUENCE: 287

Glu Asn Phe Phe Met Phe Ile Ala Glu Glu Val Arg Glu Tyr Leu
1               5                   10                  15

<210> SEQ ID NO 288
<211> LENGTH: 15
<212> TYPE: PRT
<213> ORGANISM: Mycobacterium tuberculosis

<400> SEQUENCE: 288

Gln Arg Pro Arg Met Leu Tyr Asp Tyr Phe His Gln Leu Phe Ala
1               5                   10                  15

<210> SEQ ID NO 289
<211> LENGTH: 15
<212> TYPE: PRT
<213> ORGANISM: Mycobacterium tuberculosis

<400> SEQUENCE: 289

Gln Thr Leu Val Tyr Lys Gly Met Leu Thr Thr Pro Gln Leu Lys
1               5                   10                  15

<210> SEQ ID NO 290
<211> LENGTH: 15
<212> TYPE: PRT
<213> ORGANISM: Mycobacterium tuberculosis
```

<400> SEQUENCE: 290

Ala Gln Ile Ile His Arg Ile Thr Ala Thr Ala Arg His Pro Gly
1               5                   10                  15

<210> SEQ ID NO 291
<211> LENGTH: 15
<212> TYPE: PRT
<213> ORGANISM: Mycobacterium tuberculosis

<400> SEQUENCE: 291

Gly Gln Asn Tyr Thr Tyr Lys Trp Glu Thr Phe Leu Thr Arg Glu
1               5                   10                  15

<210> SEQ ID NO 292
<211> LENGTH: 15
<212> TYPE: PRT
<213> ORGANISM: Mycobacterium tuberculosis

<400> SEQUENCE: 292

Asp Pro Met Val Gln Ile Pro Arg Leu Val Ala Asn Asn Thr Arg
1               5                   10                  15

<210> SEQ ID NO 293
<211> LENGTH: 15
<212> TYPE: PRT
<213> ORGANISM: Mycobacterium tuberculosis

<400> SEQUENCE: 293

Ala Gly Cys Gln Thr Tyr Lys Trp Glu Thr Phe Leu Thr Ser Glu
1               5                   10                  15

<210> SEQ ID NO 294
<211> LENGTH: 15
<212> TYPE: PRT
<213> ORGANISM: Mycobacterium tuberculosis

<400> SEQUENCE: 294

Pro Ser Pro Ser Met Gly Arg Asp Ile Lys Val Gln Phe Gln Ser
1               5                   10                  15

<210> SEQ ID NO 295
<211> LENGTH: 15
<212> TYPE: PRT
<213> ORGANISM: Mycobacterium tuberculosis

<400> SEQUENCE: 295

Gln Val Pro Ser Ala Ser Met Gly Arg Asp Ile Lys Val Gln Phe
1               5                   10                  15

<210> SEQ ID NO 296
<211> LENGTH: 15
<212> TYPE: PRT
<213> ORGANISM: Mycobacterium tuberculosis

<400> SEQUENCE: 296

Phe Leu Met Ser Val Gly Ala Leu Ile Ile Gly Trp Leu Leu Gln
1               5                   10                  15

<210> SEQ ID NO 297
<211> LENGTH: 15
<212> TYPE: PRT
<213> ORGANISM: Mycobacterium tuberculosis

<400> SEQUENCE: 297

Ala Gly Ile Ser Ser Leu Ile Ile Asp Pro Asn Pro Met Phe Val
1               5                   10                  15

<210> SEQ ID NO 298
<211> LENGTH: 15
<212> TYPE: PRT
<213> ORGANISM: Mycobacterium tuberculosis

<400> SEQUENCE: 298

Arg Val Leu Leu Ala Gly Trp Glu Gln Phe Asp Glu Pro Val Asp
1               5                   10                  15

<210> SEQ ID NO 299
<211> LENGTH: 15
<212> TYPE: PRT
<213> ORGANISM: Mycobacterium tuberculosis

<400> SEQUENCE: 299

Glu His Ile His Arg Pro Asn Thr Asn Asn Val Gly Pro Ile Ile
1               5                   10                  15

<210> SEQ ID NO 300
<211> LENGTH: 15
<212> TYPE: PRT
<213> ORGANISM: Mycobacterium tuberculosis

<400> SEQUENCE: 300

Ser Ile Leu Asp Met Arg Gln Leu Phe Asp Gly Ile Asp Leu Ser
1               5                   10                  15

<210> SEQ ID NO 301
<211> LENGTH: 15
<212> TYPE: PRT
<213> ORGANISM: Mycobacterium tuberculosis

<400> SEQUENCE: 301

His Pro Gln Gln Phe Ile Tyr Ala Gly Ser Leu Ser Ala Leu Leu
1               5                   10                  15

<210> SEQ ID NO 302
<211> LENGTH: 15
<212> TYPE: PRT
<213> ORGANISM: Mycobacterium tuberculosis

<400> SEQUENCE: 302

Ile Gly Leu Val Leu Ile Ala Val Leu Val Phe Val Pro Arg Val
1               5                   10                  15

<210> SEQ ID NO 303
<211> LENGTH: 15
<212> TYPE: PRT
<213> ORGANISM: Mycobacterium tuberculosis

<400> SEQUENCE: 303

Ser Glu Phe Asn Glu Val Phe Phe Asn Asp Val Phe Val Pro Asp
1               5                   10                  15

<210> SEQ ID NO 304
<211> LENGTH: 15
<212> TYPE: PRT
<213> ORGANISM: Mycobacterium tuberculosis

<400> SEQUENCE: 304

Asp Pro Val Lys Gly Ala Asp Glu Val Val Ala Phe Ala Glu Glu

-continued

```
<210> SEQ ID NO 305
<211> LENGTH: 15
<212> TYPE: PRT
<213> ORGANISM: Mycobacterium tuberculosis

<400> SEQUENCE: 305

Glu His Phe Gly His Glu Arg Tyr Asp Ala Phe Phe Ser Leu Ala
1               5                   10                  15

<210> SEQ ID NO 306
<211> LENGTH: 15
<212> TYPE: PRT
<213> ORGANISM: Mycobacterium tuberculosis

<400> SEQUENCE: 306

Phe Ser Leu Val Asn Phe Phe Asp Ala Gln Val Gly Pro Leu Ser
1               5                   10                  15

<210> SEQ ID NO 307
<211> LENGTH: 15
<212> TYPE: PRT
<213> ORGANISM: Mycobacterium tuberculosis

<400> SEQUENCE: 307

Ala Val Val Val Leu Lys Arg Leu Pro Asp Ala Leu Ala Asp Gly
1               5                   10                  15

<210> SEQ ID NO 308
<211> LENGTH: 15
<212> TYPE: PRT
<213> ORGANISM: Mycobacterium tuberculosis

<400> SEQUENCE: 308

Glu Ser Val Phe Ala Ala Thr Val Ala Glu Leu Glu Ser Leu Ile
1               5                   10                  15

<210> SEQ ID NO 309
<211> LENGTH: 15
<212> TYPE: PRT
<213> ORGANISM: Mycobacterium tuberculosis

<400> SEQUENCE: 309

Ile Thr Pro Asp Glu Gly Ala Tyr Ala Phe Glu Ala Leu Leu Arg
1               5                   10                  15

<210> SEQ ID NO 310
<211> LENGTH: 15
<212> TYPE: PRT
<213> ORGANISM: Mycobacterium tuberculosis

<400> SEQUENCE: 310

Leu Asp Trp Phe Cys Leu Phe Ser Ser Ala Ala Ala Leu Thr Gly
1               5                   10                  15

<210> SEQ ID NO 311
<211> LENGTH: 15
<212> TYPE: PRT
<213> ORGANISM: Mycobacterium tuberculosis

<400> SEQUENCE: 311

Ala Gln Glu Tyr Gln Ala Leu Ser Ala Gln Ala Ala Phe His
1               5                   10                  15
```

-continued

<210> SEQ ID NO 312
<211> LENGTH: 15
<212> TYPE: PRT
<213> ORGANISM: Mycobacterium tuberculosis

<400> SEQUENCE: 312

Gly Gln Gln Tyr Gln Ala Met Ser Ala Gln Ala Ala Phe His
1               5                   10                  15

<210> SEQ ID NO 313
<211> LENGTH: 15
<212> TYPE: PRT
<213> ORGANISM: Mycobacterium tuberculosis

<400> SEQUENCE: 313

Ala Gln Ile Tyr Gln Ala Val Ser Ala Gln Ala Ala Ile His
1               5                   10                  15

<210> SEQ ID NO 314
<211> LENGTH: 15
<212> TYPE: PRT
<213> ORGANISM: Mycobacterium tuberculosis

<400> SEQUENCE: 314

Gly Ser Thr Ile Asn Ala Ala Asn Ala Ala Ala Ala Leu Pro Thr
1               5                   10                  15

<210> SEQ ID NO 315
<211> LENGTH: 15
<212> TYPE: PRT
<213> ORGANISM: Mycobacterium tuberculosis

<400> SEQUENCE: 315

Glu Arg Tyr Val Gly Leu Tyr Leu Pro Phe Leu Asp Met Ser Phe
1               5                   10                  15

<210> SEQ ID NO 316
<211> LENGTH: 15
<212> TYPE: PRT
<213> ORGANISM: Mycobacterium tuberculosis

<400> SEQUENCE: 316

Ala Glu Ala Pro Ala Ala Ala Ala Pro Glu Glu Gln Val Gln
1               5                   10                  15

<210> SEQ ID NO 317
<211> LENGTH: 15
<212> TYPE: PRT
<213> ORGANISM: Mycobacterium tuberculosis

<400> SEQUENCE: 317

Gly Ala Met Val Ala Thr Asn Phe Phe Gly Ile Asn Thr Ile Pro
1               5                   10                  15

<210> SEQ ID NO 318
<211> LENGTH: 15
<212> TYPE: PRT
<213> ORGANISM: Mycobacterium tuberculosis

<400> SEQUENCE: 318

Ala Val Leu Val Ala Thr Asn Phe Phe Gly Ile Asn Thr Ile Pro
1               5                   10                  15

<210> SEQ ID NO 319

```
<211> LENGTH: 15
<212> TYPE: PRT
<213> ORGANISM: Mycobacterium tuberculosis

<400> SEQUENCE: 319

His Thr Val Leu Val Ala Thr Asn Phe Phe Gly Ile Asn Thr Ile
1               5                   10                  15

<210> SEQ ID NO 320
<211> LENGTH: 15
<212> TYPE: PRT
<213> ORGANISM: Mycobacterium tuberculosis

<400> SEQUENCE: 320

Gln Ala Val Leu Thr Ala Thr Asn Phe Phe Gly Ile Asn Thr Ile
1               5                   10                  15

<210> SEQ ID NO 321
<211> LENGTH: 15
<212> TYPE: PRT
<213> ORGANISM: Mycobacterium tuberculosis

<400> SEQUENCE: 321

Ala Arg Met Trp Ile Gln Ala Ala Thr Thr Met Ala Ser Tyr Gln
1               5                   10                  15

<210> SEQ ID NO 322
<211> LENGTH: 15
<212> TYPE: PRT
<213> ORGANISM: Mycobacterium tuberculosis

<400> SEQUENCE: 322

Leu Ala Trp Leu Val Gln Ala Ser Ala Asn Ser Ala Ala Met Ala
1               5                   10                  15

<210> SEQ ID NO 323
<211> LENGTH: 15
<212> TYPE: PRT
<213> ORGANISM: Mycobacterium tuberculosis

<400> SEQUENCE: 323

Asp Pro Ile Asn Glu Phe Phe Leu Ala Asn Thr Gly Arg Pro Leu
1               5                   10                  15

<210> SEQ ID NO 324
<211> LENGTH: 15
<212> TYPE: PRT
<213> ORGANISM: Mycobacterium tuberculosis

<400> SEQUENCE: 324

Gly Ile Asn Thr Ile Pro Ile Ala Ile Asn Glu Ala Glu Tyr Val
1               5                   10                  15

<210> SEQ ID NO 325
<211> LENGTH: 15
<212> TYPE: PRT
<213> ORGANISM: Mycobacterium tuberculosis

<400> SEQUENCE: 325

Gln Leu Ser Ala Glu Tyr Ala Ser Thr Ala Ala Glu Leu Ser Gly
1               5                   10                  15

<210> SEQ ID NO 326
<211> LENGTH: 15
<212> TYPE: PRT
```

<213> ORGANISM: Mycobacterium tuberculosis

<400> SEQUENCE: 326

Tyr Ala Ala Leu Val Ala Met Pro Thr Leu Ala Glu Leu Ala
1               5                   10                  15

<210> SEQ ID NO 327
<211> LENGTH: 15
<212> TYPE: PRT
<213> ORGANISM: Mycobacterium tuberculosis

<400> SEQUENCE: 327

Leu Thr Val Asp Ala Gly Ala Tyr Ala Ser Ala Glu Ala Ala Asn
1               5                   10                  15

<210> SEQ ID NO 328
<211> LENGTH: 15
<212> TYPE: PRT
<213> ORGANISM: Mycobacterium tuberculosis

<400> SEQUENCE: 328

Ala Pro Trp Gln Gln Val Leu Arg Asn Leu Gly Ile Asp Ile Gly
1               5                   10                  15

<210> SEQ ID NO 329
<211> LENGTH: 15
<212> TYPE: PRT
<213> ORGANISM: Mycobacterium tuberculosis

<400> SEQUENCE: 329

Ala Trp Met Ser Ala Ala Ala Gln Ala Glu Gln Ala Ala Thr
1               5                   10                  15

<210> SEQ ID NO 330
<211> LENGTH: 15
<212> TYPE: PRT
<213> ORGANISM: Mycobacterium tuberculosis

<400> SEQUENCE: 330

Tyr Leu Ala Trp Leu Ser Thr Ala Ala Ala Gln Ala Glu Gln Ala
1               5                   10                  15

<210> SEQ ID NO 331
<211> LENGTH: 15
<212> TYPE: PRT
<213> ORGANISM: Mycobacterium tuberculosis

<400> SEQUENCE: 331

Gly Trp Ser Ser Leu Gly Arg Glu Tyr Ala Ala Val Ala Glu Glu
1               5                   10                  15

<210> SEQ ID NO 332
<211> LENGTH: 15
<212> TYPE: PRT
<213> ORGANISM: Mycobacterium tuberculosis

<400> SEQUENCE: 332

Ala Gly Ala Met Gly Ala Tyr Ala Ala Ala Glu Ala Ala Asn Ala
1               5                   10                  15

<210> SEQ ID NO 333
<211> LENGTH: 15
<212> TYPE: PRT
<213> ORGANISM: Mycobacterium tuberculosis

<400> SEQUENCE: 333

Ala Gly Gly Phe Gly Gly Ala Gly Ala Gly Ile Ala Asn Phe Leu
1               5                   10                  15

<210> SEQ ID NO 334
<211> LENGTH: 15
<212> TYPE: PRT
<213> ORGANISM: Mycobacterium tuberculosis

<400> SEQUENCE: 334

Gly Ala Tyr Ala Ala Ala Glu Ala Ala Asn Val Ser Ala Ala Gln
1               5                   10                  15

<210> SEQ ID NO 335
<211> LENGTH: 15
<212> TYPE: PRT
<213> ORGANISM: Mycobacterium tuberculosis

<400> SEQUENCE: 335

Ser Ala Ala Gly Ser Tyr Ala Ala Ala Glu Ala Ala Asn Ala Ser
1               5                   10                  15

<210> SEQ ID NO 336
<211> LENGTH: 15
<212> TYPE: PRT
<213> ORGANISM: Mycobacterium tuberculosis

<400> SEQUENCE: 336

Ala Leu Leu Pro Arg Ala Gly Ala Ala Ala Ala Ala Ala Leu Pro
1               5                   10                  15

<210> SEQ ID NO 337
<211> LENGTH: 15
<212> TYPE: PRT
<213> ORGANISM: Mycobacterium tuberculosis

<400> SEQUENCE: 337

Ala Leu Ser Arg Val His Ser Met Phe Leu Gly Thr Gly Gly Ser
1               5                   10                  15

<210> SEQ ID NO 338
<211> LENGTH: 15
<212> TYPE: PRT
<213> ORGANISM: Mycobacterium tuberculosis

<400> SEQUENCE: 338

Ala Pro Gln Ile Asn Phe Phe Tyr Tyr Leu Gly Glu Pro Ile Val
1               5                   10                  15

<210> SEQ ID NO 339
<211> LENGTH: 15
<212> TYPE: PRT
<213> ORGANISM: Mycobacterium tuberculosis

<400> SEQUENCE: 339

Met Ser Phe Val Thr Thr Gln Pro Glu Ala Leu Ala Ala Ala Ala
1               5                   10                  15

<210> SEQ ID NO 340
<211> LENGTH: 15
<212> TYPE: PRT
<213> ORGANISM: Mycobacterium tuberculosis

<400> SEQUENCE: 340

```
Met His Val Ser Phe Val Met Ala Tyr Pro Glu Met Leu Ala Ala
1               5                   10                  15
```

<210> SEQ ID NO 341
<211> LENGTH: 15
<212> TYPE: PRT
<213> ORGANISM: Mycobacterium tuberculosis

<400> SEQUENCE: 341

```
Ser Ser Tyr Ala Ala Thr Glu Val Ala Asn Ala Ala Ala Ala Ser
1               5                   10                  15
```

<210> SEQ ID NO 342
<211> LENGTH: 15
<212> TYPE: PRT
<213> ORGANISM: Mycobacterium tuberculosis

<400> SEQUENCE: 342

```
Leu Gly Gly Leu Trp Thr Ala Val Ser Pro His Leu Ser Pro Leu
1               5                   10                  15
```

<210> SEQ ID NO 343
<211> LENGTH: 15
<212> TYPE: PRT
<213> ORGANISM: Mycobacterium tuberculosis

<400> SEQUENCE: 343

```
Leu Ser Pro Ile Ser Asn Met Val Ser Met Ala Asn Asn His Met
1               5                   10                  15
```

<210> SEQ ID NO 344
<211> LENGTH: 15
<212> TYPE: PRT
<213> ORGANISM: Mycobacterium tuberculosis

<400> SEQUENCE: 344

```
Ala Glu Leu Met Ile Leu Ile Ala Thr Asn Leu Leu Gly Gln Asn
1               5                   10                  15
```

<210> SEQ ID NO 345
<211> LENGTH: 15
<212> TYPE: PRT
<213> ORGANISM: Mycobacterium tuberculosis

<400> SEQUENCE: 345

```
Ala Gln Asn Gly Val Gln Ala Met Ser Ser Leu Gly Ser Ser Leu
1               5                   10                  15
```

<210> SEQ ID NO 346
<211> LENGTH: 15
<212> TYPE: PRT
<213> ORGANISM: Mycobacterium tuberculosis

<400> SEQUENCE: 346

```
Ala Ser Val Gly Ser Tyr Ala Ala Ala Glu Ala Ala Asn Ala Ser
1               5                   10                  15
```

<210> SEQ ID NO 347
<211> LENGTH: 15
<212> TYPE: PRT
<213> ORGANISM: Mycobacterium tuberculosis

<400> SEQUENCE: 347

```
Glu Ser Gly Ala Ser Tyr Ala Ala Arg Asp Ala Leu Ala Ala Ala
1               5                   10                  15
```

<210> SEQ ID NO 348
<211> LENGTH: 15
<212> TYPE: PRT
<213> ORGANISM: Mycobacterium tuberculosis

<400> SEQUENCE: 348

Ala Arg Phe His Gln Gln Phe Val Gln Ala Leu Thr Ala Ser Val
1               5                   10                  15

<210> SEQ ID NO 349
<211> LENGTH: 15
<212> TYPE: PRT
<213> ORGANISM: Mycobacterium tuberculosis

<400> SEQUENCE: 349

Ile Gly Ser Ser Ile Gly Ala Ala Asn Ala Ala Ala Ala Gly Ser
1               5                   10                  15

<210> SEQ ID NO 350
<211> LENGTH: 15
<212> TYPE: PRT
<213> ORGANISM: Mycobacterium tuberculosis

<400> SEQUENCE: 350

Ala Pro Tyr Val Ala Trp Met Arg Ala Thr Ala Ile Gln Ala Glu
1               5                   10                  15

<210> SEQ ID NO 351
<211> LENGTH: 15
<212> TYPE: PRT
<213> ORGANISM: Mycobacterium tuberculosis

<400> SEQUENCE: 351

Trp Phe Ile Asn Trp Tyr Leu Pro Ile Ser Gln Leu Phe Tyr Asn
1               5                   10                  15

<210> SEQ ID NO 352
<211> LENGTH: 15
<212> TYPE: PRT
<213> ORGANISM: Mycobacterium tuberculosis

<400> SEQUENCE: 352

Ala Ala Ala Gln Ala Ser Ala Ala Ala Ala Tyr Glu Ala Ala
1               5                   10                  15

<210> SEQ ID NO 353
<211> LENGTH: 15
<212> TYPE: PRT
<213> ORGANISM: Mycobacterium tuberculosis

<400> SEQUENCE: 353

Ala Ala Thr Gln Ala Arg Ala Ala Ala Ala Phe Glu Ala Ala
1               5                   10                  15

<210> SEQ ID NO 354
<211> LENGTH: 15
<212> TYPE: PRT
<213> ORGANISM: Mycobacterium tuberculosis

<400> SEQUENCE: 354

Phe Gly Gln Asn Thr Ser Ala Ile Ala Ala Ala Glu Ala Gln Tyr
1               5                   10                  15

-continued

```
<210> SEQ ID NO 355
<211> LENGTH: 15
<212> TYPE: PRT
<213> ORGANISM: Mycobacterium tuberculosis

<400> SEQUENCE: 355

Phe Phe Gly Gln Asn Thr Ala Ala Ile Ala Ala Thr Glu Ala Gln
1               5                   10                  15

<210> SEQ ID NO 356
<211> LENGTH: 15
<212> TYPE: PRT
<213> ORGANISM: Mycobacterium tuberculosis

<400> SEQUENCE: 356

Phe Gly Gln Asn Thr Ala Ser Ile Ala Ala Thr Glu Ala Gln Tyr
1               5                   10                  15

<210> SEQ ID NO 357
<211> LENGTH: 15
<212> TYPE: PRT
<213> ORGANISM: Mycobacterium tuberculosis

<400> SEQUENCE: 357

Leu Ala Ala Ala Ala Ala Trp Asp Ala Leu Ala Ala Glu Leu Tyr
1               5                   10                  15

<210> SEQ ID NO 358
<211> LENGTH: 15
<212> TYPE: PRT
<213> ORGANISM: Mycobacterium tuberculosis

<400> SEQUENCE: 358

Ala Ala Ala Ser Trp Asp Ala Leu Ala Ala Glu Leu Ala Ser Ala
1               5                   10                  15

<210> SEQ ID NO 359
<211> LENGTH: 15
<212> TYPE: PRT
<213> ORGANISM: Mycobacterium tuberculosis

<400> SEQUENCE: 359

Ala Ala Ile His Glu Met Phe Val Asn Thr Leu Gln Met Ser Ser
1               5                   10                  15

<210> SEQ ID NO 360
<211> LENGTH: 15
<212> TYPE: PRT
<213> ORGANISM: Mycobacterium tuberculosis

<400> SEQUENCE: 360

Ala Ala Ile His Glu Met Phe Val Asn Thr Leu Val Ala Ser Ser
1               5                   10                  15

<210> SEQ ID NO 361
<211> LENGTH: 15
<212> TYPE: PRT
<213> ORGANISM: Mycobacterium tuberculosis

<400> SEQUENCE: 361

Asn Arg Ala Ser Leu Met Gln Leu Ile Ser Thr Asn Val Phe Gly
1               5                   10                  15

<210> SEQ ID NO 362
<211> LENGTH: 15
```

```
<212> TYPE: PRT
<213> ORGANISM: Mycobacterium tuberculosis

<400> SEQUENCE: 362

Phe Gly Gln Asn Thr Gly Ala Ile Ala Ala Ala Glu Ala Arg Tyr
1               5                   10                  15

<210> SEQ ID NO 363
<211> LENGTH: 15
<212> TYPE: PRT
<213> ORGANISM: Mycobacterium tuberculosis

<400> SEQUENCE: 363

Pro Pro Glu Val Asn Ser Ala Arg Val Phe Ala Gly Ala Gly Ser
1               5                   10                  15

<210> SEQ ID NO 364
<211> LENGTH: 15
<212> TYPE: PRT
<213> ORGANISM: Mycobacterium tuberculosis

<400> SEQUENCE: 364

Tyr Val Ala Trp Met Ser Ala Thr Ala Ala Leu Ala Arg Glu Ala
1               5                   10                  15

<210> SEQ ID NO 365
<211> LENGTH: 15
<212> TYPE: PRT
<213> ORGANISM: Mycobacterium tuberculosis

<400> SEQUENCE: 365

Ala Met Asn Glu Ala Phe Val Ala Met Leu Gly Ala Ser Ala Asp
1               5                   10                  15

<210> SEQ ID NO 366
<211> LENGTH: 15
<212> TYPE: PRT
<213> ORGANISM: Mycobacterium tuberculosis

<400> SEQUENCE: 366

Ala Gln Leu Ser Gln Leu Ile Ser Leu Leu Pro Ser Thr Leu Gln
1               5                   10                  15

<210> SEQ ID NO 367
<211> LENGTH: 15
<212> TYPE: PRT
<213> ORGANISM: Mycobacterium tuberculosis

<400> SEQUENCE: 367

Phe Phe Gly Gln Asn Ala Pro Ala Ile Ala Ala Ile Glu Ala Ala
1               5                   10                  15

<210> SEQ ID NO 368
<211> LENGTH: 15
<212> TYPE: PRT
<213> ORGANISM: Mycobacterium tuberculosis

<400> SEQUENCE: 368

Ala Asp Tyr Leu Arg Met Trp Ile Gln Ala Ala Thr Val Met Ser
1               5                   10                  15

<210> SEQ ID NO 369
<211> LENGTH: 15
<212> TYPE: PRT
<213> ORGANISM: Mycobacterium tuberculosis
```

<400> SEQUENCE: 369

Asp Tyr Val Arg Met Trp Val Gln Ala Ala Thr Val Met Ser Ala
1               5                   10                  15

<210> SEQ ID NO 370
<211> LENGTH: 15
<212> TYPE: PRT
<213> ORGANISM: Mycobacterium tuberculosis

<400> SEQUENCE: 370

Leu Pro Leu Leu Val Pro Leu Arg Ala Ile Pro Leu Leu Gly Asn
1               5                   10                  15

<210> SEQ ID NO 371
<211> LENGTH: 15
<212> TYPE: PRT
<213> ORGANISM: Mycobacterium tuberculosis

<400> SEQUENCE: 371

Phe Val Gln Ala Leu Thr Thr Ala Ala Ala Ser Tyr Ala Ser Val
1               5                   10                  15

<210> SEQ ID NO 372
<211> LENGTH: 15
<212> TYPE: PRT
<213> ORGANISM: Mycobacterium tuberculosis

<400> SEQUENCE: 372

Tyr Ala Ser Val Glu Ala Ala Asn Ala Ser Pro Leu Gln Val Ala
1               5                   10                  15

<210> SEQ ID NO 373
<211> LENGTH: 15
<212> TYPE: PRT
<213> ORGANISM: Mycobacterium tuberculosis

<400> SEQUENCE: 373

Glu Ile Val Gln Phe Leu Glu Glu Thr Phe Ala Ala Tyr Asp Gln
1               5                   10                  15

<210> SEQ ID NO 374
<211> LENGTH: 15
<212> TYPE: PRT
<213> ORGANISM: Mycobacterium tuberculosis

<400> SEQUENCE: 374

Ala Ala Val Pro Ala Val Gly Ala Ala Gly Ala Pro Ala Ala
1               5                   10                  15

<210> SEQ ID NO 375
<211> LENGTH: 15
<212> TYPE: PRT
<213> ORGANISM: Mycobacterium tuberculosis

<400> SEQUENCE: 375

Ala Leu Ser Ala Glu Tyr Ala Ala Val Ala Gln Glu Leu Ser Val
1               5                   10                  15

<210> SEQ ID NO 376
<211> LENGTH: 15
<212> TYPE: PRT
<213> ORGANISM: Mycobacterium tuberculosis

<400> SEQUENCE: 376

```
Glu Leu Phe Val Ala Ala Tyr Val Pro Tyr Val Ala Trp Leu Val
1               5                   10                  15

<210> SEQ ID NO 377
<211> LENGTH: 15
<212> TYPE: PRT
<213> ORGANISM: Mycobacterium tuberculosis

<400> SEQUENCE: 377

Gly Trp Ile Ile Ser Asn Ile Phe Gly Ala Ile Pro Val Leu Gly
1               5                   10                  15

<210> SEQ ID NO 378
<211> LENGTH: 15
<212> TYPE: PRT
<213> ORGANISM: Mycobacterium tuberculosis

<400> SEQUENCE: 378

Leu Leu Glu Phe Ala Val Val Leu Glu Leu Ala Ile Leu Ser Ile
1               5                   10                  15

<210> SEQ ID NO 379
<211> LENGTH: 15
<212> TYPE: PRT
<213> ORGANISM: Mycobacterium tuberculosis

<400> SEQUENCE: 379

Ala Ser Met Ser Met Ala Ala Ala Ser Pro Tyr Val Gly Trp
1               5                   10                  15

<210> SEQ ID NO 380
<211> LENGTH: 15
<212> TYPE: PRT
<213> ORGANISM: Mycobacterium tuberculosis

<400> SEQUENCE: 380

Ile Gln Ala Arg Ala Ala Ala Leu Ala Phe Glu Gln Ala Tyr Ala
1               5                   10                  15

<210> SEQ ID NO 381
<211> LENGTH: 15
<212> TYPE: PRT
<213> ORGANISM: Mycobacterium tuberculosis

<400> SEQUENCE: 381

Ala Ala Gly Gly Trp Asp Ser Leu Ala Ala Glu Leu Ala Thr Thr
1               5                   10                  15

<210> SEQ ID NO 382
<211> LENGTH: 15
<212> TYPE: PRT
<213> ORGANISM: Mycobacterium tuberculosis

<400> SEQUENCE: 382

Ala Gly Thr Leu Ser Thr Phe Phe Gly Val Pro Leu Val Leu Thr
1               5                   10                  15

<210> SEQ ID NO 383
<211> LENGTH: 15
<212> TYPE: PRT
<213> ORGANISM: Mycobacterium tuberculosis

<400> SEQUENCE: 383

Asn Pro Phe Pro Phe Leu Arg Gln Ile Ile Ala Asn Gln Gln Val
```

```
                1               5                  10                  15

<210> SEQ ID NO 384
<211> LENGTH: 15
<212> TYPE: PRT
<213> ORGANISM: Mycobacterium tuberculosis

<400> SEQUENCE: 384

Met Asp Tyr Phe Ile Arg Met Trp Asn Gln Ala Ala Leu Ala Met
1               5                  10                  15

<210> SEQ ID NO 385
<211> LENGTH: 15
<212> TYPE: PRT
<213> ORGANISM: Mycobacterium tuberculosis

<400> SEQUENCE: 385

Glu Met Leu Ser Met Leu Arg Ala Met Leu Ala Pro Glu Ser Leu
1               5                  10                  15

<210> SEQ ID NO 386
<211> LENGTH: 15
<212> TYPE: PRT
<213> ORGANISM: Mycobacterium tuberculosis

<400> SEQUENCE: 386

Thr Val Ala Trp Thr Met Leu Gly Val Ala Leu Ser Ala Tyr Glu
1               5                  10                  15

<210> SEQ ID NO 387
<211> LENGTH: 15
<212> TYPE: PRT
<213> ORGANISM: Mycobacterium tuberculosis

<400> SEQUENCE: 387

Gly Phe Thr Ile Ala Asn His Asn Ala Ala Val Gly Glu Ile
1               5                  10                  15

<210> SEQ ID NO 388
<211> LENGTH: 15
<212> TYPE: PRT
<213> ORGANISM: Mycobacterium tuberculosis

<400> SEQUENCE: 388

Leu Val Leu Val Ile Asp Asp Glu Pro Gln Ile Leu Arg Ala Leu
1               5                  10                  15

<210> SEQ ID NO 389
<211> LENGTH: 15
<212> TYPE: PRT
<213> ORGANISM: Mycobacterium tuberculosis

<400> SEQUENCE: 389

Ala Leu Leu Trp Leu Ala Asp Gln Val Asp Ala Ala Leu Glu Lys
1               5                  10                  15

<210> SEQ ID NO 390
<211> LENGTH: 15
<212> TYPE: PRT
<213> ORGANISM: Mycobacterium tuberculosis

<400> SEQUENCE: 390

Glu Ser Ala Leu Phe Phe Ile Gly Val Leu Ile Val Ala Leu Leu
1               5                  10                  15
```

<210> SEQ ID NO 391
<211> LENGTH: 15
<212> TYPE: PRT
<213> ORGANISM: Mycobacterium tuberculosis

<400> SEQUENCE: 391

Ala His Leu Ile His Phe Ala Ala Ala Asn Leu Arg Asn Pro Gly
1               5                   10                  15

<210> SEQ ID NO 392
<211> LENGTH: 15
<212> TYPE: PRT
<213> ORGANISM: Mycobacterium tuberculosis

<400> SEQUENCE: 392

Ala Leu Arg Ile Leu Val Tyr Ser Asp Asn Val Gln Thr Arg Glu
1               5                   10                  15

<210> SEQ ID NO 393
<211> LENGTH: 15
<212> TYPE: PRT
<213> ORGANISM: Mycobacterium tuberculosis

<400> SEQUENCE: 393

Ala Leu Val Glu Glu Tyr Leu Arg Gly Leu Arg Gln Ala Ala Gly
1               5                   10                  15

<210> SEQ ID NO 394
<211> LENGTH: 15
<212> TYPE: PRT
<213> ORGANISM: Mycobacterium tuberculosis

<400> SEQUENCE: 394

Ala Asp Lys Asn Pro Leu Phe Leu Asp Glu Gln Leu Thr Arg Ala
1               5                   10                  15

<210> SEQ ID NO 395
<211> LENGTH: 15
<212> TYPE: PRT
<213> ORGANISM: Mycobacterium tuberculosis

<400> SEQUENCE: 395

Ala Val Leu Glu Asp Pro Tyr Ile Leu Leu Val Ser Ser Lys Val
1               5                   10                  15

<210> SEQ ID NO 396
<211> LENGTH: 15
<212> TYPE: PRT
<213> ORGANISM: Mycobacterium tuberculosis

<400> SEQUENCE: 396

Met Ala Lys Thr Ile Ala Tyr Asp Glu Glu Ala Arg Arg Gly Leu
1               5                   10                  15

<210> SEQ ID NO 397
<211> LENGTH: 15
<212> TYPE: PRT
<213> ORGANISM: Mycobacterium tuberculosis

<400> SEQUENCE: 397

Ala Tyr Gly Ser Phe Val Arg Thr Val Ser Leu Pro Val Gly Ala
1               5                   10                  15

<210> SEQ ID NO 398

```
<211> LENGTH: 15
<212> TYPE: PRT
<213> ORGANISM: Mycobacterium tuberculosis

<400> SEQUENCE: 398

Glu Thr Leu Tyr Trp Leu Ala Gln Pro Gly Ile Arg Glu Ser Ile
1               5                   10                  15

<210> SEQ ID NO 399
<211> LENGTH: 15
<212> TYPE: PRT
<213> ORGANISM: Mycobacterium tuberculosis

<400> SEQUENCE: 399

Gly Glu Glu Tyr Leu Ile Leu Ser Ala Arg Asp Val Leu Ala Val
1               5                   10                  15

<210> SEQ ID NO 400
<211> LENGTH: 15
<212> TYPE: PRT
<213> ORGANISM: Mycobacterium tuberculosis

<400> SEQUENCE: 400

Thr Gly Ile Phe Gly Leu Val Leu Val Ile Cys Val Val Leu Ile
1               5                   10                  15

<210> SEQ ID NO 401
<211> LENGTH: 15
<212> TYPE: PRT
<213> ORGANISM: Mycobacterium tuberculosis

<400> SEQUENCE: 401

Asp Val Thr Ile Arg Phe Arg Arg Phe Phe Ser Arg Leu Gln Arg
1               5                   10                  15

<210> SEQ ID NO 402
<211> LENGTH: 15
<212> TYPE: PRT
<213> ORGANISM: Mycobacterium tuberculosis

<400> SEQUENCE: 402

Ala Pro Val Val Ile Leu Ala His Gly Phe Pro Glu Leu Ala Tyr
1               5                   10                  15

<210> SEQ ID NO 403
<211> LENGTH: 15
<212> TYPE: PRT
<213> ORGANISM: Mycobacterium tuberculosis

<400> SEQUENCE: 403

Gln Ala Phe Arg Ser Arg Phe Gly Glu Asn Phe Phe Tyr Ile Leu
1               5                   10                  15

<210> SEQ ID NO 404
<211> LENGTH: 15
<212> TYPE: PRT
<213> ORGANISM: Mycobacterium tuberculosis

<400> SEQUENCE: 404

Ala Ala Phe Gln Ala Ala His Ala Arg Phe Val Ala Ala Ala Ala
1               5                   10                  15

<210> SEQ ID NO 405
<211> LENGTH: 15
<212> TYPE: PRT
```

-continued

```
<213> ORGANISM: Mycobacterium tuberculosis

<400> SEQUENCE: 405

Ala Leu Thr Ala Leu Ile Arg Asp Pro Pro Ala Asp Ser Thr Gly
1               5                   10                  15
```